(12) United States Patent
Brower-Toland et al.

(10) Patent No.: US 11,186,843 B2
(45) Date of Patent: Nov. 30, 2021

(54) COMPOSITIONS AND METHODS FOR SITE DIRECTED GENOMIC MODIFICATION

(71) Applicant: MONSANTO TECHNOLOGY LLC, St. Louis, MO (US)

(72) Inventors: Brent Brower-Toland, St. Louis, MO (US); Andrei Y. Kouranov, St. Louis, MO (US); Rosemarie Kuehn, St. Louis, MO (US); Richard J. Lawrence, Kirkwood, MO (US); Ervin D. Nagy, St. Louis, MO (US); Linda Rymarquis, St. Louis, MO (US); Veena Veena, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 165 days.

(21) Appl. No.: 15/120,110

(22) PCT Filed: Feb. 27, 2015

(86) PCT No.: PCT/US2015/018104
§ 371 (c)(1),
(2) Date: Aug. 18, 2016

(87) PCT Pub. No.: WO2015/131101
PCT Pub. Date: Sep. 3, 2015

(65) Prior Publication Data
US 2017/0166912 A1   Jun. 15, 2017

Related U.S. Application Data

(60) Provisional application No. 61/945,700, filed on Feb. 27, 2014.

(51) Int. Cl.
*C12N 15/81* (2006.01)
*C12N 15/82* (2006.01)

(52) U.S. Cl.
CPC ..... *C12N 15/8213* (2013.01); *C12N 15/8216* (2013.01)

(58) Field of Classification Search
None
See application file for complete search history.

(56) References Cited

U.S. PATENT DOCUMENTS

| | | |
|---|---|---|
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,945,839 B2 | 2/2015 | Zhang |
| 9,840,713 B2 * | 12/2017 | Zhang .................. C12N 15/746 |
| 2012/0095080 A1 | 4/2012 | Rossi et al. |
| 2014/0068797 A1 | 3/2014 | Doudna et al. |
| 2014/0170753 A1 | 6/2014 | Zhang |
| 2014/0227787 A1 | 8/2014 | Zhang |
| 2014/0242664 A1 | 8/2014 | Zhang et al. |
| 2014/0273231 A1 | 9/2014 | Cong et al. |
| 2014/0273232 A1 | 9/2014 | Zhang et al. |
| 2014/0273234 A1 | 9/2014 | Zhang et al. |
| 2014/0302563 A1 | 10/2014 | Doudna et al. |
| 2015/0082478 A1 * | 3/2015 | Cigan .................. C12N 15/81 800/270 |

FOREIGN PATENT DOCUMENTS

| | | |
|---|---|---|
| WO | WO-2013/176772 | 11/2013 |
| WO | WO-2014/018423 | 1/2014 |
| WO | WO-2014/065596 | 5/2014 |
| WO | WO-2014/150624 | 9/2014 |
| WO | WO-2014/191518 | 12/2014 |
| WO | WO-2014/191521 | 12/2014 |
| WO | WO-2014/194190 | 12/2014 |
| WO | WO 2015/026887 | 2/2015 |

OTHER PUBLICATIONS

Connelly et al. Small nuclear RNA genes transcribed by either RNA polymerase II or RNA polymerase III in monocot plants share three promoter elements and use a strategy to regulate gene expression different from that used by their dicot plant counterparts. Mol Cell Biol. Sep. 1994;14(9):5910-9.*
Wang et al. Hairpin RNAs derived from RNA polymerase II and polymerase III promoter-directed transgenes are processed differently in plants. RNA. May 2008;14(5):903-13. Epub Mar. 26, 2008. (Year: 2008).*
Owor et al. A rep-based hairpin inhibits replication of diverse maize streak virus isolates in a transient assay. J Gen Virol. Oct. 2011; 92(Pt 10):2458-65. Epub Jun. 8, 2011. (Year: 2011).*
Cho et al.,"Targeted genome engineering in human cells with the Cas9 RNA-guided endonuclease," *Nat Biotechnol*, 31:230-232, 2013.
Cong et al., "Multiplex genome engineering using CRISPR/Cas Systems," *Science*, 339:819-823, 2013.

(Continued)

*Primary Examiner* — Cynthia E Collins
(74) *Attorney, Agent, or Firm* — Dentons US LLP; Amanda Carmany-Rampey

(57) ABSTRACT

The disclosure provides novel corn, tomato, and soybean U6, U3, U2, U5, and 7SL snRNA promoters which are useful for CRISPR/Cas-mediated targeted gene modifications in plants. The disclosure also provides methods for use for U6, U3, U2, U5, and 7SL promoters in driving expression of sgRNA polynucleotides which function in a CRISPR/Cas system of targeted gene modification in plants. The disclosure also provides methods of genome modification by insertion of blunt-end DNA fragments at a site of genomic cleavage.

17 Claims, 27 Drawing Sheets
Specification includes a Sequence Listing.

(56) References Cited

OTHER PUBLICATIONS

Connelly et al., "Small nuclear RNA genes transcribed by either RNA polymerase II or RNA polymerase III in monocot plants share three promoter elements and use a strategy to regulate gene expression different from that used by their dicot plant counterparts," *Mol Cell Biol*, 14(9):5910-5919, 1994.
Doudna et al., "The new frontier of genome engineering with CRISPR-Cas9," *Science*, 346:1258096, 2014.
Esvelt et al., "Concerning RNA-guided gene drives for the alteration of wild populations," *Elife*, 3:e03401, 2014.
Gaj et al., "ZFN, TALEN, and CRISPR/Cas-based methods for genome engineering," *Trends Biotechnol*, 31:397-405, 2013.
GenBank CG438579.1 OGTBE38TV ZM_0.7_1.5_KB *Zea mays* genomic clone ZMMBMa0854H03, genomic survey sequence [online] Sep. 17, 2003 [retrieved Jul. 13, 2015]. Available at: http://www.ncbi.nlm.nih.gov/nucgss/CG438579.
GenBank CP000494.1 *Bradyrhizobium* sp. BTAi1, complete genome [Showing 3.19kb region from base 4149455 to 4152649] [online] Jan. 14, 2014 [retrieved Jul. 13, 2015]. Available at: http://www.ncbi.nlm.nih.gov/nuccore/146403799?from=4149455&to4152649&sat=4&sat_key=105750108.
Hale et al., "Essential features and rational design of CRISPR RNAs that function with the Cas RAMP module complex to cleave RNAs," *Mol Cell*, 45:292-302, 2012.
Jiang et al., "Demonstration of CRISPR/Cas9/sgRNA-mediated targeted gene modification in *Arabidopsis*, tobacco, sorghum and rice," *Nucl Acids Res*, 41(20):e188, 2013.
Jinek et al., "A programmable dual-RNA-guided DNA endonuclease in adaptive bacterial immunity," *Science*, 337:816-821, 2012.
Li et al., "Heritable gene targeting in the mouse and rat using a CRISPR-Cas system," *Nat Biotechnol*, 31:681-683, 2013.
Li et al., "Multiplex and homologous recombination-mediated genome editing in *Arabidopsis* and Nicotiana benthamiana using guide RNA and Cas9," *Nat Biotechnol*, 31(8):688-691, 2013.
Li et al., "Simultaneous generation and germline transmission of multiple gene mutations in rat using CRISPR-Cas systems," *Nature Biotechnol*, 31:684-686, 2013.
Liang et al., "Targeted mutagenesis in *Zea mays* using TALENs and the CRISPR/Cas system," *J Genet Genomics*, 41:63-68, 2014.
Long et al., "Prevention of muscular dystrophy in mice by CRISPR/Cas9-mediated editing of germline DNA," *Science*, 345:1184-1188, 2014.
Mali et al., "RNA-guided human genome engineering via Cas9," *Science*, 339:823-826, 2013.
Marshallsay et al, "Characterization of the U3 and U6 snRNA genes from wheat: U3 snRNA genes in monocot plants are transcribed by RNA polymerase III," *Plant Mol Biol*, 19:973-983, 1992.
Nekrasov et al., "Targeted mutagenesis in the model plant Nicotaiana benthamiana using Cas9 RNA-guided endonuclease," *Nat Biotechnol*, 31(8):691-693, 2013.
Qi et al., "RNA processing enables predictable programming of gene expression," *Nat Biotechnol*, 30:1002-1006, 2012.
Sampson et al., "A CRISPR/Cas system mediates bacterial innate immune evasion and virulence," *Nature*, 497:254-257, 2013.
Shan, et al., "Targeted genome modification of crop plants using a CRISPR-Cas system," *Nat Biotechnol*, 31(8):686-688, 2013.
Van der Oost, "New tool for genome surgery," *Science*, 339:768-770, 2013.
Wang et al., "One-step generation of mice carrying mutations in multiple genes by CRISPR/Cas-mediated genome engineering," *Cell*, 153:910-918, 2013.
Westra et al., "The CRISPRs, they are a-changin': how prokaryotes generate adaptive immunity," *Annu Rev Genet*, 46:311-339, 2012.
International Search Report and Written Opinion for PCT/US15/18104 dated Jul. 31, 2015.
Belhaj et al., "Plant genome editing made easy: targeted mutagenesis in model and crop plants using the CRISPR/Cas system," *Plant Methods* 9:39, 2013.
EBI Accession No. X51447, dated Mar. 13, 1990.
EBI Accession No. Z17301, dated Oct. 16, 1992.
Partial Supplementary European Search Report regarding European Application No. EP 15755923, dated Jun. 21, 2017.
Patron, "How to Knock-Out Plant Genes Using RNA-Guided CAS9," *TSL Plasmids & Molecular Tools*. <http://synbio.tsl.ac.uk/how-to-assemble-case9crispr-constructs-for-use-in-plants/>. Retrieved from the internet on Jun. 1, 2017.
Qu et al., "Artificial MicroRNA-Mediated Virus Resistance in Plants," *Journal of Virology* 81(12):6690-6699, 2007.
Sugano et al., "CRISPR/Cas9-Mediated Targeted Mutagenesis in the Liverwort *Marchantia polymorpha* L.," *Plant & Cell Physiology* 55(3):475-481, 2014.
Veretnik et al., "Nucleotide sequence of a maize U6 gene," *Nucleic Acids Research* 18(12):3661, 1990.
Watson et al., "RNA silencing platforms in plants," *FEBS Letters* 579:5982-5987, 2005.
Xie et al., "RNA-Guided Genome Editing in Plants Using a CRISPR-Cas System," *Molecular Plant* 6(6):1975-1983, 2013.

\* cited by examiner

| GUUS target | Cas9 | sgRNA target | sgRNA promoter | GFP | GUS |
|---|---|---|---|---|---|
| Zm231 | - | - | - |  |  |
| Zm231 | - | Zm231 | ch8 |  |  |
| Zm231 | + | Zm14 | ch8 |  |  |
| Zm14 | + | Zm231 | ch8 |  |  |
| Zm231 | + | Zm231 | ch8 |  |  |
| Zm231 | + | Zm231 | ch1 |  |  |
| Zm231 | + | Zm231 | ch2 |  |  |
| Zm231 | + | Zm231 | ch3 |  |  |

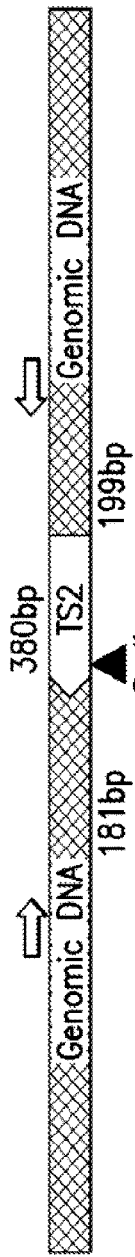
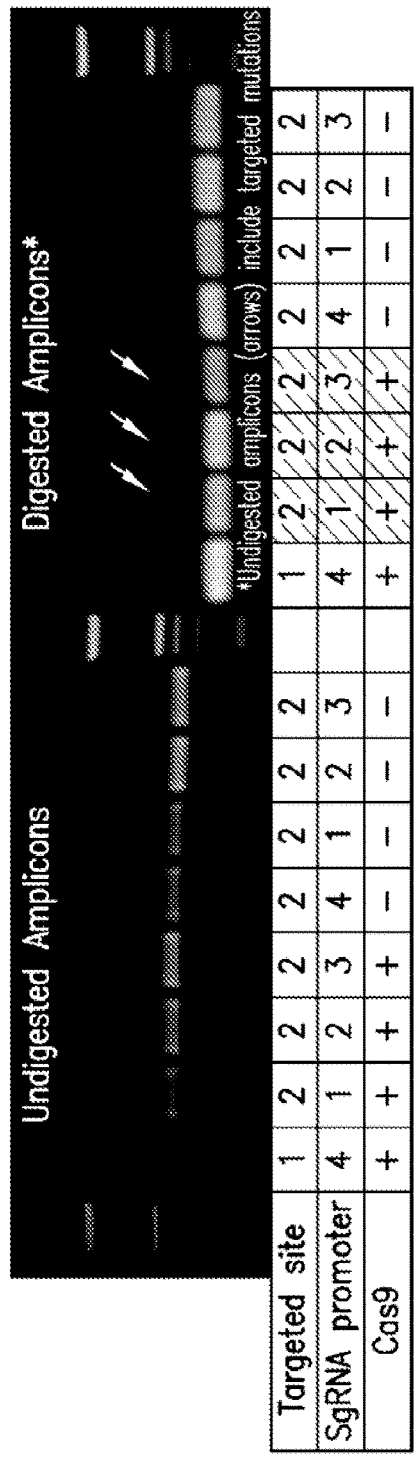
FIG. 17A
FIG. 17B
FIG. 17C

```
                              SEQUENCE LISTING

<160> NUMBER OF SEQ ID NOS: 295

<210> SEQ ID NO 1
<211> LENGTH: 397
<212> TYPE: DNA
<213> ORGANISM: Zea mays

<400> SEQUENCE: 1
aggaaaagaa gaggtgatta ctgtacctat tcgtctttgt atcggaatat aaatttatca     60
ctattttatg ataaagtaaa tctgtttccc tgtagagtta attaattaat gtaagtataa    120
gcgtaattta tagggcacta gtaggactgt cgactgtgcg ctcggcccgg ataatgcgtc    180
aaaagcgaag acgtgcacgt gggatgggaa acacgaagc gtggtctgct ttttcgcatg     240
atatctgggc cgcaccaaag aatccagccc acgcggcgtg gcgccgtcgt tacggcttgc    300
gggggaagga aacgagggac gaaccgagat ttagcaccag accggccagc gagcattgca    360
gacaccggct tataagttca gctgcgacta ccactcc                            397

<210> SEQ ID NO 2
<211> LENGTH: 200
<212> TYPE: DNA
<213> ORGANISM: Zea mays

<400> SEQUENCE: 2
cgtgggatgg gaaaacacga agcgtggtct gctttttcgc atgatatctg ggccgcacca     60
aagaatccag cccacgcggc gtggcgccgt cgttacggct tgcgggggaa ggaaacgagg    120
gacgaaccga gatttagcac cagaccggcc agcgagcatt gcagacaccg gcttataagt    180
tcagctgcga ctaccactcc                                               200

<210> SEQ ID NO 3
<211> LENGTH: 397
<212> TYPE: DNA
<213> ORGANISM: Zea mays

<400> SEQUENCE: 3
ttatatgtta ccgttgcaaa gcacgggcac tcacctagta tataatataa catcagtcgt     60
acgtaatgta ctgatgggcg ggttaacaaa tgtcactcac tatcagcacc agcagcgctt    120
agatgcatcc ggccgggcca agacccagga ccagaaagcg cgcacgttca cagcggatgc    180
tgatgggtta gatcgactga tcgaggaaga ggagagctta attaagaaac gccctgttcc    240
gctttgctag cttgcgccct gactgtccag cccacgcgct tcggtccgat tcacatgcta    300
ggctggtgca agcgagccga gacttttttt tagaaccacc ttgctcagca aaccttagga    360
acaccggctt ataagtcgaa gcgaagcgct gtgcact                            397

<210> SEQ ID NO 4
<211> LENGTH: 200
<212> TYPE: DNA
<213> ORGANISM: Zea mays

<400> SEQUENCE: 4
tgatcgagga agaggagagc ttaattaaga aacgccctgt tccgctttgc tagcttgcgc     60
```

```
cctgactgtc cagcccacgc gcttcggtcc gattcacatg ctaggctggt gcaagcgagc    120
cgagactttt ttttagaacc accttgctca gcaaaccttta ggaacaccgg cttataagtc    180
gaagcgaagc gctgtgcact                                                 200
```

<210> SEQ ID NO 5
<211> LENGTH: 397
<212> TYPE: DNA
<213> ORGANISM: Zea mays

<400> SEQUENCE: 5

```
ggattcggtg ttctttatta ggttctcgcc gaatatggtt ctcagttatg acctaacggt     60
gtccacaaga gttcgccagg atttatacaa ctattttctt atttatttct ttaacatttt    120
cccttctacg cacaatagga gataatgtca agcgttgacg gtgcacatat atttgttttt    180
ttaaaggcgt agtggcgtgt gtgcaaaaac atcctcacag gaaagacacg aagaaacatg    240
gtcaatggcc cattatataa agcaccgcca caaagcccaa ataccagttc gtcggtggag    300
caagtaacgc gctaggcaac aggcaaacag tttgtcccac ctcgtccagt cacaaaggca    360
aagcgtgact tataagccag agcggaagaa ccatacc                             397
```

<210> SEQ ID NO 6
<211> LENGTH: 200
<212> TYPE: DNA
<213> ORGANISM: Zea mays

<400> SEQUENCE: 6

```
tgtgtgcaaa aacatcctca caggaaagac acgaagaaac atggtcaatg gcccattata    60
taaagcaccg ccacaaagcc caaataccag ttcgtcggtg gagcaagtaa cgcgctaggc   120
aacaggcaaa cagtttgtcc cacctcgtcc agtcacaaag gcaaagcgtg acttataagc   180
cagagcggaa gaaccatacc                                                200
```

<210> SEQ ID NO 7
<211> LENGTH: 397
<212> TYPE: DNA
<213> ORGANISM: Zea mays

<400> SEQUENCE: 7

```
tcgtaaaata gtggtgtcca agaatttcc aggcccagtt gtaaaagcta aaatgctatt     60
cgaatttcta ctagcagtaa gtcgtgttta gaaattattt tttatatac ctttttttcct   120 tctatgtaca gtaggacaca gtgtcagcgc gcgttgacg gagaatattt gcaaaaaagt    180
aaaagagaaa gtcatagcgg cgtatgtgcc aaaaacttcg tcacagagag gccataaga    240 acatggccc acggcccaat acgaagcacc gcgacgaagc ccaaacagca gtccgtaggt    300
ggagcaaagc gctgggtaat acgcaaacgt tttgtcccac cttgactaat cacaagagtg    360
gagcgtacct tataaaccga ccgcaagca ccgaatt                              397
```

<210> SEQ ID NO 8
<211> LENGTH: 200
<212> TYPE: DNA
<213> ORGANISM: Zea mays

<400> SEQUENCE: 8

```
cggcgtatgt gccaaaaact tcgtcacaga gagggccata agaaacatgg cccacggccc     60
aatacgaagc accgcgacga agcccaaaca gcagtccgta ggtggagcaa agcgctgggt   120
aatacgcaaa cgttttgtcc caccttgact aatcacaaga gtggagcgta ccttataaac   180
```
cgagccgcaa gcaccgaatt                                                  200

<210> SEQ ID NO 9
<211> LENGTH: 540
<212> TYPE: DNA
<213> ORGANISM: Solanum lycopersicum

<400> SEQUENCE: 9
gttacgtaat tatatttctt agtcatattt tagttattcc atcttaacca cataggtgat       60
agtcaatatg tctatttcac atgtatggtt ccgtactata attaacaaca tattgatttg      120
aaattctatt tgtgctacat atattagaca aggaaaataa catatgttat tttgaaatca      180
cgtatattta ctataaatta caatgattaa caacttaaaa tatttaaatg aaaatcatat      240
taatgactct ctaaatttta tctgtgtcac ataaatgaaa acaaaaaat aacaaatatt       300
gtattcgcac gggcgcatgt gtctagttag ttataaacga agaaataagg ggctgatttc      360
gaaataaacg ttcttagaat tggaagaaat gttcagtttc taaacttgta ggactaaagc      420
aataactttt atttaattta ttttctttta tgtttctccc acatcgatca tacatataac      480
tatacagcag tataagaact ctagcgaagc aataatgctc gtcccgttgg ggacatccga      540

<210> SEQ ID NO 10
<211> LENGTH: 600
<212> TYPE: DNA
<213> ORGANISM: Solanum lycopersicum

<400> SEQUENCE: 10
tataataata ctatgttaaa tatgcaacat gtattagaag tgaattaagt atgcaataga       60
tatgtattta aaatatatt atgcttgttt gataagaagt tgatgcattg tattataagt       120
acgttagaat gtgcaataaa tatattatct atcattagaa cttgaattat aagtgaataa      180
tagattattt tttgtaatat gaattaaaag tgtattaaac atgtattaac ggtgatcaat      240
tggttaaaaa aagtttatt attaaaatga taaatctttt taatttatag tatatttatg       300
taagttttca cgttgagtaa atagcgaaga agttgggccc aaccaagtaa ataagaagg       360
ccgggccatt acaattaagt cgtcacacaa ctgggcttca ttgaaaaaag cgcaaaaccg      420
attccaggcc cgtgttagca tgaagactca actcaaccag agatttctcc ctcatcgctt      480
acagaaaaaa gctatatgct gtttatattg cgaaatctaa cagtgtagtt tgtcccttcg      540
gggacatccg ataaaattgg aacgatacag agaagattag catggcccct gcgcaaggat      600

<210> SEQ ID NO 11
<211> LENGTH: 540
<212> TYPE: DNA
<213> ORGANISM: Solanum lycopersicum

<400> SEQUENCE: 11
ttctccaaaa aaaaaaaga aagaagaag caaacaaaca aatagaagca tatctcttga        60
tgtggaagga gatcaaaata ttcccaataa atacttatga gaagaagtaa ctgatttaaa     120
attttcacta atagggttcg aaaaatgaaa atgtaatacg tggaacttga atgtaaaacc      180
tcaaggaatt cttgtgttta agaaattcaa atctctcta aatgtataca aaagatgatt      240
tcttttttacc ttatatatag taaaataaaa ttgtcggata aattcgagtg aacaccctag     300
cacccccta atcctccccc gtagtcggcc cattacagtt aaagtccagg tacaacaaaa      360
tgggcttcga ttaagatgga ataaaaggag tccaggccca tgagcccaac aaacaagcta     420

| | |
|---|---|
| tttctccctc atcggcgcac aaagaagctt tattctctta ttatagctga atattagcat | 480 |
| gtgtgtttgt cccttcgggg acatccgata aaattggaac gatacagaga agattagcat | 540 |

<210> SEQ ID NO 12
<211> LENGTH: 540
<212> TYPE: DNA
<213> ORGANISM: Glycine max

<400> SEQUENCE: 12

| | |
|---|---|
| acctttttaa ccgcacaaag ttttaaccag atttatataa tttattttttg aatccccaat | 60 |
| acatatcatt ataacatatc aattatcaaa tatttcaata acctcatgat atggcaatga | 120 |
| atacatcttc ttctcaatga acagagattt ctgaaaaaga ttaggaaagt gaaagcatac | 180 |
| tcgtttgcaa tgtaaaactg atacttcccc aaaatcatca tattccaaat atgccctggt | 240 |
| gttactgacc aaaaccagaa aaaagaaacg gaagacatat acgtctaaac ggagaaattt | 300 |
| caaaaaacaa aaattggatc atttctcgat ttgtgggtgt catcttgtgc agggcatgct | 360 |
| aatcttctct ttacccttttc ccacaagact cagcgcatgt tgtctcgtct catccaagtc | 420 |
| ccacaccgcc taaacttaac acaatattag tatttataat gacatacaac attcaagatg | 480 |
| ttgtcccttc ggggacatcc gataaaattg gaacgataca gagaagatta gcatggcccc | 540 |

<210> SEQ ID NO 13
<211> LENGTH: 540
<212> TYPE: DNA
<213> ORGANISM: Glycine max

<400> SEQUENCE: 13

| | |
|---|---|
| cattataaaa agtaaaatat aactactttg ttttttaata aaaaaaattc aatgggagat | 60 |
| actatggatt caattacctt actgatttta tttcatatgt gccagaagta tttcagtttta | 120 |
| ttttgaaaaa tcagaaaaaa aatgtctgga ataaaatata ataagcgata ctaataaata | 180 |
| attgaacaag ataatggta aaatgtcaaa tcaaaactag gctacagagt gcagagcaga | 240 |
| gtcatgatga atgacagcta gttctactta ctacaccgat tcttgtgtac ataaaaatat | 300 |
| tttaaaataa ttgaatcttt cttttagccag cttttgacaac aatgtacacc gttcgtactt | 360 |
| cttactggta ggcaatgctt cttgtttgct ttcggtggaa ggtgtatata ctcaacatta | 420 |
| cttcttttttc agcgtgttttt cttacgggag tcccacaccg cccaaaacta atacagtatt | 480 |
| cttgttttata aagaagtgca ccacttcaat tgttgtccct tcggggacat ccgataaaat | 540 |

<210> SEQ ID NO 14
<211> LENGTH: 540
<212> TYPE: DNA
<213> ORGANISM: Glycine max

<400> SEQUENCE: 14

| | |
|---|---|
| atattcataa ttttttttttt ttgtttttttt atacaaggac ggctgattca atcatcacac | 60 |
| cacacgtcat attaaaaaaa tatagtagat ttatttttaaa atagagagaa tcgttaagaa | 120 |
| aaaaataaat agtaaagtaa atgaaaaccc aaataatatc attattatgt caataagtcg | 180 |
| gagaggatag taatcaaatg gtctatgagg tggtggttca ttcaacatat agcacctatt | 240 |
| cattgttcct aaaacataat ttaagaacaa aaacttaaac ttaaataata ataataaaag | 300 |
| agtacatcga agtatctgtg ttctctatcc ttctgactaa cattcatgtt gtttgtattc | 360 |
| agcaaagggc cgtgcaggat ttgtgcgtcg cgctccggtt agttattgca gtgaccgtct | 420 |
| cttttagtccc acatcgagta attatgcttc atacagtctg tttatataac agagatggaa | 480 |

```
caaactggtt gtcccttcgg ggacatccga taaaattgga acgatacaga gaagattagc    540
```

<210> SEQ ID NO 15
<211> LENGTH: 540
<212> TYPE: DNA
<213> ORGANISM: Glycine max

<400> SEQUENCE: 15

```
ctttcaggtc atgattttt gtttctaaat gatactcaca ctcccttcca gtttttttt      60
tttaaactca gctcccttgc ttcctccacc ggttatcata atactgaacc aaatcaaaca   120
ttacagtcaa ggtactatga atatgaaacc tgaaatccta tgaatgtcat aaatttattt   180
taaataataa atttatttag aataatattt ttttgggtaa gagttataaa ataaaataca   240
aaaaaaaaac ctaatatcaa tttttcactg actccgttta tattgagact tgagaaagat   300
ggttcccgtt tgctcccggt ggaggctccg aggctgtgta tatactcgac attactttag   360
cttgttttgt tgtttctttc cctttcccac aagactcagg tctcgttcgc aaacgagtcc   420
cacaccgtct aaacttacca caatattagc gtttataatt agatgcactg catcacttat   480
tgtcccttcg ggacatccg ataaaattgg aacgatacag agaagattag catggcccct    540
```

<210> SEQ ID NO 16
<211> LENGTH: 420
<212> TYPE: DNA
<213> ORGANISM: Glycine max

<400> SEQUENCE: 16

```
tgcagagcag agtcatgatg atactactta ctacaccgat tcttgtgtgc agaaaaatat    60
gttaaaataa ttgaatcttt ctctagccaa atttgacaac aatgtacacc gttcatattg   120
agagacgatg cttcttgttt gctttcggtg gaagctgcat atactcaaca ttactccttc   180
agcgagtttt ccaactgagt cccacattgc ccagacctaa cacggtattc ttgtttataa   240
tgaaatgtgc caccacatgg attgtccctt cggggacatc cgataaaatt ggaacgatac   300
agagaagatt agcatggccc ctgcgcaagg atgacacgca caatcgaga atggtccaa    360
attttttttg aaatttctcg tttagataga tgtctttgct tttccgcact atggttctga   420
```

<210> SEQ ID NO 17
<211> LENGTH: 397
<212> TYPE: DNA
<213> ORGANISM: Artificial Sequence
<220> FEATURE:
<223> OTHER INFORMATION: Recombinant

<400> SEQUENCE: 17

```
aggaaaagaa gaggtgatta ctgtacctat tcgtctttgt atcggaatat aaatttatca    60
ctatttatg ataaagtaaa tctgtttccc tgtagagtta attaattaat gtaagtataa   120
gcgtaattta tagggcacta gtaggactgt cgactgtgcg ctcggcccgg ataatgcgtc   180
aaaagcgaag acgtgcacgt gggatgggaa acacgaagc gtggtctgct ttttcgcatg   240
atatctgggc cgcaccaaag aatccagccc acgggcgtg gcgccgtcgt tacggcttgc    300
gggggaagga aacgagggac gaaccgagat ttagtcccac cttgactaat cacaagagtg   360
gagcgtacct tataaaccga gccgcaagca ccgaatt                            397
```

<210> SEQ ID NO 18
<211> LENGTH: 397
<212> TYPE: DNA

```
<213> ORGANISM: Artificial Sequence
<220> FEATURE:
<223> OTHER INFORMATION: Recombinant

<400> SEQUENCE: 18
aggaaaagaa gaggtgatta ctgtacctat tcgtctttgt atcggaatat aaatttatca    60
ctattttatg ataaagtaaa tctgtttccc tgtagagtta attaattaat gtaagtataa   120
gcgtaattta tagggcacta gtaggactgt cgactgtgcg ctcggccgg ataatgcgtc    180 aaaagcgaag acgtgcacgt gggatgggaa acacgaagc gtggtctgct ttttcgcatg    240
atatctgggc cgcaccaaag aatccagccc acgcggaagc ccaaacagca gtccgtaggt   300
ggagcaaagc gctgggtaat acgcaaacgt tttgtcccac cttgactaat cacaagagtg   360
gagcgtacct tataaaccga gccgcaagca ccgaatt                            397

<210> SEQ ID NO 19
<211> LENGTH: 397
<212> TYPE: DNA
<213> ORGANISM: Artificial Sequence
<220> FEATURE:
<223> OTHER INFORMATION: Recombinant

<400> SEQUENCE: 19
aagtcgtaaa atagtggtgt ccaaagaatt tccaggccca gttgtaaaag ctaaaatgct    60
attcgaattt ctactagcag taagtcgtgt ttagaaatta ttttatatac cttttttcct   120
tctatgtaca gtaggacaca gtgtcagcgc cgcgttgacg agaatatttt gcaaaaaagt   180
aaaagagaaa gtcatagcgg cgtatgtgcc aaaaacttcg tcacagagag gccataaga    240 aacatggccc acggcccaat acgaagcacc gcgacgaagc ccaaacagca gtccgtaggt   300
ggagcaaagc gctgggtaat acgcaaacgt tttgcaccag accggccagc gagcattgca   360
gacaccggct tataagttca gctgcgacta ccactcc                            397

<210> SEQ ID NO 20
<211> LENGTH: 397
<212> TYPE: DNA
<213> ORGANISM: Artificial Sequence
<220> FEATURE:
<223> OTHER INFORMATION: Recombinant

<400> SEQUENCE: 20
tcgtaaaata gtggtgtcca agaatttcc aggcccagtt gtaaaagcta aatgctatt     60 cgaatttcta ctagcagtaa gtcgtgttta gaaattattt ttttatatac cttttttcct   120
tctatgtaca gtaggacaca gtgtcagcgc cgcgttgacg agaatatttt gcaaaaaagt   180
aaaagagaaa gtcatagcgg cgtatgtgcc aaaaactgtc acagagaggg ccataagaaa   240
catggcccac ggcccaataa gcccaccagc ccaccgaagc ccaaacagca gtccgtaggt   300
ggagcaaagc gctgggtaat acgcaaacgt tttgtcccac cttgactaat cacaagagtg   360
gagcgtacct tataaaccga gccgcaagca ccgaatt                            397

<210> SEQ ID NO 21
<211> LENGTH: 83
<212> TYPE: DNA
<213> ORGANISM: Artificial Sequence
<220> FEATURE:
<223> OTHER INFORMATION: Recombinant

<400> SEQUENCE: 21
gttttagagc tagaaatagc aagttaaaat aaggctagtc cgttatcaac ttgaaaaagt    60
```

```
ggcaccgagt cggtgctttt ttt                                           83
```

<210> SEQ ID NO 22
<211> LENGTH: 23
<212> TYPE: DNA
<213> ORGANISM: Zea mays

<400> SEQUENCE: 22

```
gccggccagc atttgaaaca tgg                                           23
```

<210> SEQ ID NO 23
<211> LENGTH: 20
<212> TYPE: DNA
<213> ORGANISM: Zea mays

<400> SEQUENCE: 23

```
gccggccagc atttgaaaca                                               20
```

<210> SEQ ID NO 24
<211> LENGTH: 20
<212> TYPE: DNA
<213> ORGANISM: Zea mays

<400> SEQUENCE: 24

```
gttatcaatt tactttcaat                                               20
```

<210> SEQ ID NO 25
<211> LENGTH: 20
<212> TYPE: DNA
<213> ORGANISM: Zea mays

<400> SEQUENCE: 25

```
gcgcaaggga tcagtaattc                                               20
```

<210> SEQ ID NO 26
<211> LENGTH: 1064
<212> TYPE: PRT
<213> ORGANISM: Bradyrhizobium

<400> SEQUENCE: 26

Met Lys Arg Thr Ser Leu Arg Ala Tyr Arg Leu Gly Val Asp Leu Gly
1               5                   10                  15

Ala Asn Ser Leu Gly Trp Phe Val Val Trp Leu Asp Asp His Gly Gln
                20                  25                  30

Pro Glu Gly Leu Gly Pro Gly Gly Val Arg Ile Phe Pro Asp Gly Arg
            35                  40                  45

Asn Pro Gln Ser Lys Gln Ser Asn Ala Ala Gly Arg Arg Leu Ala Arg
        50                  55                  60

Ser Ala Arg Arg Arg Arg Asp Arg Tyr Leu Gln Arg Arg Gly Lys Leu
65                  70                  75                  80

Met Gly Leu Leu Val Lys His Gly Leu Met Pro Ala Asp Glu Pro Ala
                85                  90                  95

Arg Lys Arg Leu Glu Cys Leu Asp Pro Tyr Gly Leu Arg Ala Lys Ala
            100                 105                 110

Leu Asp Glu Val Leu Pro Leu His His Val Gly Arg Ala Leu Phe His
        115                 120                 125

Leu Asn Gln Arg Arg Gly Leu Phe Ala Asn Arg Ala Ile Glu Gln Gly
    130                 135                 140

Asp Lys Asp Ala Ser Ala Ile Lys Ala Ala Ala Gly Arg Leu Gln Thr

-continued

```
            145                 150                 155                 160
Ser Met Gln Ala Cys Gly Ala Arg Thr Leu Gly Glu Phe Leu Asn Arg
                    165                 170                 175
Arg His Gln Leu Arg Ala Thr Val Arg Ala Arg Ser Pro Val Gly Gly
                    180                 185                 190
Asp Val Gln Ala Arg Tyr Glu Phe Tyr Pro Thr Arg Ala Met Val Asp
                    195                 200                 205
Ala Glu Phe Glu Ala Ile Trp Ala Ala Gln Ala Pro His His Pro Thr
        210                 215                 220
Met Thr Ala Glu Ala His Asp Thr Ile Arg Glu Ala Ile Phe Ser Gln
225                 230                 235                 240
Arg Ala Met Lys Arg Pro Ser Ile Gly Lys Cys Ser Leu Asp Pro Ala
                    245                 250                 255
Thr Ser Gln Asp Asp Val Asp Gly Phe Arg Cys Ala Trp Ser His Pro
                    260                 265                 270
Leu Ala Gln Arg Phe Arg Ile Trp Gln Asp Val Arg Asn Leu Ala Val
                    275                 280                 285
Val Glu Thr Gly Pro Thr Ser Ser Arg Leu Gly Lys Glu Asp Gln Asp
        290                 295                 300
Lys Val Ala Arg Ala Leu Leu Gln Thr Asp Gln Leu Ser Phe Asp Glu
305                 310                 315                 320
Ile Arg Gly Leu Leu Gly Leu Pro Ser Asp Ala Arg Phe Asn Leu Glu
                    325                 330                 335
Ser Asp Arg Arg Asp His Leu Lys Gly Asp Ala Thr Gly Ala Ile Leu
                    340                 345                 350
Ser Ala Arg Arg His Phe Gly Pro Ala Trp His Asp Arg Ser Leu Asp
                    355                 360                 365
Arg Gln Ile Asp Ile Val Ala Leu Leu Glu Ser Ala Leu Asp Glu Ala
        370                 375                 380
Ala Ile Ile Ala Ser Leu Gly Thr Thr His Ser Leu Asp Glu Ala Ala
385                 390                 395                 400
Ala Gln Arg Ala Leu Ser Ala Leu Leu Pro Asp Gly Tyr Cys Arg Leu
                    405                 410                 415
Gly Leu Arg Ala Ile Lys Arg Val Leu Pro Leu Met Glu Ala Gly Arg
                    420                 425                 430
Thr Tyr Ala Glu Ala Ala Ser Ala Ala Gly Tyr Asp His Ala Leu Leu
                    435                 440                 445
Pro Gly Gly Lys Leu Ser Pro Thr Gly Tyr Leu Pro Tyr Tyr Gly Gln
        450                 455                 460
Trp Leu Gln Asn Asp Val Val Gly Ser Asp Asp Glu Arg Asp Thr Asn
465                 470                 475                 480
Glu Arg Arg Trp Gly Arg Leu Pro Asn Pro Thr Val His Ile Gly Ile
                    485                 490                 495
Gly Gln Leu Arg Arg Val Val Asn Glu Leu Ile Arg Trp His Gly Pro
                    500                 505                 510
Pro Ala Glu Ile Thr Val Glu Leu Thr Arg Asp Leu Lys Leu Ser Pro
                    515                 520                 525
Arg Arg Leu Ala Glu Leu Glu Arg Glu Gln Ala Glu Asn Gln Arg Lys
        530                 535                 540
Asn Asp Lys Arg Thr Ser Leu Leu Arg Lys Leu Gly Leu Pro Ala Ser
545                 550                 555                 560
Thr His Asn Leu Leu Lys Leu Arg Leu Trp Asp Glu Gln Gly Asp Val
                    565                 570                 575
```

```
Ala Ser Glu Cys Pro Tyr Thr Gly Glu Ala Ile Gly Leu Glu Arg Leu
            580                 585                 590

Val Ser Asp Val Asp Ile Asp His Leu Ile Pro Phe Ser Ile Ser
        595                 600                 605

Trp Asp Asp Ser Ala Ala Asn Lys Val Val Cys Met Arg Tyr Ala Asn
610                 615                 620

Arg Glu Lys Gly Asn Arg Thr Pro Phe Glu Ala Phe Gly His Arg Gln
625                 630                 635                 640

Gly Arg Pro Tyr Asp Trp Ala Asp Ile Ala Glu Arg Ala Ala Arg Leu
                645                 650                 655

Pro Arg Gly Lys Arg Trp Arg Phe Gly Pro Gly Ala Arg Ala Gln Phe
            660                 665                 670

Glu Glu Leu Gly Asp Phe Gln Ala Arg Leu Leu Asn Glu Thr Ser Trp
        675                 680                 685

Leu Ala Arg Val Ala Lys Gln Tyr Leu Ala Ala Val Thr His Pro His
    690                 695                 700

Arg Ile His Val Leu Pro Gly Arg Leu Thr Ala Leu Leu Arg Ala Thr
705                 710                 715                 720

Trp Glu Leu Asn Asp Leu Leu Pro Gly Ser Asp Asp Arg Ala Ala Lys
                725                 730                 735

Ser Arg Lys Asp His Arg His Ala Ile Asp Ala Leu Val Ala Ala
            740                 745                 750

Leu Thr Asp Gln Ala Leu Leu Arg Arg Met Ala Asn Ala His Asp Asp
        755                 760                 765

Thr Arg Arg Lys Ile Glu Val Leu Leu Pro Trp Pro Thr Phe Arg Ile
    770                 775                 780

Asp Leu Glu Thr Arg Leu Lys Ala Met Leu Val Ser His Lys Pro Asp
785                 790                 795                 800

His Gly Leu Gln Ala Arg Leu His Glu Asp Thr Ala Tyr Gly Thr Val
                805                 810                 815

Glu His Pro Glu Thr Glu Asp Gly Ala Asn Leu Val Tyr Arg Lys Thr
            820                 825                 830

Phe Val Asp Ile Ser Glu Lys Glu Ile Asp Arg Ile Arg Asp Arg Arg
        835                 840                 845

Leu Arg Asp Leu Val Arg Ala His Val Ala Gly Glu Arg Gln Gln Gly
    850                 855                 860

Lys Thr Leu Lys Ala Ala Val Leu Ser Phe Ala Gln Arg Arg Asp Ile
865                 870                 875                 880

Ala Gly His Pro Asn Gly Ile Arg His Val Arg Leu Thr Lys Ser Ile
                885                 890                 895

Lys Pro Asp Tyr Leu Val Pro Ile Arg Asp Lys Ala Gly Arg Ile Tyr
            900                 905                 910

Lys Ser Tyr Asn Ala Gly Glu Asn Ala Phe Val Asp Ile Leu Gln Ala
        915                 920                 925

Glu Ser Gly Arg Trp Ile Ala Arg Ala Thr Thr Val Phe Gln Ala Asn
    930                 935                 940

Gln Ala Asn Glu Ser His Asp Ala Pro Ala Ala Gln Pro Ile Met Arg
945                 950                 955                 960

Val Phe Lys Gly Asp Met Leu Arg Ile Asp His Ala Gly Ala Glu Lys
                965                 970                 975

Phe Val Lys Ile Val Arg Leu Ser Pro Ser Asn Asn Leu Leu Tyr Leu
            980                 985                 990
```

| | | |
|---|---|---|
| Val Glu His His Gln Ala Gly Val Phe Gln Thr Arg His Asp Asp Pro | | |
| 995 | 1000 | 1005 |

| | | |
|---|---|---|
| Glu Asp Ser Phe Arg Trp Leu Phe Ala Ser Phe Asp Lys Leu Arg | | |
| 1010 | 1015 | 1020 |

| | | |
|---|---|---|
| Glu Trp Asn Ala Glu Leu Val Arg Ile Asp Thr Leu Gly Gln Pro | | |
| 1025 | 1030 | 1035 |

| | | |
|---|---|---|
| Trp Arg Arg Lys Arg Gly Leu Glu Thr Gly Ser Glu Asp Ala Thr | | |
| 1040 | 1045 | 1050 |

| | |
|---|---|
| Arg Ile Gly Trp Thr Arg Pro Lys Lys Trp Pro | |
| 1055 | 1060 |

<210> SEQ ID NO 27
<211> LENGTH: 3195
<212> TYPE: DNA
<213> ORGANISM: Artificial Sequence
<220> FEATURE:
<223> OTHER INFORMATION: Recombinant

<400> SEQUENCE: 27

```
atgaagagaa cgagtttacg ggcctaccgt ctgggcgtgg atctcggcgc caattcgctg      60
ggatggttcg tggtctggct cgacgatcac ggacagcccg agggccttgg cccggggcggc    120
gtcaggattt tccccgacgg tcgtaacccg caatccaagc aatccaatgc ggccggtcgc    180
cgcctcgcac gcagtgcacg acgacgacga gaccgctatc tgcagcgacg cggaaagctg    240
atgggcttgc tggtcaagca cggcttgatg cccgccgatg agccggcccg aaagcgattg    300
gaatgcctcg atccctatgg tctccgcgcg aaagcgctcg atgaagtgct gcctttgcat    360
catgtcggcc gggcgctgtt tcacctcaac cagcggcgcg gcctgtttgc caatcgagcg    420
atcgagcaag gcgacaagga cgccagcgcg atcaaggccg cggccggcag actgcagaca    480
tcgatgcagg cgtgcggcgc gcgcacgctc ggcgaattcc tcaaccgccg tcatcagctc    540
cgcgccacag tgcgcgcccg cagccctgtc ggcggcgacg tccaggcgcg gtatgaattc    600
tatccgacac gcgcgatggt tgatgcggag ttcaagccaa tctgggcggc acaggcaccg    660
catcacccaa cgatgacggc cgaagcgcat gacacgatcc gcgaggcgat cttctctcaa    720
cgcgcgatga agcggccgtc gatcgggaaa tgctcgctcg accccgccac cagccaggac    780
gacgtcgacg gctttcgctg cgcctggtcg catcccctgg cgcagcgttt ccgcatctgg    840
caggacgtcc gcaatctagc cgtggtggag actggcccca cgtcttccag gcttggcaag    900
gaggatcagg acaaggtcgc acgggcactg ctacagaccg accaactcag cttcgatgag    960
atccgcggcc ttctcggatt gccgtcggac gcgcggttca accttgaaag cgaccggcgt   1020
gatcacctca agggcgacgc gaccggcgcg atcctgtccg ccaggaggca ttttggcccg   1080
gcatggcatg accggtccct ggatcgtcag atcgacatcg tcgcgctgct ggagagcgcg   1140
ctcgatgaag cagcgatcat cgcctcgctc gggacaactc acagccttga tgaagcagct   1200
gcgcagcggg cgttgtccgc cttgctgcct gacggatatt gcaggcttgg actgagggcg   1260
atcaagcggg tcctgccgct catggaagct ggcaggacct acgcggaggc cgccagcgcg   1320
gccggctatg atcacgctct gctgccgggc ggcaagctct ctcccaccgg ctacctgccc   1380
tattatggac aatggctgca gaacgatgtc gtgggctcgg acgatgagcg cgacaccaac   1440
gaacggcgct ggggccgctt gccgaatccc accgttcaca tcgggatcgg ccagttgcga   1500
cgcgtcgtca atgagctcat cagatggcat ggaccgccgg ccgagatcac cgtcgagttg   1560
acgcgtgacc tgaagctgtc gccccgacgg ctggcggagc tcgaacgcga gcaggccgag   1620
```

```
aaccagcgca agaacgacaa gcgtacctcc ctattgcgca agctcgggct ccccgcgagc    1680
acgcacaatc tcctcaagct tcggctctgg gacgagcaag gcgatgttgc aagcgaatgc    1740
ccctatacgg gcgaggcgat cggcctcgaa cgtctggtct ctgatgatgt ggatatcgat    1800
cacctcatcc cattctcgat cagctgggac gacagcgcgg ccaacaaagt ggtctgcatg    1860
cgctacgcca atcgtgagaa gggcaatcga acgccgttcg aggcctttgg ccatcgccaa    1920
ggcaggcctt acgattgggc ggacattgca gaacgcgcag cgcgcctgcc gcgcggcaag    1980
cgctggcgct tcggtccagg cgcgcgggcg caattcgagg agctcggcga ctttcaggca    2040
cgcctgctca acgagaccag ctggctggcg cgcgtcgcca agcaatatct cgcagcggtc    2100
acccacccgc acaggatcca cgttctgccg ggccggctga cagcgctgct ccgcgcaaca    2160
tgggagctca acgatttgct gcccggaagc gacgacagag ccgcgaagag ccgcaaggac    2220
caccgtcatc atgccatcga cgcgctggtg gcggcactga cagaccaggc gctgctgcgc    2280
cgcatggcga acgcgcatga cgatacgcga cggaagatcg aagttctcct gccctggccg    2340
acgttccgga tcgatctcga gaccaggctg aaggcgatgc tcgtatcgca caagcccgat    2400
cacggcctcc aggcccgcct gcatgaagac accgcctatg ggaccgtcga acaccccgaa    2460
accgaggatg gtgcaaatct ggtctatcgg aagaccttcg tggacatcag cgaaaaggag    2520
atcgaccgca ttcgcgatcg ccgcttgcgt gacctcgtca gagcccatgt ggccggcgaa    2580
aggcagcagg gcaagacgct caaagcggcg gtgctgtcat cgcgcagcg cagggacatt    2640 gctggtcacc cgaatggcat tcgccatgtc cgcctgacca aatcgatcaa gccggactat    2700
ctggtaccga tccgcgacaa agccggccgc atctacaagt cctacaatgc aggcgagaat    2760
gccttcgtcg acatcctgca agccgagagt ggccgatgga tcgcgcgggc cacgaccgtc    2820
tttcaggcca atcaagccaa tgagtcgcat gacgcgccag cggcgcaacc gatcatgcgg    2880
gtcttcaagg gcgacatgct gcgcatcgat cacgctggcg cggagaagtt cgtgaagatc    2940
gtcaggcttt cgccctcgaa caacctgctc tacctcgtcg aacatcatca ggcgggcgtg    3000
tttcagaccc gccatgacga cccggaagat tcctttcggt ggctcttcgc cagttttgac    3060
aagcttcgcg aatggaacgc cgagcttgtc cggatcgata cgctgggaca gccctggcgg    3120
cgcaagcgcg gccttgaaac aggaagcgag gacgccactc gcatcggctg gacgcgacca    3180
aaaaaatggc cctga                                                    3195
```

<210> SEQ ID NO 28
<211> LENGTH: 1378
<212> TYPE: PRT
<213> ORGANISM: Artificial Sequence
<220> FEATURE:
<223> OTHER INFORMATION: Recombinant

<400> SEQUENCE: 28

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80
```

```
Tyr Leu Gln Glu Ile Phe Ser Asn Glu Met Ala Lys Val Asp Asp Ser
             85                  90                  95

Phe Phe His Arg Leu Glu Glu Ser Phe Leu Val Glu Glu Asp Lys Lys
        100                 105                 110

His Glu Arg His Pro Ile Phe Gly Asn Ile Val Asp Glu Val Ala Tyr
    115                 120                 125

His Glu Lys Tyr Pro Thr Ile Tyr His Leu Arg Lys Lys Leu Val Asp
130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
```

```
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
            530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
                610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
                675                 680                 685
Ala Asn Arg Asn Phe Met Gln Leu Ile His Asp Asp Ser Leu Thr Phe
                690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
                755                 760                 765
Thr Thr Gln Lys Gly Gln Lys Asn Ser Arg Glu Arg Met Lys Arg Ile
770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
            835                 840                 845
Asp Asp Ser Ile Asp Asn Lys Val Leu Thr Arg Ser Asp Lys Asn Arg
850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
            915                 920                 925
```

```
Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320
```

```
Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Gly Ser Lys Lys Arg Arg Ile Lys Gln Asp
    1370                1375
```

<210> SEQ ID NO 29
<211> LENGTH: 4137
<212> TYPE: DNA
<213> ORGANISM: Artificial Sequence
<220> FEATURE:
<223> OTHER INFORMATION: Recombinant

<400> SEQUENCE: 29

| | | | | | |
|---|---|---|---|---|---|
| atggacaaga | agtacagcat | tggtctggac | atcggaacga | actcggtcgg | ctgggccgtg | 60 |
| attactgacg | agtacaaagt | tcccagcaaa | aaattcaagg | ttctaggcaa | cacagaccgc | 120 |
| cactcgatta | aaaagaatct | aatcggcgcg | cttctgttcg | actctggtga | aacggccgag | 180 |
| gccacacgct | taaagaggac | cgcgcgccgc | cgctacacgc | ggcgcaagaa | ccgaatctgt | 240 |
| tacctccagg | agatcttcag | taatgagatg | gctaaggtcg | atgacagctt | cttccacagg | 300 |
| cttgaagagt | cctttctggt | cgaagaggac | aaaaaacacg | aacgtcaccc | aatcttcggg | 360 |
| aacattgtgg | atgaagtcgc | ataccacgag | aagtatccta | cgatctatca | cctccgcaag | 420 |
| aagctcgtgg | atagtaccga | caaagccgac | ctgcgcttaa | tctaccttgc | gctcgcgcac | 480 |
| atgattaagt | ccgaggaca | cttccttatt | gagggtgatc | tgaatccgga | caattccgat | 540 |
| gtggataaac | tgttcattca | gttggtccag | acatacaatc | agctattcga | ggagaatccg | 600 |
| atcaatgctt | ccggcgtgga | cgcaaaggct | attctgtcag | caagactttc | aaagagcaga | 660 |
| aggttggaga | atctgatcgc | acaacttccc | ggagagaaga | gaatgggct | cttcggcaac | 720 |
| ctcattgcgc | tgtctttggg | tctgacaccg | aactttaagt | ctaacttcga | cctcgctgag | 780 |
| gatgctaaac | ttcagcttag | caaagacacc | tatgatgatg | acctggacaa | cctcctcgcc | 840 |
| cagattggag | accagtacgc | ggatctattc | ttggctgcca | agaacctgtc | cgatgcgatt | 900 |
| ctgcttagtg | acatcctccg | agtgaacact | gaaattacga | agcacccctt | gtcggctagt | 960 |
| atgattaagc | gatacgatga | gcaccatcaa | gacctgacat | tgctaaaggc | gctcgtaaga | 1020 |
| cagcaacttc | ctgagaagta | caaggagata | ttttttgatc | agtctaagaa | tggctacgct | 1080 |
| ggttacatcg | acggtggagc | tagtcaggag | gaattctata | aattcatcaa | gcctatcctg | 1140 |
| gaaaaaatgg | acggtacgga | ggaattgctc | gttaaactaa | atcgagagga | tctgctgaga | 1200 |
| aagcagcgga | ctttcgacaa | tggttctatt | ccgcatcaga | ttcacctcgg | agaacttcac | 1260 |
| gccatcctga | cgacagga | ggacttctac | cctttcctga | agacaaccg | ggaaaaaatc | 1320 |
| gagaagatcc | tgacattcag | gattccttac | tatgtaggcc | ctttagcgag | aggcaacagt | 1380 |
| agattcgcct | ggatgaccag | aaagtctgag | gaaacaatca | caccgtggaa | cttcgaggaa | 1440 |
| gtggttgata | gggtgctag | tgcccaatca | ttcattgaga | gatgacgaa | cttcgacaag | 1500 |
| aatctgccta | acgagaaggt | tctccctaaa | catagcttgc | tttacgagta | tttcacggtg | 1560 |
| tacaatgagc | taacgaaggt | caagtatgtc | acagagggaa | tgcggaaacc | ggctttcctt | 1620 |
| tcgggtgaac | agaagaaagc | aattgtggat | ttgctcttca | agacaaaccg | aaaggtgaca | 1680 |
| gtgaagcagc | taaaggagga | ctacttcaaa | aaaatagagt | gcttcgactc | agttgagatc | 1740 |

```
agcggagtgg aggaccggtt taacgcttcc ctcggcactt accacgactt gctcaagatc    1800
atcaaggaca aagacttcct tgataacgag gagaacgaag catccttga ggacattgtg     1860 ctgacattga cgttgttcga ggatcggag atgatcgagg aacgcctcaa gacgtacgcc     1920
catctgttcg atgataaggt gatgaagcag ttaaagagga gacgttacac tggctggggc    1980
cgtctctctc gcaaactgat aaacgggata agggataaac aaagcggaaa gacaatcctc    2040
gatttcctta aatccgacgg cttcgctaac cggaacttca tgcagctcat ccatgatgac    2100
tcactgacgt tcaaggagga catccagaaa gctcaagtgt ctggccaggg tgacagcttg    2160
cacgagcaca tcgcaaatct agccggttca ccggcgataa agaagggcat tctacaaacg    2220
gtgaaagtgg tggacgagct tgtgaaggtc atgggtcgcc ataagccaga gaacattgtt    2280
atcgaaatgg cgagggagaa ccagacaacg cagaagggaa aaaaaacag tagggagcgg     2340 atgaagcgca tcgaggaagg cattaaggaa cttggaagcc aaatcctgaa agagcacccg    2400
gtggagaata cgcagttgca gaacgagaaa ctgtacctct actacttgca gaatggacgt    2460
gatatgtatg tggatcaaga gttggacatc aaccgattgt ctgactatga cgtggatcac    2520
atagtaccac agtccttcct caaggatgat agcatagaca acaaggttct tactcgtagc    2580
gacaagaatc gtggcaaatc ggacaatgtt ccatctgagg aagttgtcaa aaagatgaaa    2640
aattattgga ggcaacttct gaacgcgaag ctaattacac aaaggaaatt cgacaatctc    2700
actaaggccg agagaggagg gttaagtgag ttagacaagg ctggcttcat caagcggcag    2760
ttggtcgaga ctcgtcagat tactaagcac gtggctcaga tcctggattc gcgcatgaac    2820
accaaatacg acgagaatga caaactcatc cgtgaagtta aggtgattac actgaaatcc    2880
aagctggtct ctgactttag gaaagacttc caattctaca aggtgagaga gattaacaac    2940
taccaccacg cgcatgacgc ctacttgaat gctgtggttg ggactgccct gataaagaaa    3000
tatcctaaac ttgagtctga gttcgtttac ggtgactaca aggtttatga cgttaggaag    3060
atgatcgcca aatccgaaca ggagattggg aaagcaactg ccaaatattt cttttactcc    3120
aacattatga acttttttcaa gacagaaatc acactcgcca atggcgagat tcggaagaga    3180
ccactaatcg aaacaaacgg cgaaactggt gaaatcgttt gggataaggg tagggacttc    3240
gcaactgtta ggaaggtctt gtcgatgcct caagtgaaca tagtcaaaaa aacagaggtc    3300
cagaccggtg ggttctcaaa ggagtctatt ctgccaaagc gtaacagcga caaactcatc    3360
gctcgcaaaa aggactggga tcctaaaaag tacggtggat cgacagccc gaccgttgct     3420 tattctgttc tcgtagttgc taaagtcgag aagggcaagt ccaaaaaact caaatcggtt    3480
aaggaactgc tcggaatcac gataatggaa cgaagcagtt tcgaaaaaaa tccaattgac    3540
ttcctggaag ctaaaggtta caaggaggtc aagaaggatc ttatcatcaa gctacccaag    3600
tacagtctgt tcgaactgga gaacggtcgc aagagaatgc tggcctcggc tggtgaactc    3660
cagaagggca atgagctggc cctgccgtcc aagtacgtga actttctgta cctggcatct    3720
cattacgaga agctcaaggg ctcaccagag gacaacgagc agaagcagtt gttcgttgaa    3780
cagcacaaac actatcttga tgagatcatt gagcaaatta gcgagttcag taagcgagtt    3840
attctggctg atgctaacct ggataaggtg ctctctgcct acaacaagca ccgggataaa    3900
cctattaggg aacaggcgga gaacataatc cacctcttca ctctgacgaa tctcggcgcg    3960
cctgcggcct tcaaatattt tgataccacc atcgacagga gcgctacac aagcactaaa    4020 gaggtgctgg acgccactct cattcaccag tctattaccg ggctctacga gacacggatt    4080
```
gacctctccc agctaggtgg cgatggatct aagaagagaa gaattaaaca agattaa    4137

<210> SEQ ID NO 30
<211> LENGTH: 500
<212> TYPE: DNA
<213> ORGANISM: Artificial Sequence
<220> FEATURE:
<223> OTHER INFORMATION: Recombinant

<400> SEQUENCE: 30
aggaaaagaa gaggtgatta ctgtacctat tcgtctttgt atcggaatat aaatttatca    60
ctattttatg ataaagtaaa tctgtttccc tgtagagtta attaattaat gtaagtataa   120
gcgtaattta tagggcacta gtaggactgt cgactgtgcg ctcggcccgg ataatgcgtc   180
aaaagcgaag acgtgcacgt gggatgggaa acacgaagc gtggtctgct ttttcgcatg    240
atatctgggc cgcaccaaag aatccagccc acgcggcgtg gcgccgtcgt tacggcttgc   300
ggggaagga acgagggac gaaccgagat ttagcaccag accggccagc gagcattgca    360
gacaccggct ataagttca gctgcgacta ccactccgcc ggccagcatt tgaaacagtt    420
ttagagctag aaatagcaag ttaaaataag gctagtccgt tatcaacttg aaaaagtggc   480
accgagtcgg tgcttttttt                                              500

<210> SEQ ID NO 31
<211> LENGTH: 303
<212> TYPE: DNA
<213> ORGANISM: Artificial Sequence
<220> FEATURE:
<223> OTHER INFORMATION: Recombinant

<400> SEQUENCE: 31
cgtgggatgg gaaaacacga agcgtggtct gcttttttcgc atgatatctg ggccgcacca    60
aagaatccag cccacgcggc gtggcgccgt cgttacggct gcgggggaa ggaaacgagg   120
gacgaaccga gatttagcac cagaccggcc agcgagcatt gcagacaccg gcttataagt   180
tcagctgcga ctaccactcc gccggccagc atttgaaaca gttttagagc tagaaatagc   240
aagttaaaat aaggctagtc cgttatcaac ttgaaaaagt ggcaccgagt cggtgctttt   300
ttt                                                                303

<210> SEQ ID NO 32
<211> LENGTH: 500
<212> TYPE: DNA
<213> ORGANISM: Artificial Sequence
<220> FEATURE:
<223> OTHER INFORMATION: Recombinant

<400> SEQUENCE: 32
ttatatgtta ccgttgcaaa gcacgggcac tcacctagta tataatataa catcagtcgt    60
acgtaatgta ctgatgggcg ggttaacaaa tgtcactcac tatcagcacc agcagcgctt   120
agatgcatcc ggccgggcca agacccagga ccagaaagcg cgcacgttca cagcggatgc   180
tgatgggtta gatcgactga tcgaggaaga ggagagctta attaagaaac gccctgttcc   240
gctttgctag cttgcgccct gactgtccag cccacgcgct tcgtccgat tcacatgcta    300
ggctggtgca agcgagccga cttttttttt tagaaccacc ttgctcagca aaccttagga   360
acaccggctt ataagtcgaa gcgaagcgct gtgcactgcc ggccagcatt tgaaacagtt   420
ttagagctag aaatagcaag ttaaaataag gctagtccgt tatcaacttg aaaaagtggc   480
accgagtcgg tgcttttttt                                              500

<210> SEQ ID NO 33
<211> LENGTH: 303
<212> TYPE: DNA
<213> ORGANISM: Artificial Sequence
<220> FEATURE:
<223> OTHER INFORMATION: Recombinant

<400> SEQUENCE: 33

```
tgatcgagga agaggagagc ttaattaaga aacgccctgt tccgctttgc tagcttgcgc      60
cctgactgtc cagcccacgc gcttcggtcc gattcacatg ctaggctggt gcaagcgagc     120
cgagactttt ttttagaacc accttgctca gcaaacctta ggaacaccgg cttataagtc     180
gaagcgaagc gctgtgcact gccggccagc atttgaaaca gttttagagc tagaaatagc     240
aagttaaaat aaggctagtc cgttatcaac ttgaaaaagt ggcaccgagt cggtgctttt     300
ttt                                                                    303
```

<210> SEQ ID NO 34
<211> LENGTH: 500
<212> TYPE: DNA
<213> ORGANISM: Artificial Sequence
<220> FEATURE:
<223> OTHER INFORMATION: Recombinant

<400> SEQUENCE: 34

```
ggattcggtg ttctttatta ggttctcgcc gaatatggtt ctcagttatg acctaacggt      60
gtccacaaga gttcgccagg atttatacaa ctattttctt atttatttct ttaacatttt     120
cccttctacg cacaatagga gataatgtca agcgttgacg gtgcacatat atttgttttt     180
ttaaaggcgt agtggcgtgt gtgcaaaaac atcctcacag gaaagacacg aagaaacatg     240
gtcaatggcc cattatataa agcaccgcca caaagcccaa ataccagttc gtcggtggag     300
caagtaacgc gctaggcaac aggcaaacag tttgtcccac ctcgtccagt cacaaaggca     360
aagcgtgact tataagccag agcggaagaa ccataccgcc ggccagcatt tgaaacagtt     420
ttagagctag aaatagcaag ttaaaataag gctagtccgt tatcaacttg aaaaagtggc     480
accgagtcgg tgcttttttt                                                  500
```

<210> SEQ ID NO 35
<211> LENGTH: 303
<212> TYPE: DNA
<213> ORGANISM: Artificial Sequence
<220> FEATURE:
<223> OTHER INFORMATION: Recombinant

<400> SEQUENCE: 35

```
tgtgtgcaaa aacatcctca caggaaagac acgaagaaac atggtcaatg gcccattata      60
taaagcaccg ccacaaagcc caaataccag ttcgtcggtg gagcaagtaa cgcgctaggc     120
aacaggcaaa cagtttgtcc cacctcgtcc agtcacaaag gcaaagcgtg acttataagc     180
cagagcggaa gaaccatacc gccggccagc atttgaaaca gttttagagc tagaaatagc     240
aagttaaaat aaggctagtc cgttatcaac ttgaaaaagt ggcaccgagt cggtgctttt     300
ttt                                                                    303
```

<210> SEQ ID NO 36
<211> LENGTH: 500
<212> TYPE: DNA
<213> ORGANISM: Artificial Sequence
<220> FEATURE:

<223> OTHER INFORMATION: Recombinant

<400> SEQUENCE: 36

| | |
|---|---|
| tcgtaaaata gtggtgtcca agaatttcc aggcccagtt gtaaaagcta aaatgctatt | 60 |
| cgaatttcta ctagcagtaa gtcgtgttta gaattatttt ttttatatac ctttttcct | 120 |
| tctatgtaca gtaggacaca gtgtcagcgc cgcgttgacg gagaatattt gcaaaaaagt | 180 |
| aaaagagaaa gtcatagcgg cgtatgtgcc aaaaacttcg tcacagagag gccataaga | 240 |
| aacatggccc acggcccaat acgaagcacc gcgacgaagc ccaaacagca gtccgtaggt | 300 |
| ggagcaaagc gctgggtaat acgcaaacgt tttgtcccac cttgactaat cacaagagtg | 360 |
| gagcgtacct tataaaccga ccgcaagca ccgaattgcc ggccagcatt tgaaacagtt | 420 |
| ttagagctag aaatagcaag ttaaaataag gctagtccgt tatcaacttg aaaaagtggc | 480 |
| accgagtcgg tgcttttttt | 500 |

<210> SEQ ID NO 37
<211> LENGTH: 303
<212> TYPE: DNA
<213> ORGANISM: Artificial Sequence
<220> FEATURE:
<223> OTHER INFORMATION: Recombinant

<400> SEQUENCE: 37

| | |
|---|---|
| cggcgtatgt gccaaaaact tcgtcacaga gagggccata agaaacatgg cccacggccc | 60 |
| aatacgaagc accgcgacga agcccaaaca gcagtccgta ggtggagcaa agcgctgggt | 120 |
| aatacgcaaa cgttttgtcc caccttgact aatcacaaga gtggagcgta ccttataaac | 180 |
| cgagccgcaa gcaccgaatt gccggccagc atttgaaaca gttttagagc tagaaatagc | 240 |
| aagttaaaat aaggctagtc cgttatcaac ttgaaaaagt ggcaccgagt cggtgctttt | 300 |
| ttt | 303 |

<210> SEQ ID NO 38
<211> LENGTH: 500
<212> TYPE: DNA
<213> ORGANISM: Artificial Sequence
<220> FEATURE:
<223> OTHER INFORMATION: Recombinant

<400> SEQUENCE: 38

| | |
|---|---|
| aggaaaagaa gaggtgatta ctgtacctat tcgtctttgt atcggaatat aaatttatca | 60 |
| ctatttatg ataaagtaaa tctgtttccc tgtagagtta attaattaat gtaagtataa | 120 |
| gcgtaattta tagggcacta gtaggactgt cgactgtgcg ctcggcccgg ataatgcgtc | 180 |
| aaaagcgaag acgtgcacgt gggatgggaa acacgaagc gtggtctgct tttcgcatg | 240 |
| atatctgggc cgcaccaaag aatccagccc acgcggcgtg gcgccgtcgt tacggcttgc | 300 |
| gggggaagga aacgagggac gaaccgagat ttagcaccag accggccagc gagcattgca | 360 |
| gacaccggct tataagttca gctgcgacta ccactccgcg caagggatca gtaattcgtt | 420 |
| ttagagctag aaatagcaag ttaaaataag gctagtccgt tatcaacttg aaaaagtggc | 480 |
| accgagtcgg tgcttttttt | 500 |

<210> SEQ ID NO 39
<211> LENGTH: 500
<212> TYPE: DNA
<213> ORGANISM: Artificial Sequence
<220> FEATURE:
<223> OTHER INFORMATION: Recombinant

<400> SEQUENCE: 39

```
ttatatgtta ccgttgcaaa gcacgggcac tcacctagta tataatataa catcagtcgt    60
acgtaatgta ctgatgggcg ggttaacaaa tgtcactcac tatcagcacc agcagcgctt   120
agatgcatcc ggccgggcca agacccagga ccagaaagcg cgcacgttca cagcggatgc   180
tgatgggtta gatcgactga tcgaggaaga ggagagctta attaagaaac gccctgttcc   240
gctttgctag cttgcgccct gactgtccag cccacgcgct tcggtccgat tcacatgcta   300
ggctggtgca agcgagccga gactttttt tagaaccacc ttgctcagca aaccttagga    360
acaccggctt ataagtcgaa gcgaagcgct gtgcactgcg caagggatca gtaattcgtt   420
ttagagctag aaatagcaag ttaaaataag gctagtccgt tatcaacttg aaaaagtggc   480
accgagtcgg tgcttttttt                                               500
```

<210> SEQ ID NO 40
<211> LENGTH: 500
<212> TYPE: DNA
<213> ORGANISM: Artificial Sequence
<220> FEATURE:
<223> OTHER INFORMATION: Recombinant

<400> SEQUENCE: 40

```
ggattcggtg ttctttatta ggttctcgcc gaatatggtt ctcagttatg acctaacggt    60
gtccacaaga gttcgccagg atttatacaa ctatttctt atttatttct ttaacatttt   120
cccttctacg cacaatagga gataatgtca agcgttgacg gtgcacatat atttgttttt   180
ttaaaggcgt agtggcgtgt gtgcaaaaac atcctcacag gaaagacacg aagaaacatg   240
gtcaatggcc cattatataa agcaccgcca caaagcccaa ataccagttc gtcggtggag   300
caagtaacgc gctaggcaac aggcaaacag tttgtcccac ctcgtccagt cacaaaggca   360
aagcgtgact tataagccag agcggaagaa ccataccgcg caagggatca gtaattcgtt   420
ttagagctag aaatagcaag ttaaaataag gctagtccgt tatcaacttg aaaaagtggc   480
accgagtcgg tgcttttttt                                               500
```

<210> SEQ ID NO 41
<211> LENGTH: 500
<212> TYPE: DNA
<213> ORGANISM: Artificial Sequence
<220> FEATURE:
<223> OTHER INFORMATION: Recombinant

<400> SEQUENCE: 41

```
tcgtaaaata gtggtgtcca agaatttcc aggcccagtt gtaaaagcta aatgctatt     60
cgaatttcta ctagcagtaa gtcgtgttta gaaattattt ttttatatac cttttttcct   120
tctatgtaca gtaggacaca gtgtcagcgc cgcgttgacg gagaatattt gcaaaaaagt   180
aaaagagaaa gtcatagcgg cgtatgtgcc aaaaacttcg tcacagagag gccataagaa   240
aacatggccc acggcccaat acgaagcacc gcgacgaagc ccaaacagca gtccgtaggt   300
ggagcaaagc gctgggtaat acgcaaacgt tttgtcccac cttgactaat cacaagagtg   360
gagcgtacct tataaaccga gccgcaagca ccgaattgcg caagggatca gtaattcgtt   420
ttagagctag aaatagcaag ttaaaataag gctagtccgt tatcaacttg aaaaagtggc   480
accgagtcgg tgcttttttt                                               500
```

<210> SEQ ID NO 42

```
<211> LENGTH: 500
<212> TYPE: DNA
<213> ORGANISM: Artificial Sequence
<220> FEATURE:
<223> OTHER INFORMATION: Recombinant

<400> SEQUENCE: 42
tcgtaaaata gtggtgtcca agaatttcc  aggcccagtt gtaaaagcta aaatgctatt      60
cgaatttcta ctagcagtaa gtcgtgttta gaaattattt ttttatatac cttttttcct     120
tctatgtaca gtaggacaca gtgtcagcgc cgcgttgacg gagaatattt gcaaaaaagt     180
aaaagagaaa gtcatagcgg cgtatgtgcc aaaaacttcg tcacagagag gccataaga     240 aacatggccc acggcccaat acgaagcacc gcgacgaagc ccaaacagca gtccgtaggt     300
ggagcaaagc gctgggtaat acgcaaacgt tttgtcccac cttgactaat cacaagagtg     360
gagcgtacct tataaaccga ccgcaagca  ccgaattgtt atcaatttac ttcaatgtt      420 ttagagctag aaatagcaag ttaaaataag gctagtccgt tatcaacttg aaaaagtggc     480
accgagtcgg tgcttttttt                                                500

<210> SEQ ID NO 43
<211> LENGTH: 23
<212> TYPE: DNA
<213> ORGANISM: Zea mays

<400> SEQUENCE: 43
gttatcaatt tactttcaat cgg                                             23

<210> SEQ ID NO 44
<211> LENGTH: 23
<212> TYPE: DNA
<213> ORGANISM: Zea mays

<400> SEQUENCE: 44
gcgcaaggga tcagtaattc agg                                             23

<210> SEQ ID NO 45
<211> LENGTH: 86
<212> TYPE: DNA
<213> ORGANISM: Artificial Sequence
<220> FEATURE:
<223> OTHER INFORMATION: Recombinant

<400> SEQUENCE: 45
gggataacag ggtaatatag cgtaactata acggtcctaa ggtagcgaat tacgatacaa      60
ggctacctag cttcgcagtt acgcta                                          86

<210> SEQ ID NO 46
<211> LENGTH: 86
<212> TYPE: DNA
<213> ORGANISM: Artificial Sequence
<220> FEATURE:
<223> OTHER INFORMATION: Recombinant

<400> SEQUENCE: 46
tagcgtaact gcgaagctag gtagccttgt atcgtaattc gctaccttag gaccgttata      60
gttacgctat attccctgt tatccc                                           86

<210> SEQ ID NO 47
<211> LENGTH: 23
<212> TYPE: DNA
<213> ORGANISM: Zea mays
```

<400> SEQUENCE: 47
gatatgccaa acggtacttg agg					23

<210> SEQ ID NO 48
<211> LENGTH: 500
<212> TYPE: DNA
<213> ORGANISM: Artificial Sequence
<220> FEATURE:
<223> OTHER INFORMATION: Recombinant

<400> SEQUENCE: 48
tcgtaaaata gtggtgtcca agaatttcc aggcccagtt gtaaaagcta aaatgctatt		60 cgaatttcta ctagcagtaa gtcgtgttta gaaattattt ttttatatac cttttttcct		120 tctatgtaca gtaggacaca gtgtcagcgc cgcgttgacg gagaatattt gcaaaaaagt		180 aaaagagaaa gtcatagcgg cgtatgtgcc aaaaacttcg tcacagagag ggccataaga		240 aacatggccc acggcccaat acgaagcacc gcgacgaagc ccaaacagca gtccgtaggt		300 ggagcaaagc gctgggtaat acgcaaacgt tttgtcccac cttgactaat cacaagagtg		360 gagcgtacct tataaaccga ccgcaagca ccgaattgta caaccaact cggcaatgtt		420 ttagagctag aaatagcaag ttaaaataag gctagtccgt tatcaacttg aaaaagtggc		480 accgagtcgg tgcttttttt					500

<210> SEQ ID NO 49
<211> LENGTH: 20
<212> TYPE: DNA
<213> ORGANISM: Artificial Sequence
<220> FEATURE:
<223> OTHER INFORMATION: Recombinant

<400> SEQUENCE: 49
gcgtaactgc gaagctaggt					20

<210> SEQ ID NO 50
<211> LENGTH: 20
<212> TYPE: DNA
<213> ORGANISM: Artificial Sequence
<220> FEATURE:
<223> OTHER INFORMATION: Recombinant

<400> SEQUENCE: 50
ctcacgcctt catttcaaag					20

<210> SEQ ID NO 51
<211> LENGTH: 20
<212> TYPE: DNA
<213> ORGANISM: Artificial Sequence
<220> FEATURE:
<223> OTHER INFORMATION: Recombinant

<400> SEQUENCE: 51
gtaatgggta atcacaaagg					20

<210> SEQ ID NO 52
<211> LENGTH: 22
<212> TYPE: DNA
<213> ORGANISM: Artificial Sequence
<220> FEATURE:
<223> OTHER INFORMATION: Recombinant

<400> SEQUENCE: 52

```
ggattatatt agtttaggct tg                                              22

<210> SEQ ID NO 53
<211> LENGTH: 20
<212> TYPE: DNA
<213> ORGANISM: Artificial Sequence
<220> FEATURE:
<223> OTHER INFORMATION: Recombinant

<400> SEQUENCE: 53
cgaccaactc tccaccaatc                                                 20

<210> SEQ ID NO 54
<211> LENGTH: 21
<212> TYPE: DNA
<213> ORGANISM: Artificial Sequence
<220> FEATURE:
<223> OTHER INFORMATION: Recombinant

<400> SEQUENCE: 54
taaggagatg agtttgagac c                                               21

<210> SEQ ID NO 55
<211> LENGTH: 20
<212> TYPE: DNA
<213> ORGANISM: Artificial Sequence
<220> FEATURE:
<223> OTHER INFORMATION: Recombinant

<400> SEQUENCE: 55
tagaggtgga agcatcaaag                                                 20

<210> SEQ ID NO 56
<211> LENGTH: 20
<212> TYPE: DNA
<213> ORGANISM: Artificial Sequence
<220> FEATURE:
<223> OTHER INFORMATION: Recombinant

<400> SEQUENCE: 56
gtaccgtttg gcatatcaac                                                 20

<210> SEQ ID NO 57
<211> LENGTH: 20
<212> TYPE: DNA
<213> ORGANISM: Artificial Sequence
<220> FEATURE:
<223> OTHER INFORMATION: Recombinant

<400> SEQUENCE: 57
gagcatctaa ccaccaaaac                                                 20

<210> SEQ ID NO 58
<211> LENGTH: 500
<212> TYPE: DNA
<213> ORGANISM: Artificial Sequence
<220> FEATURE:
<223> OTHER INFORMATION: Recombinant

<400> SEQUENCE: 58
tcgtaaaata gtggtgtcca agaatttcc aggcccagtt gtaaaagcta aaatgctatt      60
cgaatttcta ctagcagtaa gtcgtgttta gaattattt ttttatatac ctttttcct     120 tctatgtaca gtaggacaca gtgtcagcgc gcgttgacg gagaatattt gcaaaaagt     180 aaaagagaaa gtcatagcgg cgtatgtgcc aaaaacttcg tcacagagag ggccataaga   240
```

```
aacatggccc acggcccaat acgaagcacc gcgacgaagc ccaaacagca gtccgtaggt    300
ggagcaaagc gctgggtaat acgcaaacgt tttgtcccac cttgactaat cacaagagtg    360
gagcgtacct tataaaccga gccgcaagca ccgaattgat atgccaaacg gtacttggtt    420
ttagagctag aaatagcaag ttaaaataag gctagtccgt tatcaacttg aaaaagtggc    480
accgagtcgg tgctttttt                                                  500

<210> SEQ ID NO 59
<211> LENGTH: 23
<212> TYPE: DNA
<213> ORGANISM: Zea mays

<400> SEQUENCE: 59
gatatgccaa acggtacttg agg                                             23

<210> SEQ ID NO 60
<211> LENGTH: 500
<212> TYPE: DNA
<213> ORGANISM: Artificial Sequence
<220> FEATURE:
<223> OTHER INFORMATION: Recombinant

<400> SEQUENCE: 60
tcgtaaaata gtggtgtcca agaatttcc aggcccagtt gtaaaagcta aaatgctatt      60
cgaatttcta ctagcagtaa gtcgtgttta gaaattattt ttttatatac cttttttcct    120
tctatgtaca gtaggacaca gtgtcagcgc gcgttgacg gagaatattt gcaaaaaagt     180
aaaagagaaa gtcatagcgg cgtatgtgcc aaaaacttcg tcacagagag ggccataaga   240
aacatggccc acggcccaat acgaagcacc gcgacgaagc ccaaacagca gtccgtaggt   300
ggagcaaagc gctgggtaat acgcaaacgt tttgtcccac cttgactaat cacaagagtg   360
gagcgtacct tataaaccga gccgcaagca ccgaattgga tctcctatca taacgttgtt   420
ttagagctag aaatagcaag ttaaaataag gctagtccgt tatcaacttg aaaaagtggc   480
accgagtcgg tgctttttt                                                 500

<210> SEQ ID NO 61
<211> LENGTH: 23
<212> TYPE: DNA
<213> ORGANISM: Zea mays

<400> SEQUENCE: 61
ggatctccta tcataacgtt tgg                                             23

<210> SEQ ID NO 62
<211> LENGTH: 92
<212> TYPE: DNA
<213> ORGANISM: Artificial Sequence
<220> FEATURE:
<223> OTHER INFORMATION: Recombinant

<400> SEQUENCE: 62
ggcgggataa cagggtaata tagcgtaact ataacggtcc taaggtagcg aattacgata     60
caaggctacc tagcttcgca gttacgctaa at                                   92

<210> SEQ ID NO 63
<211> LENGTH: 92
<212> TYPE: DNA
<213> ORGANISM: Artificial Sequence
<220> FEATURE:
```

<223> OTHER INFORMATION: Recombinant

<400> SEQUENCE: 63

```
atttagcgta actgcgaagc taggtagcct tgtatcgtaa ttcgctacct taggaccgtt    60
atagttacgc tatattaccc tgttatcccg cc                                  92
```

<210> SEQ ID NO 64
<211> LENGTH: 92
<212> TYPE: DNA
<213> ORGANISM: Artificial Sequence
<220> FEATURE:
<223> OTHER INFORMATION: Recombinant

<400> SEQUENCE: 64

```
tacgggataa cagggtaata tagcgtaact ataacggtcc taaggtagcg aattacgata    60
caaggctacc tagcttcgca gttacgctat tg                                  92
```

<210> SEQ ID NO 65
<211> LENGTH: 92
<212> TYPE: DNA
<213> ORGANISM: Artificial Sequence
<220> FEATURE:
<223> OTHER INFORMATION: Recombinant

<400> SEQUENCE: 65

```
caatagcgta actgcgaagc taggtagcct tgtatcgtaa ttcgctacct taggaccgtt    60
atagttacgc tatattaccc tgttatcccg ta                                  92
```

<210> SEQ ID NO 66
<211> LENGTH: 92
<212> TYPE: DNA
<213> ORGANISM: Artificial Sequence
<220> FEATURE:
<223> OTHER INFORMATION: Recombinant

<400> SEQUENCE: 66

```
aacgggataa cagggtaata tagcgtaact ataacggtcc taaggtagcg aattacgata    60
caaggctacc tagcttcgca gttacgctag tt                                  92
```

<210> SEQ ID NO 67
<211> LENGTH: 92
<212> TYPE: DNA
<213> ORGANISM: Artificial Sequence
<220> FEATURE:
<223> OTHER INFORMATION: Recombinant

<400> SEQUENCE: 67

```
aactagcgta actgcgaagc taggtagcct tgtatcgtaa ttcgctacct taggaccgtt    60
atagttacgc tatattaccc tgttatcccg tt                                  92
```

<210> SEQ ID NO 68
<211> LENGTH: 3366
<212> TYPE: DNA
<213> ORGANISM: Artificial Sequence
<220> FEATURE:
<223> OTHER INFORMATION: Recombinant

<400> SEQUENCE: 68

```
atgagtgacc tggtgctagg gttggatata ggcattggct ccgtgggggt tggcattctt    60
aataaggtga ccggcgaaat aattcataaa aactcacgca tctttccagc agcccaggct   120
gagaacaatc tggtccgtag aaccaaccgg cagggtcgaa ggttagccag gcgcaagaag   180
```

```
cacagacggg tccggctcaa caggcttttc gaggagtctg gtttgatcac cgatttcact    240
aagatttcta tcaacctgaa tccttatcag ctgcgcgtta aggtctcac agacgaactt     300 agcaacgaag agttgttcat cgccctgaaa atatggtca agcatcgcgg cattagctac     360
ctggacgacg cttcggatga tggcaacagt agtgtaggtg actacgctca gatcgtgaaa    420
gagaactcga agcaattgga gaccaagacc ccgggccaaa ttcaactcga aggtaccag     480 acgtatggac agttacgagg cgattttacc gttgaaaagg atggtaagaa gcacaggctg    540
attaatgtgt ttccgacctc agcttatcgc tctgaggcgc tgcgtatttt gcagacccaa    600
caggaattta acccgcaaat aacggacgag ttcataaacc gatacttaga gattcttaca    660
ggtaaacgta atactatca cggcccagga atgaaaagt ccaggacaga ttatggtcga     720
tatcgcactt ccggagagac tctcgacaat atctttggca ttcttatagg caaatgtacc    780
ttctaccctg acgaatttag agcagcgaag gcttcatata cagcacaaga gtttaatctt    840
ctcaacgacc tcaacaactt gactgtgcct actgaaacca aaaagcttag caaggagcaa    900
aaaaatcaaa tcattaacta tgttaagaat gagaaagcta tggggcccgc aaaattgttc    960
aagtacatag ctaagttact tagctgtgac gttgctgata ttaagggtta ccgtattgac   1020
aagtctggta agctgaaat tcacaccttt gaggcttata ggaagatgaa gacccttgag    1080
acacttgaca ttgagcagat ggataggag actttggaca aactggcata cgtcttgaca    1140
ttgaacaccg aagggaagg catccaggaa gctctggaac atgaatttgc agatggttcg    1200
ttcagccaaa acaggttga cgagctggtc caatttagaa aggcaaactc aagcatattc    1260
ggtaaaggtt ggcacaactt cagcgttaag ctgatgatgg aactcattcc agaattatat   1320
gaaacctctg aggaacagat gacgattctc acaagattgg gtaagcagaa acaaccagc    1380 tctagcaata agactaaata cattgacgaa aagctcctca ccgaagagat ttataacccg    1440
gtcgtggcaa agagtgtacg gcaagccatc aagatcgtta atgccgctat caaggagtat    1500
ggtgattttg ataatattgt gattgaaatg gcacgcgaga ctaacgagga cgacgagaag    1560
aaagctatac agaagattca aaaggctaat aaggacgaga aggacgccgc aatgctaaag    1620
gcggccaatc aatataatgg gaaggctgaa ctacctcata gcgtcttcca tggacataag    1680
caattagcaa ctaaaataag attatggcac cagcaaggcg aacggtgtct ttatacaggt    1740
aaaacgatat ctattcacga cctgattaac aactctaacc agtttgaagt ggatcatatc    1800
ttaccactaa gtatcacctt cgacgattca cttgctaaca aggtgctcgt ttacgccact    1860
gcgaaccaag agaaagggca gaggactcca taccaggccc ttgacagcat ggacgacgcc    1920
tggagtttta gggaattaaa agctttcgta cgtgagtcaa agacgctttc aaataaaaaa    1980
aaggagtact gctcactga agaagacatc tcaaaattcg acgtgcgcaa aaaattcatt    2040
gagcggaact tagtcgacac tcggtacgca tcaagagtag tgttgaacgc cctccaggag    2100
cactttaggg cacataagat cgacaccaag gtttcagttg ttaggggtca gtttacatcg    2160
cagcttagac gccattgggg tatagaaaaa acacgtgata cctaccatca ccatgcagtt    2220
gacgctctca tcattgcagc atcttctcaa cttaatttgt ggaaaaagca aaagaacact    2280
ctggtctcat atagcgaaga tcagctgctt gatattgaaa ccggcgagct gatttctgac    2340
gacgaataca agaatctgt gtttaaggca ccatatcaac actttgtaga cacgcttaaa    2400
tctaaagagt ttgaggattc gatccttttc agttaccaag tcgactcaaa atttaaccgt    2460
aagatctctg atgcaacaat ttatgcgacg aggcaggcca aggtaggtaa ggataaggct    2520
```

```
gacgaaacct acgtgctcgg aaaaatcaaa gatatttaca ctcaagatgg atatgatgca    2580
ttcatgaaga tatataaaaa ggacaaatct aaattcctta tgtatcgtca tgacccacag    2640
acattcgaga agttattga gcctatcctg gagaactatc cgaacaagca ataaatgag      2700 aagggcaaag aagttccatg taatccgttc ctaaagtaca aggaggaaca cggatatatt    2760
agaaaataca gcaaaaggg caacggccca gaaatcaaaa gccttaagta ctacgatagt     2820
aaactaggaa accacatcga cattacacca aaagactcta ataataaggt cgtactgcaa    2880
agcgtttccc catggcgcgc cgatgtgtat tttaataaga caacagggaa gtacgaaatc    2940
ttggggttaa aatatgcgga tctgcaattc gaaaagggaa ccggcacata caaaatttct    3000
caagaaaagt acaacgacat aaagaagaag gaagggtcg attctgattc tgaattcaag     3060
ttcacactct ataagaatga tcttctgctc gtcaaggaca cagagacaaa ggagcagcag    3120
ttgttcaggt tcttgtctag aactatgcca aaacaaaagc actacgttga actgaagcct    3180
tacgataagc aaaaattcga gggggcgag gcgcttataa aggtcctagg aaatgttgca     3240
aactctgggc agtgtaagaa gggcctgggc aagagcaaca ttagcatcta taaggttcga    3300
acggatgtgc ttgggaacca gcatatcatc aaaaacgagg gagataaacc aaagctggac    3360
ttctag                                                               3366
```

<210> SEQ ID NO 69
<211> LENGTH: 1121
<212> TYPE: PRT
<213> ORGANISM: Streptococcus thermophilus

<400> SEQUENCE: 69

```
Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
            20                  25                  30

Arg Ile Phe Pro Ala Ala Gln Ala Glu Asn Asn Leu Val Arg Arg Thr
        35                  40                  45

Asn Arg Gln Gly Arg Arg Leu Ala Arg Arg Lys Lys His Arg Arg Val
    50                  55                  60

Arg Leu Asn Arg Leu Phe Glu Glu Ser Gly Leu Ile Thr Asp Phe Thr
65                  70                  75                  80

Lys Ile Ser Ile Asn Leu Asn Pro Tyr Gln Leu Arg Val Lys Gly Leu
                85                  90                  95

Thr Asp Glu Leu Ser Asn Glu Glu Leu Phe Ile Ala Leu Lys Asn Met
            100                 105                 110

Val Lys His Arg Gly Ile Ser Tyr Leu Asp Asp Ala Ser Asp Asp Gly
        115                 120                 125

Asn Ser Ser Val Gly Asp Tyr Ala Gln Ile Val Lys Glu Asn Ser Lys
    130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Gln Glu Phe Asn Pro Gln Ile Thr
        195                 200                 205

Asp Glu Phe Ile Asn Arg Tyr Leu Glu Ile Leu Thr Gly Lys Arg Lys
    210                 215                 220
```

```
Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
            245                 250                 255

Gly Lys Cys Thr Phe Tyr Pro Asp Glu Phe Arg Ala Ala Lys Ala Ser
        260                 265                 270

Tyr Thr Ala Gln Glu Phe Asn Leu Leu Asn Asp Leu Asn Asn Leu Thr
        275                 280                 285

Val Pro Thr Glu Thr Lys Lys Leu Ser Lys Glu Gln Lys Asn Gln Ile
    290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
            325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
            355                 360                 365

Arg Glu Thr Leu Asp Lys Leu Ala Tyr Val Leu Thr Leu Asn Thr Glu
370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
            405                 410                 415

Ser Ser Ile Phe Gly Lys Gly Trp His Asn Phe Ser Val Lys Leu Met
            420                 425                 430

Met Glu Leu Ile Pro Glu Leu Tyr Glu Thr Ser Glu Glu Gln Met Thr
        435                 440                 445

Ile Leu Thr Arg Leu Gly Lys Gln Lys Thr Thr Ser Ser Asn Lys
        450                 455                 460

Thr Lys Tyr Ile Asp Glu Lys Leu Leu Thr Glu Glu Ile Tyr Asn Pro
465                 470                 475                 480

Val Val Ala Lys Ser Val Arg Gln Ala Ile Lys Ile Val Asn Ala Ala
            485                 490                 495

Ile Lys Glu Tyr Gly Asp Phe Asp Asn Ile Val Ile Glu Met Ala Arg
        500                 505                 510

Glu Thr Asn Glu Asp Asp Glu Lys Lys Ala Ile Gln Lys Ile Gln Lys
        515                 520                 525

Ala Asn Lys Asp Glu Lys Asp Ala Ala Met Leu Lys Ala Ala Asn Gln
        530                 535                 540

Tyr Asn Gly Lys Ala Glu Leu Pro His Ser Val Phe His Gly His Lys
545                 550                 555                 560

Gln Leu Ala Thr Lys Ile Arg Leu Trp His Gln Gln Gly Glu Arg Cys
            565                 570                 575

Leu Tyr Thr Gly Lys Thr Ile Ser Ile His Asp Leu Ile Asn Asn Ser
            580                 585                 590

Asn Gln Phe Glu Val Asp His Ile Leu Pro Leu Ser Ile Thr Phe Asp
        595                 600                 605

Asp Ser Leu Ala Asn Lys Val Leu Val Tyr Ala Thr Ala Asn Gln Glu
        610                 615                 620

Lys Gly Gln Arg Thr Pro Tyr Gln Ala Leu Asp Ser Met Asp Asp Ala
625                 630                 635                 640
```

```
Trp Ser Phe Arg Glu Leu Lys Ala Phe Val Arg Glu Ser Lys Thr Leu
                645                 650                 655

Ser Asn Lys Lys Lys Glu Tyr Leu Leu Thr Glu Glu Asp Ile Ser Lys
        660                 665                 670

Phe Asp Val Arg Lys Lys Phe Ile Glu Arg Asn Leu Val Asp Thr Arg
            675                 680                 685

Tyr Ala Ser Arg Val Val Leu Asn Ala Leu Gln Glu His Phe Arg Ala
690                 695                 700

His Lys Ile Asp Thr Lys Val Ser Val Val Arg Gly Gln Phe Thr Ser
705                 710                 715                 720

Gln Leu Arg Arg His Trp Gly Ile Glu Lys Thr Arg Asp Thr Tyr His
                725                 730                 735

His His Ala Val Asp Ala Leu Ile Ile Ala Ala Ser Ser Gln Leu Asn
            740                 745                 750

Leu Trp Lys Lys Gln Lys Asn Thr Leu Val Ser Tyr Ser Glu Asp Gln
        755                 760                 765

Leu Leu Asp Ile Glu Thr Gly Glu Leu Ile Ser Asp Asp Glu Tyr Lys
    770                 775                 780

Glu Ser Val Phe Lys Ala Pro Tyr Gln His Phe Val Asp Thr Leu Lys
785                 790                 795                 800

Ser Lys Glu Phe Glu Asp Ser Ile Leu Phe Ser Tyr Gln Val Asp Ser
                805                 810                 815

Lys Phe Asn Arg Lys Ile Ser Asp Ala Thr Ile Tyr Ala Thr Arg Gln
            820                 825                 830

Ala Lys Val Gly Lys Asp Lys Ala Asp Glu Thr Tyr Val Leu Gly Lys
        835                 840                 845

Ile Lys Asp Ile Tyr Thr Gln Asp Gly Tyr Asp Ala Phe Met Lys Ile
    850                 855                 860

Tyr Lys Lys Asp Lys Ser Lys Phe Leu Met Tyr Arg His Asp Pro Gln
865                 870                 875                 880

Thr Phe Glu Lys Val Ile Glu Pro Ile Leu Glu Asn Tyr Pro Asn Lys
                885                 890                 895

Gln Ile Asn Glu Lys Gly Lys Glu Val Pro Cys Asn Pro Phe Leu Lys
            900                 905                 910

Tyr Lys Glu Glu His Gly Tyr Ile Arg Lys Tyr Ser Lys Lys Gly Asn
        915                 920                 925

Gly Pro Glu Ile Lys Ser Leu Lys Tyr Tyr Asp Ser Lys Leu Gly Asn
    930                 935                 940

His Ile Asp Ile Thr Pro Lys Asp Ser Asn Asn Lys Val Val Leu Gln
945                 950                 955                 960

Ser Val Ser Pro Trp Arg Ala Asp Val Tyr Phe Asn Lys Thr Thr Gly
                965                 970                 975

Lys Tyr Glu Ile Leu Gly Leu Lys Tyr Ala Asp Leu Gln Phe Glu Lys
            980                 985                 990

Gly Thr Gly Thr Tyr Lys Ile Ser  Gln Glu Lys Tyr Asn  Asp Ile Lys
        995                 1000                1005

Lys Lys  Glu Gly Val Asp Ser  Asp Ser Glu Phe Lys  Phe Thr Leu
    1010                1015                1020

Tyr Lys  Asn Asp Leu Leu  Val Lys Asp Thr Glu  Thr Lys Glu
    1025                1030                1035

Gln Gln  Leu Phe Arg Phe Leu  Ser Arg Thr Met Pro  Lys Gln Lys
    1040                1045                1050

His Tyr  Val Glu Leu Lys Pro  Tyr Asp Lys Gln Lys  Phe Glu Gly
```

```
                1055                1060                1065

Gly  Glu  Ala  Leu  Ile  Lys  Val  Leu  Gly  Asn  Val  Ala  Asn  Ser  Gly
         1070                1075                1080

Gln  Cys  Lys  Lys  Gly  Leu  Gly  Lys  Ser  Asn  Ile  Ser  Ile  Tyr  Lys
    1085                1090                1095

Val  Arg  Thr  Asp  Val  Leu  Gly  Asn  Gln  His  Ile  Ile  Lys  Asn  Glu
1100                1105                1110

Gly  Asp  Lys  Pro  Lys  Leu  Asp  Phe
         1115                1120

<210> SEQ ID NO 70
<211> LENGTH: 188
<212> TYPE: DNA
<213> ORGANISM: Artificial Sequence
<220> FEATURE:
<223> OTHER INFORMATION: Recombinant

<400> SEQUENCE: 70
gacattctcc ccaaaatata gttattgtac tctcaagatt tattttttcca aaagggttat      60 tgtactctca agatttattt ttccaaaagg gttacttaaa tcttgcagaa gctacaaaga     120
taaggcttca tgccgaaatc aacaccctgt cattttatgg cagggtgttt tcgttattta     180
attttttt                                                              188

<210> SEQ ID NO 71
<211> LENGTH: 20
<212> TYPE: DNA
<213> ORGANISM: Zea mays

<400> SEQUENCE: 71
gacattctcc ccaaaatata                                                  20

<210> SEQ ID NO 72
<211> LENGTH: 29
<212> TYPE: DNA
<213> ORGANISM: Zea mays

<400> SEQUENCE: 72
gtttatcttt catgagcttt ttagagaat                                        29

<210> SEQ ID NO 73
<211> LENGTH: 29
<212> TYPE: DNA
<213> ORGANISM: Zea mays

<400> SEQUENCE: 73
gtaatactct atggtctgta aggtagaat                                        29

<210> SEQ ID NO 74
<211> LENGTH: 28
<212> TYPE: DNA
<213> ORGANISM: Zea mays

<400> SEQUENCE: 74
gagatccaac gtgttgggac tctagaaa                                         28

<210> SEQ ID NO 75
<211> LENGTH: 27
<212> TYPE: DNA
<213> ORGANISM: Zea mays

<400> SEQUENCE: 75
```

```
gacattctcc ccaaaatata cgagaaa                                          27

<210> SEQ ID NO 76
<211> LENGTH: 103
<212> TYPE: DNA
<213> ORGANISM: Artificial Sequence
<220> FEATURE:
<223> OTHER INFORMATION: Recombinant

<400> SEQUENCE: 76
gccggccagc atttgaaaca gttttagagc tagaaatagc aagttaaaat aaggctagtc      60
cgttatcaac ttgaaaaagt ggcaccgagt cggtgctttt ttt                       103

<210> SEQ ID NO 77
<211> LENGTH: 103
<212> TYPE: DNA
<213> ORGANISM: Artificial Sequence
<220> FEATURE:
<223> OTHER INFORMATION: Recombinant

<400> SEQUENCE: 77
gcgcaaggga tcagtaattc gttttagagc tagaaatagc aagttaaaat aaggctagtc      60
cgttatcaac ttgaaaaagt ggcaccgagt cggtgctttt ttt                       103

<210> SEQ ID NO 78
<211> LENGTH: 103
<212> TYPE: DNA
<213> ORGANISM: Artificial Sequence
<220> FEATURE:
<223> OTHER INFORMATION: Recombinant

<400> SEQUENCE: 78
gttatcaatt tactttcaat gttttagagc tagaaatagc aagttaaaat aaggctagtc      60
cgttatcaac ttgaaaaagt ggcaccgagt cggtgctttt ttt                       103

<210> SEQ ID NO 79
<211> LENGTH: 103
<212> TYPE: RNA
<213> ORGANISM: Artificial Sequence
<220> FEATURE:
<223> OTHER INFORMATION: Recombinant

<400> SEQUENCE: 79
gccggccagc auugaaaca guuuuagagc uagaaauagc aaguuaaaau aaggcuaguc       60
cguuaucaac uugaaaaagu ggcaccgagu cggugcuuuu uuu                       103

<210> SEQ ID NO 80
<211> LENGTH: 103
<212> TYPE: RNA
<213> ORGANISM: Artificial Sequence
<220> FEATURE:
<223> OTHER INFORMATION: Recombinant

<400> SEQUENCE: 80
gcgcaaggga ucaguaauuc guuuuagagc uagaaauagc aaguuaaaau aaggcuaguc      60
cguuaucaac uugaaaaagu ggcaccgagu cggugcuuuu uuu                       103

<210> SEQ ID NO 81
<211> LENGTH: 103
<212> TYPE: RNA
<213> ORGANISM: Artificial Sequence
<220> FEATURE:
```

<223> OTHER INFORMATION: Recombinant

<400> SEQUENCE: 81
guuaucaauu uacuuucaau guuuuagagc uagaaauagc aaguuaaaau aaggcuaguc      60
cguuaucaac uugaaaaagu ggcaccgagu cggugcuuuu uuu                       103

<210> SEQ ID NO 82
<211> LENGTH: 103
<212> TYPE: DNA
<213> ORGANISM: Artificial Sequence
<220> FEATURE:
<223> OTHER INFORMATION: Recombinant

<400> SEQUENCE: 82
gtacaaacca actcggcaat gttttagagc tagaaatagc aagttaaaat aaggctagtc      60
cgttatcaac ttgaaaaagt ggcaccgagt cggtgctttt ttt                       103

<210> SEQ ID NO 83
<211> LENGTH: 103
<212> TYPE: DNA
<213> ORGANISM: Artificial Sequence
<220> FEATURE:
<223> OTHER INFORMATION: Recombinant

<400> SEQUENCE: 83
gatatgccaa acggtacttg gttttagagc tagaaatagc aagttaaaat aaggctagtc      60
cgttatcaac ttgaaaaagt ggcaccgagt cggtgctttt ttt                       103

<210> SEQ ID NO 84
<211> LENGTH: 103
<212> TYPE: DNA
<213> ORGANISM: Artificial Sequence
<220> FEATURE:
<223> OTHER INFORMATION: Recombinant

<400> SEQUENCE: 84
ggatctccta tcataacgtt gttttagagc tagaaatagc aagttaaaat aaggctagtc      60
cgttatcaac ttgaaaaagt ggcaccgagt cggtgctttt ttt                       103

<210> SEQ ID NO 85
<211> LENGTH: 103
<212> TYPE: RNA
<213> ORGANISM: Artificial Sequence
<220> FEATURE:
<223> OTHER INFORMATION: Recombinant

<400> SEQUENCE: 85
guacaaacca acucggcaau guuuuagagc uagaaauagc aaguuaaaau aaggcuaguc      60
cguuaucaac uugaaaaagu ggcaccgagu cggugcuuuu uuu                       103

<210> SEQ ID NO 86
<211> LENGTH: 103
<212> TYPE: RNA
<213> ORGANISM: Artificial Sequence
<220> FEATURE:
<223> OTHER INFORMATION: Recombinant

<400> SEQUENCE: 86
gauaugccaa acgguacuug guuuuagagc uagaaauagc aaguuaaaau aaggcuaguc      60
cguuaucaac uugaaaaagu ggcaccgagu cggugcuuuu uuu                       103

<210> SEQ ID NO 87
<211> LENGTH: 103
<212> TYPE: RNA
<213> ORGANISM: Artificial Sequence
<220> FEATURE:
<223> OTHER INFORMATION: Recombinant

<400> SEQUENCE: 87
ggaucuccua ucauaacguu guuuuagagc uagaaauagc aaguuaaaau aaggcuaguc    60
cguuaucaac uugaaaaagu ggcaccgagu cggugcuuuu uuu                    103

<210> SEQ ID NO 88
<211> LENGTH: 190
<212> TYPE: DNA
<213> ORGANISM: Artificial Sequence
<220> FEATURE:
<223> OTHER INFORMATION: Recombinant

<400> SEQUENCE: 88
gtttatcttt catgagcttt ttgttattgt actctcaaga tttattttc caaaagggtt     60 attgtactct caagatttat ttttccaaaa gggttactta atcttgcag aagctacaaa   120 gataaggctt catgccgaaa tcaacaccct gtcatttat ggcagggtgt tttcgttatt   180
taattttttt                                                        190

<210> SEQ ID NO 89
<211> LENGTH: 190
<212> TYPE: DNA
<213> ORGANISM: Artificial Sequence
<220> FEATURE:
<223> OTHER INFORMATION: Recombinant

<400> SEQUENCE: 89
gtaatactct atggtctgta aggttattgt actctcaaga tttattttc caaaagggtt     60 attgtactct caagatttat ttttccaaaa gggttactta atcttgcag aagctacaaa   120 gataaggctt catgccgaaa tcaacaccct gtcatttat ggcagggtgt tttcgttatt   180
taattttttt                                                        190

<210> SEQ ID NO 90
<211> LENGTH: 189
<212> TYPE: DNA
<213> ORGANISM: Artificial Sequence
<220> FEATURE:
<223> OTHER INFORMATION: Recombinant

<400> SEQUENCE: 90
gagatccaac gtgttgggac tgttattgta ctctcaagat ttattttcc aaaagggtta     60 ttgtactctc aagatttatt ttccaaaag gttacttaa atcttgcaga agctacaaag   120
ataaggcttc atgccgaaat caacaccctg tcatttatg gcagggtgtt tcgttatttt   180
aattttttt                                                         189

<210> SEQ ID NO 91
<211> LENGTH: 188
<212> TYPE: DNA
<213> ORGANISM: Artificial Sequence
<220> FEATURE:
<223> OTHER INFORMATION: Recombinant

<400> SEQUENCE: 91
gacattctcc ccaaaatata gttattgtac tctcaagatt tattttcca aaagggttat     60

```
tgtactctca agatttattt ttccaaaagg gttacttaaa tcttgcagaa gctacaaaga    120
taaggcttca tgccgaaatc aacaccctgt catttatgg cagggtgttt tcgttattta    180
attttttt                                                            188
```

```
<210> SEQ ID NO 92
<211> LENGTH: 190
<212> TYPE: RNA
<213> ORGANISM: Artificial Sequence
<220> FEATURE:
<223> OTHER INFORMATION: Recombinant

<400> SEQUENCE: 92
guuuaucuuu caugagcuuu uuguuauugu acucucaaga uuuauuuuc caaaagggu     60 auuguacucu caagauuuau uuuccaaaa ggguuacuua aaucuugcag aagcuacaaa    120
gauaaggcuu caugccgaaa ucaacacccu gucauuuau ggcagggugu uucguuauu    180 uaauuuuuu                                                          190
```

```
<210> SEQ ID NO 93
<211> LENGTH: 190
<212> TYPE: RNA
<213> ORGANISM: Artificial Sequence
<220> FEATURE:
<223> OTHER INFORMATION: Recombinant

<400> SEQUENCE: 93
guaauacucu auggucugua agguuauugu acucucaaga uuuauuuuc caaaagggu     60 auuguacucu caagauuuau uuuccaaaa ggguuacuua aaucuugcag aagcuacaaa    120
gauaaggcuu caugccgaaa ucaacacccu gucauuuau ggcagggugu uucguuauu    180 uaauuuuuuu                                                         190
```

```
<210> SEQ ID NO 94
<211> LENGTH: 189
<212> TYPE: RNA
<213> ORGANISM: Artificial Sequence
<220> FEATURE:
<223> OTHER INFORMATION: Recombinant

<400> SEQUENCE: 94
gagauccaac guguugggac uguuauugua cucucaagau uuauuuucc aaagggguua    60 uuguacucuc aagauuuauu uuccaaaag gguuacuuaa aucuugcaga agcuacaaag    120
auaaggcuuc augccgaaau caacacccug ucauuuaug gcagggguu uucguuauuu    180 aauuuuuuu                                                          189
```

```
<210> SEQ ID NO 95
<211> LENGTH: 188
<212> TYPE: RNA
<213> ORGANISM: Artificial Sequence
<220> FEATURE:
<223> OTHER INFORMATION: Recombinant

<400> SEQUENCE: 95
gacauucucc ccaaaauaua guuauuguac ucucaagauu uauuuuucca aaagggguau    60
uguacucuca agauuuauuu uuccaaaagg guuacuuaaa ucuugcagaa gcuacaaaga   120
uaaggcuuca ugccgaaauc aacacccugu cauuuauugg caggguguuu ucguuauua    180 auuuuuuu                                                           188
```

<210> SEQ ID NO 96
<211> LENGTH: 1368
<212> TYPE: PRT
<213> ORGANISM: Streptococcus pyogenes

<400> SEQUENCE: 96

| | | | | | | | | | | | | | | | |
|---|---|---|---|---|---|---|---|---|---|---|---|---|---|---|---|
| Met | Asp | Lys | Lys | Tyr | Ser | Ile | Gly | Leu | Asp | Ile | Gly | Thr | Asn | Ser | Val |
| 1 | | | | 5 | | | | | 10 | | | | | 15 | |
| Gly | Trp | Ala | Val | Ile | Thr | Asp | Glu | Tyr | Lys | Val | Pro | Ser | Lys | Lys | Phe |
| | | | 20 | | | | | 25 | | | | | 30 | | |
| Lys | Val | Leu | Gly | Asn | Thr | Asp | Arg | His | Ser | Ile | Lys | Lys | Asn | Leu | Ile |
| | | | 35 | | | | | 40 | | | | | 45 | | |
| Gly | Ala | Leu | Leu | Phe | Asp | Ser | Gly | Glu | Thr | Ala | Glu | Ala | Thr | Arg | Leu |
| | 50 | | | | | 55 | | | | | 60 | | | | |
| Lys | Arg | Thr | Ala | Arg | Arg | Arg | Tyr | Thr | Arg | Arg | Lys | Asn | Arg | Ile | Cys |
| 65 | | | | | 70 | | | | | 75 | | | | | 80 |
| Tyr | Leu | Gln | Glu | Ile | Phe | Ser | Asn | Glu | Met | Ala | Lys | Val | Asp | Asp | Ser |
| | | | | 85 | | | | | 90 | | | | | 95 | |
| Phe | Phe | His | Arg | Leu | Glu | Glu | Ser | Phe | Leu | Val | Glu | Glu | Asp | Lys | Lys |
| | | | 100 | | | | | 105 | | | | | 110 | | |
| His | Glu | Arg | His | Pro | Ile | Phe | Gly | Asn | Ile | Val | Asp | Glu | Val | Ala | Tyr |
| | | | 115 | | | | | 120 | | | | | 125 | | |
| His | Glu | Lys | Tyr | Pro | Thr | Ile | Tyr | His | Leu | Arg | Lys | Lys | Leu | Val | Asp |
| | | | 130 | | | | | 135 | | | | | 140 | | |
| Ser | Thr | Asp | Lys | Ala | Asp | Leu | Arg | Leu | Ile | Tyr | Leu | Ala | Leu | Ala | His |
| 145 | | | | | 150 | | | | | 155 | | | | | 160 |
| Met | Ile | Lys | Phe | Arg | Gly | His | Phe | Leu | Ile | Glu | Gly | Asp | Leu | Asn | Pro |
| | | | | 165 | | | | | 170 | | | | | 175 | |
| Asp | Asn | Ser | Asp | Val | Asp | Lys | Leu | Phe | Ile | Gln | Leu | Val | Gln | Thr | Tyr |
| | | | 180 | | | | | 185 | | | | | 190 | | |
| Asn | Gln | Leu | Phe | Glu | Glu | Asn | Pro | Ile | Asn | Ala | Ser | Gly | Val | Asp | Ala |
| | | | 195 | | | | | 200 | | | | | 205 | | |
| Lys | Ala | Ile | Leu | Ser | Ala | Arg | Leu | Ser | Lys | Ser | Arg | Arg | Leu | Glu | Asn |
| | 210 | | | | | 215 | | | | | 220 | | | | |
| Leu | Ile | Ala | Gln | Leu | Pro | Gly | Glu | Lys | Lys | Asn | Gly | Leu | Phe | Gly | Asn |
| 225 | | | | | 230 | | | | | 235 | | | | | 240 |
| Leu | Ile | Ala | Leu | Ser | Leu | Gly | Leu | Thr | Pro | Asn | Phe | Lys | Ser | Asn | Phe |
| | | | | 245 | | | | | 250 | | | | | 255 | |
| Asp | Leu | Ala | Glu | Asp | Ala | Lys | Leu | Gln | Leu | Ser | Lys | Asp | Thr | Tyr | Asp |
| | | | 260 | | | | | 265 | | | | | 270 | | |
| Asp | Asp | Leu | Asp | Asn | Leu | Leu | Ala | Gln | Ile | Gly | Asp | Gln | Tyr | Ala | Asp |
| | | | 275 | | | | | 280 | | | | | 285 | | |
| Leu | Phe | Leu | Ala | Ala | Lys | Asn | Leu | Ser | Asp | Ala | Ile | Leu | Leu | Ser | Asp |
| | 290 | | | | | 295 | | | | | 300 | | | | |
| Ile | Leu | Arg | Val | Asn | Thr | Glu | Ile | Thr | Lys | Ala | Pro | Leu | Ser | Ala | Ser |
| 305 | | | | | 310 | | | | | 315 | | | | | 320 |
| Met | Ile | Lys | Arg | Tyr | Asp | Glu | His | His | Gln | Asp | Leu | Thr | Leu | Leu | Lys |
| | | | | 325 | | | | | 330 | | | | | 335 | |
| Ala | Leu | Val | Arg | Gln | Gln | Leu | Pro | Glu | Lys | Tyr | Lys | Glu | Ile | Phe | Phe |
| | | | 340 | | | | | 345 | | | | | 350 | | |
| Asp | Gln | Ser | Lys | Asn | Gly | Tyr | Ala | Gly | Tyr | Ile | Asp | Gly | Gly | Ala | Ser |
| | | | 355 | | | | | 360 | | | | | 365 | | |
| Gln | Glu | Glu | Phe | Tyr | Lys | Phe | Ile | Lys | Pro | Ile | Leu | Glu | Lys | Met | Asp |
| | | | 370 | | | | | 375 | | | | | 380 | | |

```
Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
        420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
```

-continued

```
                805                 810                 815
Gln Asn Gly Arg Asp Met Tyr Val Asp Gln Glu Leu Asp Ile Asn Arg
            820                 825                 830
Leu Ser Asp Tyr Asp Val Asp His Ile Val Pro Gln Ser Phe Leu Lys
            835                 840                 845
Asp Asp Ser Ile Asp Asn Lys Val Leu Thr Arg Ser Asp Lys Asn Arg
        850                 855                 860
Gly Lys Ser Asp Asn Val Pro Ser Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
        930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
            980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
```

```
Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 97
<211> LENGTH: 4107
<212> TYPE: DNA
<213> ORGANISM: Artificial Sequence
<220> FEATURE:
<223> OTHER INFORMATION: Recombinant

<400> SEQUENCE: 97
atggacaaga agtacagcat tggtctggac atcggaacga actcggtcgg ctgggccgtg      60
attactgacg agtacaaagt tcccagcaaa aaattcaagg ttctaggcaa cacagaccgc     120
cactcgatta aaagaatctc aatcggcgcg cttctgttcg actctggtga acggccgag      180 gccacacgct taaagaggac cgcgcgccgc cgctacacgc ggcgcaagaa ccgaatctgt     240
tacctccagg agatcttcag taatgagatg gctaaggtcg atgacagctt cttccacagg     300
cttgaagagt cctttctggt cgaagaggac aaaaaacacg aacgtcaccc aatcttcggg     360
aacattgtgg atgaagtcgc ataccacgag aagtatccta cgatctatca cctccgcaag     420
aagctcgtgg atagtaccga caaagccgac ctgcgcttaa tctaccttgc gctcgcgcac     480
atgattaagt ccgaggaca cttccttatt gagggtgatc tgaatccgga caattccgat     540
gtggataaac tgttcattca gttggtccag acatacaatc agctattcga ggagaatccg     600
atcaatgctt ccgcgtgga cgcaaaggct attctgtcag caagactttc aaagagcaga     660
aggttggaga atctgatcgc acaacttccc ggagagaaga gaatgggct cttcggcaac     720 ctcattgcgc tgtctttggg tctgacaccg aactttaagt ctaacttcga cctcgctgag     780
gatgctaaac ttcagcttag caaagacacc tatgatgatg acctggacaa cctcctcgcc     840
cagattggag accagtacgc ggatctattc ttggctgcca agaacctgtc cgatgcgatt     900
ctgcttagtg acatcctccg agtgaacact gaaattacga agcacccctt gtcggctagt     960
atgattaagc gatacgatga gcaccatcaa gacctgacat tgctaaaggc gctcgtaaga    1020
cagcaacttc ctgagaagta caaggagata tttttgatc agtctaagaa tggctacgct    1080
ggttacatcg acggtggagc tagtcaggag gaattctata aattcatcaa gcctatcctg    1140
```

```
gaaaaaatgg acggtacgga ggaattgctc gttaaactaa atcgagagga tctgctgaga   1200
aagcagcgga cttttcgacaa tggttctatt ccgcatcaga ttcacctcgg agaacttcac   1260
gccatcctga gacgacagga ggacttctac cctttcctga agacaaccg ggaaaaaatc    1320 gagaagatcc tgacattcag gattccttac tatgtaggcc ctttagcgag aggcaacagt   1380
agattcgcct ggatgaccag aaagtctgag gaaacaatca caccgtggaa cttcgaggaa   1440
gtggttgata agggtgctag tgcccaatca ttcattgaga gaatgacgaa cttcgacaag   1500
aatctgccta acgagaaggt tctccctaaa catagcttgc tttacgagta tttcacggtg   1560
tacaatgagc taacgaaggt caagtatgtc acagagggaa tgcggaaacc ggctttcctt   1620
tcgggtgaac agaagaaagc aattgtggat ttgctcttca agacaaaccg aaaggtgaca   1680
gtgaagcagc taaggagga ctacttcaaa aaaatagagt gcttcgactc agttgagatc    1740
agcggagtgg aggaccggtt taacgcttcc ctcggcactt accacgactt gctcaagatc   1800
atcaaggaca aagacttcct tgataacgag gagaacgaag acatccttga ggacattgtg   1860
ctgacattga cgttgttcga ggatcggag atgatcgagg aacgcctcaa gacgtacgcc    1920
catctgttcg atgataaggt gatgaagcag ttaaagagga gacgttacac tggctggggc   1980
cgtctctctc gcaaactgat aaacgggata agggataaac aaagcggaaa gacaatcctc   2040
gatttcctta aatccgacgg cttcgctaac cggaacttca tgcagctcat ccatgatgac   2100
tcactgacgt tcaaggagga catccagaaa gctcaagtgt ctggccaggg tgacagcttg   2160
cacgagcaca tcgcaaatct agccggttca ccggcgataa agaagggcat tctacaaacg   2220
gtgaaagtgg tggacgagct tgtgaaggtc atgggtcgcc ataagccaga gaacattgtt   2280
atcgaaatgg cgagggagaa ccagacaacg cagaagggac aaaaaaacag tagggagcgg   2340
atgaagcgca tcgaggaagg cattaaggaa cttggaagcc aaatcctgaa agagcacccg   2400
gtggagaata cgcagttgca gaacgagaaa ctgtacctct actacttgca gaatggacgt   2460
gatatgtatg tggatcaaga gttggacatc aaccgattgt ctgactatga cgtggatcac   2520
atagtaccac agtccttcct caaggatgat agcatagaca acaaggttct tactcgtagc   2580
gacaagaatc gtggcaaatc ggacaatgtt ccatctgagg aagttgtcaa aaagatgaaa   2640
aattattgga ggcaacttct gaacgcgaag ctaattacac aaaggaaatt cgacaatctc   2700
actaaggccg agagaggagg gttaagtgag ttagacaagg ctggcttcat caagcggcag   2760
ttggtcgaga ctcgtcagat tactaagcac gtggctcaga tcctggattc gcgcatgaac   2820
accaaatacg acgagaatga caaactcatc cgtgaagtta aggtgattac actgaaatcc   2880
aagctggtct ctgactttag gaaagacttc caattctaca aggtgagaga gattaacaac   2940
taccaccacg cgcatgacgc ctacttgaat gctgtggttg ggactgccct gataaagaaa   3000
tatcctaaac ttgagtctga gttcgtttac ggtgactaca aggtttatga cgttaggaag   3060
atgatcgcca aatccgaaca ggagattggg aaagcaactg ccaaatattt cttttactcc   3120
aacattatga acttttttcaa gacagaaatc acactcgcca atggcgagat tcggaagaga   3180
ccactaatcg aaacaaacgg cgaaactggt gaaatcgttt gggataaggg tagggacttc   3240
gcaactgtta ggaaggtctt gtcgatgcct caagtgaaca tagtcaaaaa aacagaggtc   3300
cagaccggtg ggttctcaaa ggagtctatt ctgccaaagc gtaacagcga caaactcatc   3360
gctcgcaaaa aggactggga tcctaaaaag tacggtggat tcgacagccc gaccgttgct   3420
tattctgttc tcgtagttgc taaagtcgag aagggcaagt ccaaaaaaact caaatcggtt   3480 aaggaactgc tcggaatcac gataatggaa cgaagcagtt tcgaaaaaaa tccaattgac   3540
```

```
ttcctggaag ctaaaggtta caaggaggtc aagaaggatc ttatcatcaa gctacccaag    3600
tacagtctgt tcgaactgga gaacggtcgc aagagaatgc tggcctcggc tggtgaactc    3660
cagaagggca atgagctggc cctgccgtcc aagtacgtga actttctgta cctggcatct    3720
cattacgaga agctcaaggg ctcaccagag acaacgagc agaagcagtt gttcgttgaa     3780
cagcacaaac actatcttga tgagatcatt gagcaaatta gcgagttcag taagcgagtt    3840
attctggctg atgctaacct ggataaggtg ctctctgcct acaacaagca ccgggataaa    3900
cctattaggg aacaggcgga gaacataatc cacctcttca ctctgacgaa tctcggcgcg    3960
cctgcggcct tcaaatattt tgataccacc atcgacagga agcgctacac aagcactaaa    4020
gaggtgctgg acgccactct cattcaccag tctattaccg ggctctacga gacacggatt    4080
gacctctccc agctaggtgg cgattaa                                       4107

<210> SEQ ID NO 98
<211> LENGTH: 469
<212> TYPE: DNA
<213> ORGANISM: Artificial Sequence
<220> FEATURE:
<223> OTHER INFORMATION: Recombinant

<400> SEQUENCE: 98
cgtctttgta tcggaatata aatttatcac tattttatga taaagtaaat ctgtttccct     60
gtagagttaa ttaattaatg taagtataag cgtaatttat agggcactag taggactgtc    120
gactgtgcgc tcggcccgga taatgcgtca aaagcgaaga cgtgcacgtg ggatgggaaa    180
acacgaagcg tggtctgctt tttcgcatga tatctgggcc gcaccaaaga atccagccca    240
cgcggcgtgg cgccgtcgtt acttgcgggg aaggaaacg agggacgaac cgagatttag     300
caccagaccg gccagcgagc attgcagaca ccggcttata agttcagctg cgactaccac    360
tccgtctctt cggagacatc cgataaaatt ggaacgatac agagaagatt agcatggccc    420
ctgcgcaagg atgacacgca caaatcgaga atggtccaa atttttttg                 469

<210> SEQ ID NO 99
<211> LENGTH: 268
<212> TYPE: DNA
<213> ORGANISM: Artificial Sequence
<220> FEATURE:
<223> OTHER INFORMATION: Recombinant

<400> SEQUENCE: 99
cctgttccgc tttgctagct tgcgccctga ctgtccagcc cacgcgcttc ggtccgattc     60
tgctaggctg gtgcaagcga gccgagactt ttttttagaa ccaccttgct cagcaaacct    120
taggaacacc ggcttataag tcgaagcgaa gcgctgtgca ctgtctcttc ggagacatcc    180
gataaaattg gaacgataca gagaagatta gcatggcccc tgcgcaagga tgacacgcac    240
aaatcgagaa atggtccaaa ttttttg                                       268

<210> SEQ ID NO 100
<211> LENGTH: 426
<212> TYPE: DNA
<213> ORGANISM: Artificial Sequence
<220> FEATURE:
<223> OTHER INFORMATION: Recombinant

<400> SEQUENCE: 100
gccaggattt atacaactat tttcttattt atttctttaa cattttccct tctacgcaca     60
```

| | |
|---|---:|
| ataggagata atgtcaagcg ttgacggtgc acatatattt gttttttaa aggcgtagtg | 120 |
| gcgtgtgtgc aaaaacatcc tcacaggaaa gacacgaaga aacatggtca atggcccatt | 180 |
| atataaagca ccgccacaaa gcccaaatac cagttcgttg gagcaagtaa cgcgctaggc | 240 |
| aacaggcaaa cagtttgtcc cacctcgtcc agtcacaaag gcaaagcgtg acttataagc | 300 |
| cagagcggaa gaaccatacc gtctcttcgg agacatccga taaaattgga acgatacaga | 360 |
| gaagattagc atggcccctg cgcaaggatg acacgcacaa atcgagaaat ggtccaaatt | 420 |
| tttttg | 426 |

<210> SEQ ID NO 101
<211> LENGTH: 469
<212> TYPE: DNA
<213> ORGANISM: Artificial Sequence
<220> FEATURE:
<223> OTHER INFORMATION: Recombinant

<400> SEQUENCE: 101

| | |
|---|---:|
| ggcccagttg taaaagctaa aatgctattc gaatttctac tagcagtaag tcgtgtttag | 60 |
| aaattatttt tttatatacc ttttttcctt ctatgtacag taggacacag tgtcagcgcc | 120 |
| gcgttgacgg agaatatttg caaaaaagta aagagaaag tcatagcggc gtatgtgcca | 180 |
| aaaacttcgt cacagagagg gccataagaa acatggccca cggcccaata cgaagcaccg | 240 |
| cgacgaagcc caaacagcag ttaggtggag caaagcgctg gtaatacgc aaacgttttg | 300 |
| tcccaccttg actaatcaca agagtggagc gtaccttata aaccgagccg caagcaccga | 360 |
| attgtctctt cggagacatc cgataaaatt ggaacgatac agagaagatt agcatggccc | 420 |
| ctgcgcaagg atgacacgca caaatcgaga aatggtccaa attttttg | 469 |

<210> SEQ ID NO 102
<211> LENGTH: 80
<212> TYPE: DNA
<213> ORGANISM: Artificial Sequence
<220> FEATURE:
<223> OTHER INFORMATION: Recombinant

<400> SEQUENCE: 102

| | |
|---|---:|
| acacttaatc ggctctcaag aagtcctcaa gggataacag ggtaatatag cgtaactata | 60 |
| acggtcctaa ggtagcgaat | 80 |

<210> SEQ ID NO 103
<211> LENGTH: 80
<212> TYPE: DNA
<213> ORGANISM: Artificial Sequence
<220> FEATURE:
<223> OTHER INFORMATION: Recombinant

<400> SEQUENCE: 103

| | |
|---|---:|
| acacttaatc ggctctcaag aagtcctcaa gggataacag ggtaatatag cgtaactata | 60 |
| acggtcctaa ggtagcgaat | 80 |

<210> SEQ ID NO 104
<211> LENGTH: 59
<212> TYPE: DNA
<213> ORGANISM: Artificial Sequence
<220> FEATURE:
<223> OTHER INFORMATION: Recombinant

<400> SEQUENCE: 104

| | |
|---|---:|
| acacttaatc ggctctcaag aagtcctcaa gtaactataa cggtcctaag gtagcgaat | 59 |

```
<210> SEQ ID NO 105
<211> LENGTH: 8
<212> TYPE: DNA
<213> ORGANISM: Artificial Sequence
<220> FEATURE:
<223> OTHER INFORMATION: Recombinant

<400> SEQUENCE: 105 ccaaaagg                                                                    8

<210> SEQ ID NO 106
<211> LENGTH: 7
<212> TYPE: DNA
<213> ORGANISM: Artificial Sequence
<220> FEATURE:
<223> OTHER INFORMATION: Recombinant
<220> FEATURE:
<221> NAME/KEY: misc_feature
<222> LOCATION: (1)..(2)
<223> OTHER INFORMATION: n is a, c, g, or t

<400> SEQUENCE: 106 nnagaaw                                                                     7

<210> SEQ ID NO 107
<211> LENGTH: 155
<212> TYPE: DNA
<213> ORGANISM: Artificial Sequence
<220> FEATURE:
<223> OTHER INFORMATION: Recombinant

<400> SEQUENCE: 107 gtttatctttt catgagcttt tgttattgt actctcaaga tttatttttc caaaagggtt         60
acttaaatct tgcagaagct acaaagataa ggcttcatgc cgaaatcaac accctgtcat        120
tttatggcag ggtgttttcg ttatttaatt ttttt                                   155

<210> SEQ ID NO 108
<211> LENGTH: 155
<212> TYPE: DNA
<213> ORGANISM: Artificial Sequence
<220> FEATURE:
<223> OTHER INFORMATION: Recombinant

<400> SEQUENCE: 108
gtaatactct atggtctgta aggttattgt actctcaaga tttatttttc caaaagggtt         60
acttaaatct tgcagaagct acaaagataa ggcttcatgc cgaaatcaac accctgtcat        120
tttatggcag ggtgttttcg ttatttaatt ttttt                                   155

<210> SEQ ID NO 109
<211> LENGTH: 154
<212> TYPE: DNA
<213> ORGANISM: Artificial Sequence
<220> FEATURE:
<223> OTHER INFORMATION: Recombinant

<400> SEQUENCE: 109
gagatccaac gtgttgggac tgttattgta ctctcaagat ttattttcc aaaagggtta          60 cttaaatctt gcagaagcta caaagataag gcttcatgcc gaaatcaaca ccctgtcatt       120
ttatggcagg gtgttttcgt tatttaattt tttt                                    154

<210> SEQ ID NO 110
```

```
<211> LENGTH: 153
<212> TYPE: DNA
<213> ORGANISM: Artificial Sequence
<220> FEATURE:
<223> OTHER INFORMATION: Recombinant

<400> SEQUENCE: 110
gacattctcc ccaaaatata gttattgtac tctcaagatt tattttttcca aaagggttac    60 ttaaatcttg cagaagctac aaagataagg cttcatgccg aaatcaacac cctgtcattt   120
tatggcaggg tgttttcgtt atttaattttt ttt                                153

<210> SEQ ID NO 111
<211> LENGTH: 155
<212> TYPE: RNA
<213> ORGANISM: Artificial Sequence
<220> FEATURE:
<223> OTHER INFORMATION: Recombinant

<400> SEQUENCE: 111
guuuaucuuu caugagcuuu uuguuauugu acucucaaga uuuauuuuuc caaaagggguu    60 acuuaaaucu ugcagaagcu acaaagauaa ggcuucaugc cgaaaucaac acccugucau   120
uuuauggcag ggguguuuucg uuauuuaauu uuuuu                              155

<210> SEQ ID NO 112
<211> LENGTH: 155
<212> TYPE: RNA
<213> ORGANISM: Artificial Sequence
<220> FEATURE:
<223> OTHER INFORMATION: Recombinant

<400> SEQUENCE: 112
guaauacucu auggucugua agguuauugu acucucaaga uuuauuuuuc caaaagggguu    60 acuuaaaucu ugcagaagcu acaaagauaa ggcuucaugc cgaaaucaac acccugucau   120
uuuauggcag ggguguuuucg uuauuuaauu uuuuu                              155

<210> SEQ ID NO 113
<211> LENGTH: 154
<212> TYPE: RNA
<213> ORGANISM: Artificial Sequence
<220> FEATURE:
<223> OTHER INFORMATION: Recombinant

<400> SEQUENCE: 113
gagauccaac guguugggac uguuauugua cucucaagau uuauuuuucc aaaagggguua    60 cuuaaaucuu gcagaagcua caaagauaag gcuucaugcc gaaaucaaca cccugucauu   120
uuauggcagg guguuuucgu uauuuaauuu uuuu                                154

<210> SEQ ID NO 114
<211> LENGTH: 153
<212> TYPE: RNA
<213> ORGANISM: Artificial Sequence
<220> FEATURE:
<223> OTHER INFORMATION: Recombinant

<400> SEQUENCE: 114
gacauucucc ccaaaauaua guuauuguac ucucaagauu uauuuuucca aaggguuac      60 uuaaaucuug cagaagcuac aaagauaagg cuucaugccg aaaucaacac ccugucauuu   120
uauggcaggg uguuuucguu auuuaauuuu uuu                                 153
```

<210> SEQ ID NO 115
<211> LENGTH: 90
<212> TYPE: DNA
<213> ORGANISM: Artificial Sequence
<220> FEATURE:
<223> OTHER INFORMATION: Recombinant

<400> SEQUENCE: 115

```
ttaagggata acagggtaat atagcgtaac tataacggtc ctaaggtagc gaattacgat      60
acaaggctac ctagcttcgc agttacgcta                                      90
```

<210> SEQ ID NO 116
<211> LENGTH: 90
<212> TYPE: DNA
<213> ORGANISM: Artificial Sequence
<220> FEATURE:
<223> OTHER INFORMATION: Recombinant

<400> SEQUENCE: 116

```
tagcgtaact gcgaagctag gtagccttgt atcgtaattc gctaccttag gaccgttata      60
gttacgctat attaccctgt tatcccttaa                                      90
```

<210> SEQ ID NO 117
<211> LENGTH: 20
<212> TYPE: DNA
<213> ORGANISM: Artificial Sequence
<220> FEATURE:
<223> OTHER INFORMATION: Recombinant

<400> SEQUENCE: 117

```
ctatattacc ctgttatccc                                                 20
```

<210> SEQ ID NO 118
<211> LENGTH: 1388
<212> TYPE: PRT
<213> ORGANISM: Artificial Sequence
<220> FEATURE:
<223> OTHER INFORMATION: Recombinant

<400> SEQUENCE: 118

```
Met Gly Ser Lys Lys Arg Arg Ile Lys Gln Asp Asp Lys Lys Tyr Ser
1               5                   10                  15

Ile Gly Leu Asp Ile Gly Thr Asn Ser Val Gly Trp Ala Val Ile Thr
            20                  25                  30

Asp Glu Tyr Lys Val Pro Ser Lys Lys Phe Lys Val Leu Gly Asn Thr
        35                  40                  45

Asp Arg His Ser Ile Lys Lys Asn Leu Ile Gly Ala Leu Leu Phe Asp
    50                  55                  60

Ser Gly Glu Thr Ala Glu Ala Thr Arg Leu Lys Arg Thr Ala Arg Arg
65                  70                  75                  80

Arg Tyr Thr Arg Arg Lys Asn Arg Ile Cys Tyr Leu Gln Glu Ile Phe
                85                  90                  95

Ser Asn Glu Met Ala Lys Val Asp Asp Ser Phe His Arg Leu Glu
            100                 105                 110

Glu Ser Phe Leu Val Glu Glu Asp Lys Lys His Glu Arg His Pro Ile
        115                 120                 125

Phe Gly Asn Ile Val Asp Glu Val Ala Tyr His Glu Lys Tyr Pro Thr
    130                 135                 140

Ile Tyr His Leu Arg Lys Lys Leu Val Asp Ser Thr Asp Lys Ala Asp
145                 150                 155                 160
```

```
Leu Arg Leu Ile Tyr Leu Ala Leu Ala His Met Ile Lys Phe Arg Gly
                165                 170                 175

His Phe Leu Ile Glu Gly Asp Leu Asn Pro Asp Asn Ser Asp Val Asp
            180                 185                 190

Lys Leu Phe Ile Gln Leu Val Gln Thr Tyr Asn Gln Leu Phe Glu Glu
            195                 200                 205

Asn Pro Ile Asn Ala Ser Gly Val Asp Ala Lys Ala Ile Leu Ser Ala
            210                 215                 220

Arg Leu Ser Lys Ser Arg Arg Leu Glu Asn Leu Ile Ala Gln Leu Pro
225                 230                 235                 240

Gly Glu Lys Lys Asn Gly Leu Phe Gly Asn Leu Ile Ala Leu Ser Leu
                245                 250                 255

Gly Leu Thr Pro Asn Phe Lys Ser Asn Phe Asp Leu Ala Glu Asp Ala
            260                 265                 270

Lys Leu Gln Leu Ser Lys Asp Thr Tyr Asp Asp Asp Leu Asp Asn Leu
            275                 280                 285

Leu Ala Gln Ile Gly Asp Gln Tyr Ala Asp Leu Phe Leu Ala Ala Lys
            290                 295                 300

Asn Leu Ser Asp Ala Ile Leu Leu Ser Asp Ile Leu Arg Val Asn Thr
305                 310                 315                 320

Glu Ile Thr Lys Ala Pro Leu Ser Ala Ser Met Ile Lys Arg Tyr Asp
                325                 330                 335

Glu His His Gln Asp Leu Thr Leu Leu Lys Ala Leu Val Arg Gln Gln
            340                 345                 350

Leu Pro Glu Lys Tyr Lys Glu Ile Phe Phe Asp Gln Ser Lys Asn Gly
            355                 360                 365

Tyr Ala Gly Tyr Ile Asp Gly Gly Ala Ser Gln Glu Glu Phe Tyr Lys
            370                 375                 380

Phe Ile Lys Pro Ile Leu Glu Lys Met Asp Gly Thr Glu Glu Leu Leu
385                 390                 395                 400

Val Lys Leu Asn Arg Glu Asp Leu Leu Arg Lys Gln Arg Thr Phe Asp
                405                 410                 415

Asn Gly Ser Ile Pro His Gln Ile His Leu Gly Glu Leu His Ala Ile
            420                 425                 430

Leu Arg Arg Gln Glu Asp Phe Tyr Pro Phe Leu Lys Asp Asn Arg Glu
            435                 440                 445

Lys Ile Glu Lys Ile Leu Thr Phe Arg Ile Pro Tyr Tyr Val Gly Pro
            450                 455                 460

Leu Ala Arg Gly Asn Ser Arg Phe Ala Trp Met Thr Arg Lys Ser Glu
465                 470                 475                 480

Glu Thr Ile Thr Pro Trp Asn Phe Glu Glu Val Val Asp Lys Gly Ala
                485                 490                 495

Ser Ala Gln Ser Phe Ile Glu Arg Met Thr Asn Phe Asp Lys Asn Leu
            500                 505                 510

Pro Asn Glu Lys Val Leu Pro Lys His Ser Leu Leu Tyr Glu Tyr Phe
            515                 520                 525

Thr Val Tyr Asn Glu Leu Thr Lys Val Lys Tyr Val Thr Glu Gly Met
            530                 535                 540

Arg Lys Pro Ala Phe Leu Ser Gly Glu Gln Lys Lys Ala Ile Val Asp
545                 550                 555                 560

Leu Leu Phe Lys Thr Asn Arg Lys Val Thr Val Lys Gln Leu Lys Glu
                565                 570                 575

Asp Tyr Phe Lys Lys Ile Glu Cys Phe Asp Ser Val Glu Ile Ser Gly
```

```
                    580                 585                 590
Val Glu Asp Arg Phe Asn Ala Ser Leu Gly Thr Tyr His Asp Leu Leu
            595                 600                 605

Lys Ile Ile Lys Asp Lys Asp Phe Leu Asp Asn Glu Asn Glu Asp
610                 615                 620

Ile Leu Glu Asp Ile Val Leu Thr Leu Thr Leu Phe Glu Asp Arg Glu
625                 630                 635                 640

Met Ile Glu Glu Arg Leu Lys Thr Tyr Ala His Leu Phe Asp Asp Lys
            645                 650                 655

Val Met Lys Gln Leu Lys Arg Arg Tyr Thr Gly Trp Gly Arg Leu
            660                 665                 670

Ser Arg Lys Leu Ile Asn Gly Ile Arg Asp Lys Gln Ser Gly Lys Thr
            675                 680                 685

Ile Leu Asp Phe Leu Lys Ser Asp Gly Phe Ala Asn Arg Asn Phe Met
            690                 695                 700

Gln Leu Ile His Asp Asp Ser Leu Thr Phe Lys Glu Asp Ile Gln Lys
705                 710                 715                 720

Ala Gln Val Ser Gly Gln Gly Asp Ser Leu His Glu His Ile Ala Asn
            725                 730                 735

Leu Ala Gly Ser Pro Ala Ile Lys Lys Gly Ile Leu Gln Thr Val Lys
            740                 745                 750

Val Val Asp Glu Leu Val Lys Val Met Gly Arg His Lys Pro Glu Asn
            755                 760                 765

Ile Val Ile Glu Met Ala Arg Glu Asn Gln Thr Thr Gln Lys Gly Gln
            770                 775                 780

Lys Asn Ser Arg Glu Arg Met Lys Arg Ile Glu Glu Gly Ile Lys Glu
785                 790                 795                 800

Leu Gly Ser Gln Ile Leu Lys Glu His Pro Val Glu Asn Thr Gln Leu
            805                 810                 815

Gln Asn Glu Lys Leu Tyr Leu Tyr Tyr Leu Gln Asn Gly Arg Asp Met
            820                 825                 830

Tyr Val Asp Gln Glu Leu Asp Ile Asn Arg Leu Ser Asp Tyr Asp Val
            835                 840                 845

Asp His Ile Val Pro Gln Ser Phe Leu Lys Asp Asp Ser Ile Asp Asn
            850                 855                 860

Lys Val Leu Thr Arg Ser Asp Lys Asn Arg Gly Lys Ser Asp Asn Val
865                 870                 875                 880

Pro Ser Glu Glu Val Val Lys Lys Met Lys Asn Tyr Trp Arg Gln Leu
            885                 890                 895

Leu Asn Ala Lys Leu Ile Thr Gln Arg Lys Phe Asp Asn Leu Thr Lys
            900                 905                 910

Ala Glu Arg Gly Gly Leu Ser Glu Leu Asp Lys Ala Gly Phe Ile Lys
            915                 920                 925

Arg Gln Leu Val Glu Thr Arg Gln Ile Thr Lys His Val Ala Gln Ile
            930                 935                 940

Leu Asp Ser Arg Met Asn Thr Lys Tyr Asp Glu Asn Asp Lys Leu Ile
945                 950                 955                 960

Arg Glu Val Lys Val Ile Thr Leu Lys Ser Lys Leu Val Ser Asp Phe
            965                 970                 975

Arg Lys Asp Phe Gln Phe Tyr Lys Val Arg Glu Ile Asn Asn Tyr His
            980                 985                 990

His Ala His Asp Ala Tyr Leu Asn Ala Val Val Gly Thr Ala Leu Ile
            995                 1000                1005
```

-continued

| | | | | | | | | | | | |
|---|---|---|---|---|---|---|---|---|---|---|---|
| Lys | Lys | Tyr | Pro | Lys | Leu | Glu | Ser | Glu | Phe | Val | Tyr | Gly | Asp | Tyr |
| 1010 | | | | 1015 | | | | 1020 | | | |

Lys Lys Tyr Pro Lys Leu Glu Ser Glu Phe Val Tyr Gly Asp Tyr
    1010                1015               1020

Lys Val Tyr Asp Val Arg Lys Met Ile Ala Lys Ser Glu Gln Glu
    1025                1030               1035

Ile Gly Lys Ala Thr Ala Lys Tyr Phe Phe Tyr Ser Asn Ile Met
    1040                1045               1050

Asn Phe Phe Lys Thr Glu Ile Thr Leu Ala Asn Gly Glu Ile Arg
    1055                1060               1065

Lys Arg Pro Leu Ile Glu Thr Asn Gly Glu Thr Gly Glu Ile Val
    1070                1075               1080

Trp Asp Lys Gly Arg Asp Phe Ala Thr Val Arg Lys Val Leu Ser
    1085                1090               1095

Met Pro Gln Val Asn Ile Val Lys Lys Thr Glu Val Gln Thr Gly
    1100                1105               1110

Gly Phe Ser Lys Glu Ser Ile Leu Pro Lys Arg Asn Ser Asp Lys
    1115                1120               1125

Leu Ile Ala Arg Lys Lys Asp Trp Asp Pro Lys Lys Tyr Gly Gly
    1130                1135               1140

Phe Asp Ser Pro Thr Val Ala Tyr Ser Val Leu Val Val Ala Lys
    1145                1150               1155

Val Glu Lys Gly Lys Ser Lys Lys Leu Lys Ser Val Lys Glu Leu
    1160                1165               1170

Leu Gly Ile Thr Ile Met Glu Arg Ser Ser Phe Glu Lys Asn Pro
    1175                1180               1185

Ile Asp Phe Leu Glu Ala Lys Gly Tyr Lys Glu Val Lys Lys Asp
    1190                1195               1200

Leu Ile Ile Lys Leu Pro Lys Tyr Ser Leu Phe Glu Leu Glu Asn
    1205                1210               1215

Gly Arg Lys Arg Met Leu Ala Ser Ala Gly Glu Leu Gln Lys Gly
    1220                1225               1230

Asn Glu Leu Ala Leu Pro Ser Lys Tyr Val Asn Phe Leu Tyr Leu
    1235                1240               1245

Ala Ser His Tyr Glu Lys Leu Lys Gly Ser Pro Glu Asp Asn Glu
    1250                1255               1260

Gln Lys Gln Leu Phe Val Glu Gln His Lys His Tyr Leu Asp Glu
    1265                1270               1275

Ile Ile Glu Gln Ile Ser Glu Phe Ser Lys Arg Val Ile Leu Ala
    1280                1285               1290

Asp Ala Asn Leu Asp Lys Val Leu Ser Ala Tyr Asn Lys His Arg
    1295                1300               1305

Asp Lys Pro Ile Arg Glu Gln Ala Glu Asn Ile Ile His Leu Phe
    1310                1315               1320

Thr Leu Thr Asn Leu Gly Ala Pro Ala Ala Phe Lys Tyr Phe Asp
    1325                1330               1335

Thr Thr Ile Asp Arg Lys Arg Tyr Thr Ser Thr Lys Glu Val Leu
    1340                1345               1350

Asp Ala Thr Leu Ile His Gln Ser Ile Thr Gly Leu Tyr Glu Thr
    1355                1360               1365

Arg Ile Asp Leu Ser Gln Leu Gly Gly Asp Gly Ser Lys Lys Arg
    1370                1375               1380

Arg Ile Lys Gln Asp
    1385

<210> SEQ ID NO 119
<211> LENGTH: 4542
<212> TYPE: DNA
<213> ORGANISM: Artificial Sequence
<220> FEATURE:
<223> OTHER INFORMATION: Recombinant

<400> SEQUENCE: 119

| | | | | | |
|---|---|---|---|---|---|
| atgggatcta | agaagagaag | aattaaacaa | gatgacaaga | agtacagcat | tggtctggac | 60 |
| atcggaacga | actcggtcgg | ctgggccgtg | attactgacg | agtacaaagt | tcccagcaaa | 120 |
| aaattcaagg | ttctaggcaa | cacagaccgc | cactcgatta | aaagaatctc | aatcggtgcg | 180 |
| cttctgttcg | actctggtga | acggccgag | gccacacgct | taaagaggac | cgcgcgccgc | 240 |
| cgctacacgc | ggcgcaagaa | ccgaatctgt | tacctccagg | taagtttctg | cttctacctt | 300 |
| tgatatatat | ataataatta | tcattaatta | gtagtaatat | aatatttcaa | atattttttt | 360 |
| caaaataaaa | gaatgtagta | tatagcaatt | gcttttctgt | agtttataag | tgtgtatatt | 420 |
| ttaatttata | acttttctaa | tatatgacca | aaatttgttg | atgtgcaggt | aagtttctgc | 480 |
| ttctaccttt | gatatatata | taataattat | cattaattag | tagtaatata | atatttcaaa | 540 |
| tatttttttc | aaaataaaag | aatgtagtat | atagcaattg | cttttctgta | gtttataagt | 600 |
| gtgtatattt | taatttataa | cttttctaat | atatgaccaa | aatttgttga | tgtgcaggag | 660 |
| atcttcagta | atgagatggc | taaggtcgat | gacagcttct | ccacaggct | gaagagtcc | 720 |
| tttctggtcg | aagaggacaa | aaaacacgaa | cgtcacccaa | tcttcgggaa | cattgtggat | 780 |
| gaagtcgcat | accacgagaa | gtatcctacg | atctatcacc | tccgcaagaa | gctcgtggat | 840 |
| agtaccgaca | aagccgacct | gcgcttaatc | taccttgcgc | tcgcgcacat | gattaagttc | 900 |
| cgaggacact | tccttattga | gggtgatctg | aatccgaca | attccgatgt | ggataaactg | 960 |
| ttcattcagt | tggtccagac | atacaatcag | ctattcgagg | agaatccgat | caatgcttcc | 1020 |
| ggcgtggacg | caaaggctat | tctgtcagca | agactttcaa | agagcagaag | gttggagaat | 1080 |
| ctgatcgcac | aacttccgg | agagaagaag | aatgggctct | tcggcaacct | cattgcgctg | 1140 |
| tctttgggtc | tgacaccgaa | ctttaagtct | aacttcgacc | tcgctgagga | tgctaaactt | 1200 |
| cagcttagca | aagacaccta | tgatgatgac | ctggacaacc | tcctcgccca | gattggagac | 1260 |
| cagtacgcgg | atctattctt | ggctgccaag | aacctgtccg | atgcgattct | gcttagtgac | 1320 |
| atcctccgag | tgaacactga | aattacgaaa | gcacccttgt | cggctagtat | gattaagcga | 1380 |
| tacgatgagc | accatcaaga | cctgacattg | ctaaaggcgc | tcgtaagaca | gcaacttcct | 1440 |
| gagaagtaca | aggagatatt | ttttgatcag | tctaagaatg | gctacgctgg | ttacatcgac | 1500 |
| ggtggagcta | gtcaggagga | attctataaa | ttcatcaagc | ctatcctgga | aaaaatggac | 1560 |
| ggtacggagg | aattgctcgt | aaactaaat | cgagaggatc | tgctgagaaa | gcagcggact | 1620 |
| ttcgacaatg | gttctattcc | gcatcagatt | cacctcggag | aacttcacgc | catcctgaga | 1680 |
| cgacaggagg | acttctaccc | tttcctgaaa | gacaaccggg | aaaaaatcga | agatcctg | 1740 |
| acattcagga | ttccttacta | tgtaggccct | ttagcgagag | gcaacagtag | attcgcctgg | 1800 |
| atgaccagaa | agtctgagga | aacaatcaca | ccgtggaact | tcgaggaagt | ggttgataag | 1860 |
| ggtgctagtg | cccaatcatt | cattgagaga | atgacgaact | tcgacaagaa | tctgcctaac | 1920 |
| gagaaggttc | tccctaaaca | tagcttgctt | tacgagtatt | tcacggtgta | caatgagcta | 1980 |
| acgaaggtca | agtatgtcac | agagggaatg | cggaaaccgg | cttccttc | gggtgaacag | 2040 |
| aagaaagcaa | ttgtggattt | gctcttcaag | acaaaccgaa | aggtgacagt | gaagcagcta | 2100 |

```
aaggaggact acttcaaaaa aatagagtgc ttcgactcag ttgagatcag cggagtggag    2160
gaccggttta acgcttccct cggcacttac cacgacttgc tcaagatcat caaggacaaa    2220
gacttccttg ataacgagga gaacgaagac atccttgagg acattgtgct gacattgacg    2280
ttgttcgagg atcgggagat gatcgaggaa cgcctcaaga cgtacgccca tctgttcgat    2340
gataaggtga tgaagcagtt aaagaggaga cgttacactg gctggggccg tctctctcgc    2400
aaactgataa acgggataag ggataaacaa agcggaaaga caatcctcga tttccttaaa    2460
tccgacggct tcgctaaccg gaacttcatg cagctcatcc atgatgactc actgacgttc    2520
aaggaggaca tccagaaagc tcaagtgtct ggccagggtg acagcttgca cgagcacatc    2580
gcaaatctag ccggttcacc ggcgataaag aagggcattc tacaaacggt gaaagtggtg    2640
gacgagcttg tgaaggtcat gggtcgccat aagccagaga acattgttat cgaaatggcg    2700
agggagaacc agacaacgca gaagggacaa aaaaacagta gggagcggat gaagcgcatc    2760
gaggaaggca ttaaggaact tggaagccaa atcctgaaag agcacccggt ggagaatacg    2820
cagttgcaga acgagaaact gtacctctac tacttgcaga atggacgtga tatgtatgtg    2880
gatcaagagt tggacatcaa ccgattgtct gactatgacg tggatcacat agtaccacag    2940
tccttcctca aggatgatag catagacaac aaggttctta ctcgtagcga caagaatcgt    3000
ggcaaatcgg acaatgttcc atctgaggaa gttgtcaaaa agatgaaaaa ttattggagg    3060
caacttctga acgcgaagct aattacacaa aggaaattcg acaatctcac taaggccgag    3120
agaggagggt aagtgagtt agacaaggct ggcttcatca agcggcagtt ggtcgagact    3180
cgtcagatta ctaagcacgt ggctcagatc ctggattcgc gcatgaacac caaatacgac    3240
gagaatgaca aactcatccg tgaagttaag gtgattacac tgaaatccaa gctggtctct    3300
gactttagga aagacttcca attctacaag gtgagagaga ttaacaacta ccaccacgcg    3360
catgacgcct acttgaatgc tgtggttggg actgccctga taaagaaata tcctaaactt    3420
gagtctgagt tcgtttacgg tgactacaag gtttatgacg ttaggaagat gatcgccaaa    3480
tccgaacagg agattgggaa agcaactgcc aaatatttct tttactccaa cattatgaac    3540
tttttcaaga cagaaatcac actcgccaat ggcgagattc ggaagagacc actaatcgaa    3600
acaaacggcg aaactggtga atcgtttgg gataagggta gggacttcgc aactgttagg    3660
aaggtcttgt cgatgcctca agtgaacata gtcaaaaaaa cagaggtcca gaccggtggg    3720
ttctcaaagg agtctattct gccaaagcgt aacagcgaca aactcatcgc tcgcaaaaag    3780
gactgggatc ctaaaaagta cggtggattc gacagcccga ccgttgctta ttctgttctc    3840
gtagttgcta aagtcgagaa gggcaagtcc aaaaaactca aatcggttaa ggaactgctc    3900
ggaatcacga taatgaacg aagcagtttc gaaaaaaatc caattgactt cctggaagct    3960
aaaggttaca aggaggtcaa gaaggatctt atcatcaagc tacccaagta cagtctgttc    4020
gaactggaga acgtcgcaa gagaatgctg gcctcggctg tgaactcca gaagggcaat    4080 gagctggccc tgccgtccaa gtacgtgaac tttctgtacc tggcatctca ttacgagaag    4140
ctcaagggct caccgagga caacgagcag aagcagttgt tcgttgaaca gcacaaacac    4200
tatcttgatg agatcattga gcaaattagc gagttcagta gcgagttat tctggctgat    4260 gctaacctgg ataaggtgct ctctgcctac aacaagcacc gggataaacc tattagggaa    4320
caggcggaga acataatcca cctcttcact ctgacgaatc tcggcgcgcc tgcggccttc    4380
aaatattttg ataccaccat cgacaggaag cgctacacaa gcactaaaga ggtgctggac    4440
```
gccactctca ttcaccagtc tattaccggg ctctacgaga cacggattga cctctcccag    4500
ctaggtggcg atggatctaa gaagagaaga attaaacaag at                        4542

<210> SEQ ID NO 120
<211> LENGTH: 10
<212> TYPE: PRT
<213> ORGANISM: Artificial Sequence
<220> FEATURE:
<223> OTHER INFORMATION: Recombinant

<400> SEQUENCE: 120

Gly Ser Lys Lys Arg Arg Ile Lys Gln Asp
1               5                   10

<210> SEQ ID NO 121
<211> LENGTH: 92
<212> TYPE: DNA
<213> ORGANISM: Artificial Sequence
<220> FEATURE:
<223> OTHER INFORMATION: Recombinant

<400> SEQUENCE: 121
caagggataa cagggtaata tagcgtaact ataacggtcc taaggtagcg aattacgata    60
caaggctacc tagcttcgca gttacgctag ta                                   92

<210> SEQ ID NO 122
<211> LENGTH: 92
<212> TYPE: DNA
<213> ORGANISM: Artificial Sequence
<220> FEATURE:
<223> OTHER INFORMATION: Recombinant

<400> SEQUENCE: 122
tactagcgta actgcgaagc taggtagcct tgtatcgtaa ttcgctacct taggaccgtt    60
atagttacgc tatattaccc tgttatccct tg                                   92

<210> SEQ ID NO 123
<211> LENGTH: 73
<212> TYPE: DNA
<213> ORGANISM: Artificial Sequence
<220> FEATURE:
<223> OTHER INFORMATION: Recombinant

<400> SEQUENCE: 123
catgccctct taggcagtag ccggccagca tttgaattaa gggataacag ggtaatatag    60
cgtaactata acg                                                        73

<210> SEQ ID NO 124
<211> LENGTH: 73
<212> TYPE: DNA
<213> ORGANISM: Artificial Sequence
<220> FEATURE:
<223> OTHER INFORMATION: Recombinant

<400> SEQUENCE: 124
catgccctct taggcagtag ccggccagca tttgaattaa gggataacag ggtaatatag    60
cgtaactata acg                                                        73

<210> SEQ ID NO 125
<211> LENGTH: 68
<212> TYPE: DNA
<213> ORGANISM: Artificial Sequence
<220> FEATURE:

<223> OTHER INFORMATION: Recombinant

<400> SEQUENCE: 125

```
catgccctct taggcagtag ccggccagca tttaagggat aacagggtaa tatagcgtaa    60
ctataacg                                                             68
```

<210> SEQ ID NO 126
<211> LENGTH: 73
<212> TYPE: DNA
<213> ORGANISM: Artificial Sequence
<220> FEATURE:
<223> OTHER INFORMATION: Recombinant

<400> SEQUENCE: 126

```
aaagcaacac ttaatcggct ctcaagaagt cctcaaggga taacagggta atatagcgta    60
actataacgg tcc                                                       73
```

<210> SEQ ID NO 127
<211> LENGTH: 73
<212> TYPE: DNA
<213> ORGANISM: Artificial Sequence
<220> FEATURE:
<223> OTHER INFORMATION: Recombinant

<400> SEQUENCE: 127

```
aaagcaacac ttaatcggct ctcaagaagt cctcaaggga taacagggta atatagcgta    60
actataacgg tcc                                                       73
```

<210> SEQ ID NO 128
<211> LENGTH: 52
<212> TYPE: DNA
<213> ORGANISM: Artificial Sequence
<220> FEATURE:
<223> OTHER INFORMATION: Recombinant

<400> SEQUENCE: 128

```
aaagcaacac ttaatcggct ctcaagaagt cctcaagtaa ctataacggt cc            52
```

<210> SEQ ID NO 129
<211> LENGTH: 73
<212> TYPE: DNA
<213> ORGANISM: Artificial Sequence
<220> FEATURE:
<223> OTHER INFORMATION: Recombinant

<400> SEQUENCE: 129

```
aaagcaacac ttaatcggct ctcaagaagt cctcaaggga taacagggta atatagcgta    60
actataacgg tcc                                                       73
```

<210> SEQ ID NO 130
<211> LENGTH: 71
<212> TYPE: DNA
<213> ORGANISM: Artificial Sequence
<220> FEATURE:
<223> OTHER INFORMATION: Recombinant

<400> SEQUENCE: 130

```
aaagcaacac ttaatcggct ctcaagaagt cctcaaggga taacagggta atatagcgta    60
actataagtc c                                                         71
```

<210> SEQ ID NO 131
<211> LENGTH: 69

-continued

<210> SEQ ID NO 131
<211> LENGTH: 69
<212> TYPE: DNA
<213> ORGANISM: Artificial Sequence
<220> FEATURE:
<223> OTHER INFORMATION: Recombinant

<400> SEQUENCE: 131
aaagcaacac ttaatcggct ctcaagaagt cctcaagata acagggtaat atagcgtaac    60
tataagtcc                                                           69

<210> SEQ ID NO 132
<211> LENGTH: 18
<212> TYPE: DNA
<213> ORGANISM: Artificial Sequence
<220> FEATURE:
<223> OTHER INFORMATION: Recombinant

<400> SEQUENCE: 132
gaaacggttc ggcatgca                                                 18

<210> SEQ ID NO 133
<211> LENGTH: 15
<212> TYPE: DNA
<213> ORGANISM: Artificial Sequence
<220> FEATURE:
<223> OTHER INFORMATION: Recombinant

<400> SEQUENCE: 133
tgagctggca cgaac                                                    15

<210> SEQ ID NO 134
<211> LENGTH: 20
<212> TYPE: DNA
<213> ORGANISM: Artificial Sequence
<220> FEATURE:
<223> OTHER INFORMATION: Recombinant

<400> SEQUENCE: 134
ccctgtcgtc cgtccaagta                                               20

<210> SEQ ID NO 135
<211> LENGTH: 1142
<212> TYPE: PRT
<213> ORGANISM: Artificial Sequence
<220> FEATURE:
<223> OTHER INFORMATION: Recombinant

<400> SEQUENCE: 135

Met Gly Ser Lys Lys Arg Arg Ile Lys Gln Asp Met Ser Asp Leu Val
1               5                   10                  15

Leu Gly Leu Asp Ile Gly Ile Gly Ser Val Gly Val Gly Ile Leu Asn
            20                  25                  30

Lys Val Thr Gly Glu Ile Ile His Lys Asn Ser Arg Ile Phe Pro Ala
        35                  40                  45

Ala Gln Ala Glu Asn Asn Leu Val Arg Arg Thr Asn Arg Gln Gly Arg
    50                  55                  60

Arg Leu Ala Arg Arg Lys Lys His Arg Val Arg Leu Asn Arg Leu
65                  70                  75                  80

Phe Glu Glu Ser Gly Leu Ile Thr Asp Phe Thr Lys Ile Ser Ile Asn
                85                  90                  95

Leu Asn Pro Tyr Gln Leu Arg Val Lys Gly Leu Thr Asp Glu Leu Ser
            100                 105                 110

Asn Glu Glu Leu Phe Ile Ala Leu Lys Asn Met Val Lys His Arg Gly

```
            115                 120                 125
Ile Ser Tyr Leu Asp Asp Ala Ser Asp Asp Gly Asn Ser Val Gly
            130                 135                 140

Asp Tyr Ala Gln Ile Val Lys Glu Asn Ser Lys Gln Leu Glu Thr Lys
145                 150                 155                 160

Thr Pro Gly Gln Ile Gln Leu Glu Arg Tyr Gln Thr Tyr Gly Gln Leu
                165                 170                 175

Arg Gly Asp Phe Thr Val Glu Lys Asp Gly Lys Lys His Arg Leu Ile
                180                 185                 190

Asn Val Phe Pro Thr Ser Ala Tyr Arg Ser Glu Ala Leu Arg Ile Leu
            195                 200                 205

Gln Thr Gln Gln Glu Phe Asn Pro Gln Ile Thr Asp Glu Phe Ile Asn
            210                 215                 220

Arg Tyr Leu Glu Ile Leu Thr Gly Lys Arg Lys Tyr Tyr His Gly Pro
225                 230                 235                 240

Gly Asn Glu Lys Ser Arg Thr Asp Tyr Gly Arg Tyr Arg Thr Ser Gly
                245                 250                 255

Glu Thr Leu Asp Asn Ile Phe Gly Ile Leu Ile Gly Lys Cys Thr Phe
            260                 265                 270

Tyr Pro Asp Glu Phe Arg Ala Ala Lys Ala Ser Tyr Thr Ala Gln Glu
            275                 280                 285

Phe Asn Leu Leu Asn Asp Leu Asn Asn Leu Thr Val Pro Thr Glu Thr
            290                 295                 300

Lys Lys Leu Ser Lys Glu Gln Lys Asn Gln Ile Ile Asn Tyr Val Lys
305                 310                 315                 320

Asn Glu Lys Ala Met Gly Pro Ala Lys Leu Phe Lys Tyr Ile Ala Lys
                325                 330                 335

Leu Leu Ser Cys Asp Val Ala Asp Ile Lys Gly Tyr Arg Ile Asp Lys
                340                 345                 350

Ser Gly Lys Ala Glu Ile His Thr Phe Glu Ala Tyr Arg Lys Met Lys
                355                 360                 365

Thr Leu Glu Thr Leu Asp Ile Glu Gln Met Asp Arg Glu Thr Leu Asp
            370                 375                 380

Lys Leu Ala Tyr Val Leu Thr Leu Asn Thr Glu Arg Glu Gly Ile Gln
385                 390                 395                 400

Glu Ala Leu Glu His Glu Phe Ala Asp Gly Ser Phe Ser Gln Lys Gln
                405                 410                 415

Val Asp Glu Leu Val Gln Phe Arg Lys Ala Asn Ser Ser Ile Phe Gly
                420                 425                 430

Lys Gly Trp His Asn Phe Ser Val Lys Leu Met Met Glu Leu Ile Pro
                435                 440                 445

Glu Leu Tyr Glu Thr Ser Glu Glu Gln Met Thr Ile Leu Thr Arg Leu
            450                 455                 460

Gly Lys Gln Lys Thr Thr Ser Ser Ser Asn Lys Thr Lys Tyr Ile Asp
465                 470                 475                 480

Glu Lys Leu Leu Thr Glu Glu Ile Tyr Asn Pro Val Val Ala Lys Ser
                485                 490                 495

Val Arg Gln Ala Ile Lys Ile Val Asn Ala Ala Ile Lys Glu Tyr Gly
                500                 505                 510

Asp Phe Asp Asn Ile Val Ile Glu Met Ala Arg Glu Thr Asn Glu Asp
                515                 520                 525

Asp Glu Lys Lys Ala Ile Gln Lys Ile Gln Lys Ala Asn Lys Asp Glu
                530                 535                 540
```

```
Lys Asp Ala Ala Met Leu Lys Ala Ala Asn Gln Tyr Asn Gly Lys Ala
545                 550                 555                 560

Glu Leu Pro His Ser Val Phe His Gly His Lys Gln Leu Ala Thr Lys
                565                 570                 575

Ile Arg Leu Trp His Gln Gln Gly Glu Arg Cys Leu Tyr Thr Gly Lys
            580                 585                 590

Thr Ile Ser Ile His Asp Leu Ile Asn Asn Ser Asn Gln Phe Glu Val
        595                 600                 605

Asp His Ile Leu Pro Leu Ser Ile Thr Phe Asp Asp Ser Leu Ala Asn
    610                 615                 620

Lys Val Leu Val Tyr Ala Thr Ala Asn Gln Glu Lys Gly Gln Arg Thr
625                 630                 635                 640

Pro Tyr Gln Ala Leu Asp Ser Met Asp Asp Ala Trp Ser Phe Arg Glu
                645                 650                 655

Leu Lys Ala Phe Val Arg Glu Ser Lys Thr Leu Ser Asn Lys Lys Lys
            660                 665                 670

Glu Tyr Leu Leu Thr Glu Glu Asp Ile Ser Lys Phe Asp Val Arg Lys
        675                 680                 685

Lys Phe Ile Glu Arg Asn Leu Val Asp Thr Arg Tyr Ala Ser Arg Val
    690                 695                 700

Val Leu Asn Ala Leu Gln Glu His Phe Arg Ala His Lys Ile Asp Thr
705                 710                 715                 720

Lys Val Ser Val Val Arg Gly Gln Phe Thr Ser Gln Leu Arg Arg His
                725                 730                 735

Trp Gly Ile Glu Lys Thr Arg Asp Thr Tyr His His His Ala Val Asp
            740                 745                 750

Ala Leu Ile Ile Ala Ala Ser Ser Gln Leu Asn Leu Trp Lys Lys Gln
        755                 760                 765

Lys Asn Thr Leu Val Ser Tyr Ser Glu Asp Gln Leu Leu Asp Ile Glu
    770                 775                 780

Thr Gly Glu Leu Ile Ser Asp Asp Glu Tyr Lys Glu Ser Val Phe Lys
785                 790                 795                 800

Ala Pro Tyr Gln His Phe Val Asp Thr Leu Lys Ser Lys Glu Phe Glu
                805                 810                 815

Asp Ser Ile Leu Phe Ser Tyr Gln Val Asp Ser Lys Phe Asn Arg Lys
            820                 825                 830

Ile Ser Asp Ala Thr Ile Tyr Ala Thr Arg Gln Ala Lys Val Gly Lys
        835                 840                 845

Asp Lys Ala Asp Glu Thr Tyr Val Leu Gly Lys Ile Lys Asp Ile Tyr
    850                 855                 860

Thr Gln Asp Gly Tyr Asp Ala Phe Met Lys Ile Tyr Lys Lys Asp Lys
865                 870                 875                 880

Ser Lys Phe Leu Met Tyr Arg His Asp Pro Gln Thr Phe Glu Lys Val
                885                 890                 895

Ile Glu Pro Ile Leu Glu Asn Tyr Pro Asn Lys Gln Ile Asn Glu Lys
            900                 905                 910

Gly Lys Glu Val Pro Cys Asn Pro Phe Leu Lys Tyr Lys Glu Glu His
        915                 920                 925

Gly Tyr Ile Arg Lys Tyr Ser Lys Lys Gly Asn Gly Pro Glu Ile Lys
    930                 935                 940

Ser Leu Lys Tyr Tyr Asp Ser Lys Leu Gly Asn His Ile Asp Ile Thr
945                 950                 955                 960
```

```
Pro Lys Asp Ser Asn Asn Lys Val Val Leu Gln Ser Val Ser Pro Trp
                965                 970                 975
Arg Ala Asp Val Tyr Phe Asn Lys Thr Thr Gly Lys Tyr Glu Ile Leu
            980                 985                 990
Gly Leu Lys Tyr Ala Asp Leu Gln Phe Glu Lys Gly Thr Gly Thr Tyr
        995                 1000                1005
Lys Ile Ser Gln Glu Lys Tyr Asn Asp Ile Lys Lys Lys Glu Gly
    1010                1015                1020
Val Asp Ser Asp Ser Glu Phe Lys Phe Thr Leu Tyr Lys Asn Asp
    1025                1030                1035
Leu Leu Leu Val Lys Asp Thr Glu Thr Lys Glu Gln Gln Leu Phe
    1040                1045                1050
Arg Phe Leu Ser Arg Thr Met Pro Lys Gln Lys His Tyr Val Glu
    1055                1060                1065
Leu Lys Pro Tyr Asp Lys Gln Lys Phe Glu Gly Glu Ala Leu
    1070                1075                1080
Ile Lys Val Leu Gly Asn Val Ala Asn Ser Gly Gln Cys Lys Lys
    1085                1090                1095
Gly Leu Gly Lys Ser Asn Ile Ser Ile Tyr Lys Val Arg Thr Asp
    1100                1105                1110
Val Leu Gly Asn Gln His Ile Ile Lys Asn Glu Gly Asp Lys Pro
    1115                1120                1125
Lys Leu Asp Phe Gly Ser Lys Lys Arg Arg Ile Lys Gln Asp
    1130                1135                1140

<210> SEQ ID NO 136
<211> LENGTH: 3618
<212> TYPE: DNA
<213> ORGANISM: Artificial Sequence
<220> FEATURE:
<223> OTHER INFORMATION: Recombinant

<400> SEQUENCE: 136
atgggatcta agaagagaag aattaaacaa gatatgagtg acctggtgct agggttggat      60
ataggcattg gctccgtggg ggttggcatt cttaataagg tgaccggcga ataattcat     120
aaaaactcac gcatctttcc agcagcccag gctgagaaca atctggtccg tagaaccaac    180
cggcagggtc gaaggttagc caggcgcaag aagcacagac gggtccggct caacaggctt    240
ttcgaggagt ctggtttgat caccgatttc actaagattt ctatcaacct gaatccttat    300
cagctgcgcg ttaaaggtct cacagacgaa cttagcaacg aagagttgtt catcgccctg    360
aaaaatatgg tcaagcatcg cggcattagc tacctggacg acgcttcgga tgatggcaac    420
agtagtgtag gtgactacgc tcagatcgtg aaagagaact cgaagcaatt ggagaccaag    480
accccgggcc aaattcaact cgaaaggtaa gtttctgctt ctaccttgta tatatata    540
ataattatca ttaattagta gtaatataat atttcaaata ttttttttcaa aataaaagaa    600
tgtagtatat agcaattgct tttctgtagt ttataagtgt gtatatttta atttataact    660
tttctaatat atgaccaaaa tttgttgatg tgcaggtacc agacgtatgg acagttacga    720
ggcgatttta ccgttgaaaa ggatggtaag aagcacaggc tgattaatgt gtttccgacc    780
tcagcttatc gctctgaggc gctgcgtatt ttgcagaccc aacaggaatt taacccgcaa    840
ataacggacg agttcataaa ccgatactta gagattctta caggtaaacg taaatactat    900
cacggcccag gaaatgaaaa gtccaggaca gattatggtc gatatcgcac ttccggagag    960
actctcgaca atatctttgg cattcttata ggcaaatgta ccttctaccc tgacgaattt   1020
```

```
agagcagcga aggcttcata tacagcacaa gagtttaatc ttctcaacga cctcaacaac    1080
ttgactgtgc ctactgaaac caaaaagctt agcaaggagc aaaaaaatca aatcattaac    1140
tatgttaaga atgagaaagc tatggggccc gcaaaattgt tcaagtacat agctaagtta    1200
cttagctgtg acgttgctga tattaagggt taccgtattg acaagtctgg taaagctgaa    1260
attcacacct ttgaggctta taggaagatg aagacccttg agacacttga cattgagcag    1320 atggatagggg agactttgga caaactggca tacgtcttga cattgaacac cgaaagggaa    1380
ggcatccagg aagctctgga acatgaattt gcagatggtt cgttcagcca aaaacaggtt    1440
gacgagctgg tccaatttag aaaggcaaac tcaagcatat tcggtaaagg ttggcacaac    1500
ttcagcgtta agctgatgat ggaactcatt ccagaattat atgaaacctc tgaggaacag    1560
atgacgattc tcacaagatt gggtaagcag aaaacaacca gctctagcaa taagactaaa    1620
tacattgacg aaaagctcct caccgaagag atttataacc cggtcgtggc aaagagtgta    1680
cggcaagcca tcaagatcgt taatgccgct atcaaggagt atggtgattt tgataatatt    1740
gtgattgaaa tggcacgcga gactaacgag gacgacgaga agaaagctat acagaagatt    1800
caaaaggcta ataaggacga gaaggacgcc gcaatgctaa aggcggccaa tcaatataat    1860
gggaaggctg aactacctca tagcgtcttc catggacata agcaattagc aactaaaata    1920
agattatggc accagcaagg cgaacggtgt ctttatacag gtaaaacgat atctattcac    1980
gacctgatta acaactctaa ccagtttgaa gtggatcata tcttaccact aagtatcacc    2040
ttcgacgatt cacttgctaa caaggtgctc gtttacgcca ctgcgaacca agagaaaggg    2100
cagaggactc cataccaggc ccttgacagc atggacgacg cctggagttt tagggaatta    2160
aaagctttcg tacgtgagtc aaagacgctt tcaaataaaa aaaaggagta cttgctcact    2220
gaagaagaca tctcaaaatt cgacgtgcgc aaaaaattca ttgagcggaa cttagtcgac    2280
actcggtacg catcaagagt agtgttgaac gccctccagg agcactttag ggcacataag    2340
atcgacacca aggtttcagt tgttaggggt cagtttacat cgcagcttag acgccattgg    2400
ggtatagaaa aaaacacgtga tacctaccat caccatgcag ttgacgctct catcattgca    2460
gcatcttctc aacttaattt gtggaaaaag caaagaacaa ctctggtctc atatagcgaa    2520
gatcagctgc ttgatattga aaccggcgag ctgatttctg acgacgaata caaagaatct    2580
gtgtttaagg caccatatca acactttgta gacacgctta atctaaaga gtttgaggat    2640 tcgatccttt tcagttacca agtcgactca aaatttaacc gtaagatctc tgatgcaaca    2700
atttatgcga cgaggcaggc caaggtaggt aaggataagg ctgacgaaac ctacgtgctc    2760
ggaaaaatca aagatattta cactcaagat ggatatgatg cattcatgaa gatatataaa    2820
aaggacaaat ctaaattcct tatgtatcgt catgacccac agacattcga gaagttatt     2880 gagcctatcc tggagaacta tccgaacaag caaataaatg agaagggcaa agaagttcca    2940
tgtaatccgt tcctaaagta caaggaggaa cacggatata ttagaaaata cagcaaaaag    3000
ggcaacggcc cagaaatcaa aagccttaag tactacgata gtaaactagg aaaccacatc    3060
gacattacac caaagactc taataataag gtcgtactgc aaagcgtttc cccatgcgc     3120 gccgatgtgt attttaataa gacaacaggg aagtacgaaa tcttggggtt aaaatatgcg    3180
gatctgcaat tcgaaagggg aaccggcaca tacaaaattt ctcaagaaaa gtacaacgac    3240
ataaagaaga aggaaggggt cgattctgat tctgaattca agttcacact ctataagaat    3300
gatcttctgc tcgtcaagga cacagagaca aaggagcagc agtgttcag gttcttgtct    3360
```

```
agaactatgc caaaacaaaa gcactacgtt gaactgaagc cttacgataa gcaaaaattc    3420 gagggggggcg aggcgcttat aaaggtccta ggaaatgttg caaactctgg gcagtgtaag    3480
aagggcctgg gcaagagcaa cattagcatc tataaggttc gaacggatgt gcttgggaac    3540
cagcatatca tcaaaaacga gggagataaa ccaaagctgg acttcggatc taagaagaga    3600
agaattaaac aagattag                                                  3618

<210> SEQ ID NO 137
<211> LENGTH: 26
<212> TYPE: DNA
<213> ORGANISM: Artificial Sequence
<220> FEATURE:
<223> OTHER INFORMATION: Recombinant

<400> SEQUENCE: 137
ccttgtatcg taattcgcta ccttag                                         26

<210> SEQ ID NO 138
<211> LENGTH: 20
<212> TYPE: DNA
<213> ORGANISM: Artificial Sequence
<220> FEATURE:
<223> OTHER INFORMATION: Recombinant

<400> SEQUENCE: 138
ctatattacc ctgttatccc                                                20

<210> SEQ ID NO 139
<211> LENGTH: 20
<212> TYPE: DNA
<213> ORGANISM: Artificial Sequence
<220> FEATURE:
<223> OTHER INFORMATION: Recombinant

<400> SEQUENCE: 139
taatcggctc tcaagaagtc                                                20

<210> SEQ ID NO 140
<211> LENGTH: 20
<212> TYPE: DNA
<213> ORGANISM: Artificial Sequence
<220> FEATURE:
<223> OTHER INFORMATION: Recombinant

<400> SEQUENCE: 140
gggactctag aaaaaacttg                                                20

<210> SEQ ID NO 141
<211> LENGTH: 21
<212> TYPE: DNA
<213> ORGANISM: Artificial Sequence
<220> FEATURE:
<223> OTHER INFORMATION: Recombinant

<400> SEQUENCE: 141
taaggagatg agtttgagac c                                              21

<210> SEQ ID NO 142
<211> LENGTH: 20
<212> TYPE: DNA
<213> ORGANISM: Artificial Sequence
<220> FEATURE:
<223> OTHER INFORMATION: Recombinant

<400> SEQUENCE: 142
```

```
aacatttcag taatcacgag                                                  20
```

<210> SEQ ID NO 143
<211> LENGTH: 20
<212> TYPE: DNA
<213> ORGANISM: Artificial Sequence
<220> FEATURE:
<223> OTHER INFORMATION: Recombinant

<400> SEQUENCE: 143

```
taatatgatg gcatgccctc                                                  20
```

<210> SEQ ID NO 144
<211> LENGTH: 68
<212> TYPE: DNA
<213> ORGANISM: Artificial Sequence
<220> FEATURE:
<223> OTHER INFORMATION: Recombinant

<400> SEQUENCE: 144

```
ctatctagtg aagatgtaat actctatggt ctgtttaagg gataacaggg taatatagcg      60
taactata                                                               68
```

<210> SEQ ID NO 145
<211> LENGTH: 55
<212> TYPE: DNA
<213> ORGANISM: Artificial Sequence
<220> FEATURE:
<223> OTHER INFORMATION: Recombinant

<400> SEQUENCE: 145

```
ctatctagtg aagatgtaat actctatggt ctgtgggtaa tatagcgtaa ctata           55
```

<210> SEQ ID NO 146
<211> LENGTH: 397
<212> TYPE: DNA
<213> ORGANISM: Solanum lycopersicum

<400> SEQUENCE: 146

```
aataaatata ttatctatca ttagaacttg aattataagt gaataataga ttatttttg       60 taatatgaat taaagtgta ttaaacatgt attaacggtg atcaattggt taaaaaaaag      120
tttattatta aaatgataaa tcttttaat ttatagtata tttatgtaag ttttcacgtt      180
gagtaaatag cgaagaagtt gggcccaacc aagtaaaata agaaggccgg gccattacaa     240
ttaagtcgtc acacaactgg gcttcattga aaaaagcgca aaaccgattc caggcccgtg     300
ttagcatgaa gactcaactc aaccagagat ttctccctca tcgcttacag aaaaagcta      360 tatgctgttt atattgcgaa atctaacagt gtagttt                              397
```

<210> SEQ ID NO 147
<211> LENGTH: 397
<212> TYPE: DNA
<213> ORGANISM: Solanum lycopersicum

<400> SEQUENCE: 147

```
tacttatgag aagaagtaac tgatttaaaa ttttcactaa tagggttcga aaatgaaaa       60 tgtaatacgt ggaacttgaa tgtaaaacct caaggaattc ttgtgtttaa gaaattcaaa    120
atctctctaa atgtatacaa aagatgattt cttttttacct tatatatagt aaaataaaat   180
tgtcggataa attcgagtga acaccctagc accccctaaa tcctcccccg tagtcggccc    240
```

```
attacagtta aagtccaggt acaacaaaat gggcttcgat taagatggaa taaaaggagt    300
ccaggcccat gagcccaaca aacaagctat ttctccctca tcggcgcaca aagaagcttt    360
attctcttat tatagctgaa tattagcatg tgtgttt                             397

<210> SEQ ID NO 148
<211> LENGTH: 397
<212> TYPE: DNA
<213> ORGANISM: Solanum lycopersicum

<400> SEQUENCE: 148
ttctatttgt gctacatata ttagacaagg aaaataacat atgttatttt gaaatcacgt    60
atatttacta taaattacaa tgattaacaa cttaaaatat ttaaatgaaa atcatattaa    120
tgactctcta aattttatct gtgtcacata atgaaaaac aaaaaataac aaatattgta    180
ttcgcacggg cgcatgtgtc tagttagtta taaacgaaga aataagggc tgatttcgaa     240 ataaacgttc ttagaattgg aagaaatgtt cagtttctaa acttgtagga ctaaagcaat    300 aactttatt taatttattt tcttttatgt ttctcccaca tcgatcatac ataactat      360 acagcagtat aagaactcta gcgaagcaat aatgctc                             397

<210> SEQ ID NO 149
<211> LENGTH: 261
<212> TYPE: DNA
<213> ORGANISM: Solanum lycopersicum

<400> SEQUENCE: 149
ataaatcttt ttaatttata gtatatttat gtaagttttc acgttgagta aatagcgaag    60
aagttgggcc caaccaagta aaataagaag gccgggccat tacaattaag tcgtcacaca    120
actgggcttc attgaaaaaa gcgcaaaacc gattccaggc ccgtgttagc atgaagactc    180
aactcaacca gagatttctc cctcatcgct tacagaaaaa agctatatgc tgtttatatt    240
gcgaatctaa cagtgtagtt t                                              261

<210> SEQ ID NO 150
<211> LENGTH: 103
<212> TYPE: DNA
<213> ORGANISM: Solanum lycopersicum

<400> SEQUENCE: 150
ggatctttcc aagcttgagg gttttagagc tagaaatagc aagttaaaat aaggctagtc    60
cgttatcaac ttgaaaaagt ggcaccgagt cggtgctttt ttt                      103

<210> SEQ ID NO 151
<211> LENGTH: 119
<212> TYPE: DNA
<213> ORGANISM: Solanum lycopersicum

<400> SEQUENCE: 151
aagctaatca agctgctaat actatttcaa aacttaggca ttctaatcct cctcaagctt    60
ggaaagatcc tttgaagaat tgtgcctttt cgtataaggt aatgtttatt cgttcgtcg     119

<210> SEQ ID NO 152
<211> LENGTH: 120
<212> TYPE: DNA
<213> ORGANISM: Artificial Sequence
<220> FEATURE:
<223> OTHER INFORMATION: Recombinant

<400> SEQUENCE: 152
```

```
aagctaatca agctgctaat actatttcaa aacttaggca ttctaatcct cctacaagct    60
tggaaagatc ctttgaagaa ttgtgccttt tcgtataagg taatgtttat tcgttcgtcg   120
```

<210> SEQ ID NO 153
<211> LENGTH: 120
<212> TYPE: DNA
<213> ORGANISM: Artificial Sequence
<220> FEATURE:
<223> OTHER INFORMATION: Recombinant

<400> SEQUENCE: 153

```
aagctaatca agctgctaat actatttcaa aacttaggca ttctaatcct cctgcaagct    60
tggaaagatc ctttgaagaa ttgtgccttt tcgtataagg taatgtttat tcgttcgtcg   120
```

<210> SEQ ID NO 154
<211> LENGTH: 117
<212> TYPE: DNA
<213> ORGANISM: Artificial Sequence
<220> FEATURE:
<223> OTHER INFORMATION: Recombinant

<400> SEQUENCE: 154

```
aagctaatca agctgctaat actatttcaa aacttaggca ttctaatcct cctagcttgg    60
aaagatcctt tgaagaattg tgccttttcg tataaggtaa tgtttattcg ttcgtcg     117
```

<210> SEQ ID NO 155
<211> LENGTH: 116
<212> TYPE: DNA
<213> ORGANISM: Artificial Sequence
<220> FEATURE:
<223> OTHER INFORMATION: Recombinant

<400> SEQUENCE: 155

```
aagctaatca agctgctaat actatttcaa aacttaggca ttctaatcct cctgcttgga    60
aagatccttt gaagaattgt gccttttcgt ataaggtaat gtttattcgt tcgtcg      116
```

<210> SEQ ID NO 156
<211> LENGTH: 114
<212> TYPE: DNA
<213> ORGANISM: Artificial Sequence
<220> FEATURE:
<223> OTHER INFORMATION: Recombinant

<400> SEQUENCE: 156

```
aagctaatca agctgctaat actatttcaa aacttaggca ttctaatcct cctttggaaa    60
gatcctttga agaattgtgc cttttcgtat aaggtaatgt ttattcgttc gtcg        114
```

<210> SEQ ID NO 157
<211> LENGTH: 20
<212> TYPE: DNA
<213> ORGANISM: Artificial Sequence
<220> FEATURE:
<223> OTHER INFORMATION: Recombinant

<400> SEQUENCE: 157

```
tagagacaac atgcaagaac                                                20
```

<210> SEQ ID NO 158
<211> LENGTH: 20
<212> TYPE: DNA
<213> ORGANISM: Artificial Sequence
<220> FEATURE:

<223> OTHER INFORMATION: Recombinant

<400> SEQUENCE: 158
taagcaacca gtaagatagg 20

<210> SEQ ID NO 159
<211> LENGTH: 380
<212> TYPE: DNA
<213> ORGANISM: Artificial Sequence
<220> FEATURE:
<223> OTHER INFORMATION: Recombinant

<400> SEQUENCE: 159
tagagacaac atgcaagaac acaccaaatt ataatttgtg tgtgaaaact ttgtctttag 60
acaaaagaag tgaaaaagca ggagatatta caacattagc attaattatg gttgatgcta 120
ttaaatctaa agctaatcaa gctgctaata ctatttcaaa acttaggcat tctaatcctc 180
ctcaagcttg gaaagatcct ttgaagaatt gtgcctttc gtataaggta atgtttattc 240
gttcgtcgtt tcaatttgtt tgtcctaaca aaactcgact atgatgaatt aggattttat 300 gtttatttt tctgtctcaa tttgcttgtc ttacttcttt ttttggctaa agtttcgac 360 cctatcttac tggttgctta 380

<210> SEQ ID NO 160
<211> LENGTH: 246
<212> TYPE: DNA
<213> ORGANISM: Glycine max

<400> SEQUENCE: 160
ggaaacttct gtttgtcccc atactccaaa acaaaacca ttttttttt atcttcgttt 60 ttgtttgctt tgactgtgag ttgaggccca actttctgct tctgtccgac tctatttgat 120
gaattttgtt tgcctcctgt gatgtgaagg atgtatcatt gaaagggaac gtgtctcaat 180
gatcccacat cggccaaata tgctcattac attgcgttta tatagtccca ggaaaacata 240
tggatt 246

<210> SEQ ID NO 161
<211> LENGTH: 493
<212> TYPE: DNA
<213> ORGANISM: Glycine max

<400> SEQUENCE: 161
tctacaaaac attataaaaa gtaagatata caacttttt ttttaaaaaa atcaatagga 60
aatattatcg gttcagttaa tttacagaga gatatttatt tcatatgtgc cagaagtatt 120
tcagttcctt atgaaaaatc agaaaaatgt atggaataaa atataataat cgatactaat 180
aatagaacaa aataaatggt aaaatgtcaa atcaaaacta ggctgcagta tgcagagcag 240
agtcatgatg atactactta ctacaccgat tcttgtgtgc agaaaatat gttaaaataa 300 ttgaatcttt ctctagccaa atttgacaac aatgtacacc gttcatattg agagacgatg 360
cttcttgttt gctttcggtg gaagctgcat atactcaaca ttactccttc agcgagtttt 420
ccaactgagt cccacattgc ccagacctaa cacggtattc ttgtttataa tgaaatgtgc 480
caccacatgg att 493

<210> SEQ ID NO 162
<211> LENGTH: 559
<212> TYPE: DNA
<213> ORGANISM: Glycine max

<400> SEQUENCE: 162

```
aggtggagtt gttccagatt tagttttcga cttagatgat gcatggaact ggctagtgac    60
gtggatggtg gtaggttact ttcaggtcat gatttttgt ttctaaatga tactcacact   120
cccttccagt tttttttttt taaactcagc tcccttgctt cctccaccgg ttatcataat   180
actgaaccaa atcaaacatt acagtcaagg tactatgaat atgaaacctg aaatcctatg   240
aatgtcataa atttatttta ataataaat ttatttagaa taatatttt ttgggtaaga   300
gttataaaat aaaatacaaa aaaaaaacct aatatcaatt tttcactgac tccgtttata   360
ttgagacttg agaagatgg ttcccgtttg ctcccggtgg aggctccgag gctgtgtata   420
tactcgacat tactttagct tgttttgttg tttctttccc tttcccacaa gactcaggtc   480
tcgttcgcaa acgagtccca caccgtctaa acttaccaca atattagcgt ttataattag   540
atgcactgca tcacttatt                                                559
```

<210> SEQ ID NO 163
<211> LENGTH: 596
<212> TYPE: DNA
<213> ORGANISM: Glycine max

<400> SEQUENCE: 163

```
aaattacacg gtagtacatc ctattataga tcgatgaatt cttaactact cgtgtccctt    60
aggccaggcc tgttttcttg cacaatttct gaaatgtata cggttccac ttcaacctt   120
ttaaccgcac aaagttttaa ccagatttat ataatttatt tttgaatccc caatacatat   180
cattataaca tatcaattat caaatatttc ataacctca tgatatggca atgaatacat   240
cttcttctca atgaacagag atttctgaaa aagattagga aagtgaaagc atactcgttt   300
gcaatgtaaa actgatactt ccccaaaatc atcatattcc aaatatgccc tggtgttact   360
gaccaaaacc agaaaaaaga aacggaagac atatacgtct aaacggagaa atttcaaaaa   420
acaaaaattg gatcatttct cgatttgtgg gtgtcatctt gtgcagggca tgctaatctt   480
ctctttaccc tttcccacaa gactcagcgc atgttgtctc gtctcatcca agtcccacac   540
cgcctaaact taacacaata ttagtattta taatgacata caacattcaa gatgtt      596
```

<210> SEQ ID NO 164
<211> LENGTH: 737
<212> TYPE: DNA
<213> ORGANISM: Glycine max

<400> SEQUENCE: 164

```
aattatttaa tcctaaaaat caatcttaca aggaaccact ataaaactag ttgaacccat    60
cgaaaactaa ctacagttga caaaatctat ttggttggtt gatttttttt aattaaaaac   120
atccaatctt aatgatataa ttatagctta atattataag attttataa aaattatatt   180
tattttgttt ctaattatgc taagagatat tattatttgt tatttaactt aaatattatc   240
acaaacttga ttgaaactta tgtttaattt aaaatattat atgtcatgag ttatgactcc   300
aataatcaca attataaagt gaagtttaat ttttagtatt acaaatattt ttttgttgtt   360
taattttaat tacttaatgt attatgttaa taattaaaaa tacaaattat ttattattaa   420
tgcaatcaca gtttgtggat ttgacaaaag aaatagggga tctaaaattg tagataagcc   480
aaagttaaaa cttgaattga ctattttttg ctctttactc tgcaccaact ttactattcc   540
ttcttttagt gtgagcttca tgcatcttgt tcaccgcaat tccgctcggt gaaagttgca   600
```

```
caattcactc acaatctgtt tctggtctgt taggtttgtt acttggagtg acacgatgac    660
gcaacagtac aagtcccaca tcgtttgagt atacagtttt caagcagttt atattcccat    720
agccttagca agagctt                                                   737
```

<210> SEQ ID NO 165
<211> LENGTH: 484
<212> TYPE: DNA
<213> ORGANISM: Glycine max

<400> SEQUENCE: 165

```
tttttaata aaaaaattc aatgggagat actatggatt caattacctt actgatttta     60
tttcatatgt gccagaagta tttcagttta ttttgaaaaa tcagaaaaaa aatgtctgga    120
ataaaatata ataagcgata ctaataaata attgaacaag ataaatggta aaatgtcaaa    180
tcaaaactag gctacagagt gcagagcaga gtcatgatga atgacagcta gttctactta    240
ctacaccgat tcttgtgtac ataaaaatat tttaaaataa ttgaatcttt ctttagccag    300
ctttgacaac aatgtacacc gttcgtactt cttactggta ggcaatgctt cttgtttgct    360
ttcggtggaa ggtgtatata ctcaacatta cttcttttc agcgtgtttt cttacgggag    420
tcccacaccg cccaaaacta atacagtatt cttgtttata aagaagtgca ccacttcaat    480
tgtt                                                                 484
```

<210> SEQ ID NO 166
<211> LENGTH: 427
<212> TYPE: DNA
<213> ORGANISM: Glycine max

<400> SEQUENCE: 166

```
cgataaaaat gttttaaacg atatatatta taaaaaaaaa cgtttcaaaa ataaatacaa     60
aaatgttttt aaatatatat aatttaactc attaagaaaa ataaaaatgc aagtgcggtg    120
acaagacaag ctaaaagttg caaaagaaat ggcagggcta taaggctcac ctactcctgg    180
atttaccaaa ttttggttcg tccctatact cgaaaaataa aacaaaataa atttcagtat    240
cttcgttttt gtatgctttg actgtgaggc gaggccaact ttcttcttct gtctgagatg    300
aattttgttt gcctcctgtg aaggatgtat cattcaaagt gaatgttttg caactgccag    360
tagtcccaca tcgaccaaat attcttatta cagtgtgttt atatagcacc tggagaagga    420
atgggtt                                                              427
```

<210> SEQ ID NO 167
<211> LENGTH: 400
<212> TYPE: DNA
<213> ORGANISM: Glycine max

<400> SEQUENCE: 167

```
gaaaagcatt cagaatattt gagcctctaa aaactttct tctttttctt tgaggagtgt     60
aatgtggatc ccaagtaacc aagaaaagca atccgaaaat tcaatttcaa gcaaactgtt    120
ctcaagtttt cgagggatat agtaatagca gagcaaaaaa acactggaaa aagcttgtac    180
ctattgaaac aaaggataat taaaaatcca aaatgtatca aaagcctaga caatttaat    240 cactattgcc tcttaacaat ttgcgcacta tgacaatcat gctctcataa tgtaacaaaa    300
gacacattag gatactagta ctgacactga caccaaggtt acatagtccc acatcgaagg    360
agtttaggta gagacatcgg tttatataac taagcgtgac                          400
```

```
<210> SEQ ID NO 168
<211> LENGTH: 434
<212> TYPE: DNA
<213> ORGANISM: Glycine max

<400> SEQUENCE: 168
ttgccaacaa gatataacaa gaagcctaat atttcaaaag gccttttggt ccttaaaaac      60
taaggaatgc atctccagaa agaagtacaa tcataatagt tgctaagaat gcagcaaaat     120
tgataaatta atcgagaaac cacaccacaa atcacacatg ccattagag  aaaaagaaag     180 gtttcaggaa aataaaagaa agaaaaagt  caattactgc ttagctacct ctctatattc     240
ccatgtgccc cttgcttgaa attggaacca ctaccaggca acagagttgt tcccttcaa      300 gcaataagag ttagaaatat ttttatatca accgaagtgg caaaaagtca gaaaccatga     360
catacgttta ctttgttagt cccacattgg atagttttag taaaacacag gtcattatat     420
agctaaacgc taac                                                       434

<210> SEQ ID NO 169
<211> LENGTH: 436
<212> TYPE: DNA
<213> ORGANISM: Glycine max

<400> SEQUENCE: 169
aatatttcaa agcacactta ggtccttaaa aatgcaatgt tacaattcca aaaggaagta      60
taatcatagt agaagccaag aatgcagaaa aattaacaaa gtgatcgagg aatcattgcc     120
acaaatcact catggctatt agagaaaaaa aaaagtttca agaaaagaaa agaaaaagtt     180
aattactact tagctacttc tttgtaaact caggtgcccc ttgcatgcaa ttgataccac     240
accaggcacc agagctgttc cttttcatgc aataagagta agagacattt ttttatgaac     300
tcagatggcg aagtgtttga aaccatgaca ggcgttactc tggtagtccg acatagagag     360
ttttaataaa acacaaatgt agtcccacat tgaacagttt aataaaaca  cagtctttat     420 ataactaaac gctgag                                                     436

<210> SEQ ID NO 170
<211> LENGTH: 428
<212> TYPE: DNA
<213> ORGANISM: Glycine max

<400> SEQUENCE: 170
cttaggtggc tcttgcttga aatgggtact gtactggaat tagagtttat cttttcatgc      60
acaaagtttt ggccctcgtt ctactacagt atacagcagt atggatatgg ttcacattaa     120
ttctccgaaa gtaatctatc cctgcgggct agcctgagaa agggtgttta taatcttgta     180
gtgatagaat caagcatcat aagagctttc aaagcctcta atgagtattt ctttttctag     240
aaaagatgaa tatttgggat caatgctgct gctgttatgt aggaaacacc gtggcaggaa     300
gattgtattt gtatccttgt gcaatactca gaccaattct gttagaaaaa tgacacaaag     360
gccgtgatgc tagtcccaca tcgagtgttt ttaacaaaac aggcgcatat atattactgg     420
acgctgag                                                              428

<210> SEQ ID NO 171
<211> LENGTH: 432
<212> TYPE: DNA
<213> ORGANISM: Glycine max

<400> SEQUENCE: 171
```

```
catgctgtgt agtgaaagac atagacagtc aaaaggcctg agaagggtat atattgtaaa      60
gatgatgatt tttcttacag atggtttata ccgctttatg cttcttcagc gtagaactta     120
tcaaagagaa cactatccat agctgaatca agttggttca ggcttttgtt ataatcacag     180
tctaggagtc taggacactt ttattttgca ttcattttcg gattgttgac gcctttgtat     240 aaatttttaca atctctcagt aaaagatcga acacttctga taatgtttta ggaatttaac    300
tctcattcta taagctttga ccaagtctga accctagaca attgcctctt taacaacttg     360
acacagaaat aataatagtc ccacatcgag agcgtttagc tacaaacatg tgtttatata    420
attaagcata ac                                                         432
```

<210> SEQ ID NO 172
<211> LENGTH: 434
<212> TYPE: DNA
<213> ORGANISM: Glycine max

<400> SEQUENCE: 172

```
gtttatgttt ggcattcttt aatctttagt atcagaataa ttgatcacat tttgaaatgc     60
caatagaaag acactcctta aacaaaagct atcgtgtatg aaaagctgca gagaaaaatc    120
aaatgtacaa gattttaaat aaagacatgc taaactgtcc aatatgtaac tagttgaaca    180
ggctgcattt ctctgtgttt ttgcttccgc agggaggaat acaaacatct aacaacttat    240
accaaagcat atagtacaaa ttacaatctt ttgttttccc caaattaatc caatttatct    300
ttcatttcat ccagaaagaa gctctttgag attgttagtg ttaaactgca aactttcttc    360
ttacttatgt cccacatagg aaagaaaagg agacaacaaa atctttatat gccctctgac    420
aaagttgtct gaat                                                       434
```

<210> SEQ ID NO 173
<211> LENGTH: 417
<212> TYPE: DNA
<213> ORGANISM: Glycine max

<400> SEQUENCE: 173

```
catttaaaat aatgaatgac taatccatta actaataact atagttgatt acttttagt      60 taattaggat gttaggaata cctgaatcca ccgacttaac tattatcata atcagttcat    120
tcaatttgaa tttgtaggat gcacctctat gttttcctct tcactttcta gtggacacaa    180
gaccctgtgt cacacacagt aatagagaaa agatcattta catgtaagcg gaacccattg    240
cattctacag caatatttg gggttggtgt tataatacaa gacggataaa atagctagag     300
agaatccaat caaatcccac attccaaatt agactatcca ttgtaggcca agtcccacat    360
tggttagaat attaggcaac gaaaccttta taaatcttct gacaagcact tcagcat       417
```

<210> SEQ ID NO 174
<211> LENGTH: 439
<212> TYPE: DNA
<213> ORGANISM: Glycine max

<400> SEQUENCE: 174

```
ggcatgtgac tttttattta aattattctc agaaatatta aaatataatc aaatatattt     60
ttttataaga tactggaaat aacattttta ggaatgtaac gaaagcccca ttacaaacac    120
ttgaactcag ggatcgatcc aacttaatta ttatctgcta cttcaaattc aaatttatag    180
gccctacctt tatgttttgc tctgcacttt cttaaatgga aacaagtaac acaatagagt    240
aagatcattt acttgtaagc ggaaactgtt gcatcaactg caatattttc gggttagttt    300
```

```
tataatataa caatgaagag aattgccgag aagatcatat caagtcccat attccattta    360
ttggccttta caagtcccac atcggtccaa atattagaca aagaaacatt tatatatcgt    420
ctgacaaacc tgtaagatt                                                 439
```

<210> SEQ ID NO 175
<211> LENGTH: 169
<212> TYPE: DNA
<213> ORGANISM: Zea mays

<400> SEQUENCE: 175

```
ggattgtgcg ggcaaagtat tttcgtcgaa agagaagcaa cgaaaaagcc cactgctccg    60
agacaccgtt ccacgaaacc tgtccgcact catctcatcg tttagcacca cctcgccagt   120
ccgcagtcct ctatacctgc ttaaatattc gtccagaccg cccacccctc               169
```

<210> SEQ ID NO 176
<211> LENGTH: 200
<212> TYPE: DNA
<213> ORGANISM: Zea mays

<400> SEQUENCE: 176

```
ctgttttcat ccggcctgtg atggaaattg tgctgcaaag tgcgcagggc cgttggcccg    60
acgacaagta tttttcgtcg agagaagcaa cgaaagccca ctcctccaag ccacccttcg   120
ctcaagtcat atttagcacc acctcggcag tcgacactgc agcacaccaa cttaaatatt   180
catcccgatc tccctcactc                                               200
```

<210> SEQ ID NO 177
<211> LENGTH: 200
<212> TYPE: DNA
<213> ORGANISM: Zea mays

<400> SEQUENCE: 177

```
aaactgtgct tgtgcagggc cgttgggcca cgtgcccacg tcaaagtatt ctagtcgaaa    60
gagaagcaac gaaagcccac tactactcct aggcaccgtt ccacgagac ctgtccgcac    120 tcatctcatc gtttagcacc aatgcgccag tccgcagtcc gctgtaccag cttaaatatt   180
cgtccctacc gcgctccatc                                               200
```

<210> SEQ ID NO 178
<211> LENGTH: 200
<212> TYPE: DNA
<213> ORGANISM: Zea mays

<400> SEQUENCE: 178

```
catataggga tcagctaagc ttatcatacc ttccttttt tttctcattc agccactact    60
gcagcctaca aaggatatca taatgggccg acccagtcac ccaggacgca atatgttggt   120
caatcccacc agttagtacc acctcggtag ctcagatgag tagaagatac cttaaaagtt   180
cagctcaggc aacttgcagc                                               200
```

<210> SEQ ID NO 179
<211> LENGTH: 200
<212> TYPE: DNA
<213> ORGANISM: Zea mays

<400> SEQUENCE: 179

```
catggtccat aggtatcaag atccagcatt gcacttgggc caaagattga gctctgcgaa    60
```

```
gtgtcaacta caatcatcta gatgggctcg acctgaaagg ccacacgatt tgccagaact    120
cccaccaatt aattagtacc acctcggttg ctcgatttag tagaagccag cttaaaagtt    180
cagctctggg gtccggtagc                                                200
```

```
<210> SEQ ID NO 180
<211> LENGTH: 181
<212> TYPE: DNA
<213> ORGANISM: Zea mays

<400> SEQUENCE: 180
catccaggtg aggcatcaag ctactactgc ctcgattggc tggacccgaa gcccacatgt     60
aggataccag aatgggccga cccaggacgc agtatgttgg ccagtcccac cggttagtgc    120
catctcggtt gctcacatgc gtagaagcca gcttaaaaat ttagctttgg taactcacag    180
c                                                                    181
```

```
<210> SEQ ID NO 181
<211> LENGTH: 200
<212> TYPE: DNA
<213> ORGANISM: Zea mays

<400> SEQUENCE: 181
catcaataag ataaagctgg tgcaggctct cgacctgaag cccacacact ggagagcaac     60
gatataccag aatggagcgg cccagtacac gatctgctgg gattgctggc cagtggccag    120
tcccgcagcc gattagcacc acctcggtgg cacagacgaa cgaacgctaa tttaaaagct    180
tagctctgga gcttggcacc                                                200
```

```
<210> SEQ ID NO 182
<211> LENGTH: 200
<212> TYPE: DNA
<213> ORGANISM: Zea mays

<400> SEQUENCE: 182
gcgaggcatc aacaagataa agctggtgca ggctctcgac ctgaagccca cacacaggag     60
agcaacaata taccaggaat ggagcggccc agtacgcgat ctgctgggat tgctggctag    120
tcccgcaccc gattagcacc acctcgcttg ctcatacgag cgaacgcaaa tttaaaaggt    180
tagctctgga gtttggcagc                                                200
```

```
<210> SEQ ID NO 183
<211> LENGTH: 200
<212> TYPE: DNA
<213> ORGANISM: Zea mays

<400> SEQUENCE: 183
cctaactaat aagtatcgga ggcaacaacg cccgctgggc tgcggcccat taacatagca     60
ctagacggac accgccgcag tcagcgttca gccggatgca gtgcgatcgg cttcatccgt    120
ttagtcccac ctcgcccagc caaagcagcg gggaggcccg gactcgctac aaaaggagac    180
ggaggttggc tgtttagagc                                                200
```

```
<210> SEQ ID NO 184
<211> LENGTH: 200
<212> TYPE: DNA
<213> ORGANISM: Zea mays

<400> SEQUENCE: 184
gccagctgcg gtggaaacga ctgcggaccg ggctagcatc gacgtattgc cgtattagta     60
```

```
gcccagaaag cccacgcaac cagatagagg tctgaatgcc tgtactttgt ggtgcttcag      120
tttagtccca cctcggtggc tttcagcggg agagagcaga gaaggcttat aaaagcagac      180
ctcagtcaac ataacaattc                                                  200

<210> SEQ ID NO 185
<211> LENGTH: 200
<212> TYPE: DNA
<213> ORGANISM: Zea mays

<400> SEQUENCE: 185
tcaataaaca attggagcga gagagactct gctgaccggg ccatcattga cgtattggta       60
gcccagaaag cccacacagt catacagagg tctgaatgtc tgtgctttat ggtgcttgag      120
tttagtccca cctcggtggc tttcagcggg agagagcaga gaaggcttat aaaagcagac      180
ctcagtcaac ataacaattc                                                  200

<210> SEQ ID NO 186
<211> LENGTH: 200
<212> TYPE: DNA
<213> ORGANISM: Zea mays

<400> SEQUENCE: 186
gaccccatct atgccgtaat tctggcttca cccctgatca agctatcgta ccttaaatgc       60
gtcgtttcac gttttttcacc ttgttggagg tctgaatgtc tgtgctttgt ggtgcttcaa     120
tttagtccca ccttgtcggc tttcaacggg agggagcgga gaaggcttat aaaagcagac      180
cctagtcaac ataacaattc                                                  200

<210> SEQ ID NO 187
<211> LENGTH: 200
<212> TYPE: DNA
<213> ORGANISM: Zea mays

<400> SEQUENCE: 187
ggtggaaacg gactcgagcg agagagactc tgcggaccgg gccagcatcg atgtattggt       60
agcccagaaa gcccacgcaa ccagacagag gtatgaatgt tgtgctttgt ggtgcttcag      120
tttagtccca cctcggcggt tttcagcgga agggagcaga gaaggcttat aaaagcagac      180
ctcagtcaac ataacaattc                                                  200

<210> SEQ ID NO 188
<211> LENGTH: 200
<212> TYPE: DNA
<213> ORGANISM: Zea mays

<400> SEQUENCE: 188 tcccttttgtc gccttgctgt tcgctccgtt tgttgggccg acatgtggc tttctgggcc       60 gcgcacgtag agtcctcctg gccagtgtcg ggctctggct ggctgcctgc tcttttttct      120
gtagtcccaa accgcttgct gaggctaata tcagccggga acaacgctat ttaggattga      180
ctgaactctg tgtaagaggc                                                  200

<210> SEQ ID NO 189
<211> LENGTH: 200
<212> TYPE: DNA
<213> ORGANISM: Zea mays

<400> SEQUENCE: 189
```

```
cctttgtggc ttcgcttcat tctcttcatc cgtttgtgac cggagtcagc ggctgtcgac      60
cgcggcgcat cctctgacta gcactgcgtc tggctggctc tggctgcttc agcttgcttt     120
agttcccaaa cccgcttgct gtagctaata ccagcaggga gcgctgctat ttaggatgga     180
ctgggcgctg cgagagaagc                                                 200

<210> SEQ ID NO 190
<211> LENGTH: 200
<212> TYPE: DNA
<213> ORGANISM: Zea mays

<400> SEQUENCE: 190
ggccttcgct tcctcgctct tcgctccttt gttgggccgg acaacaagcg gctgtctggg      60
ccgcgcacgc agtcctctgg tccagtgggc aactgcctct ggctgcttgc tcttttcctt    120
aatcccaaac cgctcgatga agctaatacc agctgggggg cgctgctatt taggagagac    180
taagcgccac ccgtagatgc                                                 200

<210> SEQ ID NO 191
<211> LENGTH: 200
<212> TYPE: DNA
<213> ORGANISM: Zea mays

<400> SEQUENCE: 191
ttcgcttcat ttctcttcac tccgtttgtt gggccggaca tcaagcggct gtctgggccg      60
cgcacgcagt cctcttgact agcactgcgt ctggctggct ctggctgctt cagctttgct    120
ttagttccaa accgcttgct gtagctaata ccagcaggga gcgctgctat ttaggatgga    180
ctgggcgctg cgagagaagc                                                 200

<210> SEQ ID NO 192
<211> LENGTH: 200
<212> TYPE: DNA
<213> ORGANISM: Zea mays

<400> SEQUENCE: 192
tcaataaaca attggagcaa gagagactct gctgaccggg ccatcatcga cgtattggta      60
gcccagaaag cccacgcagt catacagagg tctgaatgtc tgtgctttgt ggtgcttgag    120
tttagtccca cctcgacggc tttcagcggg agagagcaga aaggcttat aaaagcagac    180 ctcagtcaac ataacaattc                                                 200

<210> SEQ ID NO 193
<211> LENGTH: 200
<212> TYPE: DNA
<213> ORGANISM: Zea mays

<400> SEQUENCE: 193
gactcgagaa cttagagcta gagagactct gcggaccggg ccagcatcga cgtattggta      60
gcccagaaag cccacgcaac cagacagagg tctgaatgca tgtgctttgt ggtgcttcag    120
tttagtccca cctcggcggc tttcagcggg agagagcaga aaggcttat aaaagcagac    180 ctcagttaac ataacaattc                                                 200

<210> SEQ ID NO 194
<211> LENGTH: 200
<212> TYPE: DNA
<213> ORGANISM: Zea mays

<400> SEQUENCE: 194
```

```
ggcccttct atgtcgtaaa tctaggtcca cccccaatca agcaatccta ccttaaatac    60
atcgtttcac gttttttgagc ttgttggagg tgtgaaagtt tgtgctttgt ggtgcttcag   120
tttagtccca cctcggtggc tttcagtgag agggagcgaa aaggcttat aaaagcacac   180 cccaatcaac ataacaattc                                              200

<210> SEQ ID NO 195
<211> LENGTH: 200
<212> TYPE: DNA
<213> ORGANISM: Zea mays

<400> SEQUENCE: 195
tcaatataca attggagcga gagagactct gctgaccggg ccagcatcga cgtattggta    60
gcccagaaag cccacgcagt catacagagg tctgaatgta tgtgctttgt ggtgcttgag   120
tttagtccca cctcggaggc tttcagcggg agagagcaaa gaaggcttat aaaagcagac   180
ctcagtcagc ataacaattc                                              200

<210> SEQ ID NO 196
<211> LENGTH: 200
<212> TYPE: DNA
<213> ORGANISM: Zea mays

<400> SEQUENCE: 196
gccagctgcg gtggaaacga ctgcggaccg agccagcatc gacgtattgc cgtattggta    60
gcccagaaag cccacgcaac cggacagagg tctgaatgcc tgtactttgt ggtgcttcag   120
tttagtccca cctcggtggc tttcagcggg agagagcaga gaaggcttat aaaagcagac   180
ctcagtcaat ataacaattc                                              200

<210> SEQ ID NO 197
<211> LENGTH: 200
<212> TYPE: DNA
<213> ORGANISM: Zea mays

<400> SEQUENCE: 197
gagtccagaa cttggagcga gagagactct gctgaccggg ccagcatgga cgtattggta    60
gcccagaaag cccacgcaac cagatagagg tcttaatgcc ctttctttgt ggtgctttag   120
tttagtccca cctcgacggc tttcagcggg agggagcaga gaaggcttat aaaagaagat   180
ctcaatcaaa ttaacaattc                                              200

<210> SEQ ID NO 198
<211> LENGTH: 200
<212> TYPE: DNA
<213> ORGANISM: Zea mays

<400> SEQUENCE: 198
gactcgagaa cttggagcga gagagactct gctgaccggg ccagcatgga cgtattggta    60
gcccagaaag cccacgctac cagacagagg tctgaatgac tgttctttgt ggtgcttcag   120
tttagtccca cctcgacggc tttcagcggg aggaagcaga gaaggcttat aaaagcagat   180
cctagtcaac ataacaattc                                              200

<210> SEQ ID NO 199
<211> LENGTH: 192
<212> TYPE: DNA
<213> ORGANISM: Zea mays
```

<400> SEQUENCE: 199

```
aacggactcg agcgagagag actctgcgga ccgggccagc atcgatgtat ttggtagccc    60
agagcccacg caaccagaca gaggtatgaa tgttgtgctt tgtggtgctt cagtttagtc   120
ccacctcggc ggttttcagc ggaagggagc agagaaggct tataaaagca gacctcagtc   180
aacataacaa tt                                                      192
```

<210> SEQ ID NO 200
<211> LENGTH: 199
<212> TYPE: DNA
<213> ORGANISM: Zea mays

<400> SEQUENCE: 200

```
ggcgtatgtg ccaaaaactt cgtcacagag agggccataa gaaacatggc ccacggccca    60
atacgaagca ccgcgacgaa gcccaaacag cagtccgtag gtggagcaaa gcgctgggta   120
atacgcaaac gttttgtccc accttgacta atcacaagag tggagcgtac cttataaacc   180
gagccgcaag caccgaatt                                               199
```

<210> SEQ ID NO 201
<211> LENGTH: 418
<212> TYPE: DNA
<213> ORGANISM: Zea mays

<400> SEQUENCE: 201

```
aggaaaagaa gaggtgatta ctgtacctat tcgtctttgt atcggaatat aaatttatca    60
ctattttatg ataaagtaaa tctgtttccc tgtagagtta attaattaat gtaagtataa   120
gcgtaattta tagggcacta gtaggactgt cgactgtgcg ctcggcccgg ataatgcgtc   180
aaaagcgaag acgtgcacgt gggatgggaa acacgaagc gtggtctgct ttttcgcatg    240
atatctgggc cgcaccaaag aatccagccc acgcggcgtg gcgccgtcgt tacggcttgc   300
gggggaagga aacgagggac gaaccgagat ttagcaccag accggccagc gagcattgca   360
gacaccggct tataagttca gctgcgacta ccactccggg aggtccgagt tccactcg     418
```

<210> SEQ ID NO 202
<211> LENGTH: 625
<212> TYPE: DNA
<213> ORGANISM: Artificial Sequence
<220> FEATURE:
<223> OTHER INFORMATION: Recombinant

<400> SEQUENCE: 202

```
ttctatttgt gctacatata ttagacaagg aaaataacat atgttatttt gaaatcacgt    60
atatttacta taaattacaa tgattaacaa cttaaaatat ttaaatgaaa atcatattaa   120
tgactctcta aattttatct gtgtcacata aatgaaaaac aaaaaataac aaatattgta   180
ttcgcacggg cgcatgtgtc tagttagtta taaacgaaga ataagggggc tgatttcgaa   240
ataaacgttc ttagaattgg aagaaatgtt cagtttctaa acttgtagga ctaaagcaat   300
aacttttatt taatttatt tctttttatgt ttctcccaca tcgatcatac atataactat   360
acagcagtat aagaactcta gcgaagcaat aatgctccaa gctgactcta gcagatctcc   420
atgacggcag agaaggtact ggaaaaagaa cttctggcct ggcaggagaa actgcatcag   480
ccgattatca tcaccgaata cggcgtggat acgttagccg ggctgcactc aatgtacacc   540
gacatgtgga gtgaagagta tcagtgtgca tggctggata tgtatcaccg cgtctttgat   600
cgcgtcagcg ccgtcgtctt ttttt                                        625
```

<210> SEQ ID NO 203
<211> LENGTH: 474
<212> TYPE: DNA
<213> ORGANISM: Artificial Sequence
<220> FEATURE:
<223> OTHER INFORMATION: Recombinant

<400> SEQUENCE: 203

```
ggaaacttct gtttgtcccc atactccaaa acaaaacca tttttttttt atcttcgttt      60
ttgtttgctt tgactgtgag ttgaggccca actttctgct tctgtccgac tctatttgat    120
gaattttgtt tgcctcctgt gatgtgaagg atgtatcatt gaaagggaac gtgtctcaat    180
gatcccacat cggccaaata tgctcattac attgcgttta tatagtccca ggaaaacata    240
tggattcaag ctgactctag cagatctcca tgacggcaga aaggtactg gaaaagaac      300
ttctggcctg gcaggagaaa ctgcatcagc cgattatcat caccgaatac ggcgtggata    360
cgttagccgg gctgcactca atgtacaccg acatgtggag tgaagagtat cagtgtgcat    420
ggctggatat gtatcaccgc gtctttgatc gcgtcagcgc cgtcgtcttt tttt           474
```

<210> SEQ ID NO 204
<211> LENGTH: 721
<212> TYPE: DNA
<213> ORGANISM: Artificial Sequence
<220> FEATURE:
<223> OTHER INFORMATION: Recombinant

<400> SEQUENCE: 204

```
tctacaaaac attataaaaa gtaagatata acaacttttt ttttaaaaaa atcaatagga     60
aatattatcg gttcagttaa tttacagaga gatatttatt tcatatgtgc cagaagtatt   120
tcagttcctt atgaaaaatc agaaaaatgt atggaataaa atataataat cgatactaat   180
aatagaacaa aataaatggt aaaatgtcaa atcaaaacta ggctgcagta tgcagagcag   240
agtcatgatg atactactta ctacaccgat tcttgtgtgc agaaaaatat gttaaaataa   300
ttgaatcttt ctctagccaa atttgacaac aatgtacacc gttcatattg agagacgatg   360
cttcttgttt gctttcggtg gaagctgcat atactcaaca ttactccttc agcgagtttt   420
ccaactgagt cccacattgc ccagacctaa cacggtattc ttgtttataa tgaaatgtgc   480
caccacatgg attcaagctg actctagcag atctccatga cggcagagaa ggtactggaa   540
aaagaacttc tggcctggca ggagaaactg catcagccga ttatcatcac cgaatacggc   600
gtggatacgt tagccgggct gcactcaatg tacaccgaca tgtggagtga agagtatcag   660
tgtgcatggc tggatatgta tcaccgcgtc tttgatcgcg tcagcgccgt cgtctttttt   720
t                                                                   721
```

<210> SEQ ID NO 205
<211> LENGTH: 787
<212> TYPE: DNA
<213> ORGANISM: Artificial Sequence
<220> FEATURE:
<223> OTHER INFORMATION: Recombinant

<400> SEQUENCE: 205

```
aggtggagtt gttccagatt tagttttcga cttagatgat gcatggaact ggctagtgac     60
gtggatggtg gtaggttact ttcaggtcat gattttttgt ttctaaatga tactcacact   120
cccttccagt ttttttttttt taaactcagc tcccttgctt cctccaccgg ttatcataat   180
```

| | |
|---|---|
| actgaaccaa atcaaacatt acagtcaagg tactatgaat atgaaacctg aaatcctatg | 240 |
| aatgtcataa atttatttta aataataaat ttatttagaa taatattttt ttgggtaaga | 300 |
| gttataaaat aaaatacaaa aaaaaaacct aatatcaatt tttcactgac tccgtttata | 360 |
| ttgagacttg agaaagatgg ttcccgtttg ctcccggtgg aggctccgag gctgtgtata | 420 |
| tactcgacat tactttagct tgttttgttg tttctttccc tttcccacaa gactcaggtc | 480 |
| tcgttcgcaa acgagtccca caccgtctaa acttaccaca atattagcgt ttataattag | 540 |
| atgcactgca tcacttattc aagctgactc tagcagatct ccatgacggc agagaaggta | 600 |
| ctggaaaaag aacttctggc ctggcaggag aaactgcatc agccgattat catcaccgaa | 660 |
| tacggcgtgg atacgttagc cgggctgcac tcaatgtaca ccgacatgtg gagtgaagag | 720 |
| tatcagtgtg catggctgga tatgtatcac cgcgtctttg atcgcgtcag cgccgtcgtc | 780 |
| ttttttt | 787 |

<210> SEQ ID NO 206
<211> LENGTH: 824
<212> TYPE: DNA
<213> ORGANISM: Artificial Sequence
<220> FEATURE:
<223> OTHER INFORMATION: Recombinant

<400> SEQUENCE: 206

| | |
|---|---|
| aaattacacg gtagtacatc ctattataga tcgatgaatt cttaactact cgtgtccctt | 60 |
| aggccaggcc tgttttcttg cacaatttct gaaatgtata cggtttccac ttcaaccttt | 120 |
| ttaaccgcac aaagttttaa ccagatttat ataatttatt tttgaatccc caatacatat | 180 |
| cattataaca tatcaattat caaatatttc ataacctca tgatatggca atgaatacat | 240 |
| cttcttctca atgaacagag atttctgaaa aagattagga aagtgaaagc atactcgttt | 300 |
| gcaatgtaaa actgatactt ccccaaaatc atcatattcc aaatatgccc tggtgttact | 360 |
| gaccaaaacc agaaaaaaga aacggaagac atatacgtct aaacggagaa atttcaaaaa | 420 |
| acaaaaattg gatcatttct cgatttgtgg gtgtcatctt gtgcagggca tgctaatctt | 480 |
| ctctttaccc tttcccacaa gactcagcgc atgttgtctc gtctcatcca agtcccacac | 540 |
| cgcctaaact taacacaata ttagtattta taatgacata caacattcaa gatgttcaag | 600 |
| ctgactctag cagatctcca tgacggcaga gaaggtactg gaaaagaac ttctggcctg | 660 |
| gcaggagaaa ctgcatcagc cgattatcat caccgaatac ggcgtggata cgttagccgg | 720 |
| gctgcactca atgtacaccg acatgtggag tgaagagtat cagtgtgcat ggctggatat | 780 |
| gtatcaccgc gtctttgatc gcgtcagcgc cgtcgtcttt tttt | 824 |

<210> SEQ ID NO 207
<211> LENGTH: 965
<212> TYPE: DNA
<213> ORGANISM: Artificial Sequence
<220> FEATURE:
<223> OTHER INFORMATION: Recombinant

<400> SEQUENCE: 207

| | |
|---|---|
| aattatttaa tcctaaaaat caatcttaca aggaaccact ataaaactag ttgaacccat | 60 |
| cgaaaactaa ctacagttga caaatctat ttggttggtt gattttttt aattaaaaac | 120 |
| atccaatctt aatgatataa ttatagctta atattataag atttttataa aaattatatt | 180 |
| tattttgttt ctaattatgc taagagatat tattatttgt tatttaactt aaatattatc | 240 |
| acaaacttga ttgaaactta tgtttaattt aaaatattat atgtcatgag ttatgactcc | 300 |

```
aataatcaca attataaagt gaagtttaat ttttagtatt acaaatattt ttttgttgtt      360 taatttaat  tacttaatgt attatgttaa taattaaaaa tacaaattat ttattattaa      420
tgcaatcaca gtttgtggat ttgacaaaag aatagggga  tctaaaattg tagataagcc      480
aaagttaaaa cttgaattga ctattttttg ctctttactc tgcaccaact ttactattcc      540
ttcttttagt gtgagcttca tgcatcttgt tcaccgcaat tccgctcggt gaaagttgca      600
caattcactc acaatctgtt tctggtctgt taggtttgtt acttggagtg acacgatgac      660
gcaacagtac aagtcccaca tcgtttgagt atacagtttt caagcagttt atattcccat      720
agccttagca agagcttcaa gctgactcta gcagatctcc atgacggcag agaaggtact      780 ggaaaagaa  cttctggcct ggcaggagaa actgcatcag ccgattatca tcaccgaata      840
cggcgtggat acgttagccg ggctgcactc aatgtacacc gacatgtgga gtgaagagta      900
tcagtgtgca tggctggata tgtatcaccg cgtctttgat cgcgtcagcg ccgtcgtctt      960
ttttt                                                                  965

<210> SEQ ID NO 208
<211> LENGTH: 712
<212> TYPE: DNA
<213> ORGANISM: Artificial Sequence
<220> FEATURE:
<223> OTHER INFORMATION: Recombinant

<400> SEQUENCE: 208 tttttaata  aaaaaaattc aatgggagat actatggatt caattacctt actgattta        60 tttcatatgt gccagaagta tttcagttta ttttgaaaaa tcagaaaaaa aatgtctgga      120 ataaatata  ataagcgata ctaataaata attgaacaag ataaatggta aaatgtcaaa      180
tcaaaactag gctacagagt gcagagcaga gtcatgatga atgacagcta gttctactta      240
ctacaccgat tcttgtgtac ataaaaatat tttaaaataa ttgaatcttt ctttagccag      300 cttttgacaac aatgtacacc gttcgtactt cttactggta ggcaatgctt cttgtttgct     360
ttcggtggaa ggtgtatata ctcaacatta cttcttttc  agcgtgtttt cttacgggag      420
tcccacaccg cccaaaacta atacagtatt cttgtttata aagaagtgca ccacttcaat      480
tgttcaagct gactctagca gatctccatg acggcagaga aggtactgga aaagaactt       540 ctggcctggc aggagaaact gcatcagccg attatcatca ccgaatacgg cgtggatacg      600
ttagccgggc tgcactcaat gtacaccgac atgtggagtg aagagtatca gtgtgcatgg      660
ctggatatgt atcaccgcgt ctttgatcgc gtcagcgccg tcgtcttttt tt              712

<210> SEQ ID NO 209
<211> LENGTH: 655
<212> TYPE: DNA
<213> ORGANISM: Artificial Sequence
<220> FEATURE:
<223> OTHER INFORMATION: Recombinant

<400> SEQUENCE: 209
cgataaaaat gttttaaacg atatatatta taaaaaaaaa cgtttcaaaa ataaatacaa       60
aaatgttttt aaatatatat aatttaactc attaagaaa  ataaaaatgc aagtgcggtg      120
acaagacaag ctaaaagttg caaagaaat  ggcagggcta taaggctcac ctactcctgg      180
atttaccaaa ttttggttcg tccctatact cgaaaaataa aacaaaataa atttcagtat      240
cttcgttttt gtatgctttg actgtgaggc gaggccaact ttcttcttct gtctgagatg      300
```

```
aattttgttt gcctcctgtg aaggatgtat cattcaaagt gaatgttttg caactgccag    360
tagtcccaca tcgaccaaat attcttatta cagtgtgttt atatagcacc tggagaagga    420
atgggttcaa gctgactcta gcagatctcc atgacggcag agaaggtact ggaaaaagaa    480
cttctggcct ggcaggagaa actgcatcag ccgattatca tcaccgaata cggcgtggat    540
acgttagccg ggctgcactc aatgtacacc gacatgtgga gtgaagagta tcagtgtgca    600
tggctggata tgtatcaccg cgtctttgat cgcgtcagcg ccgtcgtctt ttttt         655
```

```
<210> SEQ ID NO 210
<211> LENGTH: 628
<212> TYPE: DNA
<213> ORGANISM: Artificial Sequence
<220> FEATURE:
<223> OTHER INFORMATION: Recombinant

<400> SEQUENCE: 210
gaaaagcatt cagaatattt gagcctctaa aaactttcct tcttttctt tgaggagtgt     60 aatgtggatc ccaagtaacc aagaaaagca atccgaaaat tcaatttcaa gcaaactgtt   120
ctcaagtttt cgagggatat agtaatagca gagcaaaaaa acactggaaa aagcttgtac   180
ctattgaaac aaaggataat taaaaatcca aatgtatca aaagcctaga caattttaat    240
cactattgcc tcttaacaat ttgcgcacta tgacaatcat gctctcataa tgtaacaaaa   300
gacacattag gatactagta ctgacactga caccaaggtt acatagtccc acatcgaagg   360
agtttaggta gagacatcgg tttatataac taagcgtgac caagctgact ctagcagatc   420
tccatgacgg cagagaaggt actggaaaaa gaacttctgg cctggcagga gaaactgcat   480
cagccgatta tcatcaccga atacggcgtg gatacgttag ccgggctgca ctcaatgtac   540
accgacatgt ggagtgaaga gtatcagtgt gcatggctgg atatgtatca ccgcgtcttt   600
gatcgcgtca gcgccgtcgt cttttttt                                     628
```

```
<210> SEQ ID NO 211
<211> LENGTH: 662
<212> TYPE: DNA
<213> ORGANISM: Artificial Sequence
<220> FEATURE:
<223> OTHER INFORMATION: Recombinant

<400> SEQUENCE: 211
ttgccaacaa gatataacaa gaagcctaat atttcaaaag gccttttggt ccttaaaaac     60
taaggaatgc atctccagaa agaagtacaa tcataatagt tgctaagaat gcagcaaaat   120
tgataaatta atcgagaaac cacaccacaa atcacacatg gccattagag aaaaagaaag   180
gtttcaggaa aataaaagaa aagaaaaagt caattactgc ttagctacct ctctatattc   240
ccatgtgccc cttgcttgaa attggaacca ctaccaggca acagagttgt tcccttcaa   300 gcaataagag ttagaaatat ttttatatca accgaagtgg caaaaagtca gaaaccatga   360
catacgttta ctttgttagt cccacattgg atagttttag taaaacacag gtcattatat   420
agctaaacgc taaccaagct gactctagca gatctccatg acggcagaga aggtactgga   480
aaagaacttc tggcctggc aggagaaact gcatcagccg attatcatca ccgaatacgg   540
cgtggatacg ttagccgggc tgcactcaat gtacaccgac atgtggagtg aagagtatca   600
gtgtgcatgg ctggatatgt atcaccgcgt ctttgatcgc gtcagcgccg tcgtcttttt   660
tt                                                                 662
```

<210> SEQ ID NO 212
<211> LENGTH: 664
<212> TYPE: DNA
<213> ORGANISM: Artificial Sequence
<220> FEATURE:
<223> OTHER INFORMATION: Recombinant

<400> SEQUENCE: 212

| | | |
|---|---|---|
| aatatttcaa agcacactta ggtccttaaa aatgcaatgt tacaattcca aaaggaagta | 60 |
| taatcatagt agaagccaag aatgcagaaa aattaacaaa gtgatcgagg aatcattgcc | 120 |
| acaaatcact catggctatt agagaaaaaa aaaagtttca agaaaagaaa agaaaaagtt | 180 |
| aattactact tagctacttc tttgtaaact caggtgcccc ttgcatgcaa ttgataccac | 240 |
| accaggcacc agagctgttc cttttcatgc aataagagta agagacattt ttttatgaac | 300 |
| tcagatggcg aagtgtttga aaccatgaca ggcgttactc tggtagtccg acatagagag | 360 |
| ttttaataaa acacaaatgt agtcccacat tgaacagttt taataaaaca cagtctttat | 420 |
| ataactaaac gctgagcaag ctgactctag cagatctcca tgacggcaga gaaggtactg | 480 |
| gaaaagaac ttctggcctg caggagaaa ctgcatcagc cgattatcat caccgaatac | 540 |
| ggcgtggata cgttagccgg gctgcactca atgtacaccg acatgtggag tgaagagtat | 600 |
| cagtgtgcat ggctggatat gtatcaccgc gtctttgatc gcgtcagcgc cgtcgtcttt | 660 |
| tttt | 664 |

<210> SEQ ID NO 213
<211> LENGTH: 656
<212> TYPE: DNA
<213> ORGANISM: Artificial Sequence
<220> FEATURE:
<223> OTHER INFORMATION: Recombinant

<400> SEQUENCE: 213

| | | |
|---|---|---|
| cttaggtggc tcttgcttga aatgggtact gtactggaat tagagtttat cttttcatgc | 60 |
| acaaagtttt ggccctcgtt ctactacagt atacagcagt atggatatgg ttcacattaa | 120 |
| ttctccgaaa gtaatctatc cctgcgggct agcctgagaa agggtgttta taatcttgta | 180 |
| gtgatagaat caagcatcat aagagctttc aaagcctcta atgagtattt cttttctag | 240 |
| aaaagatgaa tatttgggat caatgctgct gctgttatgt aggaaacacc gtggcaggaa | 300 |
| gattgtattt gtatccttgt gcaatactca gaccaattct gttagaaaaa tgacacaaag | 360 |
| gccgtgatgc tagtcccaca tcgagtgttt ttaacaaaac aggcgcatat atattactgg | 420 |
| acgctgagca agctgactct agcagatctc catgacggca gagaaggtac tggaaaaaga | 480 |
| acttctggcc tggcaggaga aactgcatca gccgattatc atcaccgaat acggcgtgga | 540 |
| tacgttagcc gggctgcact caatgtacac cgacatgtgg agtgaagagt atcagtgtgc | 600 |
| atggctggat atgtatcacc gcgtctttga tcgcgtcagc gccgtcgtct tttttt | 656 |

<210> SEQ ID NO 214
<211> LENGTH: 660
<212> TYPE: DNA
<213> ORGANISM: Artificial Sequence
<220> FEATURE:
<223> OTHER INFORMATION: Recombinant

<400> SEQUENCE: 214

| | | |
|---|---|---|
| catgctgtgt agtgaaagac atagacagtc aaaaggcctg agaagggtat atattgtaaa | 60 |
| gatgatgatt tttcttacag atggtttata ccgctttatg cttcttcagc gtagaactta | 120 |

| | |
|---|---:|
| tcaaagagaa cactatccat agctgaatca agttggttca ggcttttgtt ataatcacag | 180 |
| tctaggagtc taggacactt ttattttgca ttcattttcg gattgttgac gcctttgtat | 240 |
| aaattttaca atctctcagt aaaagatcga acacttctga taatgtttta ggaatttaac | 300 |
| tctcattcta taagctttga ccaagtctga accctagaca attgcctctt taacaacttg | 360 |
| acacagaaat aataatagtc ccacatcgag agcgtttagc tacaaacatg tgtttatata | 420 |
| attaagcata accaagctga ctctagcaga tctccatgac ggcagagaag gtactggaaa | 480 |
| aagaacttct ggcctggcag gagaaactgc atcagccgat tatcatcacc gaatacggcg | 540 |
| tggatacgtt agccgggctg cactcaatgt acaccgacat gtggagtgaa gagtatcagt | 600 |
| gtgcatggct ggatatgtat caccgcgtct ttgatcgcgt cagcgccgtc gtcttttttt | 660 |

<210> SEQ ID NO 215
<211> LENGTH: 662
<212> TYPE: DNA
<213> ORGANISM: Artificial Sequence
<220> FEATURE:
<223> OTHER INFORMATION: Recombinant

<400> SEQUENCE: 215

| | |
|---|---:|
| gtttatgttt ggcattcttt aatctttagt atcagaataa ttgatcacat tttgaaatgc | 60 |
| caatagaaag acactcctta aacaaaagct atcgtgtatg aaaagctgca gagaaaaatc | 120 |
| aaatgtacaa gattttaaat aaagacatgc taaactgtcc aatatgtaac tagttgaaca | 180 |
| ggctgcattt ctctgtgttt ttgcttccgc agggaggaat acaaacatct aacaacttat | 240 |
| accaaagcat atagtacaaa ttacaatctt ttgttttccc caaattaatc caatttatct | 300 |
| ttcatttcat ccagaaagaa gctctttgag attgttagtg ttaaactgca aactttcttc | 360 |
| ttacttatgt cccacatagg aaagaaaagg agacaacaaa atctttatat gccctctgac | 420 |
| aaagttgtct gaatcaagct gactctagca gatctccatg acggcagaga aggtactgga | 480 |
| aaaagaactt ctggcctggc aggagaaact gcatcagccg attatcatca ccgaatacgg | 540 |
| cgtggatacg ttagccgggc tgcactcaat gtacaccgac atgtggagtg aagagtatca | 600 |
| gtgtgcatgg ctggatatgt atcaccgcgt ctttgatcgc gtcagcgccg tcgtcttttt | 660 |
| tt | 662 |

<210> SEQ ID NO 216
<211> LENGTH: 645
<212> TYPE: DNA
<213> ORGANISM: Artificial Sequence
<220> FEATURE:
<223> OTHER INFORMATION: Recombinant

<400> SEQUENCE: 216

| | |
|---|---:|
| catttaaaat aatgaatgac taatccatta actaataact atagttgatt acttttagt | 60 |
| taattaggat gttaggaata cctgaatcca ccgacttaac tattatcata atcagttcat | 120 |
| tcaatttgaa tttgtaggat gcacctctat gttttcctct tcactttcta gtggacacaa | 180 |
| gaccctgtgt cacacacagt taatagagaa agatcattta catgtaagcg gaacccattg | 240 |
| cattctacag caatattttg gggttggtgt tataatacaa gacggataaa atagctagag | 300 |
| agaatccaat caaatcccac attccaaatt agactatcca ttgtaggcca gtcccacat | 360 |
| tggttagaat attaggcaac gaaaccttta taaatcttct gacaagcact tcagcatcaa | 420 |
| gctgactcta gcagatctcc atgacggcag agaaggtact ggaaaaagaa cttctggcct | 480 |
| ggcaggagaa actgcatcag ccgattatca tcaccgaata cggcgtggat acgttagccg | 540 |

```
ggctgcactc aatgtacacc gacatgtgga gtgaagagta tcagtgtgca tggctggata    600
tgtatcaccg cgtctttgat cgcgtcagcg ccgtcgtctt ttttt                    645
```

<210> SEQ ID NO 217
<211> LENGTH: 667
<212> TYPE: DNA
<213> ORGANISM: Artificial Sequence
<220> FEATURE:
<223> OTHER INFORMATION: Recombinant

<400> SEQUENCE: 217

```
ggcatgtgac tttttattta aattattctc agaaatatta aaatataatc aaatatattt     60
ttttataaga tactggaaat aacattttta ggaatgtaac gaaagcccca ttacaaacac    120
ttgaactcag ggatcgatcc aacttaatta ttatctgcta cttcaaattc aaatttatag    180
gccctacctt tatgttttgc tctgcacttt cttaaatgga aacaagtaac acaatagagt    240
aagatcattt acttgtaagc ggaaactgtt gcatcaactg caatattttc gggttagttt    300
tataatataa caatgaagag aattgccgag aagatcatat caagtcccat attccattta    360 ttggcccttta caagtcccac atcggtccaa atattagaca agaaacatt tatatatcgt     420 ctgacaaacc tgtaagattc aagctgactc tagcagatct ccatgacggc agagaaggta    480
ctggaaaaag aacttctggc ctggcaggag aaactgcatc agccgattat catcaccgaa    540
tacggcgtgg atacgttagc cgggctgcac tcaatgtaca ccgacatgtg gagtgaagag    600
tatcagtgtg catggctgga tatgtatcac cgcgtctttg atcgcgtcag cgccgtcgtc    660
tttttt                                                                667
```

<210> SEQ ID NO 218
<211> LENGTH: 398
<212> TYPE: DNA
<213> ORGANISM: Artificial Sequence
<220> FEATURE:
<223> OTHER INFORMATION: Recombinant

<400> SEQUENCE: 218

```
ggattgtgcg ggcaaagtat tttcgtcgaa agagaagcaa cgaaaaagcc cactgctccg     60
agacaccgtt ccacgaaacc tgtccgcact catctcatcg tttagcacca cctcgccagt    120
ccgcagtcct ctatacctgc ttaaatattc gtccagaccg cccaccctcc aagctgactc    180
tagcagatct ccatgacggc agagaaggta ctggaaaaag aacttctggc ctggcaggag    240
aaactgcatc agccgattat catcaccgaa tacggcgtgg atacgttagc cgggctgcac    300
tcaatgtaca ccgacatgtg gagtgaagag tatcagtgtg catggctgga tatgtatcac    360
cgcgtctttg atcgcgtcag cgccgtcgtc tttttttt                             398
```

<210> SEQ ID NO 219
<211> LENGTH: 429
<212> TYPE: DNA
<213> ORGANISM: Artificial Sequence
<220> FEATURE:
<223> OTHER INFORMATION: Recombinant

<400> SEQUENCE: 219

```
ctgttttcat ccggcctgtg atggaaattg tgctgcaaag tgcgcagggc cgttggcccg     60
acgacaagta ttttcgtcg agagaagcaa cgaaagccca ctcctccaag ccacccttcg    120
ctcaagtcat atttagcacc acctcggcag tcgacactgc agcacaccaa cttaaatatt    180
```

```
catcccgatc tccctcactc caagctgact ctagcagatc tccatgacgg cagagaaggt    240
actggaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cttttttttt                                                          429

<210> SEQ ID NO 220
<211> LENGTH: 429
<212> TYPE: DNA
<213> ORGANISM: Artificial Sequence
<220> FEATURE:
<223> OTHER INFORMATION: Recombinant

<400> SEQUENCE: 220
aaactgtgct tgtgcagggc cgttgggcca cgtgcccacg tcaaagtatt ctagtcgaaa     60
gagaagcaac gaaagcccac tactactcct aggcaccgtt gccacgagac ctgtccgcac    120
tcatctcatc gtttagcacc aatgcgccag tccgcagtcc gctgtaccag cttaaatatt    180
cgtccctacc gcgctccatc caagctgact ctagcagatc tccatgacgg cagagaaggt    240
actggaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cttttttttt                                                          429

<210> SEQ ID NO 221
<211> LENGTH: 429
<212> TYPE: DNA
<213> ORGANISM: Artificial Sequence
<220> FEATURE:
<223> OTHER INFORMATION: Recombinant

<400> SEQUENCE: 221
catataggga tcagctaagc ttatcatacc ttccttttttt tttctcattc agccactact    60
gcagcctaca aaggatatca taatgggccg acccagtcac ccaggacgca atatgttggt    120
caatcccacc agttagtacc acctcggtag ctcagatgag tagaagatac cttaaaagtt    180
cagctcaggc aacttgcagc caagctgact ctagcagatc tccatgacgg cagagaaggt    240
actggaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cttttttttt                                                          429

<210> SEQ ID NO 222
<211> LENGTH: 429
<212> TYPE: DNA
<213> ORGANISM: Artificial Sequence
<220> FEATURE:
<223> OTHER INFORMATION: Recombinant

<400> SEQUENCE: 222
catggtccat aggtatcaag atccagcatt gcacttgggc caaagattga gctctgcgaa     60
gtgtcaacta caatcatcta gatgggctcg acctgaaagg ccacacgatt tgccagaact    120
cccaccaatt aattagtacc acctcggttg ctcgatttag tagaagccag cttaaaagtt    180
cagctctggg gtccggtagc caagctgact ctagcagatc tccatgacgg cagagaaggt    240
```

```
actggaaaaa gaacttctgg cctggcagga gaaactgcat cagccgatta tcatcaccga      300
atacggcgtg gatacgttag ccgggctgca ctcaatgtac accgacatgt ggagtgaaga      360
gtatcagtgt gcatggctgg atatgtatca ccgcgtcttt gatcgcgtca gcgccgtcgt      420
ctttttttt                                                              429
```

<210> SEQ ID NO 223
<211> LENGTH: 410
<212> TYPE: DNA
<213> ORGANISM: Artificial Sequence
<220> FEATURE:
<223> OTHER INFORMATION: Recombinant

<400> SEQUENCE: 223

```
catccaggtg aggcatcaag ctactactgc ctcgattggc tggacccgaa gcccacatgt       60
aggataccag aatgggccga cccaggacgc agtatgttgg ccagtcccac cggttagtgc      120
catctcggtt gctcacatgc gtagaagcca gcttaaaaat ttagctttgg taactcacag      180
ccaagctgac tctagcagat ctccatgacg gcagagaagg tactggaaaa agaacttctg      240
gcctggcagg agaaactgca tcagccgatt atcatcaccg aatacggcgt ggatacgtta      300
gccgggctgc actcaatgta caccgacatg tggagtgaag agtatcagtg tgcatggctg      360
gatatgtatc accgcgtctt tgatcgcgtc agcgccgtcg tctttttttt                410
```

<210> SEQ ID NO 224
<211> LENGTH: 429
<212> TYPE: DNA
<213> ORGANISM: Artificial Sequence
<220> FEATURE:
<223> OTHER INFORMATION: Recombinant

<400> SEQUENCE: 224

```
catcaataag ataaagctgg tgcaggctct cgacctgaag cccacacact ggagagcaac       60
gatataccag aatggagcgg cccagtacac gatctgctgg gattgctggc cagtggccag      120
tcccgcagcc gattagcacc acctcggtgg cacagacgaa cgaacgctaa tttaaaagct      180
tagctctgga gcttggcacc caagctgact ctagcagatc tccatgacgg cagagaaggt      240
actggaaaaa gaacttctgg cctggcagga gaaactgcat cagccgatta tcatcaccga      300
atacggcgtg gatacgttag ccgggctgca ctcaatgtac accgacatgt ggagtgaaga      360
gtatcagtgt gcatggctgg atatgtatca ccgcgtcttt gatcgcgtca gcgccgtcgt      420
ctttttttt                                                              429
```

<210> SEQ ID NO 225
<211> LENGTH: 429
<212> TYPE: DNA
<213> ORGANISM: Artificial Sequence
<220> FEATURE:
<223> OTHER INFORMATION: Recombinant

<400> SEQUENCE: 225

```
gcgaggcatc aacaagataa agctggtgca ggctctcgac ctgaagccca cacacaggag       60
agcaacaata taccaggaat ggagcggccc agtacgcgat ctgctgggat tgctggctag      120
tcccgcaccc gattagcacc acctcgcttg ctcatacgag cgaacgcaaa tttaaaaggt      180
tagctctgga gtttggcagc caagctgact ctagcagatc tccatgacgg cagagaaggt      240
actggaaaaa gaacttctgg cctggcagga gaaactgcat cagccgatta tcatcaccga      300
```

```
atacggcgtg gatacgttag ccgggctgca ctcaatgtac accgacatgt ggagtgaaga   360
gtatcagtgt gcatggctgg atatgtatca ccgcgtcttt gatcgcgtca gcgccgtcgt   420
cttttttttt                                                          429
```

```
<210> SEQ ID NO 226
<211> LENGTH: 442
<212> TYPE: DNA
<213> ORGANISM: Artificial Sequence
<220> FEATURE:
<223> OTHER INFORMATION: Recombinant

<400> SEQUENCE: 226
cctaactaat aagtatcgga ggcaacaacg cccgctgggc tgcggcccat taacatagca    60
ctagacggac accgccgcag tcagcgttca gccggatgca gtgcgatcgg cttcatccgt   120
ttagtcccac ctcgcccagc aaagcagcg gggaggcccg gactcgctac aaaaggagac   180
ggaggttggc tgtttagagc caagctgact ctagcagatc tccatgacgg cagagaaggt   240
actggaaaaa gaacttctgg cctggcagga gaaactgcat cagccgatta tcatcaccga   300
atacggcgtg gatacgttag ccgggctgca ctcaatgtac accgacatgt ggagtgaaga   360
gtatcagtgt gcatggctgg atatgtatca ccgcgtcttt gatcgcgtca gcgccgtcgt   420
cacaattcaa aacaagtttt at                                            442
```

```
<210> SEQ ID NO 227
<211> LENGTH: 442
<212> TYPE: DNA
<213> ORGANISM: Artificial Sequence
<220> FEATURE:
<223> OTHER INFORMATION: Recombinant

<400> SEQUENCE: 227
gccagctgcg gtggaaacga ctgcggaccg ggctagcatc gacgtattgc cgtattagta    60
gcccagaaag cccacgcaac cagatagagg tctgaatgcc tgtactttgt ggtgcttcag   120
tttagtccca cctcggtggc tttcagcggg agagagcaga aaggcttat aaaagcagac    180 ctcagtcaac ataacaattc caagctgact ctagcagatc tccatgacgg cagagaaggt   240
actggaaaaa gaacttctgg cctggcagga gaaactgcat cagccgatta tcatcaccga   300
atacggcgtg gatacgttag ccgggctgca ctcaatgtac accgacatgt ggagtgaaga   360
gtatcagtgt gcatggctgg atatgtatca ccgcgtcttt gatcgcgtca gcgccgtcgt   420
cacaattcaa aacaagtttt at                                            442
```

```
<210> SEQ ID NO 228
<211> LENGTH: 442
<212> TYPE: DNA
<213> ORGANISM: Artificial Sequence
<220> FEATURE:
<223> OTHER INFORMATION: Recombinant

<400> SEQUENCE: 228
tcaataaaca attggagcga gagagactct gctgaccggg ccatcattga cgtattggta    60
gcccagaaag cccacacagt catacagagg tctgaatgtc tgtgctttat ggtgcttgag   120
tttagtccca cctcggtggc tttcagcggg agagagcaga aaggcttat aaaagcagac    180 ctcagtcaac ataacaattc caagctgact ctagcagatc tccatgacgg cagagaaggt   240
actggaaaaa gaacttctgg cctggcagga gaaactgcat cagccgatta tcatcaccga   300
atacggcgtg gatacgttag ccgggctgca ctcaatgtac accgacatgt ggagtgaaga   360
```

```
gtatcagtgt gcatggctgg atatgtatca ccgcgtcttt gatcgcgtca gcgccgtcgt    420
cacaattcaa aacaagtttt at                                            442
```

<210> SEQ ID NO 229
<211> LENGTH: 442
<212> TYPE: DNA
<213> ORGANISM: Artificial Sequence
<220> FEATURE:
<223> OTHER INFORMATION: Recombinant

<400> SEQUENCE: 229

```
gaccccatct atgccgtaat tctggcttca ccctgatca agctatcgta ccttaaatgc     60
gtcgtttcac gttttcacc ttgttggagg tctgaatgtc tgtgctttgt ggtgcttcaa    120
tttagtccca ccttgtcggc tttcaacggg agggagcgga aaggcttat aaaagcagac    180 cctagtcaac ataacaattc aagctgact ctagcagatc tccatgacgg cagagaaggt    240
actgaaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cacaattcaa aacaagtttt at                                            442
```

<210> SEQ ID NO 230
<211> LENGTH: 442
<212> TYPE: DNA
<213> ORGANISM: Artificial Sequence
<220> FEATURE:
<223> OTHER INFORMATION: Recombinant

<400> SEQUENCE: 230

```
ggtggaaacg gactcgagcg agagagactc tgcggaccgg gccagcatcg atgtattggt     60
agcccagaaa gcccacgcaa ccagacagag gtatgaatgt tgtgctttgt ggtgcttcag    120
tttagtccca cctcggcggt tttcagcgga agggagcaga aaggcttat aaaagcagac    180 ctcagtcaac ataacaattc aagctgact ctagcagatc tccatgacgg cagagaaggt    240
actgaaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cacaattcaa aacaagtttt at                                            442
```

<210> SEQ ID NO 231
<211> LENGTH: 442
<212> TYPE: DNA
<213> ORGANISM: Artificial Sequence
<220> FEATURE:
<223> OTHER INFORMATION: Recombinant

<400> SEQUENCE: 231

```
tcccttttgtc gccttgctgt tcgctccgtt tgttgggccg acatgtggc tttctgggcc     60 gcgcacgtag agtcctcctg gccagtgtcg ggctctggct ggctgcctgc tcttttttct    120
gtagtcccaa accgcttgct gaggctaata tcagccggga acaacgctat ttaggattga    180
ctgaactctg tgtaagaggc caagctgact ctagcagatc tccatgacgg cagagaaggt    240
actgaaaaaa gaacttctgg cctggcagga gaaactgcat cagccgatta tcatcaccga    300
atacggcgtg gatacgttag ccgggctgca ctcaatgtac accgacatgt ggagtgaaga    360
```

| | |
|---|---|
| gtatcagtgt gcatggctgg atatgtatca ccgcgtcttt gatcgcgtca gcgccgtcgt | 420 |
| cacaattcaa aacaagtttt at | 442 |

<210> SEQ ID NO 232
<211> LENGTH: 442
<212> TYPE: DNA
<213> ORGANISM: Artificial Sequence
<220> FEATURE:
<223> OTHER INFORMATION: Recombinant

<400> SEQUENCE: 232

| | |
|---|---|
| cctttgtggc ttcgcttcat tctcttcatc cgtttgtgac cggagtcagc ggctgtcgac | 60 |
| cgcggcgcat cctctgacta gcactgcgtc tggctggctc tggctgcttc agcttgcttt | 120 |
| agttcccaaa cccgcttgct gtagctaata ccagcaggga gcgctgctat ttaggatgga | 180 |
| ctgggcgctg cgagagaagc caagctgact ctagcagatc tccatgacgg cagagaaggt | 240 |
| actggaaaaa gaacttctgg cctggcagga gaaactgcat cagccgatta tcatcaccga | 300 |
| atacggcgtg gatacgttag ccgggctgca ctcaatgtac accgacatgt ggagtgaaga | 360 |
| gtatcagtgt gcatggctgg atatgtatca ccgcgtcttt gatcgcgtca gcgccgtcgt | 420 |
| cacaattcaa aacaagtttt at | 442 |

<210> SEQ ID NO 233
<211> LENGTH: 442
<212> TYPE: DNA
<213> ORGANISM: Artificial Sequence
<220> FEATURE:
<223> OTHER INFORMATION: Recombinant

<400> SEQUENCE: 233

| | |
|---|---|
| ggccttcgct tcctcgctct tcgctccttt gttgggccgg acaacaagcg gctgtctggg | 60 |
| ccgcgcacgc agtcctctgg tccagtgggc aactgcctct ggctgcttgc tcttttcctt | 120 |
| aatcccaaac cgctcgatga agctaatacc agctgggggg cgctgctatt taggagagac | 180 |
| taagcgccac ccgtagatgc caagctgact ctagcagatc tccatgacgg cagagaaggt | 240 |
| actggaaaaa gaacttctgg cctggcagga gaaactgcat cagccgatta tcatcaccga | 300 |
| atacggcgtg gatacgttag ccgggctgca ctcaatgtac accgacatgt ggagtgaaga | 360 |
| gtatcagtgt gcatggctgg atatgtatca ccgcgtcttt gatcgcgtca gcgccgtcgt | 420 |
| cacaattcaa aacaagtttt at | 442 |

<210> SEQ ID NO 234
<211> LENGTH: 442
<212> TYPE: DNA
<213> ORGANISM: Artificial Sequence
<220> FEATURE:
<223> OTHER INFORMATION: Recombinant

<400> SEQUENCE: 234

| | |
|---|---|
| ttcgcttcat ttctcttcac tccgtttgtt gggccggaca tcaagcggct gtctgggccg | 60 |
| cgcacgcagt cctcttgact agcactgcgt ctggctggct ctggctgctt cagctttgct | 120 |
| ttagttccaa accgcttgct gtagctaata ccagcaggga gcgctgctat ttaggatgga | 180 |
| ctgggcgctg cgagagaagc caagctgact ctagcagatc tccatgacgg cagagaaggt | 240 |
| actggaaaaa gaacttctgg cctggcagga gaaactgcat cagccgatta tcatcaccga | 300 |
| atacggcgtg gatacgttag ccgggctgca ctcaatgtac accgacatgt ggagtgaaga | 360 |
| gtatcagtgt gcatggctgg atatgtatca ccgcgtcttt gatcgcgtca gcgccgtcgt | 420 |

```
cacaattcaa aacaagtttt at                                             442

<210> SEQ ID NO 235
<211> LENGTH: 427
<212> TYPE: DNA
<213> ORGANISM: Artificial Sequence
<220> FEATURE:
<223> OTHER INFORMATION: Recombinant

<400> SEQUENCE: 235
ggcgtatgtg ccaaaaactt cgtcacagag agggccataa gaaacatggc ccacggccca     60
atacgaagca ccgcgacgaa gcccaaacag cagtccgtag gtggagcaaa gcgctgggta    120
atacgcaaac gttttgtccc accttgacta atcacaagag tggagcgtac cttataaacc    180
gagccgcaag caccgaattc aagctgactc tagcagatct ccatgacggc agagaaggta    240
ctggaaaaag aacttctggc ctggcaggag aaactgcatc agccgattat catcaccgaa    300
tacggcgtgg atacgttagc cgggctgcac tcaatgtaca ccgacatgtg gagtgaagag    360
tatcagtgtg catggctgga tatgtatcac cgcgtctttg atcgcgtcag cgccgtcgtc    420
ttttttt                                                              427

<210> SEQ ID NO 236
<211> LENGTH: 428
<212> TYPE: DNA
<213> ORGANISM: Artificial Sequence
<220> FEATURE:
<223> OTHER INFORMATION: Recombinant

<400> SEQUENCE: 236
gcgtggtctg ctttttcgca tgatatctgg gccgcaccaa agaatccagc ccacgcggcg     60
tggcgccgtc gttacggctt gcggggaag gaaacgaggg acgaaccgag atttagcacc    120
agaccggcca gcgagcattg cagacaccgg cttataagtt cagctgcgac taccactccg    180
ggaggtccga gttccactcg caagctgact ctagcagatc tccatgacgg cagagaaggt    240
actggaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cttttttt                                                             428

<210> SEQ ID NO 237
<211> LENGTH: 21
<212> TYPE: DNA
<213> ORGANISM: Artificial Sequence
<220> FEATURE:
<223> OTHER INFORMATION: Recombinant

<400> SEQUENCE: 237
acaattcaaa acaagtttta t                                               21

<210> SEQ ID NO 238
<211> LENGTH: 4622
<212> TYPE: DNA
<213> ORGANISM: Artificial Sequence
<220> FEATURE:
<223> OTHER INFORMATION: Recombinant

<400> SEQUENCE: 238
atgggatcta agaagagaag aattaaacaa gatatgagtg acctggtgct agggttggct     60
```

| | |
|---|---|
| ataggcattg gctccgtggg ggttggcatt cttaataagg tgaccggcga aataattcat | 120 |
| aaaaactcac gcatctttcc agcagcccag gctgagaaca atctggtccg tagaaccaac | 180 |
| cggcagggtc gaaggttagc caggcgcaag aagcacagac gggtccggct caacaggctt | 240 |
| ttcgaggagt ctggtttgat caccgatttc actaagattt ctatcaacct gaatccttat | 300 |
| cagctgcgcg ttaaaggtct cacagacgaa cttagcaacg aagagttgtt catcgccctg | 360 |
| aaaaatatgg tcaagcatcg cggcattagc tacctggacg acgcttcgga tgatggcaac | 420 |
| agtagtgtag gtgactacgc tcagatcgtg aaagagaact cgaagcaatt ggagaccaag | 480 |
| accccgggcc aaattcaact cgaaaggtaa gtttctgctt ctacctttga tatatatata | 540 |
| ataattatca ttaattagta gtaatataat atttcaaata ttttttttcaa aataaaagaa | 600 |
| tgtagtatat agcaattgct tttctgtagt ttataagtgt gtatatttta atttataact | 660 |
| tttctaatat atgaccaaaa tttgttgatg tgcaggtacc agacgtatgg acagttacga | 720 |
| ggcgatttta ccgttgaaaa ggatggtaag aagcacaggc tgattaatgt gtttccgacc | 780 |
| tcagcttatc gctctgaggc gctgcgtatt ttgcagaccc aacaggaatt taacccgcaa | 840 |
| ataacggacg agttcataaa ccgatactta gagattctta caggtaaacg taaatactat | 900 |
| cacggcccag gaaatgaaaa gtccaggaca gattatggtc gatatcgcac ttccggagag | 960 |
| actctcgaca atatctttgg cattcttata ggcaaatgta ccttctaccc tgacgaattt | 1020 |
| agagcagcga aggcttcata tacagcacaa gagtttaatc ttctcaacga cctcaacaac | 1080 |
| ttgactgtgc ctactgaaac caaaaagctt agcaaggagc aaaaaaatca aatcattaac | 1140 |
| tatgttaaga atgagaaagc tatggggccc gcaaaattgt tcaagtacat agctaagtta | 1200 |
| cttagctgtg acgttgctga tattaagggt taccgtattg acaagtctgg taaagctgaa | 1260 |
| attcacacct tgaggcttta taggaagatg aagacccttg agacacttga cattgagcag | 1320 |
| atggataggg agactttgga caaactggca tacgtcttga cattgaacac cgaaagggaa | 1380 |
| ggcatccagg aagctctgga acatgaattt gcagatggtt cgttcagcca aaaacaggtt | 1440 |
| gacgagctgg tccaatttag aaaggcaaac tcaagcatat tcggtaaagg ttggcacaac | 1500 |
| ttcagcgtta agctgatgat ggaactcatt ccagaattat atgaaacctc tgaggaacag | 1560 |
| atgacgattc tcacaagatt gggtaagcag aaaacaacca gctctagcaa taagactaaa | 1620 |
| tacattgacg aaaagctcct caccgaagag atttataacc cggtcgtggc aaagagtgta | 1680 |
| cggcaagcca tcaagatcgt taatgccgct atcaaggagt atggtgattt tgataatatt | 1740 |
| gtgattgaaa tggcacgcga gactaacgag gacgacgaga agaaagctat acagaagatt | 1800 |
| caaaaggcta ataaggacga gaaggacgcc gcaatgctaa aggcggccaa tcaatataat | 1860 |
| gggaaggctg aactacctca tagcgtcttc catggacata gcaattagc aactaaaata | 1920 |
| agattatggc accagcaagg cgaacggtgt ctttatacag gtaaaacgat atctattcac | 1980 |
| gacctgatta caactctaa ccagtttgaa gtggatgcta tcttaccact aagtatcacc | 2040 |
| ttcgacgatt cacttgctaa caaggtgctc gtttacgcca ctgcgaacca agagaaaggg | 2100 |
| cagaggactc cataccaggc ccttgacagc atggacgacg cctggagttt tagggaatta | 2160 |
| aaagctttcg tacgtgagtc aaagacgctt tcaataaaaa aaaggagta cttgctcact | 2220 |
| gaagaagaca tctcaaaatt cgacgtgcgc aaaaaattca ttgagcggaa cttagtcgac | 2280 |
| actcggtacg catcaagagt agtgttgaac gccctccagg agcactttag ggcacataag | 2340 |
| atcgacacca aggtttcagt tgttaggggt cagtttacat cgcagcttag acgccattgg | 2400 |
| ggtatagaaa aaacacgtga tacctaccat caccatgcag ttgacgctct catcattgca | 2460 |

```
gcatcttctc aacttaattt gtggaaaaag caaaagaaca ctctggtctc atatagcgaa    2520
gatcagctgc ttgatattga aaccggcgag ctgattctg acgacgaata caaagaatct    2580
gtgtttaagg caccatatca acactttgta gacacgctta aatctaaaga gtttgaggat    2640
tcgatccttt tcagttacca agtcgactca aaatttaacc gtaagatctc tgatgcaaca    2700
atttatgcga cgaggcaggc caaggtaggt aaggataagg ctgacgaaac ctacgtgctc    2760
ggaaaaatca agatattta cactcaagat ggatatgatg cattcatgaa gatatataaa    2820
aaggacaaat ctaaattcct tatgtatcgt catgacccac agacattcga gaaagttatt    2880
gagcctatcc tggagaacta tccgaacaag caaataaatg agaagggcaa agaagttcca    2940
tgtaatccgt tcctaaagta caaggaggaa cacggatata ttagaaaata cagcaaaaag    3000
ggcaacggcc cagaaatcaa aagccttaag tactacgata gtaaactagg aaaccacatc    3060
gacattacac caaaagactc taataataag gtcgtactgc aaagcgtttc cccatggcgc    3120
gccgatgtgt attttaataa gacaacaggg aagtacgaaa tcttggggtt aaaatatgcg    3180
gatctgcaat tcgaaagggg aaccggcaca tacaaaattt ctcaagaaaa gtacaacgac    3240
ataaagaaga aggaagggt cgattctgat tctgaattca agttcacact ctataagaat    3300
gatcttctgc tcgtcaagga cacagagaca aaggagcagc agttgttcag gttcttgtct    3360
agaactatgc aaaacaaaa gcactacgtt gaactgaagc cttacgataa gcaaaaattc    3420
gagggggcg aggcgcttat aaaggtccta ggaaatgttg caaactctgg gcagtgtaag    3480
aagggcctgg gcaagagcaa cattagcatc tataaggttc gaacggatgt gcttgggaac    3540
cagcatatca tcaaaaacga gggagataaa ccaaagctgg acttcggatc ttctattgtg    3600
gcgcagctct caagaaggga cccggcgcta gcggctctga ctaatgacca tctcgtggct    3660
ctggcttgcc tgggggggcg gcctgctctg gacgctgtga agaaggggct cccacacgct    3720
ccagagttca tccgcagggt gaacaggagg attgctgagc ggacaagcca cagggtcgct    3780
gactacgctc atgtggtccg cgttctggag ttcttccagt gccactcgca tccggctcac    3840
gccttcgatg aggccatgac ccagttcggc atgtctcggc atgggctggt ccagctcttc    3900
aggcgggttg gcgtgactga gttcgaggct cgctacggga ccctgccacc agcgtcccag    3960
cgctgggaca ggatcctcca ggcgagcggc atgaagaggg ctaagccaag ccctacctcg    4020
gctcagacgc cagaccagac atctctccac gcgttcgctg attcactgga gagggacctc    4080
gatgctccat ccccaatgca tgagggcgac cagaccaggg cgtccagccg caagaggtca    4140
cggtccgata gggctgtgac ggggccatcg gctcagcagg ctgtcgaggt tagggtgcct    4200
gagcagaggg acgctctcca cctgccactc tcctggaggg tcaagcgccc taggacgagg    4260
atctggggcg ggctgccaga ccctggcaca ccgattgccg cggatctcgc tgcctcgtct    4320
actgttatgt gggagcagga cgctgctcca ttcgctggcg ctgctgacga tttcccagcc    4380
ttcaatgagg aggagctggc ttggctgatg gagctgctgc ctcagtcggg gtcggttggc    4440
gggacaatcg ctgccgacct ggcggcttcg tctaccgtca tgtgggagca ggacgccgcg    4500
ccgttcgctg gcgctgccga cgatttccct gcgttcaacg aggaggagct ggcgtggctg    4560
atggagctgc tgccccagag cgggagcgtc ggcgggacaa tctgaagcag aacacgcgct    4620
ga                                                                  4622

<210> SEQ ID NO 239
<211> LENGTH: 1471
<212> TYPE: PRT
```

<213> ORGANISM: Artificial Sequence
<220> FEATURE:
<223> OTHER INFORMATION: Recombinant

<400> SEQUENCE: 239

```
Met Gly Ser Lys Lys Arg Arg Ile Lys Gln Asp Met Ser Asp Leu Val
1               5                   10                  15

Leu Gly Leu Ala Ile Gly Ile Gly Ser Val Gly Val Gly Ile Leu Asn
            20                  25                  30

Lys Val Thr Gly Glu Ile Ile His Lys Asn Ser Arg Ile Phe Pro Ala
        35                  40                  45

Ala Gln Ala Glu Asn Asn Leu Val Arg Arg Thr Asn Arg Gln Gly Arg
    50                  55                  60

Arg Leu Ala Arg Arg Lys Lys His Arg Arg Val Arg Leu Asn Arg Leu
65                  70                  75                  80

Phe Glu Glu Ser Gly Leu Ile Thr Asp Phe Thr Lys Ile Ser Ile Asn
                85                  90                  95

Leu Asn Pro Tyr Gln Leu Arg Val Lys Gly Leu Thr Asp Glu Leu Ser
            100                 105                 110

Asn Glu Glu Leu Phe Ile Ala Leu Lys Asn Met Val Lys His Arg Gly
        115                 120                 125

Ile Ser Tyr Leu Asp Asp Ala Ser Asp Gly Asn Ser Ser Val Gly
    130                 135                 140

Asp Tyr Ala Gln Ile Val Lys Glu Asn Ser Lys Gln Leu Glu Thr Lys
145                 150                 155                 160

Thr Pro Gly Gln Ile Gln Leu Glu Arg Tyr Gln Thr Tyr Gly Gln Leu
                165                 170                 175

Arg Gly Asp Phe Thr Val Glu Lys Asp Gly Lys Lys His Arg Leu Ile
            180                 185                 190

Asn Val Phe Pro Thr Ser Ala Tyr Arg Ser Glu Ala Leu Arg Ile Leu
        195                 200                 205

Gln Thr Gln Gln Glu Phe Asn Pro Gln Ile Thr Asp Glu Phe Ile Asn
    210                 215                 220

Arg Tyr Leu Glu Ile Leu Thr Gly Lys Arg Lys Tyr Tyr His Gly Pro
225                 230                 235                 240

Gly Asn Glu Lys Ser Arg Thr Asp Tyr Gly Arg Tyr Arg Thr Ser Gly
                245                 250                 255

Glu Thr Leu Asp Asn Ile Phe Gly Ile Leu Ile Gly Lys Cys Thr Phe
            260                 265                 270

Tyr Pro Asp Glu Phe Arg Ala Ala Lys Ala Ser Tyr Thr Ala Gln Glu
        275                 280                 285

Phe Asn Leu Leu Asn Asp Leu Asn Asn Leu Thr Val Pro Thr Glu Thr
    290                 295                 300

Lys Lys Leu Ser Lys Glu Gln Lys Asn Gln Ile Ile Asn Tyr Val Lys
305                 310                 315                 320

Asn Glu Lys Ala Met Gly Pro Ala Lys Leu Phe Lys Tyr Ile Ala Lys
                325                 330                 335

Leu Leu Ser Cys Asp Val Ala Asp Ile Lys Gly Tyr Arg Ile Asp Lys
            340                 345                 350

Ser Gly Lys Ala Glu Ile His Thr Phe Glu Ala Tyr Arg Lys Met Lys
        355                 360                 365

Thr Leu Glu Thr Leu Asp Ile Glu Gln Met Asp Arg Glu Thr Leu Asp
    370                 375                 380

Lys Leu Ala Tyr Val Leu Thr Leu Asn Thr Glu Arg Glu Gly Ile Gln
```

-continued

```
385                 390                 395                 400
Glu Ala Leu Glu His Glu Phe Ala Asp Gly Ser Phe Ser Gln Lys Gln
                405                 410                 415
Val Asp Glu Leu Val Gln Phe Arg Lys Ala Asn Ser Ser Ile Phe Gly
                420                 425                 430
Lys Gly Trp His Asn Phe Ser Val Lys Leu Met Met Glu Leu Ile Pro
                435                 440                 445
Glu Leu Tyr Glu Thr Ser Glu Glu Gln Met Thr Ile Leu Thr Arg Leu
                450                 455                 460
Gly Lys Gln Lys Thr Thr Ser Ser Asn Lys Thr Lys Tyr Ile Asp
465                 470                 475                 480
Glu Lys Leu Leu Thr Glu Ile Tyr Asn Pro Val Val Ala Lys Ser
                485                 490                 495
Val Arg Gln Ala Ile Lys Ile Val Asn Ala Ala Ile Lys Glu Tyr Gly
                500                 505                 510
Asp Phe Asp Asn Ile Val Ile Glu Met Ala Arg Glu Thr Asn Glu Asp
                515                 520                 525
Asp Glu Lys Lys Ala Ile Gln Lys Ile Gln Lys Ala Asn Lys Asp Glu
                530                 535                 540
Lys Asp Ala Ala Met Leu Lys Ala Ala Asn Gln Tyr Asn Gly Lys Ala
545                 550                 555                 560
Glu Leu Pro His Ser Val Phe His Gly His Lys Gln Leu Ala Thr Lys
                565                 570                 575
Ile Arg Leu Trp His Gln Gln Gly Glu Arg Cys Leu Tyr Thr Gly Lys
                580                 585                 590
Thr Ile Ser Ile His Asp Leu Ile Asn Asn Ser Asn Gln Phe Glu Val
                595                 600                 605
Asp Ala Ile Leu Pro Leu Ser Ile Thr Phe Asp Asp Ser Leu Ala Asn
                610                 615                 620
Lys Val Leu Val Tyr Ala Thr Ala Asn Gln Glu Lys Gly Gln Arg Thr
625                 630                 635                 640
Pro Tyr Gln Ala Leu Asp Ser Met Asp Asp Ala Trp Ser Phe Arg Glu
                645                 650                 655
Leu Lys Ala Phe Val Arg Glu Ser Lys Thr Leu Ser Asn Lys Lys Lys
                660                 665                 670
Glu Tyr Leu Leu Thr Glu Glu Asp Ile Ser Lys Phe Asp Val Arg Lys
                675                 680                 685
Lys Phe Ile Glu Arg Asn Leu Val Asp Thr Arg Tyr Ala Ser Arg Val
                690                 695                 700
Val Leu Asn Ala Leu Gln Glu His Phe Arg Ala His Lys Ile Asp Thr
705                 710                 715                 720
Lys Val Ser Val Val Arg Gly Gln Phe Thr Ser Gln Leu Arg Arg His
                725                 730                 735
Trp Gly Ile Glu Lys Thr Arg Asp Thr Tyr His His Ala Val Asp
                740                 745                 750
Ala Leu Ile Ile Ala Ala Ser Ser Gln Leu Asn Leu Trp Lys Lys Gln
                755                 760                 765
Lys Asn Thr Leu Val Ser Tyr Ser Glu Asp Gln Leu Leu Asp Ile Glu
                770                 775                 780
Thr Gly Glu Leu Ile Ser Asp Asp Glu Tyr Lys Glu Ser Val Phe Lys
785                 790                 795                 800
Ala Pro Tyr Gln His Phe Val Asp Thr Leu Lys Ser Lys Glu Phe Glu
                805                 810                 815
```

```
Asp Ser Ile Leu Phe Ser Tyr Gln Val Asp Ser Lys Phe Asn Arg Lys
            820                 825                 830

Ile Ser Asp Ala Thr Ile Tyr Ala Thr Arg Gln Ala Lys Val Gly Lys
            835                 840                 845

Asp Lys Ala Asp Glu Thr Tyr Val Leu Gly Lys Ile Lys Asp Ile Tyr
            850                 855                 860

Thr Gln Asp Gly Tyr Asp Ala Phe Met Lys Ile Tyr Lys Lys Asp Lys
865                 870                 875                 880

Ser Lys Phe Leu Met Tyr Arg His Asp Pro Gln Thr Phe Glu Lys Val
                885                 890                 895

Ile Glu Pro Ile Leu Glu Asn Tyr Pro Asn Lys Gln Ile Asn Glu Lys
            900                 905                 910

Gly Lys Glu Val Pro Cys Asn Pro Phe Leu Lys Tyr Lys Glu Glu His
            915                 920                 925

Gly Tyr Ile Arg Lys Tyr Ser Lys Lys Gly Asn Gly Pro Glu Ile Lys
        930                 935                 940

Ser Leu Lys Tyr Tyr Asp Ser Lys Leu Gly Asn His Ile Asp Ile Thr
945                 950                 955                 960

Pro Lys Asp Ser Asn Asn Lys Val Val Leu Gln Ser Val Ser Pro Trp
                965                 970                 975

Arg Ala Asp Val Tyr Phe Asn Lys Thr Thr Gly Lys Tyr Glu Ile Leu
                980                 985                 990

Gly Leu Lys Tyr Ala Asp Leu Gln Phe Glu Lys Gly Thr Gly Thr Tyr
            995                 1000                1005

Lys Ile Ser Gln Glu Lys Tyr Asn Asp Ile Lys Lys Lys Glu Gly
        1010                1015                1020

Val Asp Ser Asp Ser Glu Phe Lys Phe Thr Leu Tyr Lys Asn Asp
        1025                1030                1035

Leu Leu Leu Val Lys Asp Thr Glu Thr Lys Glu Gln Gln Leu Phe
        1040                1045                1050

Arg Phe Leu Ser Arg Thr Met Pro Lys Gln Lys His Tyr Val Glu
        1055                1060                1065

Leu Lys Pro Tyr Asp Lys Gln Lys Phe Glu Gly Gly Glu Ala Leu
        1070                1075                1080

Ile Lys Val Leu Gly Asn Val Ala Asn Ser Gly Gln Cys Lys Lys
        1085                1090                1095

Gly Leu Gly Lys Ser Asn Ile Ser Ile Tyr Lys Val Arg Thr Asp
        1100                1105                1110

Val Leu Gly Asn Gln His Ile Ile Lys Asn Glu Gly Asp Lys Pro
        1115                1120                1125

Lys Leu Asp Phe Gly Ser Ser Ile Val Ala Gln Leu Ser Arg Arg
        1130                1135                1140

Asp Pro Ala Leu Ala Ala Leu Thr Asn Asp His Leu Val Ala Leu
        1145                1150                1155

Ala Cys Leu Gly Gly Arg Pro Ala Leu Asp Ala Val Lys Lys Gly
        1160                1165                1170

Leu Pro His Ala Pro Glu Phe Ile Arg Arg Val Asn Arg Arg Ile
        1175                1180                1185

Ala Glu Arg Thr Ser His Arg Val Ala Asp Tyr Ala His Val Val
        1190                1195                1200

Arg Val Leu Glu Phe Phe Gln Cys His Ser His Pro Ala His Ala
        1205                1210                1215
```

| | | | | | | | | | |
|---|---|---|---|---|---|---|---|---|---|
| Phe | Asp | Glu | Ala | Met | Thr | Gln | Phe | Gly | Met | Ser | Arg | His | Gly | Leu |
| | 1220 | | | | 1225 | | | | 1230 | | | | | |

Phe Asp Glu Ala Met Thr Gln Phe Gly Met Ser Arg His Gly Leu
    1220                1225            1230

Val Gln Leu Phe Arg Arg Val Gly Val Thr Glu Phe Glu Ala Arg
    1235                1240            1245

Tyr Gly Thr Leu Pro Pro Ala Ser Gln Arg Trp Asp Arg Ile Leu
    1250                1255            1260

Gln Ala Ser Gly Met Lys Arg Ala Lys Pro Ser Pro Thr Ser Ala
    1265                1270            1275

Gln Thr Pro Asp Gln Thr Ser Leu His Ala Phe Ala Asp Ser Leu
    1280                1285            1290

Glu Arg Asp Leu Asp Ala Pro Ser Pro Met His Glu Gly Asp Gln
    1295                1300            1305

Thr Arg Ala Ser Ser Arg Lys Arg Ser Arg Ser Asp Arg Ala Val
    1310                1315            1320

Thr Gly Pro Ser Ala Gln Gln Ala Val Glu Val Arg Val Pro Glu
    1325                1330            1335

Gln Arg Asp Ala Leu His Leu Pro Leu Ser Trp Arg Val Lys Arg
    1340                1345            1350

Pro Arg Thr Arg Ile Trp Gly Gly Leu Pro Asp Pro Gly Thr Pro
    1355                1360            1365

Ile Ala Ala Asp Leu Ala Ala Ser Ser Thr Val Met Trp Glu Gln
    1370                1375            1380

Asp Ala Ala Pro Phe Ala Gly Ala Ala Asp Phe Pro Ala Phe
    1385                1390            1395

Asn Glu Glu Glu Leu Ala Trp Leu Met Glu Leu Leu Pro Gln Ser
    1400                1405            1410

Gly Ser Val Gly Gly Thr Ile Ala Ala Asp Leu Ala Ala Ser Ser
    1415                1420            1425

Thr Val Met Trp Glu Gln Asp Ala Ala Pro Phe Ala Gly Ala Ala
    1430                1435            1440

Asp Asp Phe Pro Ala Phe Asn Glu Glu Glu Leu Ala Trp Leu Met
    1445                1450            1455

Glu Leu Leu Pro Gln Ser Gly Ser Val Gly Gly Thr Ile
    1460                1465            1470

<210> SEQ ID NO 240
<211> LENGTH: 27
<212> TYPE: DNA
<213> ORGANISM: Artificial Sequence
<220> FEATURE:
<223> OTHER INFORMATION: Recombinant

<400> SEQUENCE: 240
ggaggtccga gttccactcg caagaat                                         27

<210> SEQ ID NO 241
<211> LENGTH: 353
<212> TYPE: DNA
<213> ORGANISM: Artificial Sequence
<220> FEATURE:
<223> OTHER INFORMATION: Recombinant

<400> SEQUENCE: 241
ggcgtatgtg ccaaaaactt cgtcacagag agggccataa gaaacatggc ccacggccca      60
atacgaagca ccgcgacgaa gcccaaacag cagtccgtag gtggagcaaa gcgctgggta     120
atacgcaaac gttttgtccc accttgacta atcacaagag tggagcgtac cttataaacc     180

```
gagccgcaag caccgaattg ggaggtccga gttccactcg gttattgtac tctcaagatt    240 tattttcca aagggttac ttaaatcttg cagaagctac aaagataagg cttcatgccg      300
aaatcaacac cctgtcattt tatggcaggg tgttttcgtt atttaatttt ttt           353
```

<210> SEQ ID NO 242
<211> LENGTH: 350
<212> TYPE: DNA
<213> ORGANISM: Artificial Sequence
<220> FEATURE:
<223> OTHER INFORMATION: Recombinant

<400> SEQUENCE: 242

```
tttcatccgg cctgtgatgg aaattgtgct gcaaagtgcg cagggccgtt ggcccgacga     60
caagtatttt tcgtcgagag aagcaacgaa agcccactcc tccaagccac ccttcgctca   120
agtcatattt agcaccacct cggcagtcga cactgcagca caccaactta aatattcatc   180
ccgatctccc tcactcggga ggtccgagtt ccactcggtt attgtactct caagatttat   240
ttttccaaaa gggttactta aatcttgcag aagctacaaa gataaggctt catgccgaaa   300
tcaacaccct gtcattttat ggcagggtgt ttcgttatt taattttttt                 350
```

<210> SEQ ID NO 243
<211> LENGTH: 360
<212> TYPE: DNA
<213> ORGANISM: Artificial Sequence
<220> FEATURE:
<223> OTHER INFORMATION: Recombinant

<400> SEQUENCE: 243

```
aacggactcg agcgagagag actctgcgga ccgggccagc atcgatgtat ttggtagccc     60
agagcccacg caaccagaca gaggtatgaa tgttgtgctt tgtggtgctt cagtttagtc   120
ccacctcggc ggttttcagc ggaagggagc agagaaggct tataaaagca gacctcagtc   180
aacataacaa ttaggaggtc cgagttccac tcggttattg tactctcaag atttattttt   240
ccaaaagggt tacttaaatc ttgcagaagc tacaaagata aggcttcatg ccgaaatcaa   300
caccctgtca ttttatggca gggtgttttc gttatttaat caaattcaaa ttttttttaa   360
```

<210> SEQ ID NO 244
<211> LENGTH: 373
<212> TYPE: DNA
<213> ORGANISM: Artificial Sequence
<220> FEATURE:
<223> OTHER INFORMATION: Recombinant

<400> SEQUENCE: 244

```
aggcgttcgc ttcatttctc ttcactccgt ttgttgggcc ggacatcaag cggctgtctg     60
ggccgcgcac gcagtcctct tgactagcac tgcgtctggc tggctctggc tgcttcagct   120
ttgctttagt tccaaaccgc ttgctgtagc taataccagc agggagcgct gctatttagg   180
atggactggg cgctgcgaga gaagcaggag gtccgagttc cactcggtta ttgtactctc   240
aagatttatt tttccaaaag ggttacttaa atcttgcaga agctacaaag ataaggcttc   300
atgccgaaat caacaccctg tcattttatg gcagggtgtt ttcgttattt aatcaaattc   360 aaatttttt taa                                                        373
```

<210> SEQ ID NO 245
<211> LENGTH: 348
<212> TYPE: DNA
<213> ORGANISM: Artificial Sequence

```
<220> FEATURE:
<223> OTHER INFORMATION: Recombinant

<400> SEQUENCE: 245
caataagata aagctggtgc aggctctcga cctgaagccc acacactgga gagcaacgat      60
ataccagaat ggagcggccc agtacacgat ctgctgggat tgctggccag tggccagtcc     120
cgcagccgat tagcaccacc tcggtggcac agacgaacga acgctaattt aaaagcttag     180
ctctggagct tggcaggagg tccgagttcc actcggttat tgtactctca agatttattt     240
ttccaaaagg gttacttaaa tcttgcagaa gctacaaaga taaggcttca tgccgaaatc     300
aacaccctgt cattttatgg cagggtgttt tcgttattta atttttttt                 348

<210> SEQ ID NO 246
<211> LENGTH: 3131
<212> TYPE: DNA
<213> ORGANISM: Artificial Sequence
<220> FEATURE:
<223> OTHER INFORMATION: Recombinant

<400> SEQUENCE: 246
gaattcctat gataaagttg ctctgtaaca gaaaacacca tctaggtcga cttacttgcg      60
gccgcttact tggcgcgccg gaggtccgag ttccactcgc aagaatttgc ttcttgggag     120
gtccgagttc cactcgcaag aatcctctca ttaggaggtc cgagttccac tcgcaagaat     180
attattcgca agacccttcc tctatataag gaagttcatt tcatttggag aggacacgct     240
gaaatcacca gtctctctct acaaatctat ctctctctat tttccggacc gaccgtcttc     300
ggtacgcgct cactccgccc tctgcctttg ttactgccac gtttctctga atgctctctt     360
gtgtggtgat tgctgagagt ggtttagctg gatctagaat tacactctga aatcgtgttc     420
tgcctgtgct gattacttgc cgtcctttgt agcagcaaaa tatagggaca tggtagtacg     480
aaacgaagat agaacctaca cagcaatacg agaaatgtgt aatttggtgc ttagcggtat     540
ttatttaagc acatgttggt gttatagggc acttggattc agaagtttgc tgttaattta     600
ggcacaggct tcatactaca tgggtcaata gtatagggat tcatattata ggcgatacta     660
taataatttg ttcgtctgca gagcttatta tttgccaaaa ttagatattc ctattctgtt     720
tttgtttgtg tgctgttaaa ttgttaacgc ctgaaggaat aaatataaat gacgaaattt     780
tgatgtttat ctctgctcct ttattgtgac cataagtcaa gatcagatgc acttgtttta     840
aatattgttg tctgaagaaa taagtactga cagtattttg atgcattgat ctgcttgttt     900
gttgtaacaa aatttaaaaa taagagtttt ccttttttgtt gctctcctta cctcctgatg     960
gtatctagta tctaccaact gacactatat tgcttctctt tacatacgta tcttgctcga    1020
tgccttctcc ctagtgttga ccagtgttac tcacatagtc tttgctcatt tcattgtaat    1080
gcagatacca agcggggtac cctcagcgct gtgcctgttg cgatcgcacc atggtccgtc    1140
ctgtagaaac cccaacccgt gaaatcaaaa aactcgacgg cctgtgggca ttcagtctgg    1200
atcgcgaaaa ctgtggaatt gatcagcgtt ggtgggaaag cgcgttacaa gaaagccggg    1260
caattgctgt gccaggcagt tttaacgatc agttcgccga tgcagatatt cgtaattatg    1320
cgggcaacgt ctggtatcag cgcgaagtct ttataccgaa aggttgggca ggccagcgta    1380
tcgtgctgcg tttcgatgcg gtcactcatt acggcaaagt gtgggtcaat aatcaggaag    1440
tgatggagca tcaggggcgg ctatacgcca ttgaagccga tgtcacgccg tatgttattg    1500
ccgggaaaag tgtacgtaag tttctgcttc taccttttgat atatatataa taattatcat    1560
```

-continued

| | | | | |
|---|---|---|---|---|
| taattagtag | taatataata | tttcaaatat | ttttttcaaa | ataaagaat gtagtatata | 1620 |
| gcaattgctt | ttctgtagtt | tataagtgtg | tatattttaa | tttataactt ttctaatata | 1680 |
| tgaccaaaat | ttgttgatgt | gcaggtatca | ccgtttgtgt | gaacaacgaa ctgaactggc | 1740 |
| agactatccc | gccgggaatg | gtgattaccg | acgaaaacgg | caagaaaaag cagtcttact | 1800 |
| tccatgattt | ctttaactat | gccggaatcc | atcgcagcgt | aatgctctac accacgccga | 1860 |
| acacctgggt | ggacgatatc | accgtggtga | cgcatgtcgc | gcaagactgt aaccacgcgt | 1920 |
| ctgttgactg | gcaggtggtg | gccaatggtg | atgtcagcgt | tgaactgcgt gatgcggatc | 1980 |
| aacaggtggt | tgcaactgga | caaggcacta | gcgggacttt | gcaagtggtg aatccgcacc | 2040 |
| tctggcaacc | gggtgaaggt | tatctctatg | aactgtgcgt | cacagccaaa agccagacag | 2100 |
| agtgtgatat | ctacccgctt | cgcgtcggca | tccggtcagt | ggcagtgaag ggcgaacagt | 2160 |
| tcctgattaa | ccacaaaccg | ttctacttta | ctggctttgg | tcgtcatgaa gatgcggact | 2220 |
| tgcgtggcaa | aggattcgat | aacgtgctga | tggtgcacga | ccacgcatta atggactgga | 2280 |
| ttggggccaa | ctcctaccgt | acctcgcatt | acccttacgc | tgaagagatg ctcgactggg | 2340 |
| cagatgaaca | tggcatcgtg | gtgattgatg | aaactgctgc | tgtcggcttt aacctctctt | 2400 |
| taggcattgg | tttcgaagcg | ggcaacaagc | cgaaagaact | gtacagcgaa gaggcagtca | 2460 |
| acggggaaac | tcagcaagcg | cacttacagg | cgattaaaga | gctgatagcg cgtgacaaaa | 2520 |
| accacccaag | cgtggtgatg | tggagtattg | ccaacgaacc | ggatacccgt ccgcaaggtg | 2580 |
| cacgggaata | tttcgcgcca | ctggcggaag | caacgcgtaa | actcgacccg acgcgtccga | 2640 |
| tcacctgcgt | caatgtaatg | ttctgcgacg | ctcacaccga | taccatcagc gatctctttg | 2700 |
| atgtgctgtg | cctgaaccgt | tattacggat | ggtatgtcca | aagcggcgat ttggaaacgg | 2760 |
| cagagaaggt | actggaaaaa | gaacttctgg | cctggcagga | gaaactgcat cagccgatta | 2820 |
| tcatcaccga | atacggcgtg | gatacgttag | ccgggctgca | ctcaatgtac accgacatgt | 2880 |
| ggagtgaaga | gtatcagtgt | gcatggctgg | atatgtatca | ccgcgtcttt gatcgcgtca | 2940 |
| gcgccgtcgt | cggtgaacag | gtatggaatt | cgccgatttt | tgcgacctcg caaggcatat | 3000 |
| tgcgcgttgg | cggtaacaag | aaagggatct | tcactcgcga | ccgcaaaccg aagtcggcgg | 3060 |
| cttttctgct | gcaaaaacgc | tggactggca | tgaacttcgg | tgaaaaaccg cagcagggag | 3120 |
| gcaaacaatg | a | | | | 3131 |

<210> SEQ ID NO 247
<211> LENGTH: 200
<212> TYPE: DNA
<213> ORGANISM: Glycine max

<400> SEQUENCE: 247

| | | | | |
|---|---|---|---|---|
| atccaagcaa | aatacttgga | agatacgaaa | gtgtttgaaa | tcagttatta gtttcacgtt | 60 |
| tgataaaatt | gctgatttaa | atttttgact | gttgctctcg | gctaggaatg ttgcaagcga | 120 |
| agaagtccca | catttgtcag | aacattggca | ggcagctgaa | gctcactgta taaaaatgga | 180 |
| gtacttggat | agttgaaagc | | | | 200 |

<210> SEQ ID NO 248
<211> LENGTH: 200
<212> TYPE: DNA
<213> ORGANISM: Glycine max

<400> SEQUENCE: 248

| | | | | |
|---|---|---|---|---|
| acttgtttga | actcaattat | tagtctcaag | ttcgaagaat | attggataaa ctcaactgcc | 60 |

```
gatttaaatt tgaaaatgtt gttcttgtgt agagatttta ggagcatctg acaccagtga      120
caaagtccca catttgtcag aacactgaca atcagctaat gctgacagta taaaagtgga      180
gtacttggaa ggttgaaagc                                                 200
```

<210> SEQ ID NO 249
<211> LENGTH: 200
<212> TYPE: DNA
<213> ORGANISM: Glycine max

<400> SEQUENCE: 249

```
aacgtgtttg aactcaatta ttagtctcaa gtttgaagag tactggataa actcaactgc      60
tgcattaaat ttgaaactgt tagttcttgt ttggagattt tagaagcatc ttacacaagt     120
cagagcccca cattcgtcag aacactgaca agcagctaat gctcacagta taaaagttga     180
atacttagac gtttcaaagc                                                 200
```

<210> SEQ ID NO 250
<211> LENGTH: 200
<212> TYPE: DNA
<213> ORGANISM: Glycine max

<400> SEQUENCE: 250

```
tagttatctg gtttcgttaa ttgtggttga agcctgaagg catccattat ccctaactat      60
cctggatggt tgcaaatact gtcctaagta ctacagaaac aagaagactg acagtgtaac    120
gaagtaccac gtctctcaag agaaataaca agcgttgaag actaaactat aaataaaaac    180
attatttcat tgtacaaagc                                                 200
```

<210> SEQ ID NO 251
<211> LENGTH: 200
<212> TYPE: DNA
<213> ORGANISM: Glycine max

<400> SEQUENCE: 251

```
aaataaaccc gttgaatgaa tggaccgaag acaatctgaa tccaaaaaag atagctatca      60
ttgcttgtga ttgaactggc tcatgctctg catccgaaca aaacttggag acacttataa    120
cgaagtccca cattgctgag atgagataac actcgcttca gattttatta taaaaaacgc    180
attacatatt gtggaaactc                                                 200
```

<210> SEQ ID NO 252
<211> LENGTH: 200
<212> TYPE: DNA
<213> ORGANISM: Glycine max

<400> SEQUENCE: 252

```
attaattgtg gatgatggca tccattatcc gtggtatttg ttagacttgg atggttgctg      60
gtcgaccaaa caaatactgt cctaaggact acaaaaacaa gaagactgac agtgcaacaa   120
agtatcacat cattcaagag aaataacaag cgctaaagac taaacttta aaaaaatgc     180 attattccat tgttcaaagc                                                 200
```

<210> SEQ ID NO 253
<211> LENGTH: 200
<212> TYPE: DNA
<213> ORGANISM: Glycine max

<400> SEQUENCE: 253

```
tgttaattgt gtttgaggac atccattatc caacattaga acaagatttg ttagacttgg      60
atagttgcta atcgagaagt cccagcaaat actacagaaa ctagaaagct attgatgtaa     120
tgaagtccca catcgctcaa gagaaataac aagcactgaa gactgaagta taaaacaagc     180
attatttcat tgtgcaaagc                                                 200

<210> SEQ ID NO 254
<211> LENGTH: 200
<212> TYPE: DNA
<213> ORGANISM: Glycine max

<400> SEQUENCE: 254
atgaatggaa cggcttgagt ttcgctcaac tgcaggaaaa tgtggattgc agacaatctg      60
aatcccaaaa agatagttat ccttgcttgt tatcagaact agacttggac acacttatta     120
cgatggccca tatcgcttag atgagataac actcgcttca gattttatta taaaaaatgc     180
attgtatgtt gtgtaaactc                                                 200

<210> SEQ ID NO 255
<211> LENGTH: 200
<212> TYPE: DNA
<213> ORGANISM: Glycine max

<400> SEQUENCE: 255
gtttcatgat tccgatcaaa gcaagagcat ccagtctcaa ttttgtcttc tcaattcact      60
cattcatcaa aatcagcagt tttatgcatc aacaagcatg gaatgttgaa ccacccatga     120
ttaagcccca tatcgttgtg ttgagataac tatcacctga agttgtctta taaaaaacac     180
atctgaatac ttttataatc                                                 200

<210> SEQ ID NO 256
<211> LENGTH: 200
<212> TYPE: DNA
<213> ORGANISM: Glycine max

<400> SEQUENCE: 256
agtaaaatat caacgggaag attataatgt gtttgaactt tcattagtct cagatttgaa      60
cttttatgtt gctgatctaa attttttaacc atgttgctct tggctaggat gttgggatga    120
attagtccca catttgtcag aactttgtca ggaagctgaa gctcccagta taaaatttga     180
atacttacat tgtacaaagc                                                 200

<210> SEQ ID NO 257
<211> LENGTH: 200
<212> TYPE: DNA
<213> ORGANISM: Glycine max

<400> SEQUENCE: 257
attcactcat tttcagaatt atcagtgtgt ctacactcta cactctacac tcagaaacaa      60
gcttgaaaca ttggtgccca ttgtcgaaga ctccatggct aagtcaaatt gtcaccatga     120
ctaagtccca tatcgattag aagagaggac aatcactcca gagcttatta taaaacagac     180 attataaacac cgttgtactc                                                200

<210> SEQ ID NO 258
<211> LENGTH: 200
<212> TYPE: DNA
<213> ORGANISM: Glycine max

<400> SEQUENCE: 258
```

```
tgtggctgaa ggcatcaatt atccatagtt agaacaaaga tttgttagac atggatagtt    60
gctggtcgac caaacaaata ctgtcctaag gactacaaaa caagaagacc ttcagtgtaa   120
cgaagtccca cattgcgcaa gagaaataac aagcactgaa gactgaagta taaaaacaac   180
attatttcat tgaacaaatc                                               200
```

<210> SEQ ID NO 259
<211> LENGTH: 200
<212> TYPE: DNA
<213> ORGANISM: Glycine max

<400> SEQUENCE: 259

```
agtaaaatat caacgggaag attataatgt gtttgaactt ttattagtct caggtttgaa    60
cttttatgtt gctgatctaa attttttaacc atgttgctct tggctaggat gttgggatga  120
attagtccca catttgtcag aactttgtca ggcagctgaa gctcccagta taaaatttga   180
atacctacaa tgtacaaagc                                               200
```

<210> SEQ ID NO 260
<211> LENGTH: 200
<212> TYPE: DNA
<213> ORGANISM: Glycine max

<400> SEQUENCE: 260

```
agtaaaatat caacgggaag attataatgt gtttgaactt ttattagtct caggtttgaa    60
cttttatgtt gctgatctaa attttttaacc atgttgctct tggctaggat gttgggatga  120
attagtccca catttgtcag gactttgtca ggcagctgaa gctcccagta taaaatttga   180
atacttacat tgtacaaagc                                               200
```

<210> SEQ ID NO 261
<211> LENGTH: 200
<212> TYPE: DNA
<213> ORGANISM: Glycine max

<400> SEQUENCE: 261

```
ggtgccccat ctggtggcag cagagtattg taatgtgggt gtttggagac tggagtgtcc    60
atggatttct gtacggagaa atggaagatt taacacataa gggtgcgcgt tgaagtacta   120
atatggccca tatcgtttag aagagataga aataactcta tatcttatta taaaagaaga   180
ttttgaagcc atgtatactc                                               200
```

<210> SEQ ID NO 262
<211> LENGTH: 200
<212> TYPE: DNA
<213> ORGANISM: Glycine max

<400> SEQUENCE: 262

```
tgttcatgga tttgttctgt gtggagaaat tattgatcgt cacaactaca ttttctagac    60
tctgctttgc cattgtagta gaggaattac tgtttctctg ttccaggcgt tacaagtata   120
aacagtccca tatcgtttag aagagataga aataactcta tatcttatta taaaagaaga   180
ttttgaagca tagcaaactc                                               200
```

<210> SEQ ID NO 263
<211> LENGTH: 200
<212> TYPE: DNA
<213> ORGANISM: Glycine max

```
<400> SEQUENCE: 263
gttatagggg tttagcatta atccagatgg gttgtgaaat atgcaagtgt aagtgtaatc      60
taattaggat acgttataga cacaaaggtc acttgatgtt caatgtggaa ccacccatga     120
gtgagtccca catcgctgag ttaagataag aatcacctga agttttatta taaaacaaac    180
gtttcaacag ttaaaaattc                                                 200

<210> SEQ ID NO 264
<211> LENGTH: 200
<212> TYPE: DNA
<213> ORGANISM: Glycine max

<400> SEQUENCE: 264
ttttgcagga atcaggataa tggaagaatg aagaaaagat atagagacgt agaggttgaa      60
gagaaggtag tagcagaaaa tccaagttct tatgtatgtt ggcgcttaac tccttattgc    120
ccaagtccca caccggcgat gagaaagaat ctgcgccaaa gacttggcta taaaacaaac    180
aatccttgaa attcttaagc                                                 200

<210> SEQ ID NO 265
<211> LENGTH: 200
<212> TYPE: DNA
<213> ORGANISM: Glycine max

<400> SEQUENCE: 265
ggtttggact ctgtacgcac tgtcacatcc taaataagaa aacacatttc gaagaaagac      60
cggatattag aagaattaac atttcaaatt gttactattg caacagcaac gtagtcgcca    120
aagagtccca catcagtcag tcaagaaagc agtagaacat gtaacagaaa taaaagcaac    180
aacaatatac tgatcaaagc                                                 200

<210> SEQ ID NO 266
<211> LENGTH: 200
<212> TYPE: DNA
<213> ORGANISM: Glycine max

<400> SEQUENCE: 266
ctatgtaaca agtacaattt cacagacccg tgttgttct ggtcttttga gaagtggtat       60
tgtattgtgc agaatgcatg agttatgtag aaacaagctt gccctgaaga gctatcctac    120
ctaagtccca cactggtaag gagaaagaat atgcaaaaat agtttgacta taaaagaaac    180
agtctatgat agaacaaatc                                                 200

<210> SEQ ID NO 267
<211> LENGTH: 200
<212> TYPE: DNA
<213> ORGANISM: Glycine max

<400> SEQUENCE: 267
gtagcttcag attactcgtg tgttaactgg gtcatgaatc cgtgatccaa cgttagaaca      60
agaacaaaac ctgaatagaa gagaaaggct atttggtgga tgttgcagaa atactagcga    120
tgaagtctca cattgctgag aagagaaaac aatgacctga tatttatta taaaagacaa     180 ctctggagcc ttaaaagctc                                                 200

<210> SEQ ID NO 268
<211> LENGTH: 400
<212> TYPE: DNA
<213> ORGANISM: Glycine max
```

```
<400> SEQUENCE: 268
aagaatgtcc actctcaatc actaagttgt tgtttccttt ttaattcact cattttaga      60 attatcagtg ttatactgaa tctagattga acatttgtg cccgaagact ccatccatga     120
caaagcccca tcgtctag aagagatgac aatcactcca gggcttatca taaaaaagac      180 ttttgcagc tgtaacactc aagaatgtcc actctcaatc actaagttgt tgtttccttt     240
ttaattcact cattttaga attatcagtg ttatactgaa tctagattga acatttgtg      300 cccgaagact ccatccatga caaagcccca tcgtctag aagagatgac aatcactcca     360
gggcttatca taaaaaagac ttttgcagc tgtaacactc                           400

<210> SEQ ID NO 269
<211> LENGTH: 200
<212> TYPE: DNA
<213> ORGANISM: Glycine max

<400> SEQUENCE: 269
agctgaggaa ggtagcttca gattactcgt gtgttaactg ggtcatgaat ccgtgatcca     60
acgtttgaac aagagcaaaa tctgaataga agagaaaggc tgttgcagaa atactagtga    120
tgaagtctca cattgctgag aagagaaaac aatgacctga tatttatta taaaacacaa    180 ctctggagcc ttaacaactc                                                200

<210> SEQ ID NO 270
<211> LENGTH: 200
<212> TYPE: DNA
<213> ORGANISM: Glycine max

<400> SEQUENCE: 270
gttaatatta ttactcgtgt gttaactggg tcatgaatcc gcgatccaac gttagcacaa     60
gaacaaaatc tgaatagaag agaaaaggcg atttggtgga tatagcagaa gaactagtga    120
gaaagtccca cattgctgag aagagaaaac aataacatga tgtttatta taaaacgcaa    180 ctctggagtg tgaacaactc                                                200

<210> SEQ ID NO 271
<211> LENGTH: 200
<212> TYPE: DNA
<213> ORGANISM: Glycine max

<400> SEQUENCE: 271
tctgtggaaa gattgaagat tcaatacaaa ccagaccctg tcttgttttg ttttggaatt     60
atcagttctc tattgcagcc agacccagag caagcgtgga tgttgcggaa gtactagtta    120
tgaagtccca cattgctgag aagagaaaac aatgacctga tgtttatta taaaatgcaa    180 ctctggaaca tgaacaactc                                                200

<210> SEQ ID NO 272
<211> LENGTH: 200
<212> TYPE: DNA
<213> ORGANISM: Glycine max

<400> SEQUENCE: 272
agtaaaatat caacgggaag attataatgt gtttgaactt tcattagtct caggtttgaa     60
cttttatgtt gctgatctaa attttaacc atgttgctct tggctaggat gttgggatga    120
attagtccca catttgtcag aactttgtca ggcagctgaa gctcccagta taaaatttga    180
```

```
atacttacat tgtacaaagc                                            200

<210> SEQ ID NO 273
<211> LENGTH: 200
<212> TYPE: DNA
<213> ORGANISM: Glycine max

<400> SEQUENCE: 273
agttcttgtt tcttttttaa ttaattcatt ttcagaatta ttatacacaa aaactagctt   60
gaaaaatttg tgcccattgt ccaagactcc atccatgact aggcgtctaa gccgcatcga  120
ttaagtccca tatcgcttag aaaatatgac aatcactcca gagcttatta taaaagagac  180 attttttagac taaggcattc                                             200

<210> SEQ ID NO 274
<211> LENGTH: 200
<212> TYPE: DNA
<213> ORGANISM: Glycine max

<400> SEQUENCE: 274
ctaaattctt gtttcttttt taattcactc attttcagaa ttattataca caaactagct   60
tgaaaatttt gtgcccattg tcgaagactc caccatgact aagggtctaa gccccatcga  120
ataagtccca tatcacttag aaaagatgaa aatgactcca gagcttatta taaaataaac  180 attttttacac tgttatattc                                             200

<210> SEQ ID NO 275
<211> LENGTH: 200
<212> TYPE: DNA
<213> ORGANISM: Glycine max

<400> SEQUENCE: 275
ctggatccaa cttataaatc agttataggg ggtttagcat gactccagat gggttgtgaa   60
atatgcatgt gagtgcaatc acattaggac acttgaagtt taatgttaaa ccacccacga  120
ttaagtcccg tatcgatgag taaagataac aatcatctga agtatttta taaaacgcac   180 gtttcaaagc atagaaattc                                              200

<210> SEQ ID NO 276
<211> LENGTH: 200
<212> TYPE: DNA
<213> ORGANISM: Glycine max

<400> SEQUENCE: 276
tgataggtga attaattatt tttaatatac gaatgaggaa gaaagaaaaa ctattataac   60
aatctgctaa gttggggccg aagttgaagt atcaagcgca cgagtgcctc tgtatagtga  120
aaaaagccca catcgagcag cttactaagt tgaagtaaac tctaggctat aaaatgagag  180
agctactcgt cagttcaacc                                              200

<210> SEQ ID NO 277
<211> LENGTH: 200
<212> TYPE: DNA
<213> ORGANISM: Glycine max

<400> SEQUENCE: 277
catgttgaga tgaaagatca agtattcgta ttgcattgat gagtcagatc attgactttg   60
gagatgctct acatagagaa gagaaagtga aggatcaagt gtcattcttt gtttctggcg  120
aaggtccaca tcgagccgca tactgaggga aagtgagctg cttgtactat aaatttcaaa  180
```

```
ggtgcatctg taaacaaatc                                                200

<210> SEQ ID NO 278
<211> LENGTH: 200
<212> TYPE: DNA
<213> ORGANISM: Glycine max

<400> SEQUENCE: 278
caagctagtt gtcccaagcc tgcatagagt gataacagca tgctaataac tcccaaagaa     60
cacagatgaa aaatcaagta tcaagtgtgt gggtgctaac atttcagatt ctgactaaat    120
aaagcccaca tcgaatggta tacttagagc tagtaagctg cttacgctat aaaatgaaag    180
gctcattgct attgatattc                                                200

<210> SEQ ID NO 279
<211> LENGTH: 200
<212> TYPE: DNA
<213> ORGANISM: Glycine max

<400> SEQUENCE: 279
aacaccatca gaagctatga agaagaacaa aaggctcctg gagatattcc attttttcatt    60 gattccctat cttcatgata ttaacagtgt gggagccttg cctgagttta catttctgac    120
caaagcccac atcgactggt attgtaatag caagtgaact ggttatacaa taaaaggaaa    180
gggctgttag ctcattactt                                                200

<210> SEQ ID NO 280
<211> LENGTH: 200
<212> TYPE: DNA
<213> ORGANISM: Glycine max

<400> SEQUENCE: 280
caacaataag ttggtacctt tagagaaaag acatgctttc tgtgtatagc attattagcg     60
cacagttgat agaaaatgaa gtattgtata tgggtatgat cgagtgtcta tttcttgagc    120
aaagcccaca ttgagtaata taccaaatag aagtgaactg cttatgctat aaaatggaag    180
agctgcattt agttttaagc                                                200

<210> SEQ ID NO 281
<211> LENGTH: 200
<212> TYPE: DNA
<213> ORGANISM: Glycine max

<400> SEQUENCE: 281
atgtgagatg aaaaatcaag tattcataat gggtggacga gactgtgaca acttcattca     60
ggggtattac aggtgactgg aaagaaagta ttaagtgtgc gggtgctaac ttttctgact    120
aaagtccaca tcgaagggta taccaagagc aagtaagcag cttatgctat aaaatgaaag    180
ggtcgtttgt tttgttactc                                                200

<210> SEQ ID NO 282
<211> LENGTH: 200
<212> TYPE: DNA
<213> ORGANISM: Glycine max

<400> SEQUENCE: 282
aaagatcaag tattcatatt gcattgatga gtgagaccat tgactttgta gatgctaccg     60
ttgatagaag agaaagtgaa ggatcaagta tggtcatttc tttgtttccg tcttctaacg    120
```

```
aaggtccaca tcgagccgta ttctgagtga gagtgagctg cttataatat aaaattcgaa      180
ggtgtttact tactaaaaca                                                  200
```

<210> SEQ ID NO 283
<211> LENGTH: 389
<212> TYPE: DNA
<213> ORGANISM: Glycine max

<400> SEQUENCE: 283

```
tagagagaat cgttaagaaa aaataaata gtaaagtaaa tgaaaaccca aataatatca       60
ttattatgtc aataagtcgg agaggatagt aatcaaatgg tctatgaggt ggtggttcat     120
tcaacatata gcacctattc attgttccta aaacataatt taagaacaaa aacttaaact    180
taaataataa taataaaaga gtacatcgaa gtatctgtgt tctctatcct tctgactaac    240
attcatgttg tttgtattca gcaaagggcc gtgcaggatt tgtgcgtcgc gctccggtta    300
gttattgcag tgaccgtctc tttagtccca catcgagtaa ttatgcttca tacagtctgt    360
ttatataaca gagatggaac aaactggtt                                       389
```

<210> SEQ ID NO 284
<211> LENGTH: 9
<212> TYPE: PRT
<213> ORGANISM: Artificial sequence
<220> FEATURE:
<223> OTHER INFORMATION: Synthetic peptide

<400> SEQUENCE: 284

```
Leu Ala Gly Leu Ile Asp Ala Asp Gly
1               5
```

<210> SEQ ID NO 285
<211> LENGTH: 28
<212> TYPE: DNA
<213> ORGANISM: Artificial sequence
<220> FEATURE:
<223> OTHER INFORMATION: consensus sequence
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 285

```
agctannatg ttntacaaat ttctncta                                         28
```

<210> SEQ ID NO 286
<211> LENGTH: 22
<212> TYPE: DNA
<213> ORGANISM: Artificial sequence
<220> FEATURE:
<223> OTHER INFORMATION: consensus sequence
<220> FEATURE:
<221> NAME/KEY: misc_feature
<222> LOCATION: (7)..(8)
<223> OTHER INFORMATION: n is a, c, g, or t

<400> SEQUENCE: 286

```
ctatttnntt ctatagcttt tt                                               22
```

```
<210> SEQ ID NO 287
<211> LENGTH: 16
<212> TYPE: DNA
<213> ORGANISM: Artificial sequence
<220> FEATURE:
<223> OTHER INFORMATION: consensus sequence
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 287
atccntctan gnacaa                                                    16

<210> SEQ ID NO 288
<211> LENGTH: 20
<212> TYPE: DNA
<213> ORGANISM: Artificial sequence
<220> FEATURE:
<223> OTHER INFORMATION: consensus sequence
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 288
naggacanag tgtcancnag                                                20

<210> SEQ ID NO 289
<211> LENGTH: 71
<212> TYPE: DNA
<213> ORGANISM: Artificial sequence
<220> FEATURE:
<223> OTHER INFORMATION: consensus sequence
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
```

<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t

<400> SEQUENCE: 289
gcgcgttgac cgtgcanant nannggntag ttcnacagaa ngncntagng gcgtgtgtga    60
tcnaaaaaca n                                                        71

<210> SEQ ID NO 290
<211> LENGTH: 53
<212> TYPE: DNA
<213> ORGANISM: Artificial sequence
<220> FEATURE:
<223> OTHER INFORMATION: consensus sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:

<221> NAME/KEY: misc_feature
<222> LOCATION: (49)..(49)
<223> OTHER INFORMATION: n is a, c, g, or t

<400> SEQUENCE: 290 cntnanggc ntngccnnaa gaaacatggg ccanggccca nnatncaang cac    53

<210> SEQ ID NO 291
<211> LENGTH: 48
<212> TYPE: DNA
<213> ORGANISM: Artificial sequence
<220> FEATURE:
<223> OTHER INFORMATION: consensus sequence
<220> FEATURE:
<221> NAME/KEY: misc_feature
<222> LOCATION: (4)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t

<400> SEQUENCE: 291
cgcnnncaag cccanatacc agttcgtngg tggagcaanc gaggcgct    48

<210> SEQ ID NO 292
<211> LENGTH: 187
<212> TYPE: DNA
<213> ORGANISM: Artificial sequence
<220> FEATURE:
<223> OTHER INFORMATION: consensus sequence
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(49)
<223> OTHER INFORMATION: n is a, c, g, or t

```
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t

<400> SEQUENCE: 292
aacagncaaa catttngtnc cacctngncc agncacnatt gcnnannnng gcttataagn      60
cganncgcaa cgcaccncac ngtctcttcg gagacatccg ataaaattgg aacgatacag     120
agaagattag catggcccct gcgcaaggat gacacgcaca aatcgagaaa tggtccaaat     180
tttttg                                                               187

<210> SEQ ID NO 293
<211> LENGTH: 24
<212> TYPE: DNA
<213> ORGANISM: Artificial sequence
<220> FEATURE:
<223> OTHER INFORMATION: blunt-end oligonucleotide

<400> SEQUENCE: 293
agaagtcctc aagtaccgtt tggc                                            24

<210> SEQ ID NO 294
<211> LENGTH: 14
<212> TYPE: DNA
<213> ORGANISM: Artificial sequence
<220> FEATURE:
<223> OTHER INFORMATION: blunt-end oligonucleotide

<400> SEQUENCE: 294
aagtcctcaa ggga                                                       14

<210> SEQ ID NO 295
<211> LENGTH: 14
<212> TYPE: DNA
<213> ORGANISM: Artificial sequence
<220> FEATURE:
<223> OTHER INFORMATION: blunt-end oligonucleotide

<400> SEQUENCE: 295
gctagtaccg tttg                                                       14
```

COMPOSITIONS AND METHODS FOR SITE DIRECTED GENOMIC MODIFICATION

CROSS REFERENCE TO RELATED APPLICATIONS

This application is a '371 National Stage application of PCT/US15/18104, filed Feb. 27, 2015, which claims the benefit of priority to U.S. Provisional Application Ser. No. 61/945,700, filed Feb. 27, 2014, the entire disclosures of which are incorporated herein by reference.

INCORPORATION OF SEQUENCE LISTING

The sequence listing that is contained in the file named "MONS350US-updated ST25.txt", which is 248 kilobytes (measured in MS-WINDOWS) and created on Sep. 26, 2017, is filed herewith by electronic submission and incorporated herein by reference.

BACKGROUND

Field

The disclosure relates to the field of biotechnology. More specifically, the disclosure provides a method of introducing recombinant blunt-end double-strand DNA fragments into the genome of a plant by introducing a double-strand break in the genome and novel plant promoters beneficial for the expression of, for instance, non-protein-coding small RNAs for CRISPR-mediated genome modification.

Description of Related Art

Site-specific recombination has potential for application across a wide range of biotechnology-related fields. Meganucleases, zinc finger nucleases (ZFNs), and transcription activator-like effector nucleases (TALENs) containing a DNA-binding domain and a DNA-cleavage domain enable genome modification. While meganucleases, ZFNs, and TALENs, are effective and specific, these technologies require generation through protein engineering of one or more components for each genomic site chosen for modification. Recent advances in application of clustered, regularly interspaced, short palindromic repeats (CRISPR) have illustrated a method of genome modification that may be as robust as the comparable systems (meganucleases, ZFNs, and TALENs), yet has the advantage of being quick to engineer.

The Clustered Regularly Interspersed Short Palindromic Repeats (CRISPRs) system constitutes an adaptive immune system in prokaryotes that targets endonucleolytic cleavage of invading phage. The system is composed of a protein component (Cas) and a guide RNA (gRNA) that targets the protein to a specific locus for endonucleolytic cleavage. This system has been successfully engineered to target specific loci for endonucleolytic cleavage of mammalian, zebrafish, drosophila, nematode, bacteria, yeast, and plant genomes.

SUMMARY

In one aspect the invention provides a recombinant DNA construct comprising a snRNA promoter selected from the group consisting of: a U6 promoter, a U3 promoter, a U2 promoter, a U5 promoter, and a 7SL promoter; operably linked to a sequence encoding a single-guide RNA (sgRNA), wherein the sequence of said snRNA promoter comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NOs:146-149, SEQ ID NOs:160-201, or SEQ ID NOs:247-283; or a fragment thereof, wherein the fragment is at least 140 bp in length. In one embodiment the sequence of said U6 promoter may comprise any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NOs:146-149, SEQ ID NOs:160-166, SEQ ID NOs:200-201, or SEQ ID NO:283, or a fragment thereof, wherein the fragment is at least 140 bp in length. In a further embodiment, the sequence of said U6 promoter may comprise SEQ ID NO:7. In another embodiment the sequence of said U6 promoter may comprise a sequence selected from the group consisting of: SEQ ID NO:17, SEQ ID NO:18, SEQ ID NO:19, and SEQ ID NO:20. In yet another embodiment the sequence of said U3 promoter may comprise any of SEQ ID NOs:167-171 or SEQ ID NOs:178-182, or a fragment thereof; wherein the fragment is at least 140 bp in length. In still yet another embodiment the sequence of said U2 promoter comprises any of SEQ ID NOs:183-187, SEQ ID NOs:192-199, or SEQ ID NOs:247-275, or a fragment thereof; wherein the fragment is at least 140 bp in length. In another embodiment the sequence of said U5 promoter comprises any of SEQ ID NOs:188-191, or SEQ ID NOs:276-282, or a fragment thereof; wherein the fragment is at least 140 bp in length. In a further embodiment the sequence of said 7SL promoter comprises any of SEQ ID NOs:172-177, or a fragment thereof; wherein the fragment is at least 140 bp in length. The recombinant DNA construct may further comprise a transcription termination sequence.

The recombinant DNA construct may also further comprise a sequence encoding a promoter operably linked to a sequence encoding a clustered, regularly interspaced, short palindromic repeats (CRISPR)-associated Cas endonuclease gene product. In certain embodiments of the recombinant DNA construct, the Cas endonuclease gene product may be further operably linked to a nuclear localization sequence (NLS). Further, in certain embodiments of the contemplated recombinant DNA construct, the sequence encoding said Cas endonuclease may be selected from the group consisting of SEQ ID NO:27, SEQ ID NO:68, and SEQ ID NO:97, SEQ ID NO:119, and SEQ ID NO:136.

Another aspect of the invention provides a recombinant DNA construct comprising a snRNA promoter selected from the group consisting of: a U6 promoter, a U3 promoter, a U2 promoter, a U5 promoter, and a 7SL promoter; operably linked to a sequence specifying a non-coding RNA, wherein the sequence of said snRNA promoter comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NOs:146-149, SEQ ID NOs:160-201 or SEQ ID NOs:247-283, or a fragment thereof, wherein the fragment is at least 140 bp in length. In some embodiments the non-coding RNA is selected from the group consisting of: a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), and a naturally occurring antisense siRNA (nat-siRNA).

Certain embodiments if the invention further comprise such a recombinant DNA construct, wherein the sequence of said U3 promoter comprises any of SEQ ID NOs:167-171 and SEQ ID NOs:178-182, or a fragment thereof; wherein the fragment is at least 140 bp in length. In another embodiment of the recombinant DNA construct, the sequence of said U2 promoter comprises any of SEQ ID NOs:183-187, SEQ ID NOs:192-199, or SEQ ID NOs:247-275, or a fragment thereof; wherein the fragment is at least 140 bp in length. In yet another embodiment of the recombinant DNA construct, the sequence of said U5 promoter comprises any of SEQ ID NOs:188-191, or SEQ ID NOs:276-282, or a fragment thereof; wherein the fragment is at least 140 bp in length. Still further, the invention provides an embodiment wherein the sequence of said U6 promoter may comprise any of SEQ ID NOs:1-20, SEQ ID NOs:146-149, SEQ ID NOs:160-166, SEQ ID NOs:200-201, or SEQ ID NO:283, or a fragment thereof; wherein the fragment is at least 140 bp in length. Another embodiment comprises the recombinant DNA construct wherein the sequence of said 7SL promoter comprises any of SEQ ID NOs:172-177, or a fragment thereof; wherein the fragment is at least 140 bp in length.

Another aspect of the invention provides a cell comprising a recombinant DNA construct as described above. In certain embodiments the cell is a plant cell.

The invention further provides a method of introducing a double-strand break in the genome of a cell, comprising introducing in said cell: a) at least one recombinant DNA construct of claim 1; and b) a second recombinant DNA construct comprising a sequence encoding a promoter operably linked to a sequence encoding a clustered, regularly interspaced, short palindromic repeats (CRISPR)-associated Cas endonuclease gene product operably linked to a nuclear localization sequence (NLS). In one embodiment of such a method, the sequence of the U6 promoter comprises SEQ ID NO:7. In another embodiment of the method, the U6 promoter comprises a sequence selected from the group consisting of: SEQ ID NO:17, SEQ ID NO:18, SEQ ID NO:19, and SEQ ID NO:20. In yet another embodiment of the method, the sequence encoding said Cas endonuclease is selected from the group consisting of SEQ ID NO:27, SEQ ID NO:68, and SEQ ID NO:97, SEQ ID NO:119, and SEQ ID NO:136.

The invention further provides a method of introducing a double-strand break in the genome of a cell, comprising introducing to said cell at least one recombinant DNA construct which comprises a recombinant DNA construct comprising a snRNA promoter selected from the group consisting of: a U6 promoter, a U3 promoter, a U2 promoter, a U5 promoter, and a 7SL promoter; operably linked to a sequence encoding a single-guide RNA (sgRNA), wherein the sequence of said snRNA promoter comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NOs:146-149, SEQ ID NOs:160-201, or SEQ ID NOs:247-283; or a fragment thereof, wherein the fragment is at least 140 bp in length, and also further comprises a sequence encoding a promoter operably linked to a sequence encoding a clustered, regularly interspaced, short palindromic repeats (CRISPR)-associated Cas endonuclease gene product.

In certain embodiments of the method, the sequence of said U6 promoter comprises SEQ ID NO:7. In other embodiments the U6 promoter comprises a sequence selected from the group consisting of: SEQ ID NO:17, SEQ ID NO:18, SEQ ID NO:19, and SEQ ID NO:20. In some embodiments of the method the sequence encoding the Cas endonuclease is selected from the group consisting of SEQ ID NO:27, SEQ ID NO:68, and SEQ ID NO:97, SEQ ID NO:119, and SEQ ID NO:136.

Another aspect of the invention provides a method of genome modification comprising: a) introducing a double-strand break at a selected site in the genome of a plant cell, and b) introducing into said plant cell a recombinant blunt-end double-strand DNA fragment, wherein said recombinant blunt-end double-strand DNA fragment is incorporated into said double strand break by endogenous DNA repair. The method may comprise genome modification such as production of a modified linkage block, linking two or more QTLs, disrupting linkage of two or more QTLs, gene insertion, gene replacement, gene conversion, deleting or disrupting a gene, transgenic event selection, transgenic trait donor selection, transgene replacement, or targeted insertion of at least one nucleic acid of interest. In some embodiments of the method the double stranded break is introduced by an endonuclease. In certain embodiments the endonuclease may be selected from the group consisting of: a TALEN endonuclease; a CRISPR endonuclease; a meganuclease comprising a "LAGLIDADG," (SEQ ID NO:284) "GIY-YIG," "His-Cys box," or HNH sequence motif; and a Zinc finger nuclease. In particular embodiments the endonuclease is a TALEN endonuclease and TALEN expression constructs are introduced into the plant cell, wherein about 0.1 pmol of each TALEN expression construct is introduced into the plant cell.

Further, in the method the plant cell may be a protoplast or may have been, or is being, grown in a plant cell culture. In certain embodiments of the method the plant cell is selected from the group consisting of: a soybean plant cell; a corn plant cell; a rice plant cell; a wheat plant cell; a turfgrass plant cell; a cotton plant cell; and a canola plant cell. In other embodiments of the method the recombinant blunt-end double-strand DNA fragment does not comprise a region of homology to the selected site in the genome.

Embodiments of the method are contemplated wherein about 0.03 to about 0.3 fmol of recombinant blunt-end double-strand DNA fragment is introduced into said plant cell. In particular embodiments about 0.15 fmol of recombinant blunt-end double-strand DNA fragment is introduced into said plant cell. Further, the blunt-end double-strand DNA fragment may comprise on the 5' end, or the 3' end, or both the 5' and 3' ends, a region with microhomology to a sequence comprising one or both ends of said double-strand break in the genome. Some embodiments comprise a method wherein the region of microhomology is selected from a sequence 1 bp, 2 bp, 3 bp, 4, bp, 5 bp, 6 bp, 7 bp, 8 bp, 9 bp, or 10 bp in length. In a particular embodiment of the method the region of microhomology is 3 bp in length.

The method may comprise introduction of a double-strand break in step a) as described above, by providing said cell with an endonuclease designed to target a selected target site in the genome of said cell. Further, the endonuclease may be provided by at least one recombinant DNA construct encoding the endonuclease. In an embodiment, the endonuclease is provided by delivering an mRNA encoding the endonuclease or the endonuclease to the plant cell. In particular embodiments The endonuclease is selected from the group consisting of: a TALEN endonuclease; a Zinc finger endonuclease; a meganuclease; and a CRISPR endonuclease. Additional embodiments may comprise introduction of a double-strand break in step a) by providing said cell with a recombinant DNA construct encoding a promoter operably linked to a sequence encoding a clustered, regularly interspaced, short palindromic repeats (CRISPR)-associated Cas endonuclease gene product and a recombinant DNA construct comprising a U6, U3, U2, U5, or 7SL promoter operably linked to a sequence encoding a single-guide RNA (sgRNA) designed to target a selected target site in the chromosome of said cell. In particular embodiments the Cas endonuclease gene product may be further operably linked to at least one nuclear localization sequence (NLS).

In certain embodiments of the method the sequence of said U6, U3, U2, U5, or 7SL promoter may comprise SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NOs:146-149, SEQ ID NOs:160-201 or SEQ ID NOs:247-283, or a fragment thereof; wherein the fragment is at least 140 bp in length and comprises a transcription termination sequence. In particular embodiments the U6 promoter may comprise a sequence selected from the group consisting of: SEQ ID NOs:1-20, SEQ ID NOs:146-149, SEQ ID NOs:160-166, SEQ ID NOs:200-201, and SEQ ID NO:283, or a fragment thereof; wherein the fragment is at least 140 bp in length comprising a transcription termination sequence. In alternative embodiments the U6 promoter may comprise a sequence selected from the group consisting of: SEQ ID NO:17, SEQ ID NO:18, SEQ ID NO:19, and SEQ ID NO:20. In further embodiments the sequence of said U3 promoter may comprise any of SEQ ID NOs:167-171 or SEQ ID NOs:178-182, or a fragment thereof; wherein the fragment is at least 140 bp in length. In still further embodiments the sequence of said U5 promoter comprises any of SEQ ID NOs:188-191, or SEQ ID NOs:276-282, or a fragment thereof; wherein the fragment is at least 140 bp in length. Additionally, the sequence of said U2 promoter may comprise any of SEQ ID NOs:183-187, SEQ ID NOs:192-199, or SEQ ID NOs:247-275, or a fragment thereof; wherein the fragment is at least 140 bp in length. In yet other embodiments the sequence of said 7SL promoter comprises any of SEQ ID NOs:172-177, or a fragment thereof, wherein the fragment is at least 140 bp in length.

Embodiments are also contemplated wherein the recombinant DNA construct encoding a promoter operably linked to a sequence encoding a clustered, regularly interspaced, short palindromic repeats (CRISPR)-associated Cas endonuclease gene product, and the recombinant DNA construct comprising a U6, U3, U2, U5, or 7SL promoter operably linked to a sequence encoding a single-guide RNA (sgRNA) is designed to target a selected target site in the chromosome of said cell, are on the same construct. Other embodiments of the method may comprise use of a recombinant DNA construct encoding a promoter operably linked to a sequence encoding a clustered, regularly interspaced, short palindromic repeats (CRISPR)-associated Cas endonuclease gene product and the recombinant DNA construct comprising a U6, U3, U2, U5, or 7SL promoter is operably linked to a sequence encoding a single-guide RNA (sgRNA) designed to target a selected target site in the chromosome of said cell are on at least two constructs.

A further aspect of the invention comprises a plant cell comprising a targeted recombinant sited-directed integration of a blunt-end double-strand DNA fragment. Further provided are a plant, plant part, or plant seed comprising a targeted recombinant sited-directed integration of a blunt-end double-strand DNA fragment.

A still further aspect of the invention comprises: a method of genome modification comprising: a) introducing a double-strand break in the genome of a plant cell by introducing a double-strand break in the genome of a cell, comprising introducing in said cell: a) at least one recombinant DNA construct of claim 1; and b) a second recombinant DNA construct comprising a sequence encoding a promoter operably linked to a sequence encoding a clustered, regularly interspaced, short palindromic repeats (CRISPR)-associated Cas endonuclease gene product operably linked to a nuclear localization sequence (NLS); and b) introducing into said plant cell a recombinant blunt-end double-strand DNA fragment, wherein said recombinant blunt-end double-strand DNA fragment is incorporated into said double strand break by endogenous DNA repair.

A further aspect of the invention comprises a method of genome modification comprising: a) introducing a double-strand break in the genome of a plant cell as described above, and b) introducing into said plant cell a recombinant blunt-end double-strand DNA fragment, wherein said recombinant blunt-end double-strand DNA fragment is incorporated into said double strand break by endogenous DNA repair.

Yet another aspect of the invention comprises a recombinant DNA construct comprising at least a first expression cassette comprising a U6, U3, U2, U5, or 7SL promoter operably linked to a sequence encoding a single-guide RNA (sgRNA), wherein the sequence of said promoter comprises any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NOs:146-149, SEQ ID NOs:160-201, or SEQ ID NOs:247-283, or a fragment thereof; wherein the fragment is at least 140 bp in length. In certain embodiments the recombinant DNA construct further comprises at least a second expression cassette, wherein the sequence encoding the first sgRNA is distinct from the sequence encoding the second sgRNA. The recombinant DNA construct may also comprise a construct wherein the promoter operably linked to the sequence encoding the first sgRNA is distinct from the promoter operably linked to the sequence encoding the second sgRNA. In certain embodiments the construct comprises flanking left and right homology arms (HA) which are each about 200-1200 bp in length. In particular embodiments the homology arms are about 230 to about 1003 bp in length.

Another aspect of the invention provides a method of quantifying the activity of a nuclease by detecting integrated DNA fragments by determining the rate of homologous recombination (HR) mediated targeted integration by use of using digital PCR or quantitative PCR.

Yet another aspect of the invention comprises a recombinant DNA construct comprising: a) a first snRNA promoter selected from the group consisting of: a U6 promoter, a U3 promoter, a U2 promoter, a U5 promoter, and a 7SL promoter; operably linked to a sequence encoding a non-coding RNA, and b) a second snRNA promoter selected from the group consisting of: a U6 promoter, a U3 promoter, a U2 promoter, a U5 promoter, and a 7SL promoter; operably linked to a sequence encoding a non-coding RNA, wherein the first snRNA promoter and the second snRNA promoter are different. In certain embodiments the sequence encoding the first snRNA promoter and the sequence encoding the second snRNA promoter each comprise SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NOs:146-149, SEQ ID NOs:160-201, or SEQ ID NOs:247-283, or a fragment thereof; wherein the fragment is at least 140 bp in length. Further, a recombinant DNA construct, wherein the first and second snRNA promoter are U6 promoters and the sequences encoding the first and second snRNA promoters are each selected from the group consisting of: SEQ ID NOs:1-8, SEQ ID NOs:17-20, and SEQ ID NOs:200-201 is also provided in certain embodiments.

Thus, a recombinant DNA construct wherein the first and second snRNA promoter are U6 promoters and the sequences encoding the first and second snRNA promoters are each selected from the group consisting of: SEQ ID NOs:12-16, SEQ ID NOs:160-166, and SEQ ID NO:283, is also provided. Alternatively, a recombinant DNA construct, wherein the first and second snRNA promoter are U6 promoters and the sequences encoding the first and second snRNA promoters are each selected from the group consisting of: SEQ ID NOs:9-11 and SEQ ID NO:146-149, is provided.

A recombinant DNA construct, wherein the first and second snRNA promoter are U2 promoters and the sequences encoding the first and second snRNA promoters are each selected from the group consisting of SEQ ID NOs:183-187 and SEQ ID NOs:192-199 is also contemplated. Additionally, certain embodiments of the invention comprise a recombinant DNA construct wherein the first and second snRNA promoter are U2 promoters and the sequences encoding the first and second snRNA promoters are each selected from the group consisting of SEQ ID NOs:247-275.

Yet other embodiments comprise a recombinant DNA construct, wherein the first and second snRNA promoter are U3 promoters and the sequences encoding the first and second snRNA promoters are each selected from the group consisting of SEQ ID NOs:178-182. Still other embodiments of the invention comprise a recombinant DNA construct, wherein the first and second snRNA promoter are U3 promoters and the sequences encoding the first and second snRNA promoters are each selected from the group consisting of SEQ ID NOs:167-171.

Alternatively, the recombinant DNA construct may comprise first and second snRNA promoter which are U5 promoters and wherein the sequences encoding the first and second snRNA promoters are each selected from the group consisting of SEQ ID NOs:188-191. Alternatively provided are recombinant DNA constructs wherein the first and second snRNA promoter are U5 promoters and the sequences encoding the first and second snRNA promoters are each selected from the group consisting of SEQ ID NOs:276-282.

Certain embodiments of the invention provide a recombinant DNA construct wherein the first and second snRNA promoter are 7SL promoters and the sequences encoding the first and second snRNA promoters are each selected from the group consisting of SEQ ID NOs:175-177. In other embodiments the recombinant DNA construct wherein the first and second snRNA promoter are 7SL promoters and the sequences encoding the first and second snRNA promoters are each selected from the group consisting of SEQ ID NOs:172-174.

Also contemplated are embodiments wherein the recombinant DNA construct comprises a first snRNA promoter which is a U6 promoter and a second snRNA promoter is also present and is selected from the group consisting of: a U3 promoter, a U2 promoter, a U5 promoter, and a 7SL promoter. Other embodiments include a recombinant DNA construct wherein the first snRNA promoter is a U3 promoter and the second snRNA promoter is selected from the group consisting of: a U6 promoter, a U2 promoter, a U5 promoter, and a 7SL promoter. Alternatively in the recombinant DNA construct, the first snRNA promoter is a U2 promoter and the second snRNA promoter may be selected from the group consisting of: a U6 promoter, a U3 promoter, a U5 promoter, and a 7SL promoter; or the first snRNA promoter is a U5 promoter and the second snRNA promoter is selected from the group consisting of: a U6 promoter, a U2 promoter, a U3 promoter, and a 7SL promoter. Further, the recombinant DNA construct may comprise a first snRNA promoter which is a 7SL promoter and the second snRNA promoter may be selected from the group consisting of: a U6 promoter, a U2 promoter, a U3 promoter, and a U5 promoter.

Other contemplated embodiments of the invention include a recombinant DNA construct as described above, wherein the sequences encoding the first and second snRNA promoters are each selected from the group consisting of: SEQ ID NOs:1-8, SEQ ID NOs:17-20, SEQ ID NOs:200-201, SEQ ID NOs:183-187, SEQ ID NOs:192-199, SEQ ID NOs:178-182, SEQ ID NOs:188-191, and SEQ ID NOs:175-177. In certain embodiments of the recombinant DNA construct, the sequences encoding the first and second snRNA promoters are each selected from the group consisting of: SEQ ID NOs:12-16, SEQ ID NOs:160-166, SEQ ID NO:283, SEQ ID NOs:247-275, SEQ ID NOs:167-171, SEQ ID NOs:276-282, and SEQ ID NOs:172-174.

The recombinant DNA construct may further comprise a sequence specifying one or more additional snRNA promoters selected from the group consisting of: a U6 promoter, a U3 promoter, a U2 promoter, a U5 promoter, and a 7SL promoter; operably linked to a sequence encoding a non-coding RNA, wherein the first snRNA promoter, the second snRNA promoter, and each of the one or more additional snRNA promoters are different. In particular embodiments of the recombinant DNA construct, the sequence specifying said one or more additional snRNA promoters is selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NOs:146-149, SEQ ID NOs:160-201, or SEQ ID NOs:247-283; or a fragment thereof, wherein the fragment is at least 140 bp in length. Further, the recombinant DNA construct may comprise 3, 4, 5, 6, 7, 8, 9 or 10 snRNA promoters.

In some embodiments of the recombinant DNA construct, the non-coding RNAs are sgRNAs targeting different selected target sites in a chromosome of a plant cell. The recombinant DNA constructs may further comprise a sequence encoding a promoter operably linked to a sequence encoding a clustered, regularly interspaced, short palindromic repeats (CRISPR)-associated Cas endonuclease gene product.

Yet another aspect of the invention provides a method of genome modification comprising: a) introducing double-strand breaks at two or more selected sites in the genome of a plant cell by providing said cell with a clustered, regularly interspaced, short palindromic repeats (CRISPR)-associated Cas endonuclease and a recombinant DNA construct wherein the non-coding RNAs are sgRNAs targeting different selected target sites in a chromosome of a plant cell, and b) introducing into said plant cell one or more exogenous double-strand DNA fragment; wherein said exogenous double-strand DNA fragments are incorporated into said double strand breaks by endogenous DNA repair. In some embodiments said one or more exogenous double-strand DNA fragments are blunt-ended. In certain embodiments of the method, said one or more exogenous double-strand DNA fragments comprise a region of homology to a selected site in the genome. In other embodiments the exogenous double-strand DNA fragments comprise regions of homology to different selected sites in the genome.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 1A) and (FIG. 1B) The sequence consensus, and (SEQ ID NOs:285-292) percent conservation are presented below the alignments. (FIG. 1B) The thick arrow indicates the transcription start site; upstream from the transcriptional start site are a 'TATA Box', an Upstream Sequence Element (USE), and Monocot-Specific Promoter (MSP) elements, each marked with heavy lined boxes; the stretch of seven thymidine bases (poly-T) at the 3' end is the transcription termination signal. The sequences in FIG. 1.A and FIG. 1.B correspond the following: ZmU6_Ch1 represented by SEQ ID NO:98; ZmU6_Ch2 represented by SEQ ID NO:99; ZmU6_Ch3 represented by SEQ ID NO:100; ZmU6_Ch8 represented by SEQ ID NO:101.

(FIG. 5B) blunt-end oligonucleotide without microhomology used for insertion at a corn genomic target site (SEQ ID NO:293 pre-insertion and SEQ ID NOs:294 and 295 after insertion; (FIG. 5C) blunt-end oligonucleotide with microhomology ends used for insertion at a corn genomic target site (SEQ ID NO:293 pre-insertion and SEQ ID NOs:294 and 295 after insertion; (FIG. 5D) fragment analysis profile of PCR amplicons spanning the oligo-chromosome junction in test (upper panel) and negative control samples (bottom panel) of the oligonucleotide integration assay (where the arrow indicates the expected peak); and (FIG. 5E) DNA sequences of oligonucleotide-chromosome junctions (SEQ ID NOs:294 and 295) at the Zm_L70c corn genomic target site confirming integrations of both full-length (integration 1; SEQ ID NO:103) and truncated oligonucleotides (integration 2; SEQ ID NO:104), the expected sequence (template) is presented as SEQ ID NO:102.

FIG. 17. 17A. Schematic of PCR screening strategy to detect CRISPR/Cas9 induced mutation by NHEJ at tomato invertase inhibitor target site 2 (TS2), resulting in mutation of restriction endonuclease site SmlI. 17B. Photograph of PCR amplicons run on an agarose gel showing undigested amplicons and SmlI digested amplicons to detect CRISPR/Cas9 induced mutation at tomato invertase inhibitor target site 2. 17C. Multiple sequence alignment of sequences of PCR amplicons from CRISPR/Cas9 induced mutation by NHEJ at the tomato invertase inhibitor target site 2.

DETAILED DESCRIPTION

Figures 1, 1A:
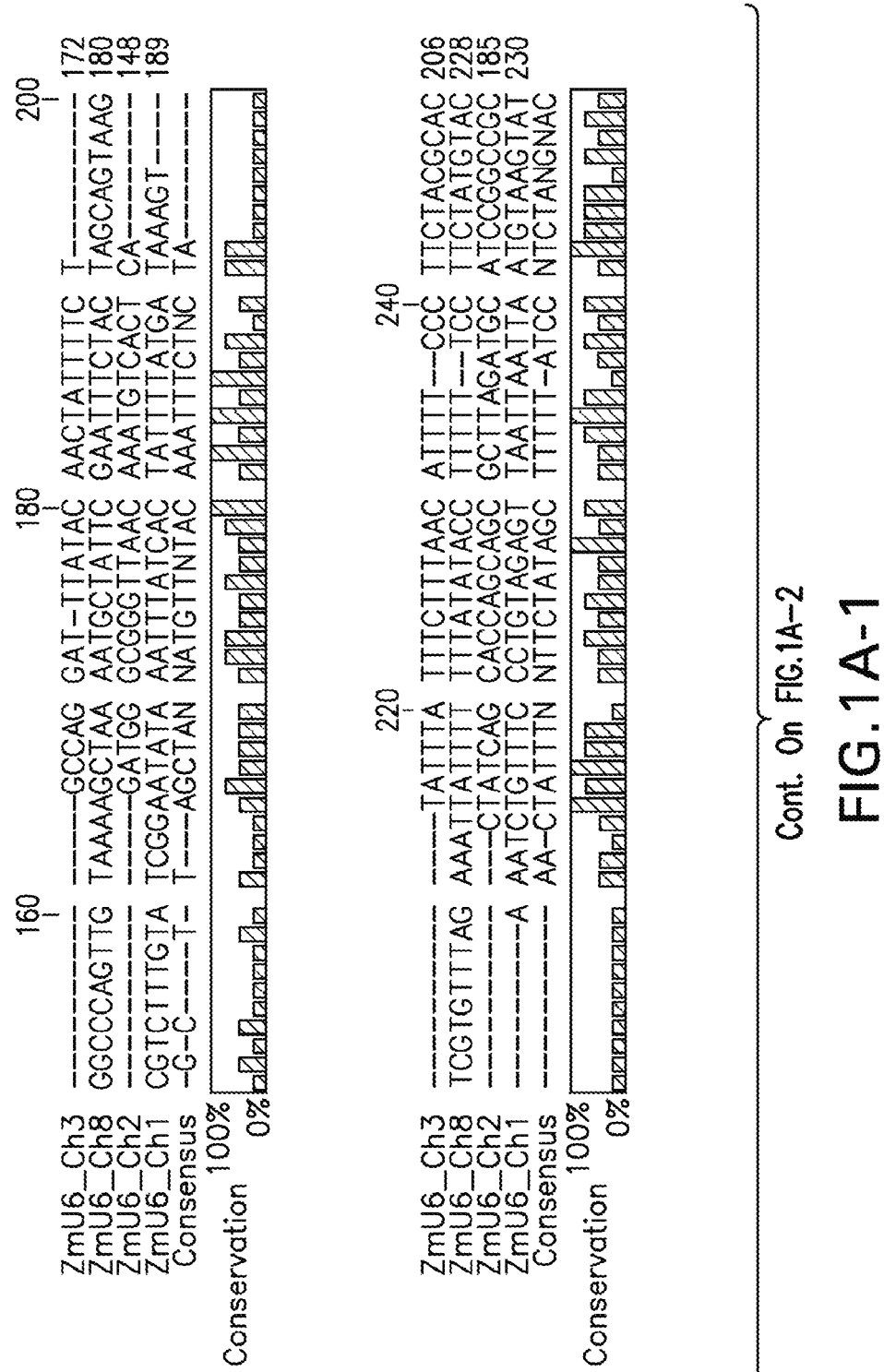
FIG. 1A-1B: Nucleotide sequence alignment of four native corn U6 small nuclear RNA (snRNA) genes, including their putative promoters from chromosomes 1, 2, 3, and 8.

The disclosure provides novel promoters from *Zea mays* and other plants, and methods for their use that include targeted gene modification of a plant genome using transgenic expression of a gene, or genes, involved in the Clustered Regularly Interspersed Short Palindromic Repeats (CRISPR) system found in many bacteria. For instance, the disclosure provides, in one embodiment, DNA constructs encoding at least one expression cassette including a U6 promoter disclosed herein and a sequence encoding a single-guide RNA (sgRNA). Methods for causing a CRISPR system to modify a target genome are also provided, as are the genomic complements of a plant modified by the use of such a system. The disclosure thus provides tools and methods that allow one to insert, remove, or modify genes, loci, linkage blocks, and chromosomes within a plant. Also disclosed are U3, U2, U5 and 7SL promoters and methods for their use that include targeted gene modification of a plant genome.

The disclosure provides, in another embodiment, DNA constructs encoding at least one expression cassette including a promoter disclosed herein and a sequence encoding a non-protein-coding small RNA (npcRNA). These constructs are useful for targeting nuclear expression of the npcRNA molecules.

The CRISPR system constitutes an adaptive immune system in prokaryotes that targets endonucleolytic cleavage of the DNA and RNA of invading phage (reviewed in Westra et al., *Annu Rev Genet*, 46:311-39, 2012). There are three known types of CRISPR systems, Type I, Type II, and Type III. The CRISPR systems rely on small RNAs for sequence-specific detection and targeting of foreign nucleic acids for destruction. The components of the bacterial CRISPR systems are CRISPR-associated (Cas) genes and CRISPR array(s) consisting of genome-target sequences (protospacers) interspersed with short palindromic repeats. Transcription of the protospacer/repeat elements into precursor CRISPR RNA (pre-crRNA) molecules is followed by enzymatic cleavage triggered by hybridization between a trans-acting CRISPR RNA (tracrRNA) molecule and a pre-crRNA palindromic repeat. The resulting crRNA:tracrRNA molecules, consisting of one copy of the spacer and one repeat, complex with a Cas nuclease. The CRISPR/Cas complex is then directed to DNA sequences (protospacer) complementary to the crRNA spacer sequence, where this RNA-Cas protein complex silences the target DNA through enzymatic cleavage of both strands (double-strand break; DSB).

The native bacterial type II CRISPR system requires four molecular components for targeted cleavage of exogenous DNAs: a Cas endonuclease (e.g., Cas9), the house-keeping RNaselll, CRISPR RNA (crRNA) and trans-acting CRISPR RNA (tracrRNA). The latter two components form a dsRNA complex and bind to Cas9 resulting in an RNA-guided DNA endonuclease complex. For targeted genome modifications in eukaryotes, this system was simplified to two components: the Cas9 endonuclease and a chimeric crRNA-tracrRNA, called guide-RNA (gRNA) or, alternatively, single-guide RNA (sgRNA). Experiments initially conducted in eukaryotic systems determined that the RNaseIII component was not necessary to achieve targeted DNA cleavage. The minimal two component system of Cas9 with the sgRNA, as the only unique component, enables this CRISPR system of targeted genome modification to be more cost effective and flexible than other targeting platforms such as meganucleases, Zn-finger nucleases, or TALE-nucleases which require protein engineering for modification at each targeted DNA site. Additionally, the ease of design and production of sgRNAs provides the CRISPR system with several advantages for application of targeted genome modification. For example, the CRISPR/Cas complex components (Cas endonuclease, sgRNA, and, optionally, exogenous DNA for integration into the genome) designed for one or more genomic target sites can be multiplexed in one transformation, or the introduction of the CRISPR/Cas complex components can be spatially and/or temporally separated.

Expression Strategies for sgRNAs

The disclosure provides, in certain embodiments, novel combinations of promoters and a sequence encoding a sgRNA, to allow for specifically introducing a double-stranded DNA cleavage event into endogenous DNA (i.e., a genome). In one embodiment, a U6 promoter from corn is operably linked to a sgRNA-encoding gene, in order to constitutively express the sgRNA in transformed cells. This may be desirable, for example, when the resulting sgRNA transcripts are retained in the nucleus and will thus be optimally located within the cell to guide nuclear processes. This may also be desirable, for example, when the activity of the CRISPR is low or the frequency of finding and cleaving the target site is low. It may also be desirable when a promoter for a specific cell type, such as the germ line, is not known for a given species of interest. In another embodiment, a U3, U2, U5, or 7SL promoter is operably linked to a sgRNA-encoding gene, for expression of an sgRNA in transformed cells.

In another embodiment, a chimeric promoter comprising all or a portion of any of the U6 promoters provided herein can be used to express a sgRNA. Alternatively, a U3, U2, U5, or 7SL chimeric promoter comprising all or a portion of any of these promoters, may be utilized. For example, the 5' portion of the U6 promoter from corn chromosome 1 (SEQ ID NO:1), including one MSP element, operably linked to the 3' portion of the U6 promoter from corn chromosome 8 (SEQ ID NO:7), including a USE element and a TATA box (SEQ ID NO:17), cloned upstream of a sgRNA, may be used to induce CRISPR-mediated cleavage under different environmental conditions.

Multiple U6 promoters with differing sequence may be utilized to minimize problems in vector stability, which is typically associated with sequence repeats. Further, highly repetitive regions in chromosomes may lead to genetic instability and silencing. Therefore, use of multiple U6 (or other disclosed) promoters in the CRISPR/Cas system of targeted gene modification may facilitate vector stacking of multiple sgRNA cassettes in the same transformation construct, wherein the differing sgRNA transcript levels are to be optimized for efficient targeting of a single target site.

Chimeric U6 promoters can result in new, functional versions with improved or otherwise modified expression levels, and four representative chimeric corn U6 promoters have been designed (SEQ ID NO:17, SEQ ID NO:18, SEQ ID NO:19, and SEQ ID NO:20).

The disclosed U6 promoters may also drive expression of other non-protein-coding RNA (npcRNA). Non-limiting examples of non-protein-coding small RNA include a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), and a naturally occurring antisense siRNA (nat-siRNA).

Promoters and transcriptional elements for additional small nuclear RNA (snRNA) genes, similar to U6 promoters and which may be transcribed by RNA polymerase II or RNA polymerase III, can also be identified, such as U3, U2, U5, and 7SL promoters. These alternate promoters can be useful in cassette design, especially where these additional elements may facilitate nuclear retention of the CRISPR system transcripts. Additional gene transcription elements that can be useful in CRISPR cassette design include intron-embedded elements and transcriptional elements of plant specific RNA polymerase IV and V promoters.

Expression Strategies for Cas-Associated Genes

The disclosure provides novel promoters for use in sequence-specific or sequence-directed CRISPR-mediated cleavage for molecular breeding by providing transcription of, for example, a sgRNA including a spacer sequence used to target a protospacer sequence within a genomic target site for endonuclease cleavage by at least one Cas protein, wherein the genomic target site is native or transgenic. In addition, CRISPR systems can be customized to catalyze cleavage at one or more genomic target sites. In certain embodiments, such a custom CRISPR system would have properties making it amenable to genetic modification such that the system's Cas endonuclease protein(s) recognition, binding and/or catalytic activity could be manipulated.

One aspect of this disclosure is to introduce into a plant cell an expression vector comprising one or more cassettes encoding a U6 corn promoter, or other disclosed promoter such as an U3, U2, U5 or 7SL promoter, operably linked to a sgRNA, including a copy of a spacer sequence complementary to a protospacer sequence within a genomic target site, and an expression vector encoding a Cas-associated gene to modify the plant cell in such a way that the plant cell, or a plant comprised of such cells, will subsequently exhibit a beneficial trait. In one non-limiting example, the trait is a trait such as improved yield, resistance to biotic or abiotic stress, herbicide tolerance, or other improvements in agronomic performance. The ability to generate such a plant cell derived therefrom depends on introducing the CRISPR system using transformation vectors and cassettes described herein.

The expression vector encoding a Cas-associated gene may comprise a promoter. In certain embodiments, the promoter is a constitutive promoter, a tissue specific promoter, a developmentally regulated promoter, or a cell cycle regulated promoter. Certain contemplated promoters include ones that only express in the germline or reproductive cells, among others. Such developmentally regulated promoters have the advantage of limiting the expression of the CRISPR system to only those cells in which DNA is inherited in subsequent generations. Therefore, a CRISPR-mediated genetic modification (i.e., chromosomal or episomal dsDNA cleavage) is limited only to cells that are involved in transmitting their genome from one generation to the next. This might be useful if broader expression of the CRISPR system were genotoxic or had other unwanted effects. Examples of such promoters include the promoters of genes encoding DNA ligases, recombinases, replicases, and so on.

Endonucleases are enzymes that cleave the phosphodiester bond within a polynucleotide chain. Examples of endonucleases that cleave only at specific nucleotide sequences are well known in the art and can include, for instance, restriction endonucleases. However, the need for targeted genome engineering as an alternative to classical plant breeding requires highly customizable tools for genome editing. The CRISPR-associated type II prokaryotic adaptive immune system provides such an alternative. As such, the DNA constructs provided herein can recognize a specific nucleotide sequence of interest within a target host genome and allow for mutation or integration at that site. In a particular embodiment, the DNA constructs contain one or more corn U6 promoter, or chimeras thereof, that express high levels of a sequence encoding a sgRNA. A DNA construct that expresses a sgRNA that targets a Cas-associated gene product with endonuclease activity to a specific genomic sequence, such that the specific genomic sequence is cleaved and produces a double-stranded break which is repaired by a double strand break repair pathway, which may include, for example, non-homologous end-joining, homologous recombination, synthesis-dependent strand annealing (SDSA), single-strand annealing (SSA), or a combination thereof thereby disrupting the native locus, may be particularly useful.

In one embodiment, a CRISPR system comprises at least one Cas-associated gene encoding a CRISPR endonuclease and one sgRNA comprising a copy of a spacer sequence complementary to a protospacer sequence within an endogenous genomic target site.

In particular embodiments, a Cas-associated gene can include any type II CRISPR system endonuclease. Such a Cas-associated gene product would have properties making it amenable to genetic modification such that its nuclease activity and its recognition and binding of crRNA, tracrRNA, and/or sgRNA could be manipulated.

The present disclosure also provides for use of CRISPR-mediated double-stranded DNA cleavage to genetically alter expression and/or activity of a gene or gene product of interest in a tissue- or cell-type specific manner to improve productivity or provide another beneficial trait, wherein the nucleic acid of interest may be endogenous or transgenic in nature. Thus, in one embodiment, a CRISPR system is engineered to mediate disruption at specific sites in a gene of interest. Genes of interest include those for which altered expression level/protein activity is desired. These DNA cleavage events can be either in coding sequences or in regulatory elements within the gene.

This disclosure provides for the introduction of a type II CRISPR system into a cell. Exemplary type II Cas-associated genes include natural and engineered (i.e., modified, including codon-optimized) nucleotide sequences encoding polypeptides with nuclease activity such as Cas9 from *Streptococcus pyogenes, Streptococcus thermophilus,* or *Bradyrhizobium* sp.

The catalytically active CRISPR-associate gene (e.g., Cas9 endonuclease) can be introduced into, or produced by, a target cell. Various methods may be used to carry this out, as disclosed herein.

Transient Expression of CRISPRs

In some embodiments, the sgRNA and/or Cas-associated gene is transiently introduced into a cell. In certain embodiments, the introduced sgRNA and/or Cas-associated gene is provided in sufficient quantity to modify the cell but does not persist after a contemplated period of time has passed or after one or more cell divisions. In such embodiments, no further steps are needed to remove or segregate the sgRNA and/or Cas-associated gene from the modified cell. In yet other embodiments of this disclosure, double-stranded DNA fragments are also transiently introduced into a cell along with sgRNA and/or Cas-associated gene. In such embodiments, the introduced double-stranded DNA fragments are provided in sufficient quantity to modify the cell but do not persist after a contemplated period of time has passed or after one or more cell divisions.

In another embodiment, mRNA encoding the Cas-associated gene is introduced into a cell. In such embodiments, the mRNA is translated to produce the type II CRISPR system endonuclease in sufficient quantity to modify the cell (in the presence of at least one sgRNA) but does not persist after a contemplated period of time has passed or after one or more cell divisions. In such embodiments, no further steps are needed to remove or segregate the Cas-associated gene from the modified cell.

In one embodiment of this disclosure, a catalytically active Cas-associated gene product is prepared in vitro prior to introduction to a cell, including a prokaryotic or eukaryotic cell. The method of preparing a Cas-associated gene product depends on its type and properties and would be known by one of skill in the art. For example, if the Cas-associated gene product is a large monomeric DNA nuclease, the active form of the Cas-associated gene product can be produced via bacterial expression, in vitro translation, via yeast cells, in insect cells, or by other protein production techniques described in the art. After expression, the Cas-associated gene product is isolated, refolded if needed, purified and optionally treated to remove any purification tags, such as a His-tag. Once crude, partially purified, or more completely purified Cas-associated gene products are obtained, the protein may be introduced to, for example, a plant cell via electroporation, by bombardment with Cas-associated gene product coated particles, by chemical transfection or by some other means of transport across a cell membrane. Methods for introducing nucleic acids into bacterial and animal cells are similarly well known in the art. The protein can also be delivered using nanoparticles, which can deliver a combination of active protein and nucleic acid. Once a sufficient quantity of the Cas-associated gene product is introduced so that an effective amount of in vivo nuclease activity is present, along with the appropriate sgRNA, the protospacer sequences within the episomal or genomic target sites are cleaved. It is also recognized that one skilled in the art might create a Cas-associated gene product that is inactive but is activated in vivo by native processing machinery; such a Cas-associated gene product is also contemplated by this disclosure.

In another embodiment, a construct that will transiently express a sgRNA and/or Cas-associated gene is created and introduced into a cell. In yet another embodiment, the vector will produce sufficient quantities of the sgRNAs and/or Cas-associated gene in order for the desired episomal or genomic target site or sites to be effectively modified by CRISPR-mediated cleavage. For instance, the disclosure contemplates preparation of a vector that can be bombarded, electroporated, chemically transfected or transported by some other means across the plant cell membrane. Such a vector could have several useful properties. For instance, in one embodiment, the vector can replicate in a bacterial host such that the vector can be produced and purified in sufficient quantities for transient expression. In another embodiment, the vector can encode a drug resistance gene to allow selection for the vector in a host, or the vector can also comprise an expression cassette to provide for the expression of the sgRNA and/or Cas-associated gene in a plant. In a further embodiment, the expression cassette could contain a promoter region, a 5' untranslated region, an optional intron to aid expression, a multiple cloning site to allow facile introduction of a sequence encoding sgRNAs and/or Cas-associated gene, and a 3' UTR. In particular embodiments, the promoters in the expression cassette would be U6 promoters from *Zea mays* In yet other embodiments, the promoters would be chimeric U6 promoters from *Zea mays*. In some embodiments, it can be beneficial to include unique restriction sites at one or at each end of the expression cassette to allow the production and isolation of a linear expression cassette, which can then be free of other vector elements. The untranslated leader regions, in certain embodiments, can be plant-derived untranslated regions. Use of an intron, which can be plant-derived, is contemplated when the expression cassette is being transformed or transfected into a monocot cell.

In other embodiments, one or more elements in the vector include a spacer complementary to a protospacer contained within an episomal or genomic target site. This facilitates CRISPR-mediated modification within the expression cassette, enabling removal and/or insertion of elements such as promoters and transgenes.

In another approach, a transient expression vector may be introduced into a cell using a bacterial or viral vector host. For example, *Agrobacterium* is one such bacterial vector that can be used to introduce a transient expression vector into a host cell. When using a bacterial, viral or other vector host system, the transient expression vector is contained within the host vector system. For example, if the *Agrobacterium* host system is used, the transient expression cassette would be flanked by one or more T-DNA borders and cloned into a binary vector. Many such vector systems have been identified in the art (reviewed in Hellens et al., 2000).

In embodiments whereby the sgRNA and/or Cas-associated gene is transiently introduced in sufficient quantities to modify a cell, a method of selecting the modified cell may be employed. In one such method, a second nucleic acid molecule containing a selectable marker is co-introduced with the transient sgRNA and/or Cas-associated gene. In this embodiment, the co-introduced marker may be part of a molecular strategy to introduce the marker at a target site. For example, the co-introduced marker may be used to disrupt a target gene by inserting between genomic target sites. In another embodiment, the co-introduced nucleic acid may be used to produce a visual marker protein such that transfected cells can be cell-sorted or isolated by some other means. In yet another embodiment, the co-introduced marker may randomly integrate or be directed via a second sgRNA:Cas-protein complex to integrate at a site independent of the primary genomic target site. In still yet another embodiment, the co-introduced molecule may be targeted to a specific locus via a double strand break repair pathway, which may include, for example, non-homologous end-joining, homologous recombination, synthesis-dependent strand annealing (SDSA), single-strand annealing (SSA), or a combination thereof, at the genomic target site(s). In the above embodiments, the co-introduced marker may be used to identify or select for cells that have likely been exposed to the sgRNA and/or Cas-associated gene and therefore are likely to have been modified by the CRISPR.

Stable Expression of CRISPRs

In another embodiment, a CRISPR expression vector is stably transformed into a cell so as to cleave a DNA sequence at or near a genomic target site in the host genome with a sgRNA and Cas-associated gene product encoded within the vector. In this embodiment, the design of the transformation vector provides flexibility for when and under what conditions the sgRNA and/or Cas-associated gene is expressed. Furthermore, the transformation vector can be designed to comprise a selectable or visible marker that will provide a means to isolate or efficiently select cell lines that contain and/or have been modified by the CRISPR.

Cell transformation systems have been described in the art and descriptions include a variety of transformation vectors. For example, for plant transformations, two principal methods include *Agrobacterium*-mediated transformation and particle gun bombardment-mediated (i.e., biolistic) transformation. In both cases, the CRISPR is introduced via an expression cassette. The cassette may contain one or more of the following elements: a promoter element that can be used to express the sgRNA and/or Cas-associated gene; a 5' untranslated region to enhance expression; an intron element to further enhance expression in certain cell types, such as monocot cells; a multiple-cloning site to provide convenient restriction sites for inserting the sgRNA and/or Cas-associated gene sequences and other desired elements; and a 3' untranslated region to provide for efficient termination of the expressed transcript. In particular embodiments, the promoters in the expression cassette would be U6 promoters from *Zea mays*. In yet other embodiments, the promoters would be chimeric U6 promoters from *Zea mays*.

For particle bombardment or with protoplast transformation, the expression cassette can be an isolated linear fragment or may be part of a larger construct that might contain bacterial replication elements, bacterial selectable markers or other elements. The sgRNA and/or Cas-associated gene expression cassette(s) may be physically linked to a marker cassette or may be mixed with a second nucleic acid molecule encoding a marker cassette. The marker cassette is comprised of necessary elements to express a visual or selectable marker that allows for efficient selection of transformed cells. In the case of *Agrobacterium*-mediated transformation, the expression cassette may be adjacent to or between flanking T-DNA borders and contained within a binary vector. In another embodiment, the expression cassette may be outside of the T-DNA. The presence of the expression cassette in a cell may be manipulated by positive or negative selection regime(s). Furthermore, a selectable marker cassette may also be within or adjacent to the same T-DNA borders or may be somewhere else within a second T-DNA on the binary vector (e.g., a 2 T-DNA system).

In another embodiment, cells that have been modified by a CRISPR, either transiently or stably, are carried forward along with unmodified cells. The cells can be sub-divided into independent clonally derived lines or can be used to regenerate independently derived plants. Individual plants or clonal populations regenerated from such cells can be used to generate independently derived lines. At any of these stages a molecular assay can be employed to screen for cells, plants or lines that have been modified. Cells, plants or lines that have been modified continue to be propagated and unmodified cells, plants or lines are discarded. In these embodiments, the presence of an active CRISPR in a cell is essential to ensure the efficiency of the overall process.

Transformation Methods

Methods for transforming or transfecting a cell are well known in the art. Methods for plant transformation using *Agrobacterium* or DNA coated particles are well known in the art and are incorporated herein. Suitable methods for transformation of host cells for use with the current disclosure are believed to include virtually any method by which DNA can be introduced into a cell, for example by *Agrobacterium*-mediated transformation (U.S. Pat. Nos. 5,563,055; 5,591,616; 5,693,512; 5,824,877; 5,981,840; and 6,384,301) and by acceleration of DNA coated particles (U.S. Pat. Nos. 5,015,580; 5,550,318; 5,538,880; 6,160,208; 6,399,861; and 6,403,865), etc. Through the application of techniques such as these, the cells of virtually any species may be stably transformed.

Various methods for selecting transformed cells have been described. For example, one might utilize a drug resistance marker such as a neomycin phosphotransferase protein to confer resistance to kanamycin or to use 5-enolpyruvyl shikimate phosphate synthase to confer tolerance to glyphosate. In another embodiment, a carotenoid synthase is used to create an orange pigment that can be visually identified. These three exemplary approaches can each be used effectively to isolate a cell or plant or tissue thereof that has been transformed and/or modified by a CRISPR.

When a nucleic acid sequence encoding a selectable or screenable marker is inserted into a genomic target site, the marker can be used to detect the presence or absence of a CRISPR or its activity. This may be useful once a cell has been modified by a CRISPR, and recovery of a genetically modified cell that no longer contains the CRISPR, or a regenerated plant from such a modified cell, is desired. In other embodiments, the marker may be intentionally designed to integrate at the genomic target site, such that it can be used to follow a modified cell independently of the CRISPR. The marker can be a gene that provides a visually detectable phenotype, such as in the seed, to allow rapid identification of seeds that carry or lack a CRISPR expression cassette.

This disclosure provides for a means to regenerate a plant from a cell with a repaired double-stranded break within a protospacer sequence at a genomic target site. The regenerant can then be used to propagate additional plants.

The disclosure additionally provides novel plant transformation vectors and expression cassettes which include novel U6 promoters, and U3, U2, U5 and 7SL promoters, and combinations thereof, with CRISPR-associated gene(s) and sgRNA expression cassettes. The disclosure further provides methods of obtaining a plant cell, a whole plant, and a seed or embryo that have been specifically modified using CRISPR-mediated cleavage. This disclosure also relates to a novel plant cell containing a CRISPR-associated Cas endonuclease expression construct and sgRNA expression cassettes.

Targeting Using Blunt-End Oligonucleotides

In certain embodiments, the CRISPR/Cas9 system can be utilized for targeting insertion of a blunt-end double-stranded DNA fragment into a genomic target site of interest. CRISPR-mediated endonuclease activity can introduce a double stand break (DSB) in the protospacer of the selected genomic target site and DNA repair, such as microhomology-driven non-homologous end-joining DNA repair, results in insertion of the blunt-end double-stranded DNA fragment into the DSB. Blunt-end double-stranded DNA fragments can be designed with 1-10 bp of microhomology, on both the 5' and 3' ends of the DNA fragment, that correspond to the 5' and 3' flanking sequence at the cut site of the protospacer in the genomic target site.

Use of Custom CRISPRs in Molecular Breeding

In some embodiments, genome knowledge is utilized for targeted genetic alteration of a genome. At least one sgRNA can be designed to target at least one region of a genome to disrupt that region from the genome. This aspect of the disclosure may be especially useful for genetic alterations. The resulting plant could have a modified phenotype or other property depending on the gene or genes that have been altered. Previously characterized mutant alleles or introduced transgenes can be targeted for CRISPR-mediated modification, enabling creation of improved mutants or transgenic lines.

In another embodiment, a gene targeted for deletion or disruption may be a transgene that was previously introduced into the target plant or cell. This has the advantage of allowing an improved version of a transgene to be introduced or by allowing disruption of a selectable marker encoding sequence. In yet another embodiment, a gene targeted for disruption via CRISPR is at least one transgene that was introduced on the same vector or expression cassette as (an)other transgene(s) of interest, and resides at the same locus as another transgene. It is understood by those skilled in the art that this type of CRISPR-mediated modification may result in deletion or insertion of additional sequences. Thus it may, in certain embodiments, be preferable to generate a plurality of plants or cells in which a deletion has occurred, and to screen such plants or cells using standard techniques to identify specific plants or cells that have minimal alterations in their genomes following CRISPR-mediated modification. Such screens may utilize genotypic and/or phenotypic information. In such embodiments, a specific transgene may be disrupted while leaving the remaining transgene(s) intact. This avoids having to create a new transgenic line containing the desired transgenes without the undesired transgene.

In another aspect, the present disclosure includes methods for inserting a DNA fragment of interest into a specific site of a plant's genome, wherein the DNA fragment of interest is from the genome of the plant or is heterologous with respect to the plant. This disclosure allows one to select or target a particular region of the genome for nucleic acid (i.e., transgene) stacking (i.e., mega-locus). A targeted region of the genome may thus display linkage of at least one transgene to a haplotype of interest associated with at least one phenotypic trait, and may also result in the development of a linkage block to facilitate transgene stacking and transgenic trait integration, and/or development of a linkage block while also allowing for conventional trait integration.

Use of Custom CRISPRs in Trait Integration

Directed insertion, in at least one genomic protospacer site, of DNA fragments of interest, via CRISPR-mediated cleavage allows for targeted integration of multiple nucleic acids of interest (i.e., a trait stack) to be added to the genome of a plant in either the same site or different sites. Sites for targeted integration can be selected based on knowledge of the underlying breeding value, transgene performance in that location, underlying recombination rate in that location, existing transgenes in that linkage block, or other factors. Once the stacked plant is assembled, it can be used as a trait donor for crosses to germplasm being advanced in a breeding pipeline or be directly advanced in the breeding pipeline.

The present disclosure includes methods for inserting at least one nucleic acid of interest into at least one site, wherein the nucleic acid of interest is from the genome of a plant, such as a QTL or allele, or is transgenic in origin. A targeted region of the genome may thus display linkage of at least one transgene to a haplotype of interest associated with at least one phenotypic trait (as described in U.S. Patent Application Publication No. 2006/0282911); development of a linkage block to facilitate transgene stacking and transgenic trait integration, development of a linkage block to facilitate QTL or haplotype stacking and conventional trait integration, and so on.

In another embodiment of this disclosure, multiple unique sgRNAs can be used to modify multiple alleles at specific loci within one linkage block contained on one chromosome by making use of knowledge of genomic sequence information and the ability to design custom sgRNAs as described in the art. A sgRNA that is specific for, or can be directed to, a genomic target site that is upstream of the locus containing the non-target allele is designed or engineered as necessary. A second sgRNA that is specific for, or can be directed to, a genomic target site that is downstream of the target locus containing the non-target allele is also designed or engineered. The sgRNAs may be designed such that they complement genomic regions where there is no homology to the non-target locus containing the target allele. Both sgRNAs may be introduced into a cell using one of the methods described above.

The ability to execute targeted integration relies on the action of the sgRNA:Cas-protein complex and the endonuclease activity of the Cas-associated gene product. This advantage provides methods for engineering plants of interest, including a plant or cell, comprising at least one genomic modification.

A custom sgRNA can be utilized in a CRISPR system to generate at least one trait donor to create a custom genomic modification event that is then crossed into at least one second plant of interest, including a plant, wherein CRISPR delivery can be coupled with the sgRNA of interest to be used for genome editing. In other aspects one or more plants of interest are directly transformed with the CRISPR system and at least one double-stranded DNA fragment of interest for directed insertion. It is recognized that this method may be executed in various cell, tissue, and developmental types, including gametes of plants. It is further anticipated that one or more of the elements described herein may be combined with use of promoters specific to particular cells, tissues, plant parts and/or developmental stages, such as a meiosis-specific promoter.

In addition, the disclosure contemplates the targeting of a transgenic element already existing within a genome for deletion or disruption. This allows, for instance, an improved version of a transgene to be introduced, or allows selectable marker removal. In yet another embodiment, a gene targeted for disruption via CRISPR-mediated cleavage is at least one transgene that was introduced on the same vector or expression cassette as (an)other transgene(s) of interest, and resides at the same locus as another transgene.

In one aspect, the disclosure thus provides a method for modifying a locus of interest in a cell comprising (a) identifying at least one locus of interest within a DNA sequence; (b) creating a modified nucleotide sequence, in or proximal to the locus of interest, that includes a protospacer sequence within a genomic target site for a first sgRNA according to the disclosure; (c) introducing into at least one cell the sgRNA and Cas-associated gene, wherein the sgRNA and/or Cas-associated gene is expressed transiently or stably; (d) assaying the cell for a CRISPR-mediated modification in the DNA making up or flanking the locus of interest; and (e) identifying the cell or a progeny cell thereof as comprising a modification in said locus of interest.

Another aspect provides a method for modifying multiple loci of interest in a cell comprising (a) identifying multiple loci of interest within a genome; (b) identifying multiple genomic protospacer sites within each locus of interest; (c) introducing into at least one cell multiple sgRNA and at least one Cas-associated gene according to the disclosure, wherein the cell comprises the genomic protospacer sites and the sgRNA and Cas-associated gene is expressed transiently or stably and creates a modified locus, or loci, that includes at least one CRISPR-mediated cleavage event; (d) assaying the cell for CRISPR-mediated modifications in the DNA making up or flanking each locus of interest; and (e) identifying a cell or a progeny cell thereof which comprises a modified nucleotide sequence at said loci of interest.

The disclosure further contemplates sequential modification of a locus of interest, by two or more sgRNAs and Cas-associated gene(s) according to the disclosure. Genes or other sequences added by the action of such a first CRISPR-mediated genomic modification may be retained, further modified, or removed by the action of a second CRISPR-mediated genomic modification.

The present invention thus includes a method for modifying a locus of interest in a crop plant such as maize (corn; *Zea mays*), soybean (*Glycine max*), cotton (*Gossypium hirsutum; Gossypium* sp.), peanut (*Arachis hypogaea*), barley (*Hordeum vulgare*); oats (*Avena sativa*); orchard grass (*Dactylis glomerata*); rice (*Oryza sativa,* including indica and japonica varieties); sorghum (*Sorghum bicolor*); sugar cane (*Saccharum* sp.); tall fescue (*Festuca arundinacea*); turf-grass species (e.g. species: *Agrostis stolonifera, Poa pratensis, Stenotaphrum secundatum*); wheat (*Triticum aestivum*); alfalfa (*Medicago sativa*); members of the genus *Brassica,* including broccoli, cabbage, carrot, cauliflower, Chinese cabbage; cucumber, dry bean, eggplant, tobacco, fennel, garden beans, gourd, leek, lettuce, melon, okra, onion, pea, pepper, pumpkin, radish, spinach, squash, sweet corn, tomato, watermelon, ornamental plants, and other fruit, vegetable, tuber, oilseed, and root crops, wherein oilseed crops include soybean, canola, oil seed rape, oil palm, sunflower, olive, corn, cottonseed, peanut, flaxseed, safflower, and coconut.

The genome modification may comprise a modified linkage block, the linking of two or more QTLs, disrupting linkage of two or more QTLs, gene insertion, gene replacement, gene conversion, deleting or disrupting a gene, transgenic event selection, transgenic trait donor selection, transgene replacement, or targeted insertion of at least one nucleic acid of interest.

Definitions

The definitions and methods provided define the present disclosure and guide those of ordinary skill in the art in the practice of the present disclosure. Unless otherwise noted, terms are to be understood according to conventional usage by those of ordinary skill in the relevant art. Definitions of common terms in molecular biology may also be found in Alberts et al., Molecular Biology of The Cell, 5th Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2247; and Lewin, Genes IX, Oxford University Press: New York, 2007. The nomenclature for DNA bases as set forth at 37 CFR § 1.822 is used.

As used herein, "CRISPR-associated genes" refers to nucleic acid sequences that encode polypeptide components of clustered regularly interspersed short palindromic repeats (CRISPR)-associated systems (Cas). Examples include, but are not limited to, Cas3 and Cas9, which encode endonucleases from the CRISPR type I and type II systems, respectively.

As used herein, "single-guide RNA (sgRNA)" refers to a crRNA:tracrRNA fused hybrid single-stranded RNA molecule encoded by a customizable DNA element that, generally, comprises a copy of a spacer sequence which is complementary to the protospacer sequence of the genomic target site, and a binding domain for an associated-Cas endonuclease of the CRISPR complex.

As used herein, "genomic target site" refers to a protospacer and a protospacer adjacent motif (PAM) located in a host genome selected for targeted mutation and/or double-strand break.

As used herein, "protospacer" refers to a short DNA sequence (12 to 40 bp) that can be targeted for mutation, and/or double-strand break, mediated by enzymatic cleavage with a CRISPR system endonuclease guided by complementary base-pairing with the spacer sequence in the crRNA or sgRNA.

As used herein, "protospacer adjacent motif (PAM)" includes a 3 to 8 bp sequence immediately adjacent to the protospacer sequence in the genomic target site.

As used herein, "microhomology" refers to the presence of the same short sequence (1 to 10 bp) of bases in different polynucleotide molecules.

As used herein, "codon-optimized" refers to a polynucleotide sequence that has been modified to exploit the codon usage bias of a particular plant. The modified polynucleotide sequence still encodes the same, or substantially similar polypeptide as the original sequence but uses codon nucleotide triplets that are found in greater frequency in a particular plant.

As used herein, "non-protein-coding RNA (npcRNA)" refers to a non-coding RNA (ncRNA) which is a precursor small non-protein coding RNA, or a fully processed non-protein coding RNA, which are functional RNA molecules that are not translated into a protein.

As used herein, the term "chimeric" refers to the product of the fusion of portions of two or more different polynucleotide molecules, or to a gene expression element produced through the manipulation of known elements or other polynucleotide molecules. Novel chimeric regulatory elements can be designed or engineered by a number of methods. In one embodiment of the present disclosure, a chimeric promoter may be produced by fusing the 5' portion of a U6 promoter from corn chromosome 1, which includes at least one Monocot-Specific Promoter (MSP) element, to the 3' portion of the U6 promoter from corn chromosome 8, which includes an Upstream Sequence Element (USE) and a TATA Box. The resultant chimeric promoter may have novel expression properties relative to the first or second promoters.

As used herein, "promoter" refers to a nucleic acid sequence located upstream or 5' to a translational start codon of an open reading frame (or protein-coding region) of a gene and that is involved in recognition and binding of RNA polymerase I, II, or III and other proteins (trans-acting transcription factors) to initiate transcription. A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively. Rather than being expressed "specifically" in a given tissue, plant part, or cell type, a promoter may display "enhanced" expression, i.e., a higher level of expression, in one cell type, tissue, or plant part of the plant compared to other parts of the plant. Temporally regulated promoters are functional only or predominantly during certain periods of plant development or at certain times of day, as in the case of genes associated with circadian rhythm, for example. Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

As used herein, an "expression cassette" refers to a polynucleotide sequence comprising at least a first polynucleotide sequence capable of initiating transcription of an operably linked second polynucleotide sequence and optionally a transcription termination sequence operably linked to the second polynucleotide sequence.

A palindromic sequence is a nucleic acid sequence that is the same whether read 5' to 3' on one strand or 3' to 5' on the complementary strand with which it forms a double helix. A nucleotide sequence is said to be a palindrome if it is equal to its reverse complement. A palindromic sequence can form a hairpin.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended.

For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability.

Having described the present disclosure in detail, it will be apparent that modifications, variations, and equivalent embodiments are possible without departing from the scope of the present disclosure defined in the appended claims. Furthermore, it should be appreciated that all examples in the present disclosure are provided as non-limiting examples.

EXAMPLES

The following examples are included to demonstrate embodiments of the disclosure. It should be appreciated by those of skill in the art that many changes can be made in the specific embodiments which are disclosed and still obtain a like or similar result without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

Example 1

Identification of Promoters to Express sgRNA

To enable genome engineering in corn, soy, and tomato using the CRISPR-based gene targeting system, novel U6 promoters native to these three genomes were identified. After BLAST searching for the highly conserved U6 gene in corn, soy, and tomato genomes, 200-600 bp of sequence upstream of these putative U6 genes was selected to test for promoter function (Table 1). Four U6 promoters were identified from the corn B73 genome, one each on chromosome 1 (SEQ ID NO:1), chromosome 2 (SEQ ID NO:3), chromosome 3 (SEQ ID NO:5), and chromosome 8 (SEQ ID NO:7). A multiple sequence alignment of these four corn U6 promoters and corresponding U6 genes was compiled as shown in FIGS. 1A and B. For each of these corn U6 promoters, conserved U6 promoter motifs (e.g., TATA Box, Upstream Sequence Element (USE), and Monocot-Specific Promoter (MSP) elements (Connelly, Mol. Cell Biol. 14:5910-5919, 1994) are present (FIG. 1B). A guanine nucleobase following the poly-T tracts was conserved among these four genes, and may have a significant role in transcription. The sequence consensus, and percent conservation are presented below the alignment (FIG. 1). Based on the multiple sequence alignment, the conserved motifs of these U6 promoters were within the 140 bp proximal to the transcription start site. Based on the proximity of these conserved U6 promoter motifs, 200 bp of the proximal upstream sequence from the transcription start site for each of the corn chromosome U6 promoters, chromosome 1 (SEQ ID NO:2), chromosome 2 (SEQ ID NO:4), chromosome 3 (SEQ ID NO:6), and chromosome 8 (SEQ ID NO:8) was selected for testing for efficient promoter activity in sgRNA expression cassettes.

In addition to the four corn U6 promoters, chimeric U6 promoters were designed. Four chimeric corn U6 promoters were designed using differing combinations of the corn U6 promoters from chromosome 1, 2, and 8, with each chimeric promoter being 397 bp in length. The breakpoints of the chimeras were determined so that the conserved elements (e.g., USE, MSP, and TATA box) of different chromosomal origins were mixed in the new chimeric U6 promoters but retained their relative spacing to the native corn U6 promoters. For example, the 5' end of the U6 promoter including MSP and USE were derived from one chromosome, while the 3' end including the TATA box and one or more MSP elements were derived from a second chromosome. Although the corn U6 promoter from chromosome 2 was not a very strong promoter in its native form, it included more than one MSP element. Consequently, chimeras that include mainly chromosome 1 and/or 8 sequence can also include one or more chromosome 2 MSP elements. Specifically, the 5' portion of chimera 1 (SEQ ID NO:17) is derived from the U6 promoter from corn chromosome 1 (SEQ ID NO:1), including one MSP element, and the 3' portion of this chimera is derived from the U6 promoter from corn chromosome 8 (SEQ ID NO:7), including a USE element and a TATA box. Similarly, the 5' portion of chimera 2 (SEQ ID NO:18) is derived from the U6 promoter from corn chromosome 1 (SEQ ID NO:1), including one MSP element, and the 3' portion of this chimera is derived from the U6 promoter from corn chromosome 8 (SEQ ID NO:7), including a second MSP element, a USE element, and a TATA box. The 5' portion of chimera 3 (SEQ ID NO:19) is derived from the U6 promoter from corn chromosome 8 (SEQ ID NO:7), including one MSP element, and the 3' portion of this chimera is derived from the U6 promoter from corn chromosome 1 (SEQ ID NO:1), including a second MSP element, a USE element, and a TATA box. Additionally, for chimera 3, there is a 3 bp deletion beginning at bp 100 of SEQ ID NO:7, and the 5' end of the chimera begins with 5'-AAG-3'. Chimera 4 (SEQ ID NO:20) was derived from the U6 promoter from corn chromosome 8 (SEQ ID NO:7), including the MSP element, the USE element and the TATA box. However, this chimera also includes two additional MSP elements (for a total of 3 MSP elements) derived from the U6 promoter of corn chromosomes 1 and 2.

TABLE 1

U6 promoters from corn (*Zea mays*), tomato (*Solanum lycopersicum*), and soybean (*Glycine max*), their chromosomal source and length.

| SEQ ID NO. | Source | Chromosome | Length (bp) |
|---|---|---|---|
| 1 | Zea mays | 1 | 397 |
| 2 | Zea mays | 1 | 200 |
| 3 | Zea mays | 2 | 397 |
| 4 | Zea mays | 2 | 200 |
| 5 | Zea mays | 3 | 397 |
| 6 | Zea mays | 3 | 200 |
| 7 | Zea mays | 8 | 397 |
| 8 | Zea mays | 8 | 200 |
| 9 | Solanum lycopersicum | 10 | 540 |
| 10 | Solanum lycopersicum | 1 | 600 |
| 11 | Solanum lycopersicum | 7 | 540 |
| 12 | Glycine max | 6 | 540 |
| 13 | Glycine max | 16 | 540 |
| 14 | Glycine max | 19 | 540 |
| 15 | Glycine max | 4 | 540 |
| 16 | Glycine max | 19 | 420 |
| 17 | Zea mays | Chimeric: 1 + 8 | 397 |
| 18 | Zea mays | Chimeric: 1 + 8 | 397 |
| 19 | Zea mays | Chimeric: 8 + 1 | 397 |
| 20 | Zea mays | Chimeric: 8 + 2 + 1 + 8 | 397 |

Example 2

Identification of Cas9 Genes to Enable Genome Engineering in Plants

The *S. pyogenes* Cas9 sequence (SEQ ID NO:28 is the polypeptide sequence of Cas9 with NLS, and SEQ ID NO:96 is the polypeptide sequence of Cas9 without NLS) was used for CRISPR-mediated site-directed targeting of a reporter construct in immature corn embryos. For expression, the codon-optimized nucleotide sequence of Cas9 was designed into an expression vector capable of expression in a plant. This Cas9 expression vector contained a 35S promoter driving expression of the Cas9 open reading frame, a NLS sequence incorporated into the 3' end of the Cas9 coding region, and a Nos transcription termination sequence (SEQ ID NO:29).

A Cas9 protein (SEQ ID NO:26), and a monocot codon-optimized version of the nucleotide sequence encoding the same (SEQ ID NO:27), were identified from the plant-related bacteria *Bradyrhizobium,* and can be useful for increasing the robustness of CRISPR/Cas-mediated genome modification in plants. A Cas9 protein (SEQ ID NO:69) and a monocotcodon-optimized version thereof (SEQ ID NO:68), were identified from *Streptococcus thermophilus*, and can be useful for increasing the robustness of CRISPR/Cas-mediated genome modification in plants. Additional Cas9 genes from plant-related bacteria (e.g., symbiotic or pathogenic bacteria) can also be identified.

Example 3

Single-Guide RNA Cassette Design

A set of single-guide RNA (sgRNA) expression cassettes were designed to target a protospacer in a corn genomic target site referred to as Zm7 (5'-GCCGGCCAGCATTT-GAAACATGG-3', SEQ ID NO:22). The different expression cassettes included one of the 397 bp U6 promoters from corn: chromosome 1 (SEQ ID NO:30), chromosome 2 (SEQ ID NO:32), chromosome 3 (SEQ ID NO:34), or chromosome 8 (SEQ ID NO:36); or one of the 200 bp U6 promoter from corn: chromosome 1 (SEQ ID NO:31), chromosome 2 (SEQ ID NO:33), chromosome 3 (SEQ ID NO:35), or chromosome 8 (SEQ ID NO:37). Each expression cassette also contained, i) the U6 poly-T terminator conserved in each of the four corn U6 genes; ii) a sgRNA including a copy of the spacer sequence 5'-GCCGGCCAGCATTT-GAAACA-3' (SEQ ID NO:23) corresponding to the protospacer of the Zm7 genomic target site (SEQ ID NO:22); and iii) the conserved 3' domain of a sgRNA providing the Cas endonuclease binding domain, and ending with the U6 poly-T tract (SEQ ID NO:21).

Similarly, a set of sgRNA cassettes were designed with one of the four corn U6 397 bp promoters (SEQ ID NO:30, SEQ ID NO:32, SEQ ID NO:34, or SEQ ID NO:36; see Table 2), and the spacer sequence of the sgRNA complementary to the protospacer of the corn genomic target site referred to as Zm231 (SEQ ID NO:24). Table 3 lists the corresponding SEQ ID NOs for the DNA and RNA sequences of the sgRNAs containing the Zm7, Zm231, and Zm14 target sites. A negative control sgRNA cassette was designed with the corn U6 397 bp promoter from corn chromosome 8 (SEQ ID NO:36) and spacer sequence of the sgRNA complementary to the protospacer of the corn genomic target site referred to as Zm14 (SEQ ID NO:24). This negative control sgRNA cassette was designed with a spacer sequence of the sgRNA that is non-complementary to the protospacer sequence of the Zm231 corn genomic target site. Inclusion of a sgRNA comprising the spacer sequence complementary to the Zm14 corn genomic target site will not result in CRISPR/Cas-mediated cleavage of the protospacer sequence of the Zm231 corn target protospacer site. These Zm231 and Zm14 sgRNA cassettes are represented by SEQ ID NO:38, SEQ ID NO:39, SEQ ID NO:40, SEQ ID NO:41, and SEQ ID NO:42 (Table 2). Each of these sgRNA cassettes also contains at the 3' end of the sgRNA sequence a U6 poly-T tract.

TABLE 2

Cassettes with the indicated corn (*Zea mays*) U6 promoters and sgRNA containing spacers complementary to the protospacer sequence of the indicated corn genomic target sites.

| SEQ ID NO. | U6 Promoter from Chromosome | U6 Promoter Length (bp) | Genomic target site |
|---|---|---|---|
| 30 | 1 | 397 | Zm7 |
| 31 | 1 | 200 | Zm7 |
| 32 | 2 | 397 | Zm7 |
| 33 | 2 | 200 | Zm7 |
| 34 | 3 | 397 | Zm7 |
| 35 | 3 | 200 | Zm7 |
| 36 | 8 | 397 | Zm7 |
| 37 | 8 | 200 | Zm7 |
| 38 | 1 | 397 | Zm231 |
| 39 | 2 | 397 | Zm231 |
| 40 | 3 | 397 | Zm231 |
| 41 | 8 | 397 | Zm231 |
| 42 | 8 | 397 | Zm14 |

TABLE 3

DNA and RNA sequences of *Streptococcus pyogenes* sgRNAs containing spacer sequences complementary to the protospacer sequence of the corn genomic target sites Zm7, Zm231, and Zm14.

| SEQ ID NO. | | |
|---|---|---|
| DNA | RNA | Genomic target site |
| 76 | 79 | Zm7 |
| 77 | 80 | Zm231 |
| 78 | 81 | Zm14 |

Example 4

CRISPR Activity in Corn—Modified GUS Reporter Assay

To determine the activity of CRISPR/Cas-mediated gene-targeting efficiency in corn, a system for the transient expression of a reporter gene in immature corn embryos was used. In addition to the sgRNA cassettes described above, the design incorporated an expression cassette containing the Cas9 endonuclease of *Streptococcus pyogenes* (SEQ ID NO:28) containing a nuclear localization signal (NLS) sequence and was codon-optimized for expression in corn.

Figures 1, 1A, 2:
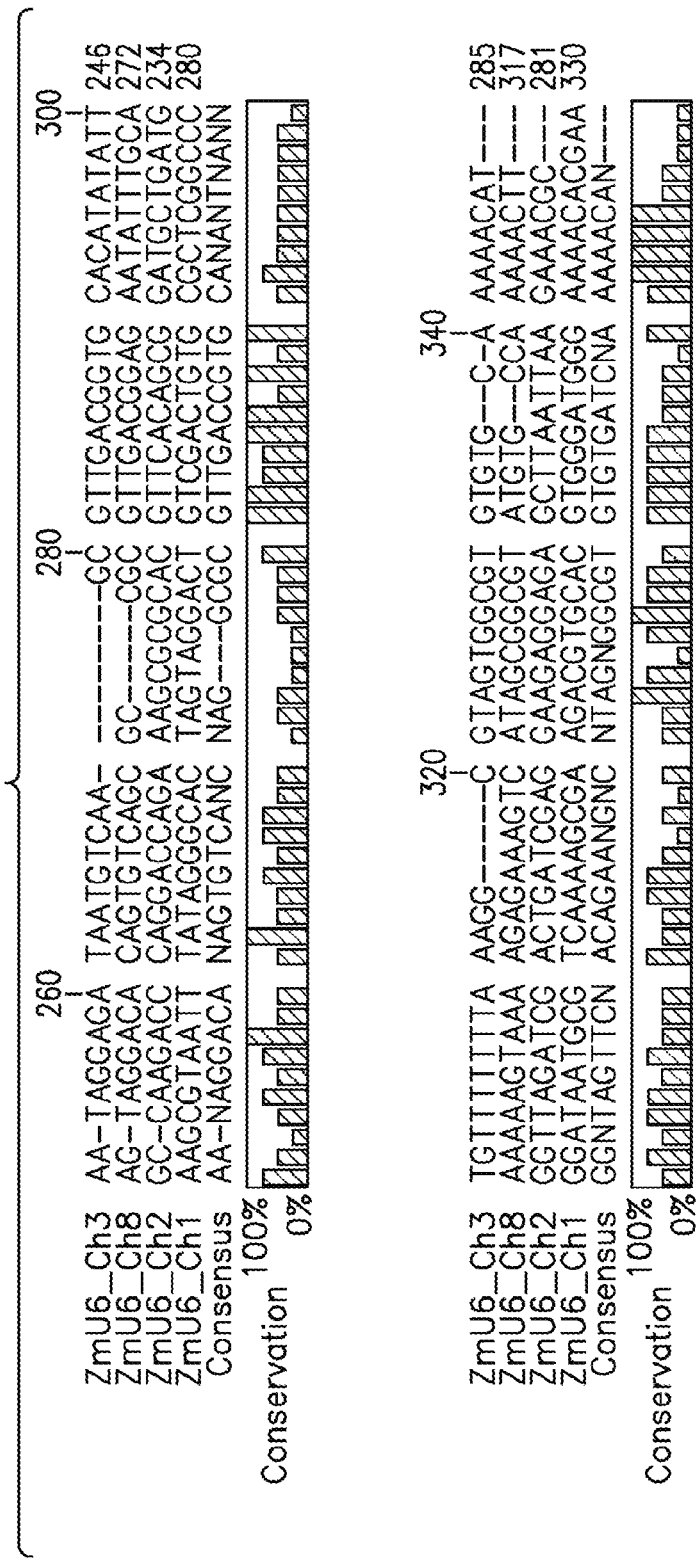
FIG. 2: Illustration of a modified GUS (f3-glucuronidase) reporter gene harboring a direct repeat of the coding sequence (GUUS) interrupted by a target site (TS) for CRISPR cleavage.
Figures 1, 1B:
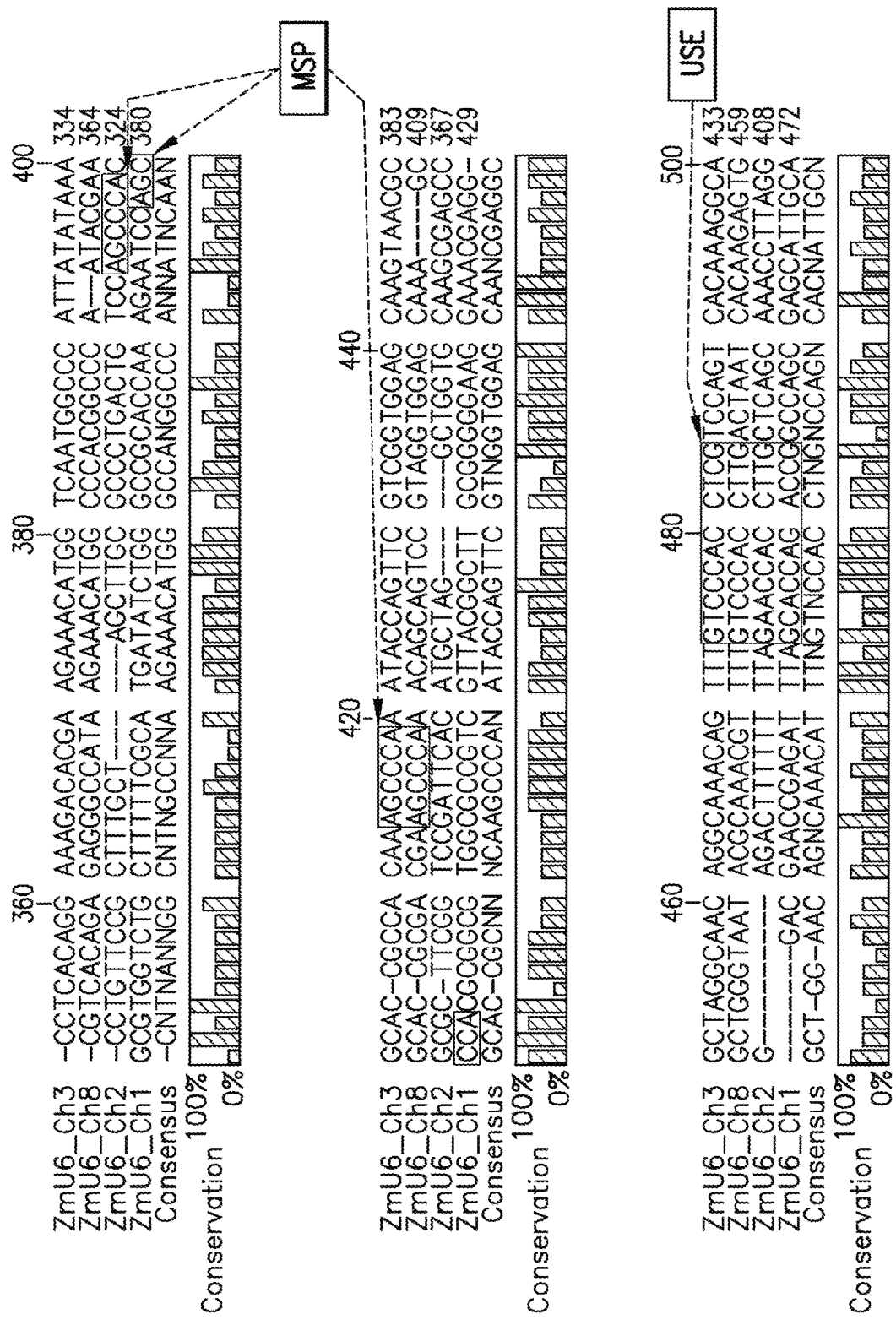
Figures 1, 1B, 2:
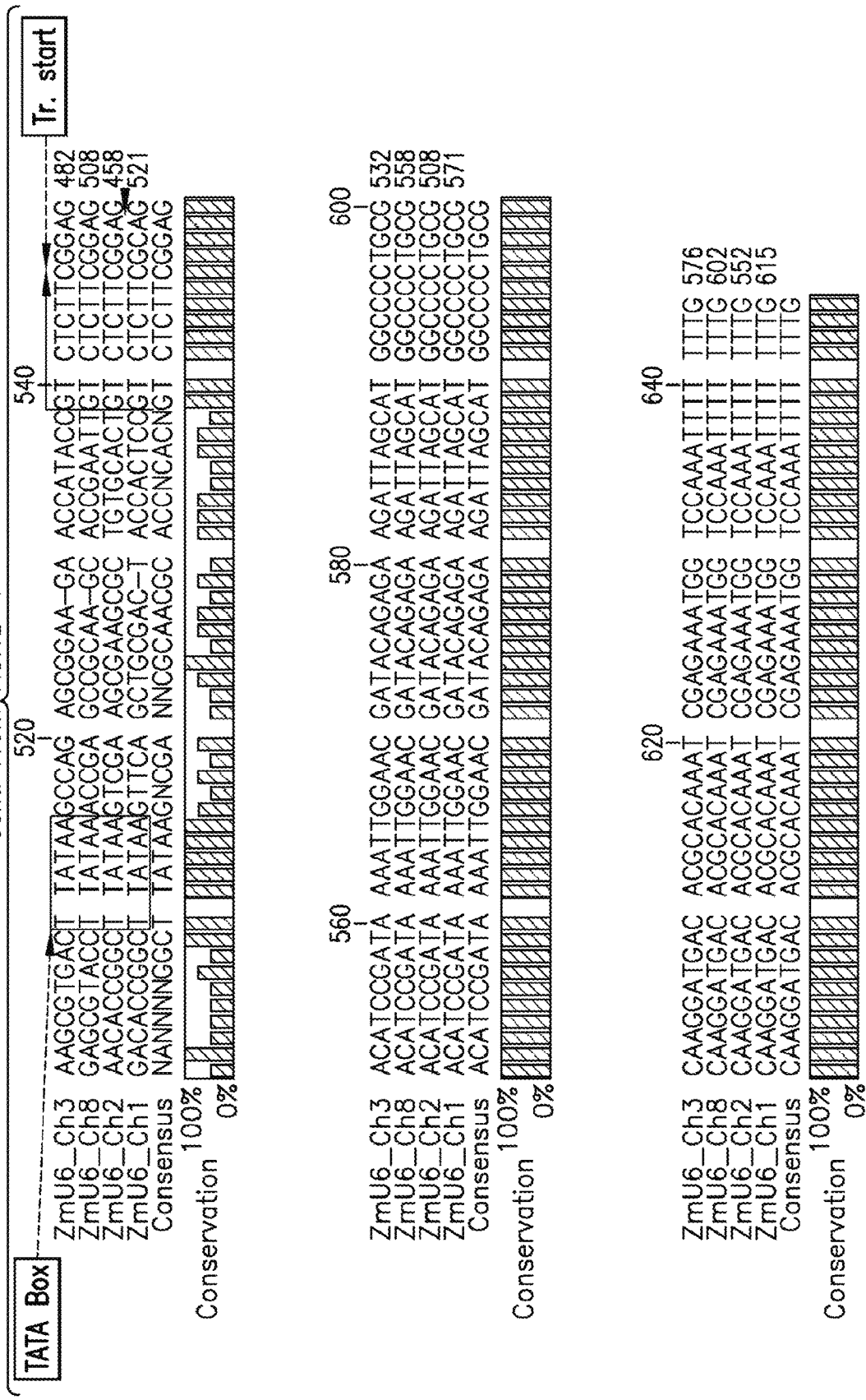
Figure 2:
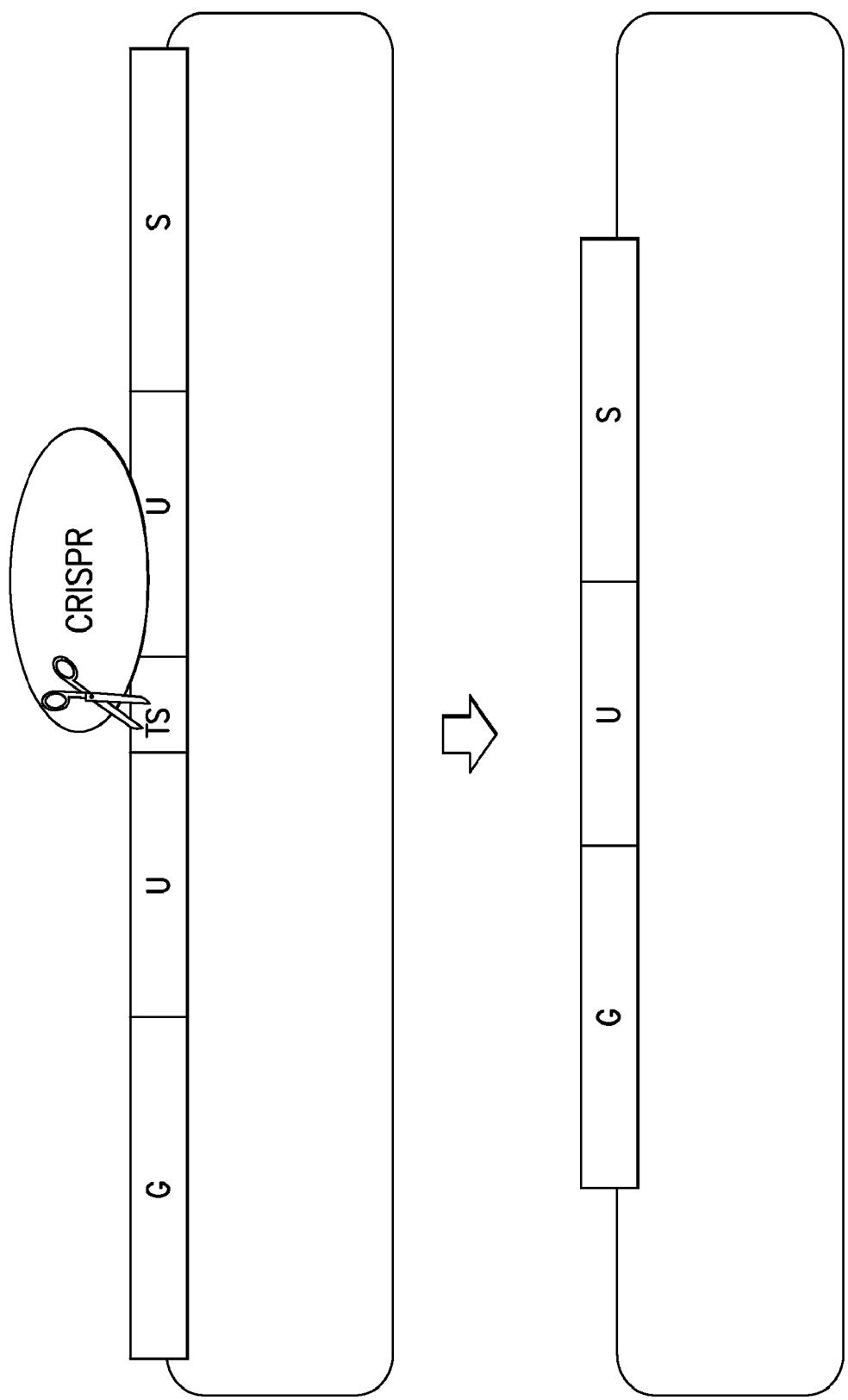

The reporter gene construct for these experiments was a cassette containing a modified β-glucuronidase (GUS) coding sequence with a corn genomic target site (protospacer and PAM) for targeted CRISPR cleavage (e.g., the Zm7 (SEQ ID NO:22), Zm231 (SEQ ID NO:44), or Zm14 (SEQ ID NO:43)) engineered into the reporter gene and surrounded by an internal direct repeat of the GUS coding sequence (FIG. 2). When co-delivered with expression vectors for CRISPR components, if the CRISPR system cleaves the protospacer sequence, the endogenous plant single-strand annealing (SSA) pathway of homologous recombination DNA repair will reconstitute a functional GUS gene. These modified GUS reporter constructs were named GU-Zm7-US, GU-Zm231-US, or GU-Zm14-US, referring to the corn genomic target site inserted into the GUS gene, Zm7, Zm231, and Zm14, respectively. One of the modified GUS reporter gene cassettes was co-delivered with expression vectors for the other CRISPR components (e.g., one of the sgRNA cassettes) and the expression cassette encoding the Cas9 endonuclease (SEQ ID NO:28). Expression cassettes were mixed and co-coated on 0.6 μM gold particles using standard protocols. 3-day old pre-cultured immature corn embryos were then bombarded with these prepared gold particles. Embryos were maintained in culture for 3-5 days after bombardment and then processed for histochemical staining using X-Gluc (5-bromo-4-chloro-3-indolyl glucuronide) and standard laboratory protocols.

Figure 3:
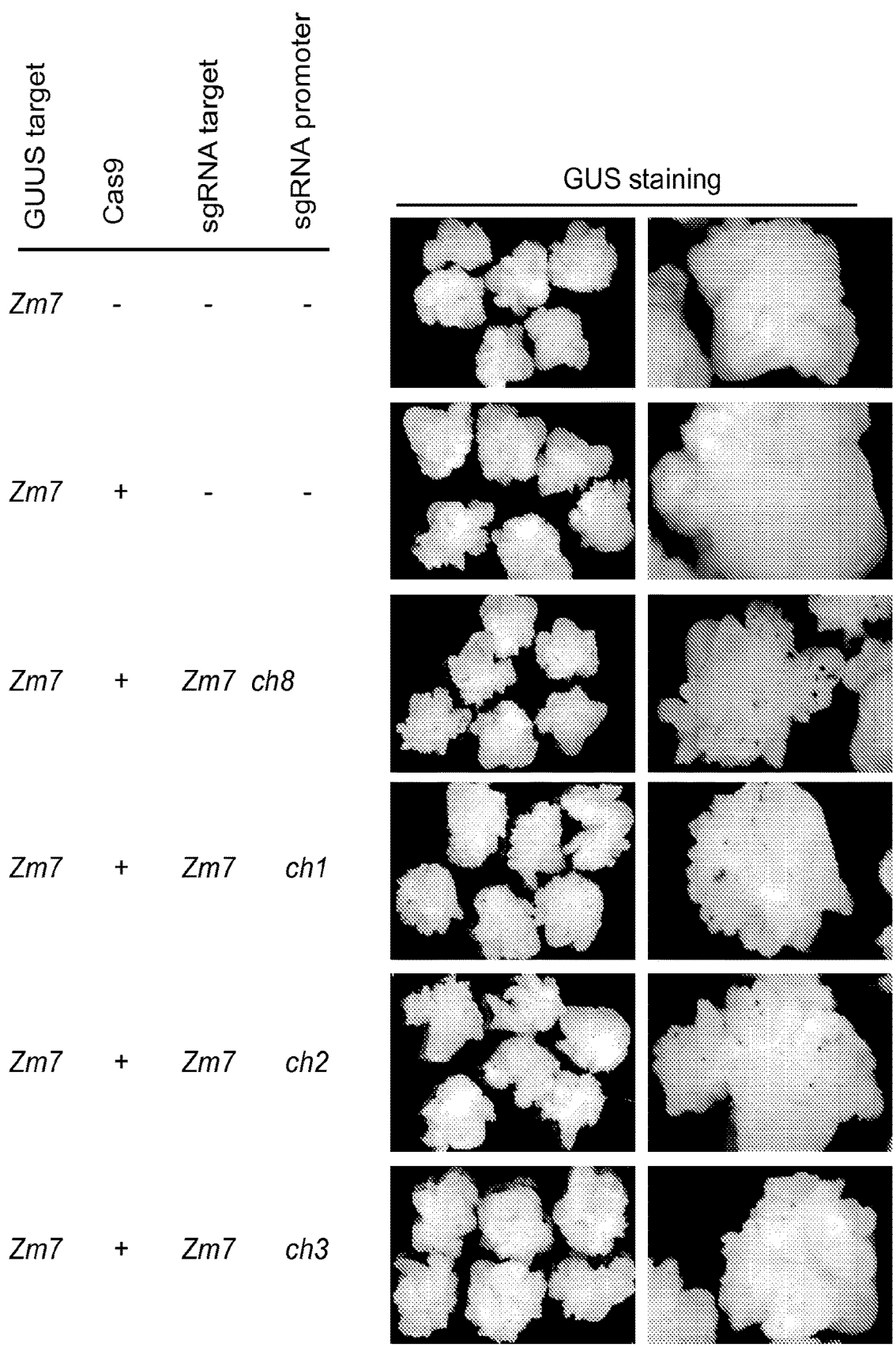
FIG. 3: GUS activities detected in corn callus after co-bombardment of a GUUS reporter construct together with CRISPR constructs designed for introducing a double-stranded break (DSB) at the Zm7 genomic target site.
Figure 4:
FIG. 4: GUS activity detected in corn callus after co-bombardment of a GUUS reporter construct together with CRISPR constructs designed for introducing a DSB at the Zm231 genomic target site. A different genomic target and single-guide RNA (sgRNA) spacer sequence, Zm14, were used as negative control. Also shown are fluorescence microscopy images of representative calli which were co-bombarded with a green fluorescent protein (GFP) expression vector with the GUUS reporter construct, Cas9 expression vector and vectors containing the various sgRNA cassettes.
Figure 4:
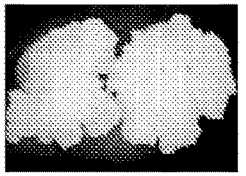
Figure 4:
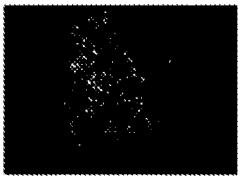
Figure 4:
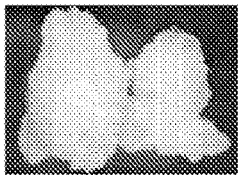
Figure 4:
Figure 4:
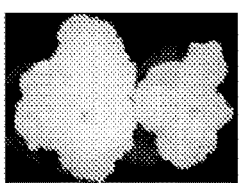
Figure 4:
Figure 4:
Figure 4:
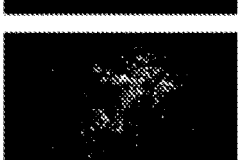
Figure 4:
Figure 4:
Figure 4:
Figure 4:
Figure 4:
Figure 4:
Figure 4:

If CRISPR-mediated Cas9 endonuclease activity occurs at the protospacer site in the modified reporter gene construct, then GUS activity is detected as blue foci using histochemical staining and X-Gluc (FIGS. 3 and 4).

Separate expression cassettes were designed to contain one of four corn U6 promoters (from chromosomes 1, 2, 3, and 8) driving expression of a sgRNA containing a spacer sequence complementary to the protospacer of the corn Zm7 genomic target site (FIG. 3). To prepare samples for the expression assay, 0.6 μM gold particles were coated with 0.6 pmol of one of the Zm7-sgRNA constructs and 0.3 pmol of each of the other constructs (Cas9 expression cassette and the Zm7-modified reporter construct (GU-Zm7-US)). Once the coated gold particles were prepared, ¼ of the mixture was used for bombardment of 3-day old immature corn embryos using standard protocols. More than 50 immature corn calli were bombarded for each set of constructs evaluated, and staining was done 5 days post-bombardment. Following staining, photographs of representative calli (overview of several calli and a close-up view of a single callus) were taken (FIG. 3). The modified reporter construct GU-Zm7-US was designed to contain the Zm7 genomic target site (SEQ ID NO:22), and the sgRNA was designed to contain a copy of the Zm7 spacer (SEQ ID NO:23). The Zm7-sgRNA spacer was incorporated into expression cassettes with one of the four 397 bp corn U6 promoters from chromosome 1 (SEQ ID NO:30), chromosome 2 (SEQ ID NO:32), chromosome 3 (SEQ ID NO:34), or chromosome 8 (SEQ ID NO:36). Negative controls used in the transformation included the modified reporter construct GU-Zm7-US with the Zm7 genomic target site and: (1) lacking both the Cas9 endonuclease expression cassette and the Zm7-sgRNA expression cassette; or (2) lacking just the Zm7-sgRNA expression cassette (FIG. 3). For both of these controls no blue sectors were detected, indicating no CRISPR-mediated cleavage of the modified reporter construct had occurred. The results from evaluation of the four different 397 bp corn U6 promoters in driving expression of the Zm7-sgRNA cassette showed that while all four 397 bp corn U6 promoters worked (i.e., blue sectors detected in the calli), the efficacy of the different promoters varied (as evidenced by the size and number of blue sectors in the calli). The U6 promoter from corn chromosome 8 showed the most efficacy, followed by the U6 promoter from chromosome 1. The U6 promoters from chromosomes 2 and 3 showed similar efficacy to each other (Chr 8>Chr 1>Chr2≈Chr3).

The specificity of the CRISPR/Cas9 system in this corn expression system was evaluated by testing mismatches between the protospacer sequence within the genomic target site in the modified GUUS reporter gene construct and the spacer sequence included in the varying sgRNA constructs (FIG. 4). As in the experiment described above, 0.6 μM gold particles were coated with one or more constructs; 0.3 pmol of the individual modified GUUS reporter construct (GUUS target), 0.16 pmol of the Cas9 endonuclease expression cassette, 0.3 pmol of the individual sgRNA cassettes, and 0.03 pmol of a transformation control construct expressing green fluorescent protein (GFP) (FIG. 4). Once the coated gold particles were prepared, ¼ of the mixture was used for bombardment of 3-day old immature corn embryos using standard protocols. More than 50 immature corn calli were bombarded for each set of constructs evaluated. Tissue was maintained in culture for 3 days post-bombardment. Determination of GFP expression by fluorescence microscopy was done on day 1 and again on day 3 to validate uniform bombardment and transformation. After the fluorescence microscopy on day 3, the calli were processed for X-Gluc staining and fluorescent and light micrographs of representative calli were taken (FIG. 4). The fluorescent staining for all calli indicated good transformation.

Negative controls used in the transformation included the modified reporter construct GU-Zm231-US with the Zm231 genomic target site (1) lacking both the Cas9 endonuclease expression cassette and any sgRNA expression cassette; or (2) having a Zm231-sgRNA expression cassette with a corn U6 promoter from chromosome 8, but lacking the Cas9 endonuclease expression cassette (FIG. 4). Both of these controls showed no blue sectors detected with X-Gluc staining, indicating no CRISPR-mediated cleavage of the modified reporter construct had occurred (FIG. 4).

The specificity of the CRISPR/Cas9 system was also evaluated using controls including a mismatch between the protospacer site in the modified GUUS reporter construct and the sgRNA spacer sequence. Specifically, the mismatch was between the modified reporter construct GU-Zm231-US with the Zm231 genomic target site and (1) the sgRNA expression cassette with the Zm14 spacer and a corn U6 promoter from chromosome 8; or (2) the sgRNA expression cassette with the Zm231 spacer sequence and a corn U6 promoter from chromosome 8 (FIG. 4).

Finally, the 397 bp corn U6 promoters (chromosome 1, 2, 3, and 8) were each used to generate sgRNA expression cassettes with the Zm231 genomic target site. These were each co-transformed with the modified reporter construct GU-Zm231-US made with the Zm231 genomic target site. Results indicated that when the sgRNA spacer sequence and the genomic target site of the reporter construct were mismatched, there was very little GUS activity detected. By contrast, when the sgRNA spacer sequence and the genomic target site of the reporter construct were matched, many large blue foci were detected (FIG. 4). The U6 promoter from corn chromosome 8 may have higher efficacy (based on the assumption that efficacy correlates to blue foci which were more numerous, larger in size, and darker in staining intensity), followed by the U6 promoter from corn chromosome 1. The U6 promoters from corn chromosomes 2 and 3 showed similar efficacy to each other (Chr 8>Chr 1>Chr2≈Chr3).

The sgRNA driven by the U6 promoter from corn chromosome 8 consistently showed high activity. These findings suggest that different corn U6 promoters have differing activities, and further highlights the usefulness of the U6 promoter derived from corn chromosome 8 in the CRISPR/Cas system of targeted genome modification.

Example 5

Blunt-End Oligonucleotide Integration

The CRISPR/Cas9 system was evaluated for targeting efficacy of insertion of a blunt-end double-stranded DNA fragment into one of three genomic target sites, identified as Zm_L70a (SEQ ID NO:47), Zm_L70c (SEQ ID NO:59), and Zm_L70d (SEQ ID NO:61) within the corn genome. Each of these three genomic target sites is unique in the corn genome. If the CRISPR components are capable of endonuclease activity and introduce a double strand break (DSB) in the protospacer of the selected genomic target site, then the endogenous corn non-homologous end-joining DNA repair system will insert the blunt-end double-stranded DNA fragment into the DSB.

Figure 5A:
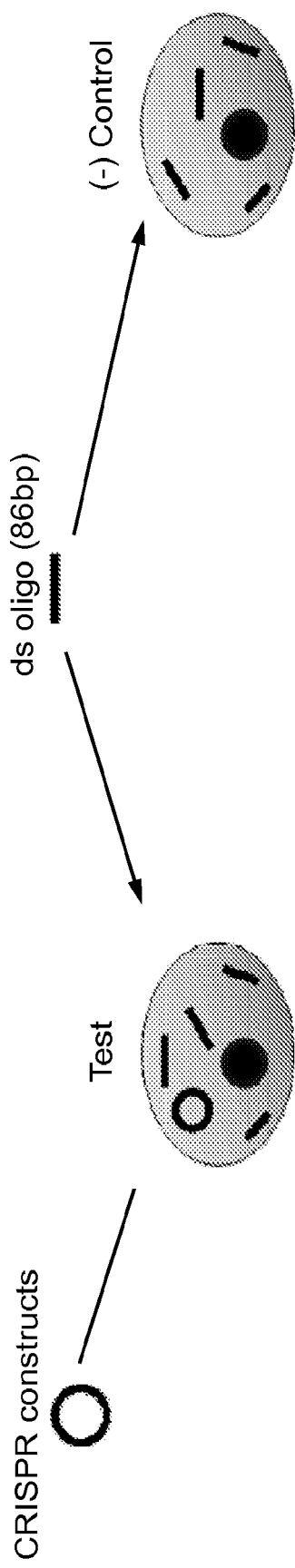
FIG. 5A-5E: Illustrations of (FIG. 5A) oligonucleotide integration assay.
Figure 5B:
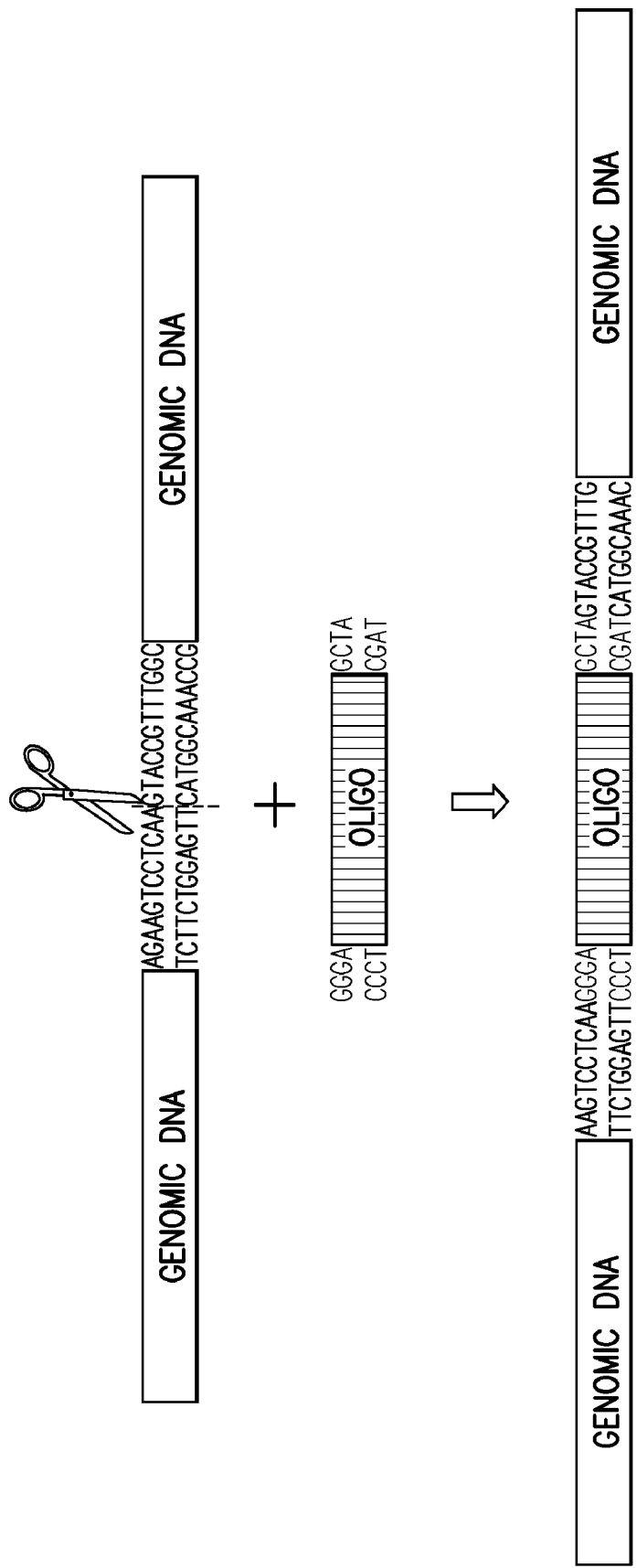
Figure 5C:
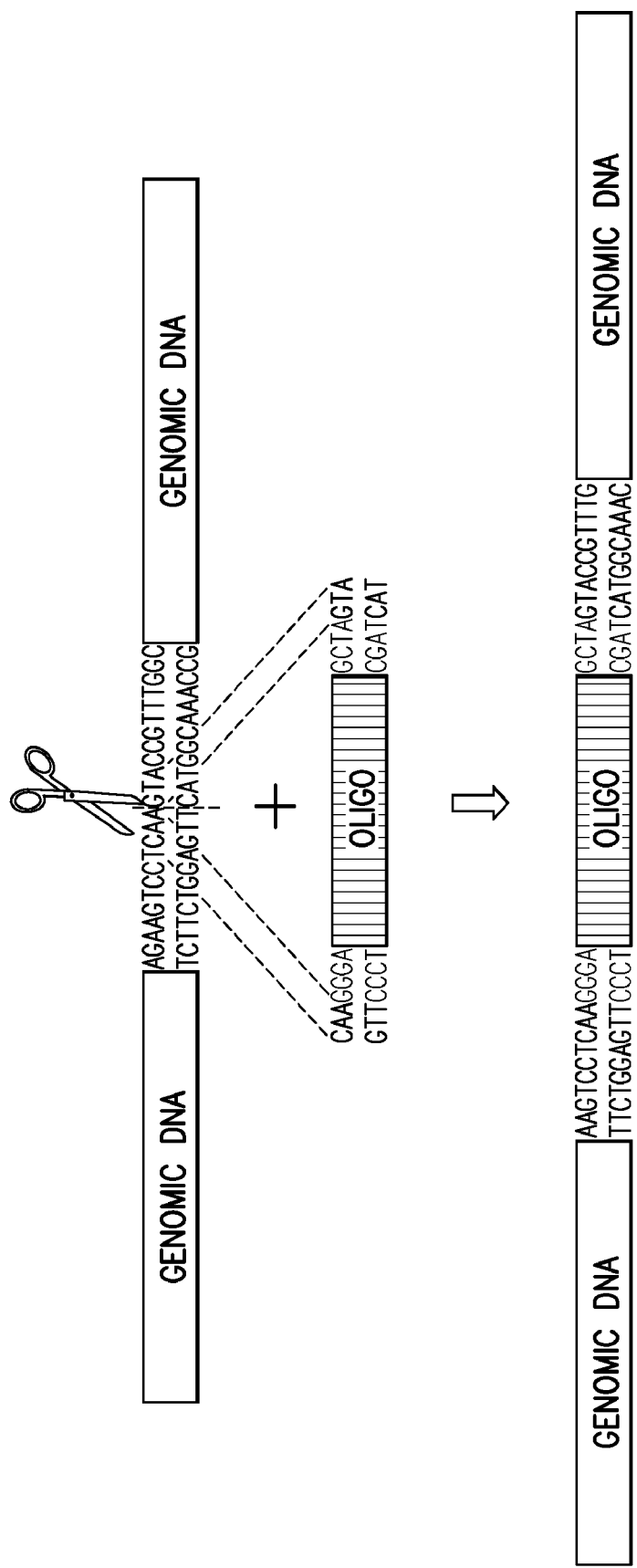

Complementary oligonucleotides were pre-annealed to form blunt-ended double-stranded DNA fragments, and these were co-transformed with CRISPR constructs into corn protoplasts (FIG. 5A). The oligonucleotide pairs were designed to either (1) not contain microhomology regions (see FIG. 5B), or (2) contain on each end (5' and 3') a 3 bp microhomology to the corresponding 5' and 3' flanking sequence at the cut site of the protospacer in the genomic target site (FIG. 5C). The microhomology sequences may promote blunt-end double-strand DNA fragment integrations through a mechanism of microhomology-driven non-homologous end-joining at the genomic target site. The two sequences of the oligonucleotide pair without microhomology sequence were SEQ ID NO:45 and SEQ ID NO:46. The three pairs of oligonucleotides, each containing microhomology to their respective genomic target site, were annealed in pairwise combinations of the following oligonucleotides: (1) SEQ ID NO:62 and SEQ ID NO:63 (microhomology to Zm_L70a); (2) SEQ ID NO:64 and SEQ ID NO:65 (microhomology to Zm_L70c); and (3) SEQ ID NO:66 and SEQ ID NO:67 (microhomology to Zm_L70d) to form blunt-end double-strand DNA fragments.

For these blunt-end double-strand DNA fragment integration assays, the CRISPR constructs used included the Cas9 endonuclease expression cassette described above, and one of three sgRNA expression cassettes. The three sgRNA expression cassettes were each driven by the 397 bp version of the U6 promoter from corn chromosome 8 (SEQ ID NO:7) and contained the spacer sequence corresponding to the genomic target sites: Zm_L70a (SEQ ID NO:48), Zm_L70c (SEQ ID NO:58), and Zm_L70d (SEQ ID NO:60). Differing combinations of the CRISPR components and oligonucleotides for these assays were mixed as follows: 0.6 pmol of the Cas9 expression cassette, 1.6 pmol of one of the sgRNA expression cassettes, and 35 pmol of the pre-annealed, oligonucleotide pair, and, using a standard PEG-mediated protocol, transformed into aliquots of corn leaf protoplast suspensions containing about 320,000 cells. Two days later, corn protoplasts were harvested and analyzed for insertion of the blunt-end double-strand DNA fragment into the particular L70 genomic target site targeted by the unique sgRNA selected in each case (Table 4). The negative control was the omission of the Cas9 expression cassette during the corn protoplast transformation.

To detect the insertion of the blunt-end double strand DNA fragment into the corn chromosome, DNA was extracted and high-throughput thermal amplification (PCR) was done with multiple pairs of primers (Table 5). As the blunt-end double strand DNA fragment may insert into the CRISPR cleaved chromosomal DNA in either orientation, primers were designed to one strand of the blunt-end double strand DNA fragment and to both flanking genomic regions, with each primer pair spanning the junction of the insertion site. The PCR amplicons were separated on a fragment analysis platform (ABI3730 DNA analyzer) from Life Technologies (Grand Island, N.Y.). This platform, which is more sensitive than gel-based electrophoresis methods and has single-bp resolution, confirmed whether the amplicons originated from the template of interest and whether they were specific to the experimental treatment conditions.

TABLE 4

DNA and RNA sequences of *Streptococcus pyogenes* sgRNA containing spacer sequences complementary to the protospacer sequence of the corn genomic target sites L70a, L70c, L70d.

| SEQ ID NO. | | |
| --- | --- | --- |
| DNA | RNA | Genomic target site |
| 82 | 85 | Zm_L70a |
| 83 | 86 | Zm_L70c |
| 84 | 87 | Zm_L70d |

Figure 5D:
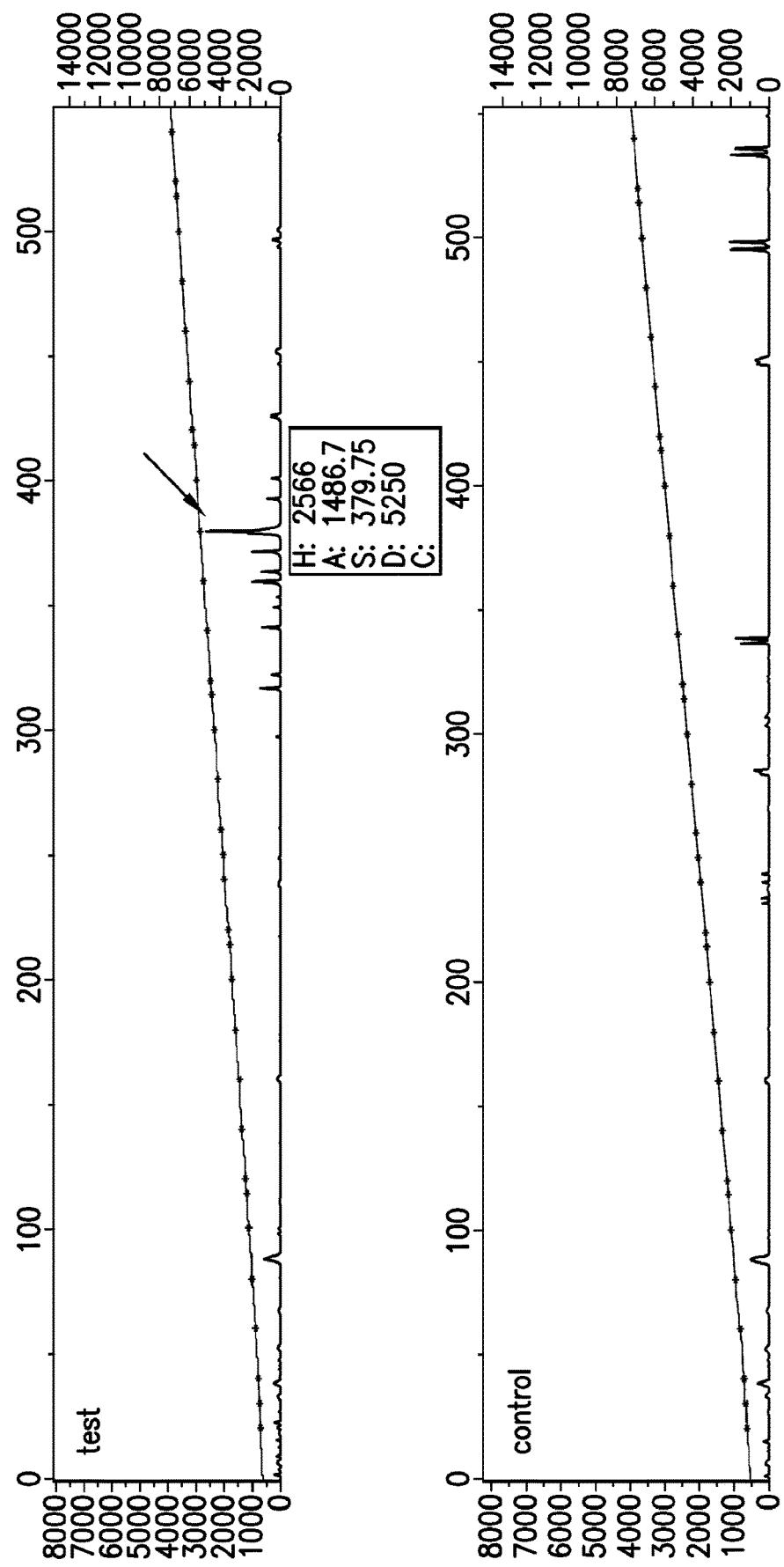

One representative fragment analysis profile is shown in FIG. 5D (Experiment T3, Table 5). Amplification of DNA extracted from corn protoplasts transformed with Cas9, sgRNA containing spacer sequences complementary to the protospacer sequence of the Zm_L70c corn genomic target site (SEQ ID NO:83), and the blunt-end double-stranded DNA fragment without microhomology, using primers at the Zm_L70c genomic target site (SEQ ID NO:49, primer specific for the inserted blunt-end double-strand DNA fragment, and SEQ ID NO:55, primer specific for flanking genomic DNA) revealed a major peak of the expected size and several additional peaks of similar sizes (arrow) (FIG. 5D, top panel). By contrast, no amplification products were seen from DNA extracted from the negative control transformations (FIG. 5D, bottom panel). This PCR profile was consistent with double-stranded breaks repaired erroneously by non-homologous end-joining, resulting in introduction of short indels at the site of repair.

Figure 5E:
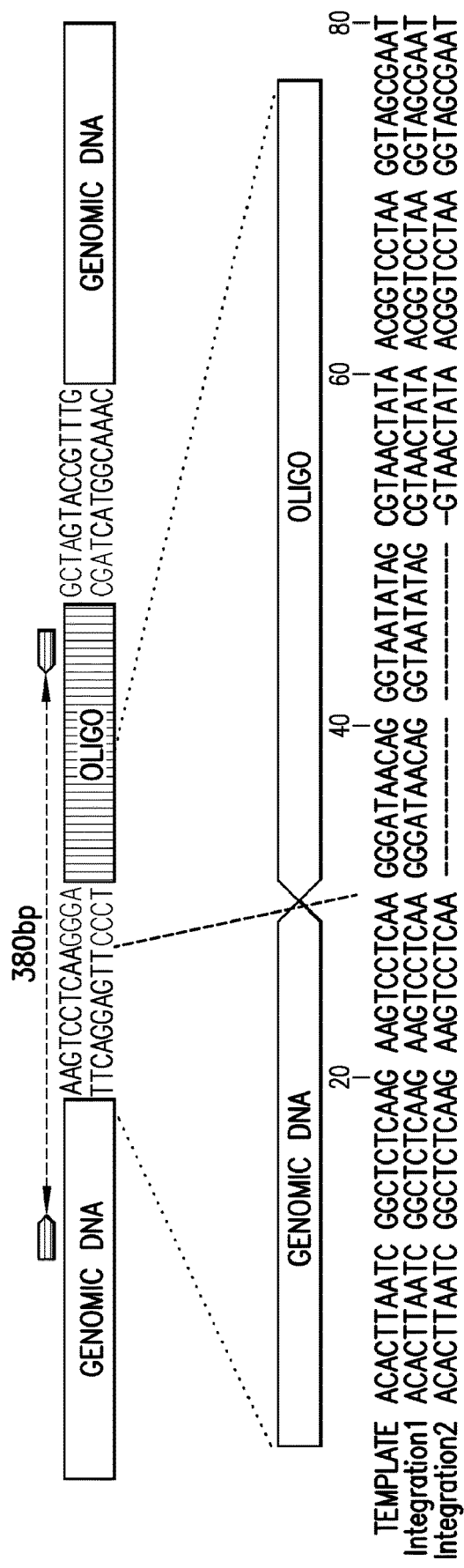

To confirm that the blunt-end double-strand DNA fragment was incorporated at the genomic target site, the PCR amplicons were cloned and sequenced (Table 5). Negative controls lacking Cas9 proteins did not produce PCR products. Seven of the ten experiments showed the expected pattern: a positive PCR product of the expected size for the test samples, and no PCR product for control samples. The seven experiments showing a positive PCR product included experiments demonstrating integrations occurring for both blunt-end double-strand DNA fragments with and without microhomology. Experiments T1 and T7 failed to detect targeted integrations in either test or control samples. PCR products from six of the experiments were cloned and sequenced, confirming the expected DNA fragment-chromosome junctions for blunt-end double-strand DNA fragment integration. Sequencing results showed the presence of both full-length and truncated DNA fragments (indels) present at the site of blunt-end double-strand DNA fragment integration (see, e.g., FIG. 5E, Experiment T1). Sequences were consistent with the fragment analysis (FIG. 5D) and demonstrated that CRISPR/Cas9 can target native, sequence-specific, chromosomal loci for cleavage in corn protoplasts. These results also demonstrated successful blunt-end double-strand DNA fragment integration with and without regions of microhomology.

Example 6

Targeted Genome Modification with CRISPR/Cas9 Complex Genes from *Streptococcus thermophilus*

Figure 6:
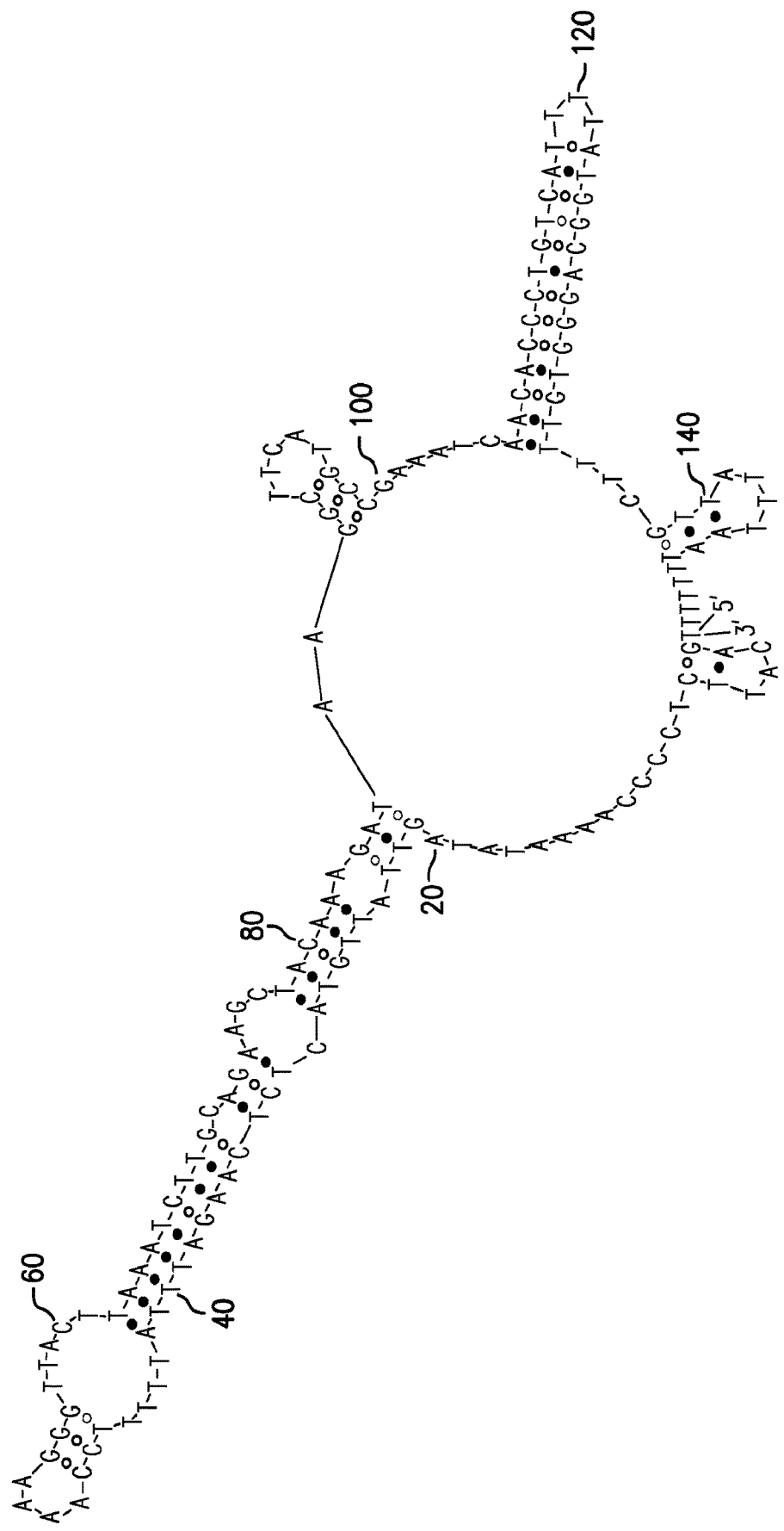
FIG. 6: Illustration of a sgRNA including a spacer sequence complementary to a native corn genomic target site and an artificial loop (5'-CCAAAAGG-3'; SEQ ID NO:105) and its predicted secondary structure designed for *Streptococcus thermophilus* Cas9-mediated targeting (SEQ ID NO:110).

It may be desirable to accomplish CRISPR-mediated genome modification of some plants (e.g., crop plants) with CRISPR complex genes derived from *Streptococcus thermophilus* instead of *S. pyogenes*. The inventors have developed an expression cassette encoding a codon-optimized nucleotide sequence with two nuclear localization signals (NLS) (SEQ ID NO:136) of the Cas9 protein from *S. thermophilus* (SEQ ID NO:69). The StCas9 was designed to encode both an N-terminal and a C-terminal nuclear-localization signal (NLS) (SEQ ID NO:120) at amino acid position 2-11 and 1133-1142 (SEQ ID NO:135). Additionally, the DNA expression cassette (SEQ ID NO:136) included an intron at nucleotide position 507-695. A series of unique *S. thermophilus* single-guide RNAs (sgRNA) have been designed. The *S. thermophilus* sgRNA was designed to link the native *S. thermophilus* crRNA and tracrRNA with a stem loop (5'-CCAAAAGG-3'; SEQ ID NO:105), and to contain the spacer sequence complementary to the protospacer of the corn genomic target sites selected from Zm_L70e (SEQ ID NO:72), Zm_L70f (SEQ ID:73), Zm_L70g (SEQ ID NO:74), or Zm_L70h (SEQ ID NO:75). The seven nucleotides at the 3' end of each of these genomic target sites represent the *S. thermophilus*-specific protospacer adjacent motif (PAM, 5'-NNAGAAW-3'; SEQ ID NO:106). FIG. 6 shows the predicted secondary structure of this *S. thermophilus* sgRNA (SEQ ID NO:70) with a copy of the spacer sequence (SEQ ID NO:71) complementary to the protospacer sequence of the corn Zm_L70h genomic target site (SEQ ID NO:75) and stem-loop linker (5'-CCAAAAGG-3'; SEQ ID NO:105). Table 6 lists the corresponding SEQ ID NOs for the DNA and RNA sequences encoding *S. thermophilus* sgRNAs containing spacer sequences complementary to the protospacer sequence of the corn genomic target sites Zm_L70e, Zm_L70f, Zm_L70g, and Zm_L70h.

TABLE 5

Blunt-end oligonucleotide insertion assay

| Experiment | Treatments | Genomic protospacer/ target site | Microhomology | Orientation | Primer pairs (SEQ ID NOs) | Expected amplicon size (bp) | Expected amplicon | Sequenced amplicon |
|---|---|---|---|---|---|---|---|---|
| T1 | test | L70a | − | + | 50/49 | 408 | − | − |
|  | (−) control | L70a | − | + | 50/49 | N/A | − | − |
| T2 | test | L70a | − | − | 51/49 | 324 | + | + |
|  | (−) control | L70a | − | − | 51/49 | N/A | − | − |
| T3 | test | L70c | − | + | 55/49 | 384 | + | + |
|  | (−) control | L70c | − | + | 55/49 | N/A | − | − |
| T4 | test | L70c | − | − | 54/49 | 411 | + | + |
|  | (−) control | L70c | − | − | 54/49 | N/A | − | − |
| T5 | test | L70c | + | + | 55/49 | 384 | + | + |
|  | (−) control | L70c | + | + | 55/49 | N/A | − | − |
| T6 | test | L70c | + | − | 54/49 | 411 | + | − |
|  | (−) control | L70c | + | − | 54/49 | N/A | − | − |
| T7 | test | L70d | − | + | 56/49 | 359 | − | − |
|  | (−) control | L70d | − | + | 56/49 | N/A | − | − |
| T8 | test | L70d | − | − | 57/49 | 356 | + | + |
|  | (−) control | L70d | − | − | 57/49 | N/A | − | − |
| T9 | test | L70d | + | + | 56/49 | 359 | + | + |
|  | (−) control | L70d | + | + | 56/49 | N/A | − | − |
| T10 | test | L70d | + | − | 57/49 | 356 | + | − |
|  | (−) control | L70d | + | − | 57/49 | N/A | * | − |

Where * = sample contaminated.

TABLE 6

DNA and RNA sequences of *Streptococcus thermophilus* sgRNA containing spacer sequences complementary to the protospacer sequence of the corn genomic target sites Zm_L70e, Zm_L70f, Zm_L70g, and Zm_L70h.

| SEQ ID NO. | | |
|---|---|---|
| DNA | RNA | Genomic target site |
| 107 | 111 | Zm_L70e |
| 108 | 112 | Zm_L70f |
| 109 | 113 | Zm_L70g |
| 110 | 114 | Zm_L70h |

The assay for *S. thermophilus* Cas9 mediated genome modification was essentially as described in example 5. Specifically, 320,000 corn protoplasts were transfected with 0.8 pmol *S. thermophilus* Cas9 (SEQ ID NO:136) expression construct, and 1.6 pmol of one of the sgRNA expression constructs driven by the 397 bp version of the U6 promoter from corn chromosome 8 (SEQ ID NO:7) containing the spacer sequence corresponding to the genomic target sites: sgRNA construct for site L70e (SEQ ID NO:107), sgRNA construct for site L70f (SEQ ID NO:108), and sgRNA construct for site L70g (SEQ ID NO:109), and 50 pmol of a pre-annealed blunt-end double-strand DNA fragment encoded by SEQ ID NO:115 and SEQ ID NO:116. To test for transformation efficiency, 2.5 ug of a construct encoding green fluorescent protein (GFP) was included. At the time of harvesting, an aliquot of the transfected protoplasts was collected to calculate transfection frequency on the PE Operetta® Imaging System (PerkinElmer, Waltham, Mass.) which calculates the ratio of GFP positive cells per total cells. Omission of the StCas9 expression cassette during the corn protoplast transformation served as the negative control. Protoplasts were harvested 48 hours post transfection and analyzed for insertion of the blunt-end double-strand DNA fragment into the L70e, or L70f, or L70g genomic target site by quantitative, high-throughput PCR analysis using a BioRad QX200™ Droplet Digital™ PCR (ddPCR™) system (BioRad, Hercules, Calif.) and TaqMan® probes. To determine the percent targeted integration rate, one set of TaqMan primers and probes was used with the ddPCR system to detect the template copy number of a junction of the inserted blunt-end double-strand DNA fragment at the chromosomal target site. The junction specific primers and probe for corn chromosomal sites L70e, L70f, L70g, and L70h are indicated in Table 7. To normalize the amount of DNA in the transfected protoplast aliquot, the ddPCR system was used with a second set of TaqMan primers and a probe (primers encoded by SEQ ID NO:132 and SEQ ID NO:134; probe encoded by SEQ ID NO:133) to determine the template copy number of a site unique in the corn genome and outside of the target site. The calculation for the percent targeted integration rate was the target site specific template copy number divided by the corn genome specific template copy number divided by the transformation frequency as determined by GFP-positive vs. total cell counts using the PE Operetta® Imaging System (PerkinElmer, Waltham, Mass.). The data points presented in the graph were determined by averaging four biological replicates. The results are presented in FIG. 15 and show that the percent integration rate for each of the sites L70e, L70f, and L70g was higher than the corresponding control.

PCR amplicons corresponding to targeted junctions from the protoplast experiments were sequenced to confirm the integration of the blunt-end double-strand DNA fragments into the selected target sites. FIG. 15B shows an alignment of the expected integration of the blunt-end, double-strand DNA fragment at the L70f target site (SEQ ID NO:144) and one example of target site integration (SEQ ID NO:145) with deletion of some of the sequence of the DNA fragment. Although these sequencing results show indels, the results confirm that the DNA fragment was integrated at the L70f target site.

TABLE 7

SEQ ID NOs for primers and probes for PCR amplification of junction at corn chromosomal target sites with inserted DNA fragment.

| Site | SEQ ID NO: of Genomic specific primer | SEQ ID NO: of Probe | SEQ ID NO: of Inserted DNA specific primer |
|---|---|---|---|
| L70e | 139 | 138 | 137 |
| L70f | 140 | 138 | 137 |
| L70g | 141 | 138 | 137 |
| L70h | 142 | 138 | 137 |

Example 7

Targeting Multiple Unique Genomic Sites by sgRNA Multiplexing

Figure 7A:
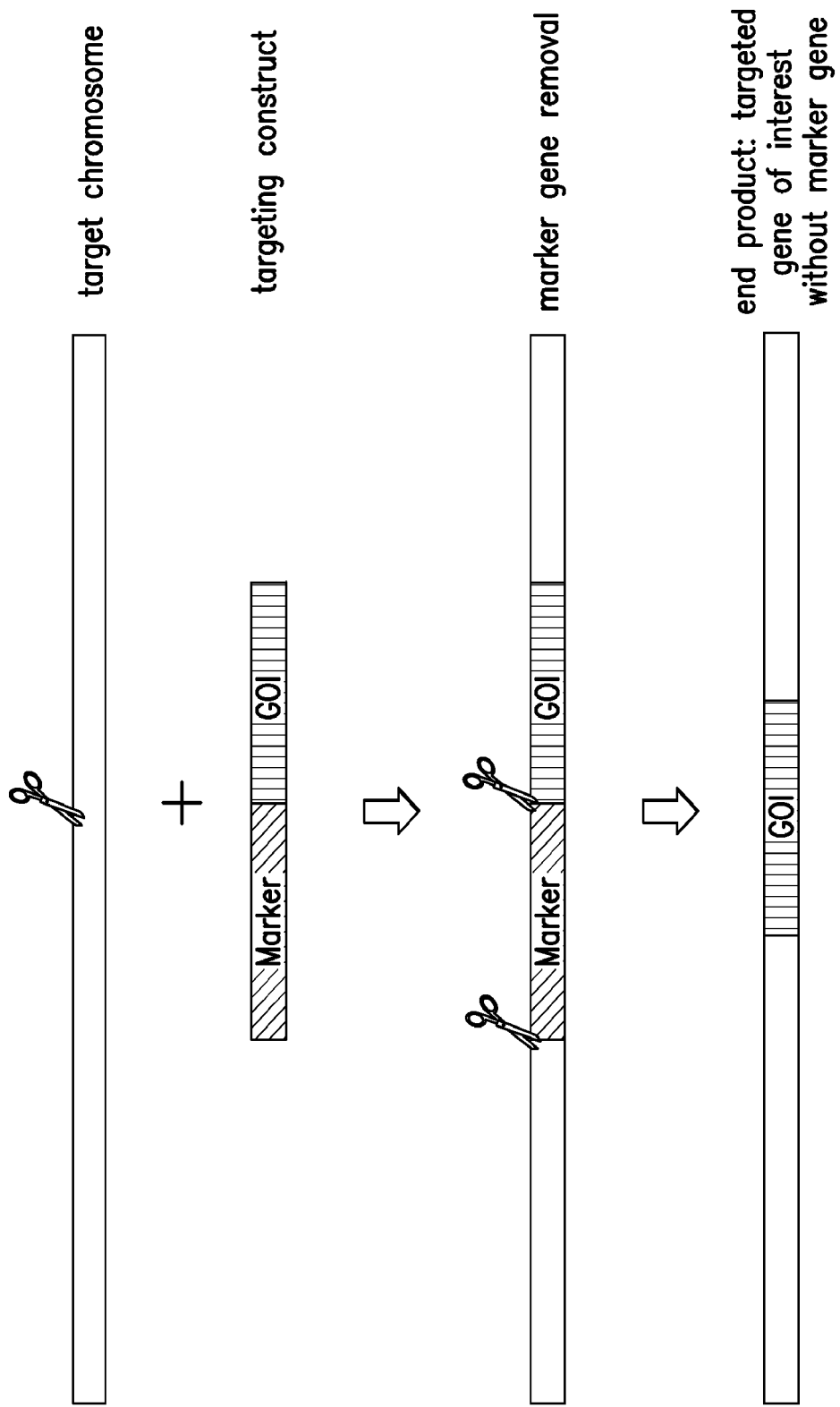
FIG. 7: Illustrations of (A) selectable marker gene removal by multiplex CRISPR activity following targeted integration of the gene of interest (GOI); and (B) a CRISPR/Cas multiplex system to evaluate gene linkage of multiple QTL candidate genes. Where likelihood of odds (LOD) is a statistical measure for genetic linkage; an LOD of 3 means that it is 1000× more likely that a QTL exists in the interval than that there is no QTL.

A key advantage of the CRISPR system, as compared to other genome engineering platforms, is that multiple sgRNAs directed to separate and unique genomic target sites can be delivered as individual components to effect targeting. Alternatively, multiple sgRNAs directed to separate and unique genomic target sites can be multiplexed (i.e., stacked) in a single expression vector to effect targeting. An example of an application that can require multiple targeted endonucleolytic cleavages includes marker-gene removal from a transgenic event (FIG. 7A). The CRISPR system can be used to remove the selectable marker from the transgenic insert, leaving behind the gene of interest.

Figure 7B:
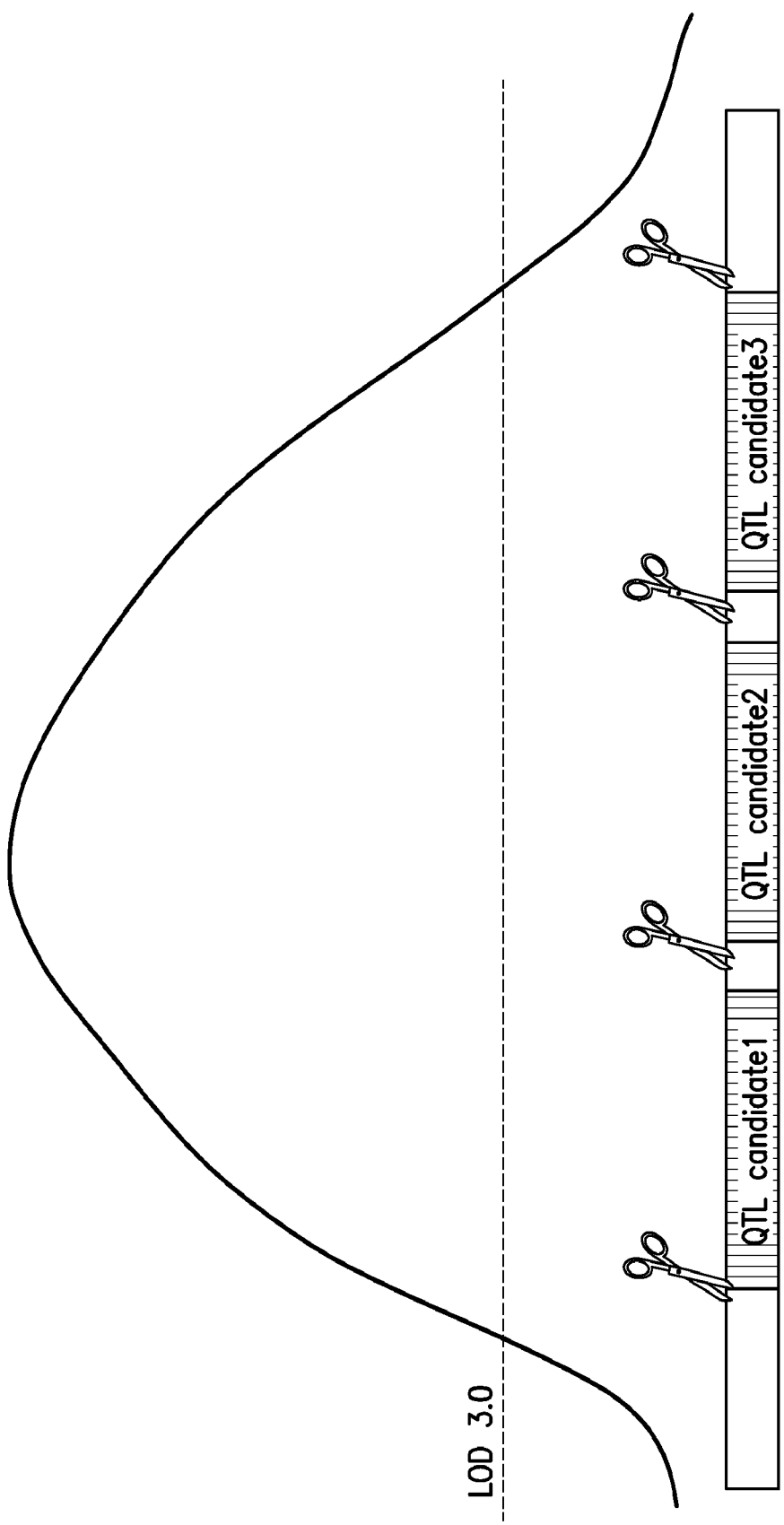

Another example of an application in which such a CRISPR/Cas system can be useful is when there is a requirement for multiple targeted endonucleolytic cleavages, such as when the identification of causal genes behind a quantitative trait is hampered by lack of meiotic recombinations in the QTL regions that would separate the gene candidates from each other. This can be circumvented by transformation with several CRISPR constructs targeting the genes of interests simultaneously. These constructs would either knock out the gene candidates by frame shift mutations or remove them by deletion. Such transformations can also lead to random combinations of intact and mutant loci that would allow for identification of casual genes (FIG. 7B).

Example 8

Integration Rates as a Function of Blunt-End DNA Fragment Concentration and Time The corn protoplast system essentially as described in Example 5 was used to determine the optimal concentration of blunt-end double-strand DNA fragment to be included in the assay mixture to achieve the highest percentage targeting integration rate. For these assays the expression construct encoding the *S. pyogenes* Cas9 was modified to include an intron from position 469-657 in the coding region (SEQ ID NO:119). Additionally, the protein sequence (SEQ ID NO:118) contained two NLS sequences (SEQ ID NO:120), one at the amino-terminal end (amino acids 2 to 11 of SEQ ID NO:118) and one at the carboxy-terminal end (amino acids 1379 to 1388 of SEQ ID NO:118).

Figure 8:
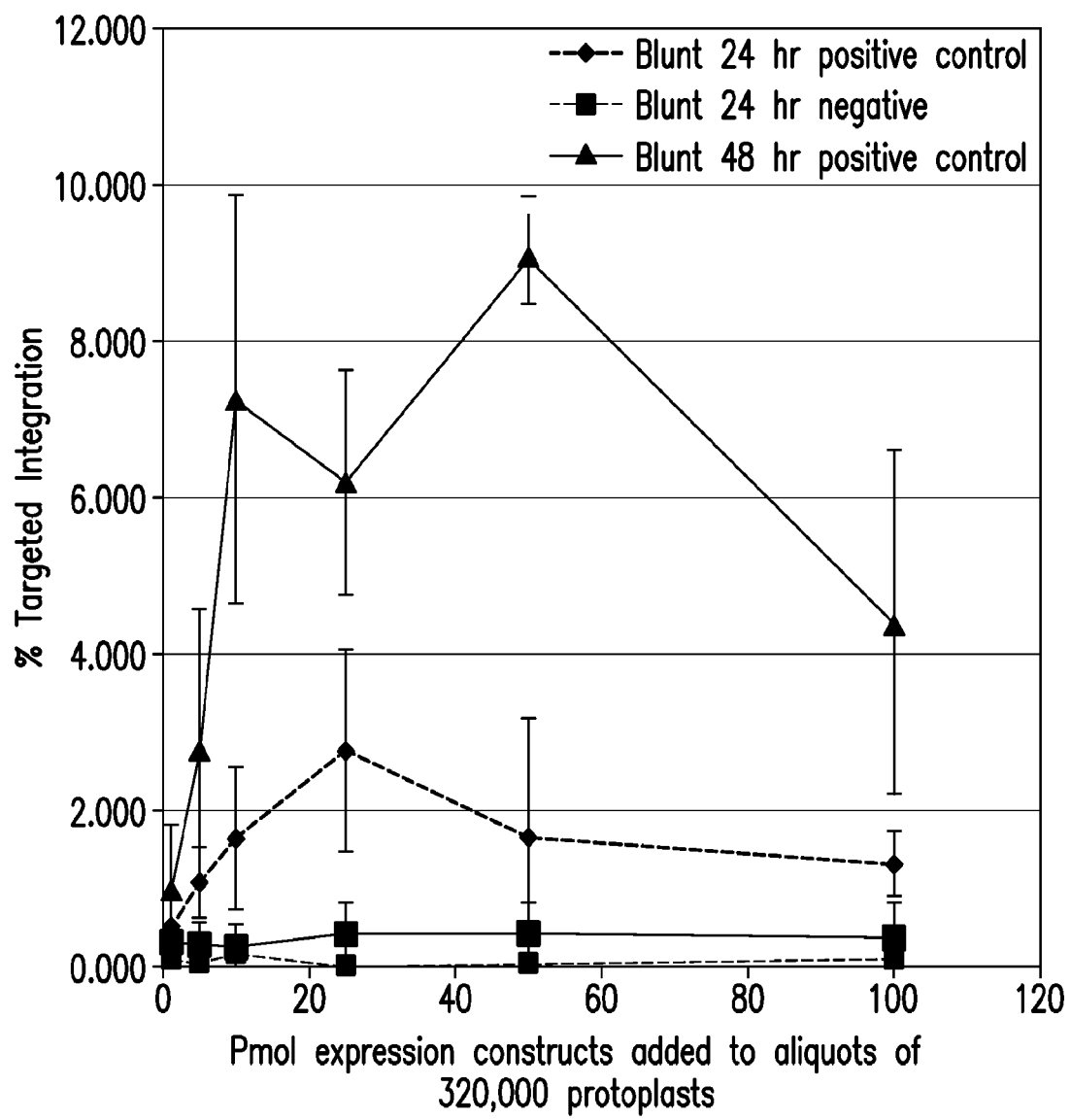
FIG. 8. Graphical presentation of data showing percentage targeted integration rates (Y-axis) detected at 24 and 48 hours post-transformation of corn protoplasts using CRISPR constructs targeting a native chromosomal target (Zm7) in corn and a titration of the pmol of blunt-end, double-stranded DNA fragment added to the transfection mixture (X-axis). The negative controls were run without added Cas9 expression constructs.

For the assay, 320,000 corn protoplasts were transfected with 0.8 pmol S. pyogenes Cas9 (SEQ ID NO:119) expression construct, and 1.6 pmol of sgRNA expression construct driven by the 397 bp version of the U6 promoter from corn chromosome 8 (SEQ ID NO:7) containing the spacer sequence corresponding to the genomic target sites: Zm7 (SEQ ID NO:23), and a pre-annealed blunt-end double-strand DNA fragment (SEQ ID NO:115 and SEQ ID NO:116) at 1, 5, 10, 25, 50, and 100 pmol. For transformation efficiency, 2.5 ug of a construct encoding green fluorescent protein (GFP) was included and the number of GFP positive protoplasts per 320,000 corn protoplasts was determined. Omission of the Cas9 expression cassette during the corn protoplast transformation served as the negative control. Protoplasts were harvested at 24 hours and 48 hours post transfection and analyzed for insertion of the blunt-end double-strand DNA fragment into the Zm7 genomic target site by quantitative, high-throughput PCR analysis using a BioRad QX200™ Droplet Digital™ PCR (ddPCR™) system (BioRad, Hercules, Calif.) and Taqman® probes. To determine the percent targeted integration rate, one set of Taqman primers (represented by SEQ ID NO:137 and SEQ ID NO:143) and a probe (represented by SEQ ID NO:138) was used with the ddPCR system to detect the template copy number of a junction of the inserted blunt-end double-strand DNA fragment at the chromosomal Zm7 target site. To normalize the amount of DNA in the transfected protoplast aliquot, the ddPCR system was used with a second set of Taqman primers and a probe (primers encoded by SEQ ID NO:132 and SEQ ID NO:134; probe encoded by SEQ ID NO:133) to determine the template copy number of a site unique in the corn genome and outside of the target site. The calculation for the percent targeted integration rate was the target site specific template copy number divided by the corn genome specific template copy number divided by the transformation frequency as determined by GFP-positive vs. total cell counts using the PE Operetta Imaging System (PerkinElmer, Waltham, Mass.). The data points presented in the graph were determined by averaging four biological replicates. The results are presented in FIG. 8 and show that the peak for percentage targeted integration rate was obtained with 50 pmol of the blunt-end, double-strand DNA fragment and incubation for 48 hours.

Example 9

Integration Rates as a Function of Cas9 Endonuclease Concentration

Figure 9:
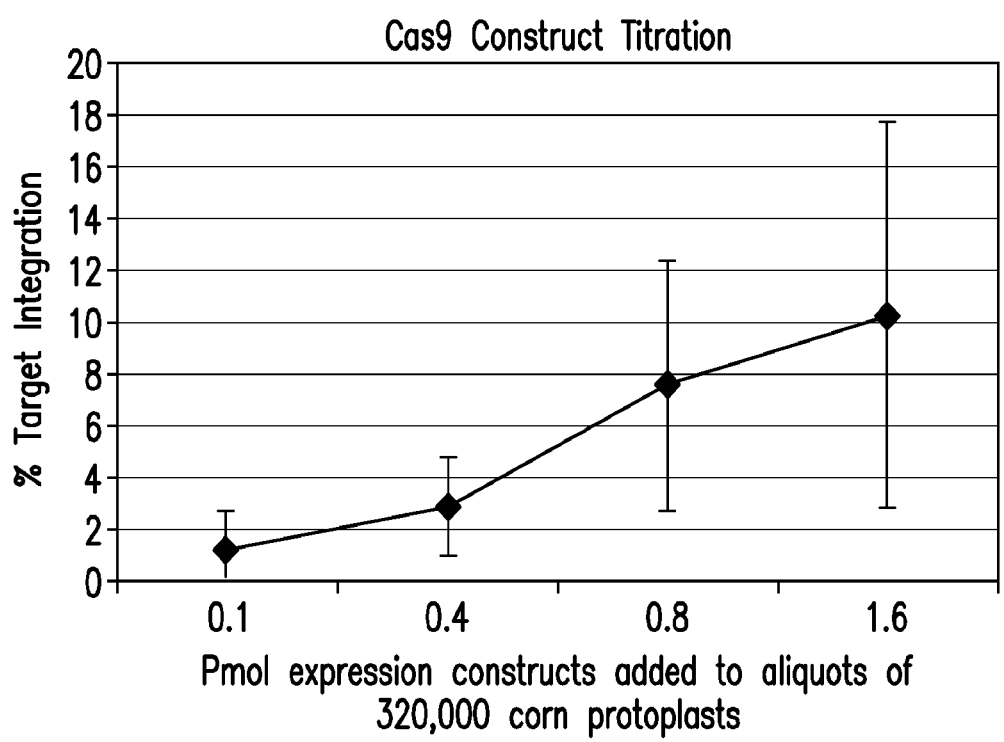
FIG. 9. Graphical presentation of the integration rate (Y-axis) as a function of the amount (in pmol) of SpCas9 expression construct added to transfection mixture of corn protoplasts (X-axis).

The corn protoplast system essentially as described in Example 8 was used to establish the optimal concentration of expression constructs encoding S. pyogenes Cas9 included in the protoplast transfection mixture to achieve the highest percentage targeted integration rate with the blunt-end double-strand DNA fragments. For these assays the expression construct encoding the modified S. pyogenes Cas9 was as described in Example 8. For the assay, 320,000 corn protoplasts were transfected with 0.1 pmol or 0.4 pmol or 0.8 pmol or 1.6 pmol of the S. pyogenes Cas9 (SEQ ID NO:119) expression construct, and 1.6 pmol of sgRNA expression construct driven by the 397 bp version of the U6 promoter from corn chromosome 8 (SEQ ID NO:7) containing the spacer sequence corresponding to the genomic target site Zm7 (SEQ ID NO:23), 50 pmol of pre-annealed blunt-end double-strand DNA fragment (SEQ ID NO:115 and SEQ ID NO:116), and a construct encoding GFP. The corn protoplasts were harvested 48 hours post-transfection and the percentage targeted integration was assessed as described in Example 8 using the ddPCR system and Taqman probes. The results of the analysis of the Cas9 expression construct titration are presented in FIG. 9 showing a linear increase in percentage targeted integration rate over the full-range of pmol of expression construct concentration tested.

Example 10

Sequence Confirmation of Insertion of Blunt-End Double-Strand DNA Fragments

PCR amplicons corresponding to targeted junctions from the protoplast experiments detailed in Example 5 and Example 8 were sequenced to confirm the integration of the blunt-end double-strand DNA fragments into the selected target site, Zm7 or L70c.

Figure 10A:
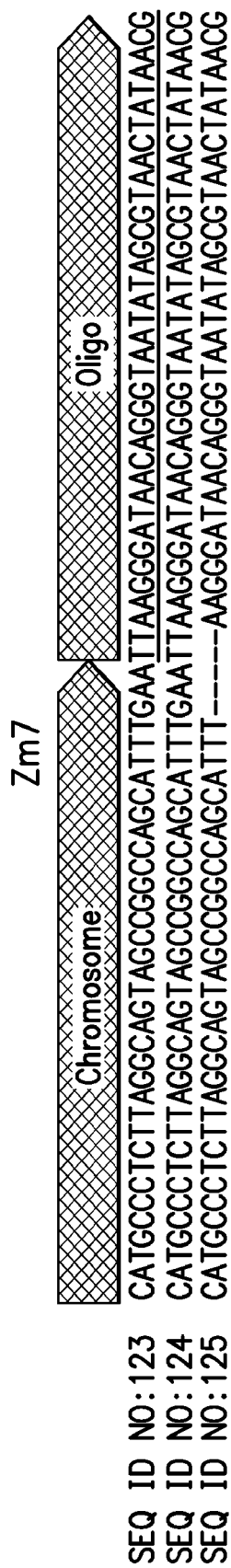
FIG. 10. Sequence confirmation for targeted integrations of blunt-end, double-strand DNA fragments into chromosomes of corn protoplasts transformed with CRISPR/Cas9 and sgRNA expression constructs. For all panels 10A, B, C, the top sequence is the expected sequence of one junction of the target site and the blunt-end double-strand DNA fragment (underlined sequence) included in the experiment. 10A. Corn chromosome site Zm7 targeted by CRISPR/Cas9 constructs and with blunt-end double-strand DNA fragment formed by annealed DNA fragments represented by SEQ ID NO:115 and SEQ ID NO:116. 10B. Corn chromosome site L70c targeted by CRISPR/Cas9 constructs and with blunt-end double-strand DNA fragment without micro-homology sequences formed by annealed DNA fragments represented by SEQ ID NO:45 and SEQ ID NO:46. 10C. Corn chromosome site L70c targeted by CRISPR/Cas9 constructs and with blunt-end double-strand DNA fragment with 3 bp micro-homology sequences at each end of the DNA fragment formed by annealed DNA fragments represented by SEQ ID NO:121 and SEQ ID NO:122.

For the corn chromosome site Zm7 targeted by CRISPR/Cas9 constructs and with blunt-end double-strand DNA fragment formed by annealed oligonucleotides encoded by SEQ ID NO:115 and SEQ ID NO:116 (see Example 8), PCR amplicons were agarose-gel purified and sequenced. The expected sequence is presented as SEQ ID NO:123, as shown in FIG. 10A. The results from the sequencing show at least one event with a base-pair perfect insertion of the blunt-end double-strand DNA fragment into the target site (SEQ ID NO:124). The results also show events with short deletions in either the chromosome or the DNA insert side of the junction, as indicated with SEQ ID NO:125 (see FIG. 10A).

Figure 10B:
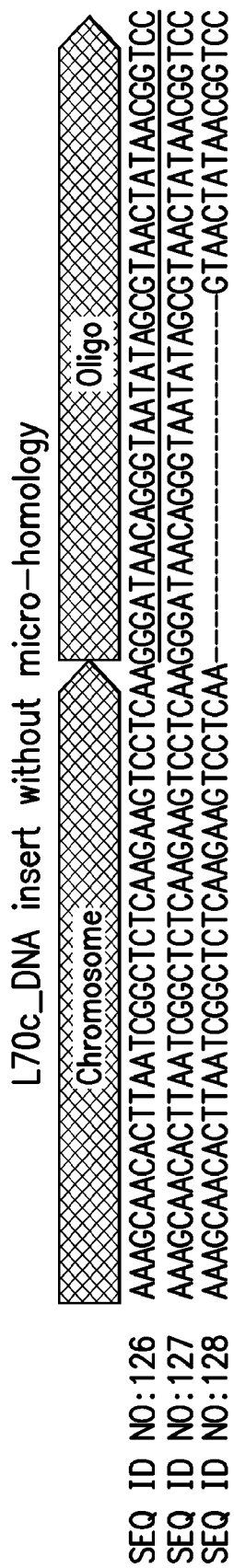

For the corn chromosome site L70c targeted by CRISPR/Cas9 constructs and with blunt-end double-strand DNA fragment without micro-homology sequences formed by annealed oligonucleotides encoded by SEQ ID NO:45 and SEQ ID NO:46 (see Example 5), PCR amplicons were agarose-gel purified and sequenced. The expected sequence is presented as SEQ ID NO:126, as shown in FIG. 10B. The results from the sequencing show at least one event that was detected with a base-pair perfect insertion of the blunt-end double-strand DNA fragment into the target site (SEQ ID NO:127). The results also show an example of events with short deletions in either the chromosome or the DNA insert side of the junction, as indicated with SEQ ID NO:128 (see FIG. 10B).

Figure 10C:
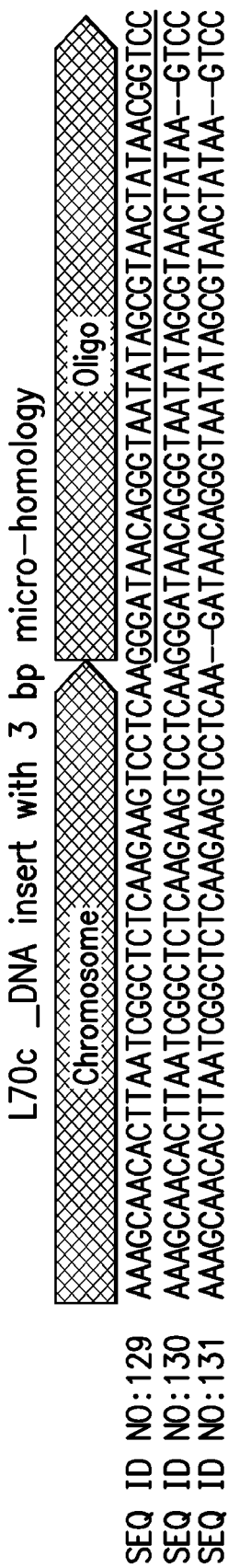

For the corn chromosome site L70c targeted by CRISPR/Cas9 constructs and with blunt-end double-strand DNA fragment with 3bp micro-homology sequences at each end of the DNA fragment formed by annealed oligonucleotides encoded by SEQ ID NO:121 and SEQ ID NO:122 (see Example 5), PCR amplicons were agarose-gel purified and sequenced. The expected sequence is presented as SEQ ID NO:129, as shown in FIG. 10C. The results from the sequencing show at least one event that was detected with a base-pair perfect insertion at the junction of the blunt-end double-strand DNA fragment into the target site (SEQ ID NO:130). The results also show an example of events with short deletions in either the chromosome or the DNA insert side of the junction (SEQ ID NO:131) and/or in the DNA insert itself (SEQ ID NO:130 and SEQ ID NO:131), as indicated (see FIG. 10C).

These results indicate that blunt-end double-strand DNA fragments are incorporated into a double-strand break (DSB)

at a target site created by a CRISPR/Cas9 system. The DNA fragments are incorporated by non-homologous end joining (NHEJ), an error-prone DNA repair mechanism that heals most somatic double-strand breaks in nature. Consistent with the endogenous NHEJ repair mechanism, the results show that blunt-end double-strand DNA fragments were incorporated with short deletions at the DSB created with CRISPR/Cas9 components, as illustrated by comparing SEQ ID NO:123 and SEQ ID NO:125 (FIG. 10A), and by comparing SEQ ID NO:126 and SEQ ID NO:128 (FIG. 10B), and by comparing SEQ ID NO:129 and SEQ ID NO:131 (FIG. 10C) (with this last pair there was also a 2bp deletion internal to the inserted DNA fragment). Blunt-end double-strand DNA fragments were incorporated in a base-pair perfect manner at the DSB created with CRISPR/Cas9 components, as illustrated by comparing SEQ ID NO:123 and SEQ ID NO:124 (FIG. 10A), and by comparing SEQ ID NO:126 and SEQ ID NO:127 (FIG. 10B), and by comparing SEQ ID NO:129 and SEQ ID NO:130 (FIG. 10C) (though in this last pair there was a 2 bp deletion internal to the inserted DNA fragment).

Example 11

Integration Rates as a Function of TALEN Endonuclease Concentration

The corn protoplast system essentially as described in Example 8 was used to establish the optimal concentration of expression constructs encoding a pair of TALEN endonucleases needed in the transfection mixture to achieve the highest percentage targeting integration rate of blunt-end double-strand DNA fragments.

Figure 11:
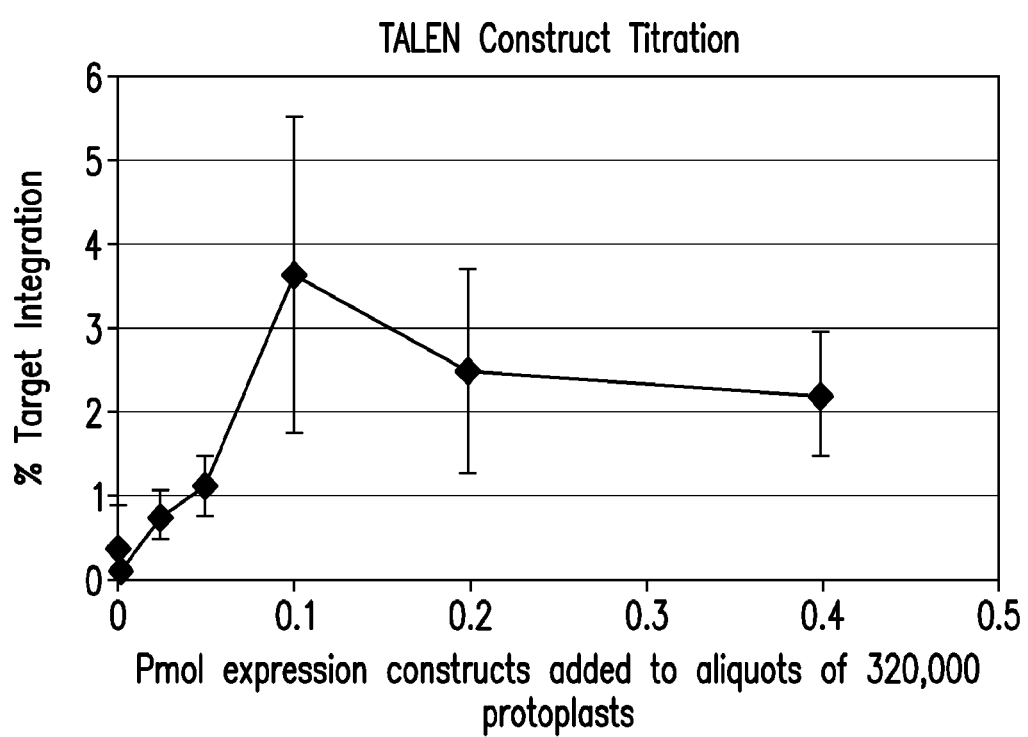
FIG. 11. Graphical presentation of the integration rate (Y-axis) as a function of the amount (in pmol) of TALEN expression constructs targeting corn chromosome site L70.4 which were added to transfection mixture of corn protoplasts (X-axis).

For these assays a pair of expression constructs with TALEN encoding cassettes was tested. The targeting site in the corn chromosome for the TALEN pair was L70.4. For the TALEN assay 0, 0.01, 0.02, 0.05, 0.1, 0.2 and 0.4 pmol of each of the constructs containing the TALEN encoding cassettes was used in the corn protoplast transformation. Also included was 50 pmol of pre-annealed blunt-end double-strand DNA fragment (SEQ ID NO:115 and SEQ ID NO:116) and 2.5 ug of the GFP encoding construct. The corn protoplasts were harvested 48 hours post-transfection and the percentage targeted integration was assessed by high-throughput PCR analysis essentially as described in previous examples. The results of the analysis of the TALEN expression construct titration are presented in FIG. 11 showing that the percentage targeted integration rate plateaus at about 0.1 pmol of each of the TALEN expression constructs included in the transfection reaction.

Example 12

Targeted Integration by Homologous Recombination—CRISPR/Cas9

Genome modification by targeted integration of a desired introduced DNA sequence will occur at sites of double strand breaks (DSB) in a chromosome. The integration of the DNA sequence is mediated by mechanisms of non-homologous end-joining (NHEJ) or homologous recombination using DNA repair mechanisms of the host cell. DSBs at specific sites in the host cell genome can be achieved using an endonuclease such as an engineered meganuclease, an engineered TALEN or a CRISPR/Cas9 system.

Figure 12B:
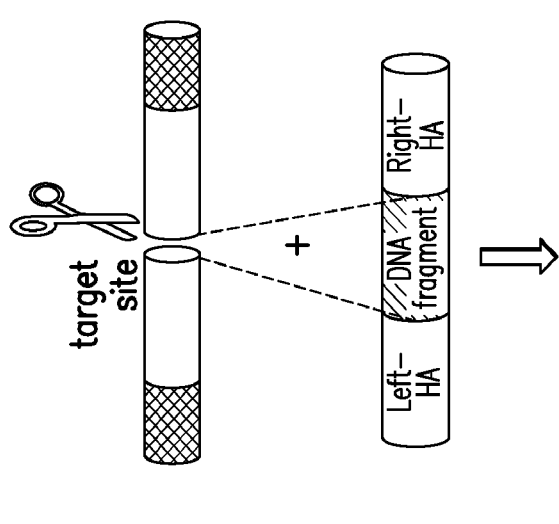
FIG. 12. Schematic representation of NHEJ and HR-mediated targeted integration and PCR primer positions for high through-put screening. Targeted integration of a DNA fragment by non-homologous end-joining (NHEJ) is presented in FIG. 12A and targeted integration of a DNA fragment by homologous recombination (HR) is presented in FIG. 12B.
Figure 12A:
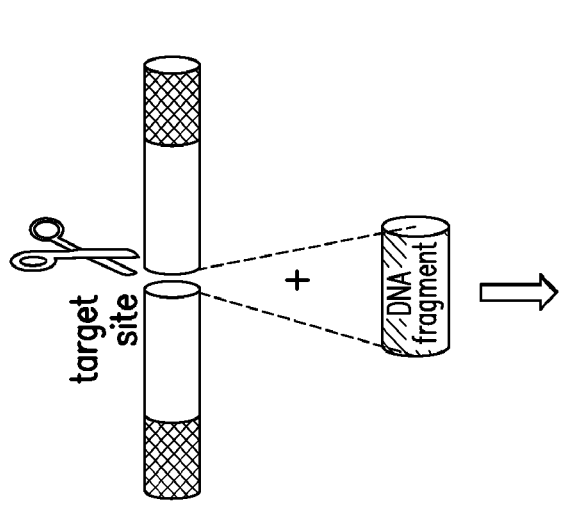

A schematic representation of a high through-put (HTP) testing method of NHEJ and HR-mediated targeted integration is presented in FIG. 12. Targeted integration of a DNA fragment by non-homologous end-joining (NHEJ) is presented in FIG. 12A and targeted integration of a DNA fragment by homologous recombination (HR) is presented in FIG. 12B. For HR, a recombinant DNA construct containing a cassette with the DNA fragment flanked with left- and right-homology arms (Left-HA and Right-HA, respectively) is introduced into the host cell. Following either NHEJ or HR targeted integration, HTP PCR analysis with primers (indicated by the short pair of arrows in FIG. 12A and 12B) designed to detect a targeted event where one primer is internal to the inserted DNA fragment and a second primer is located in the flanking chromosomal region.

The corn protoplast system as described in the above examples was used to determine homologous recombination (HR) mediated targeted integration rates. The target site Zm7 was targeted by a CRISPR/Cas9 nuclease and the sgRNA for targeting the corn Zm7 site, as described in Example 8. In addition to the constructs encoding the CRISPR/Cas9 and sgRNA cassettes, a construct containing a cassette for homologous recombination cassette was included at either 4 ug concentration or 6 ug concentration. As described above, a construct encoding GFP was also transfected and the percentage of GFP positive cells was used in the calculation of the targeted integration rate. The controls did not contain the construct encoding the SpCas9 endonuclease.

Figure 13A:
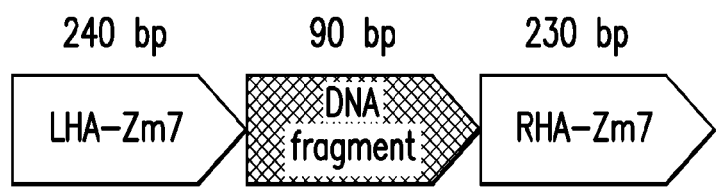
FIG. 13. Schematic representation of the constructs used for homologous integration. The blunt-end DNA arrow indicates the 90 bp sequence corresponding to the 90 bp blunt-end, double-strand DNA fragment used for NHEJ assays, LHA refers to left-homology arm, RHA refers to right-homology arm, Zm7 refers to the target site Zm7 targeted by a CRISPR/Cas9+sgRNA. The length in bp of each of the homology arms is indicated. A. Schematic for HR-cassette construct for targeting the corn chromosome site Zm7 with LHA and RHA of 240 and 230 bp in length, respectively. B. Schematic for HR-cassette construct for targeting the corn chromosome site Zm7 with LHA and RHA of 240 and 1003 bp in length, respectively.
Figure 13B:
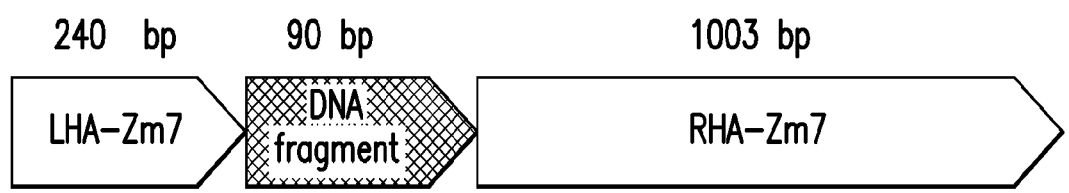

The recombinant DNA constructs containing cassettes for homologous recombination were designed to have the 90 bp sequence corresponding to the 90bp blunt-end, double-strand DNA fragment used for NHEJ assays (encoded by sequences SEQ ID NO:115 and SEQ ID NO:116) flanked by left and right homology arms (HA). The left-HA is designed based on the sequence flanking the 5'-side of the site for the double-strand break (DSB) for targeted integration. The right-HA is designed as the sequencing flanking the 3'-side of the site for the double-strand break (DSB) for targeted integration. For the Zm7 site the left-HA was 240 bp in length, and two separate right-HA sequences were included, one of 230 bp and one of 1003 bp in length (see FIGS. 13A and 13B, respectively).

Protoplasts were transfected and harvested 48 hours later and analyzed for integration by high through-put PCR with one primer designed for the region of the DNA fragment sequence (encoded by the sequences SEQ ID NO:115 and SEQ ID NO:116) and one primer in the chromosomal region flanking the left homology arm. The size of the expected PCR amplicon with successful HR using the Zm7 targeting constructs (FIGS. 13A and 13B) was 411 bp. In conventional quantitative PCR (qPCR), amplicons longer than about 160 bp cannot be quantitatively measured, and thus, are not recommended to be used. The current experiment clearly demonstrated that significantly longer PCR amplicons can also be used in the ddPCR system, which opens up a host of new opportunities in quantitative biology.

Figure 15A:
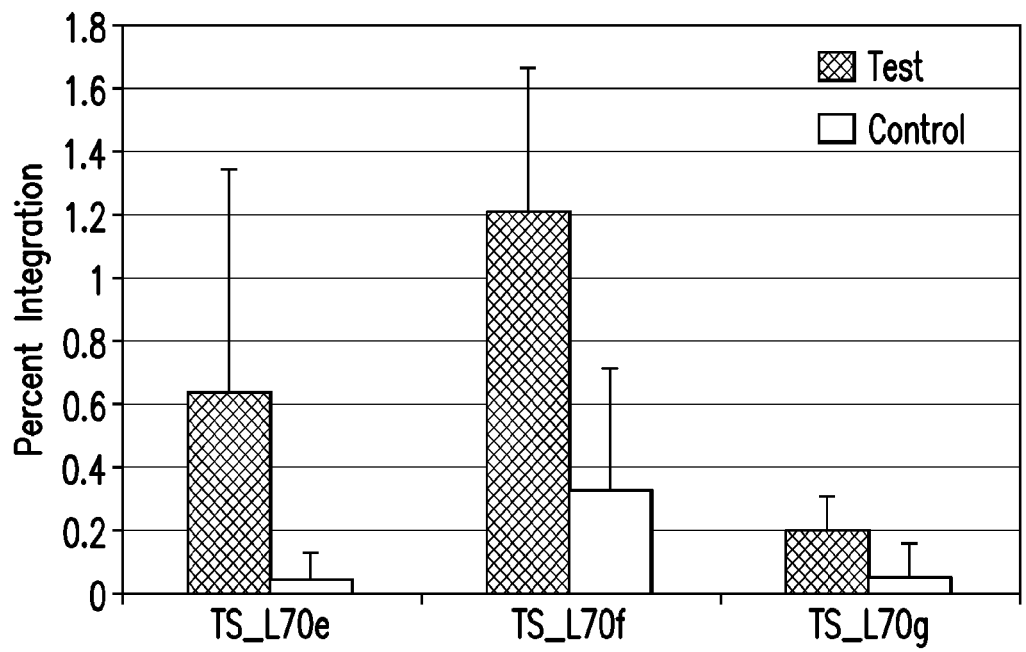
FIG. 15. 15A. Graphical presentation of data showing percent targeted integration rates in transfected corn protoplasts using StCas9 CRISPR constructs targeting native corn chromosomal target sites L70e, L70f, and L70g. The controls lacked a StCas9 expression cassette construct in the transfection mixture. 15B. Sequence alignment of expected integration of the blunt-end, double-strand DNA fragment at the L70f target site (SEQ ID NO:144) and one example of target site integration with indel of the DNA fragment sequence (SEQ ID NO:145).
Figure 15B:

The HR-mediated recombination rate for the corn chromosomal site Zm7 are presented in Table 8 and FIG. 15. When the left-HA and the right-HA were 240 bp and 230 bp, respectively, and the construct with the homology arm cassette was at a concentration of 4 ug or 6 ug, there was not a statistically significant difference in the percentage integration rate between the test sample and the control. When the left-HA was 240 bp and the right-HA was1003 bp (indicated by SL in Table 8), and the construct with the homology arm cassette was at a concentration of 4 ug there was not a statistically significant difference in the percentage integration rate between the test sample and the control. In contrast, when the left-HA was 240 bp and the right-HA was 1003 bp (indicated by SL in Table 8), and the construct with the homology arm cassette was at a concentration of 6 ug there was a statistically significant (p<0.05) difference in the percentage integration rate between the test sample and the control. This result shows that targeted integration can be achieved by the mechanism of HR at sites of DSB which are targeted by CRISPR/Cas9 system in a corn genome.

TABLE 8

HR-mediated integration rates in corn protoplasts with DSB mediated by a CRISPR/Cas9 system at the chromosomal site Zm7.

|  | Mean | | Std Dev | |
| --- | --- | --- | --- | --- |
|  | Test | Control | Test | Control |
| Zm7 + SS + 4 ug | 0.88346 | 0.15936 | 0.83999 | 0.17658 |
| Zm7 + SS + 6 ugl | 1.20057 | 0.15936 | 0.92889 | 0.17658 |
| Zm7 + SL + 4 ug | 1.297183 | 0.98692 | 0.791837 | 0.86133 |
| Zm7 + SL + 6 ug** | 2.32094 | 0.98692 | 1.35951 | 0.86133 |

**Test was statistically higher (p < 0.05) than the corresponding control based on a student's t-test.

Example 13

Targeted Integration by Homologous Recombination—TALEN

The corn protoplast system as described in the above examples was used to determine homologous recombination (HR) mediated targeted integration rates. The target site L70.4 was targeted by a pair of recombinant DNA constructs encoding a TALEN pair directed to target the corn L70.4 site, as described in Example 11. In addition to the constructs encoding the TALEN cassettes, a construct containing a cassette for homologous recombination cassette was included at either 4 ug concentration or 6 ug concentration. As described above, a construct encoding GFP was also transfected and the percentage of GFP positive cells was used in the calculation of the targeted integration rate. The controls did not contain the constructs encoding the TALENs.

Figure 14A:
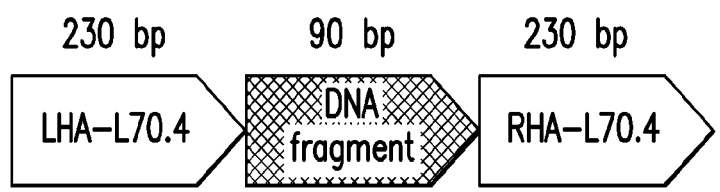
FIG. 14. Schematic representation of the constructs used for homologous integration. In the figure, blunt-end DNA arrow indicates the 90 bp sequence corresponding to the 90bp blunt-end, double-strand DNA fragment used for NHEJ assays, LHA refers to left-homology arm, RHA refers to right-homology arm, L70.4 refers to the target site L70.4 in the corn chromosome targeted by a TALEN pair. The length in bp of each of the homology arms is indicated. A. Schematic for HR-cassette construct for targeting the corn chromosome site L70.4 with both the LHA and RHA 230 bp in length. B. Schematic for HR-cassette construct for targeting the corn chromosome site L70.4 with LHA and RHA of 1027 bp and 230 bp in length, respectively.
Figure 14B:
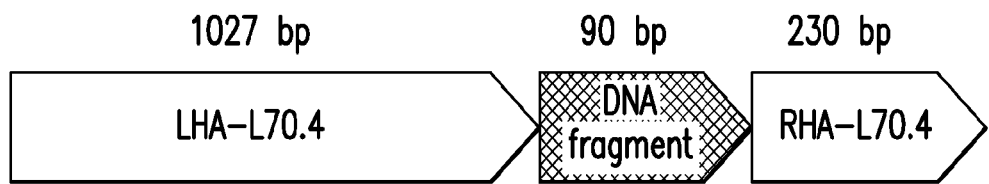

The recombinant DNA constructs containing cassettes for homologous recombination were designed to have the 90 bp sequence corresponding to the 90 bp blunt-end, double-strand DNA fragment used for NHEJ assays (encoded by sequences SEQ ID NO:115 and SEQ ID NO:116) flanked by left and right homology arms (HA). The left-HA is designed based on the sequence flanking the 5'-side of the site for the double-strand break (DSB) for targeted integration. The right-HA is designed as the sequencing flanking the 3'-side of the site for the double-strand break (DSB) for targeted integration. For the L70.4 site the right-HA was 230 bp in length, and two separate left-HA sequences were included, one of 230 bp and one of 1027 bp in length (see FIGS. 14A and 14B, respectively).

Protoplasts were transfected and harvested 48 hours later and analyzed for integration by quantitative, high throughput PCR using the ddPCR system and Taqman probes with one primer designed for the region of the DNA fragment sequence (encoded by the sequences SEQ ID NO:115 and SEQ ID NO:116) and one primer in the chromosomal region flanking the left homologous arm. The size of the expected PCR amplicon with successful HR using the L70.4 targeting construct of FIG. 14A was 383 bp. The size of the expected PCR amplicon with successful HR using the L70.4 targeting construct of FIG. 14B was 1208 bp.

The HR-mediated recombination rate for the corn chromosomal site L70.4 with two separate template DNA constructs is presented in Table 9. When the left-HA and the right-HA were both 230 bp (indicated by SS in Table 9), and the construct with the homology arm cassette was at a concentration of 4 ug there was a statistically significant (p<0.05) difference in the percentage integration rate between the test sample and the control. When the left-HA and the right-HA were both 230 bp (indicated by SS in Table 9), and the construct with the homology arm cassette was at a concentration of 6 ug there was not a statistically significant difference in the percentage integration rate between the test sample and the control. When the left-HA was 1027 bp and the right-HA was 230 bp (indicated by LS in Table 9), and the construct with the homology arm cassette was at a concentration of 4 ug or 6 ug there was not a statistically significant difference in the percentage integration rate between the test sample and the control. This result shows that targeted integration can be achieved by the mechanism of HR at sites of DSB which are targeted by TALENs directed to a specific site in a corn genome.

TABLE 9

HR-mediated Integration Rates in corn protoplasts with DSB mediated by TALENs at the chromosomal site L70.4.

|  | Mean | | Std Dev | |
| --- | --- | --- | --- | --- |
|  | Test | Control | Test | Control |
| L70.4 + SS + 4 ug** | 1.54833 | 0.12181 | 1.48997 | 0.14504 |
| L70.4 + SS + 6 ug | 0.28395 | 0.12181 | 0.20174 | 0.14504 |
| L70.4 + LS + 4 ug | 0.163347 | 0.38048 | 0.282926 | 0.67502 |
| L70.4 + LS + 6 ug | 0.51467 | 0.38048 | 0.23052 | 0.67502 |

**Test was statistically higher (p < 0.05) than the corresponding control based on a student's t-test.

Example 14

Targeting in Corn Genome with Chimeric U6 Promoters

Chimeric U6 promoters were determined to be effective at driving expression of sgRNA constructs and resulting in targeted integration of double-strand, blunt-end DNA fragments at preselected sites in corn chromosomes. These experiments were conducted using the quantitative chromosome cutting assay in corn protoplast assay as described in example 5 and example 6. The U6 promoters incorporated into the sgRNA constructs were: a) the 397 bp corn chromosome 8 U6 promoter encoded by SEQ ID NO:7, b) the 397 bp ch1:ch8 chimeric U6 promoter encoded by SEQ ID NO:18, b) the 397 bp ch8:ch1 chimeric U6 promoter encoded by SEQ ID NO:19, and c) the 397 bp ch8:ch2:ch1:ch8 chimeric U6 promoter encoded by SEQ ID NO:20. The corn chromosomal target sites were L70a, L70c, and L70d, as described in example 5. The CRISPR/Cas9 system employed an expression cassette with the S. pyogenes Cas9 modified to contain two NLS sequences and an intron and encoded by SEQ ID NO:119. The double-strand, blunt-end DNA fragment was encoded by SEQ ID NO:115 and SEQ ID NO:116.

In one assay, 48 hours post transfection of the corn protoplasts with the CRISPR/Cas9 system components, the quantitative assay was done with TaqMan probes. The results (see FIG. 16A) indicate that the targeted integration rate at target site L70a with the sgRNA construct containing the ch8 U6 promoter or the sgRNA construct containing the chimeric ch1:ch8 U6 promoter resulted in about the equivalent percent target integration rate. The targeted integration rate at target site L70c, the sgRNA construct containing the chimeric ch8:ch1 U6 promoter resulted in about double the target integration rate compared to sgRNA construct containing the ch8 U6 promoter. The targeted integration rate at target site L70d, the sgRNA construct containing the ch8 U6 promoter had higher targeted integration rate compared to the sgRNA construct containing the chimeric ch8:ch2:ch1:ch8 U6 promoter.

In another assay, 48 hours post transfection of the corn protoplasts with the CRISPR/Cas9 system components, the quantitative assay was done with EvaGreen® (BioRad, Hercules, Calif.) intercalating dye. The results (see FIG. 16B) indicate that the targeted integration rate with the sgRNA construct containing the ch8 U6 promoter was nearly the same as the targeted integration rate at target site L70a with the sgRNA construct containing the chimeric ch1:ch8 U6 promoter, and at target site L70c with the sgRNA construct containing the chimeric ch8:ch1 U6 promoter, and at target site L70d with the sgRNA construct containing the chimeric ch8:ch2:ch1:ch8 U6 promoter. These data indicate that the targeted integration rate detected by the EvaGreen intercalating dye was about ten-fold higher compared to the targeted integration rates detected using MGB TaqMan probes. This discrepancy is mostly due to differences in the chemistries of the assays. The TaqMan assay uses just two primers and an internal probe, of which one of the primers and the probe are located on the inserted DNA fragment sequence. Unfortunately, the double-strand, blunt-end DNA fragment used in the transfection often undergo degradation by endogenous exonucleases in the protoplasts, and this results in DNA fragment integrations with truncated sites where the TaqMan probe binds. These truncated integration events are not detectable by the TaqMan assay. On the other hand, the binding site for the TaqMan primer located within the inserted DNA fragment sequence is located more internally in the inserted DNA fragment and remains intact even in most truncated inserted DNA fragments. Since the assay with the intercalating Evagreen dye does not require the internal probe, and only the TaqMan primers, this assay is not affected by oligo degradations and thus can detect many more integrations than the TaqMan assay. Otherwise, the two methods of measuring the percent targeted integration showed similar patterns at the three chromosomal target sites and the three different chimeric U6 promoters driving sgRNA expression.

Figure 16A:
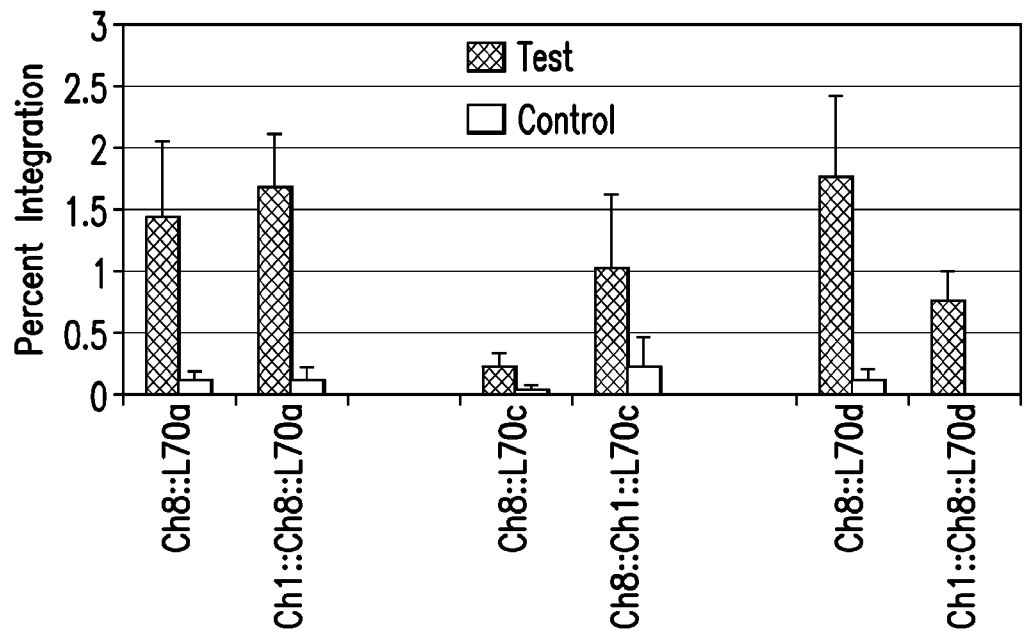
FIG. 16. 16A. Chromosomal integration rates using constructs with the corn chromosome 8 U6 promoter or one of three separate chimeric U6 promoters driving sgRNA expression in CRISPR/Cas9 system to target three different corn chromosomal target sites. Targeted integration was measured by ddPCR assay using MGB TaqMan probes. 16B. Chromosomal integration rates using constructs with the corn chromosome 8 U6 promoter or one of three separate chimeric U6 promoters driving sgRNA expression in CRISPR/Cas9 system to target three different corn chromosomal target sites. Targeted integration was measured by ddPCR assay using EvaGreen® intercalating dye.
Figure 16B:
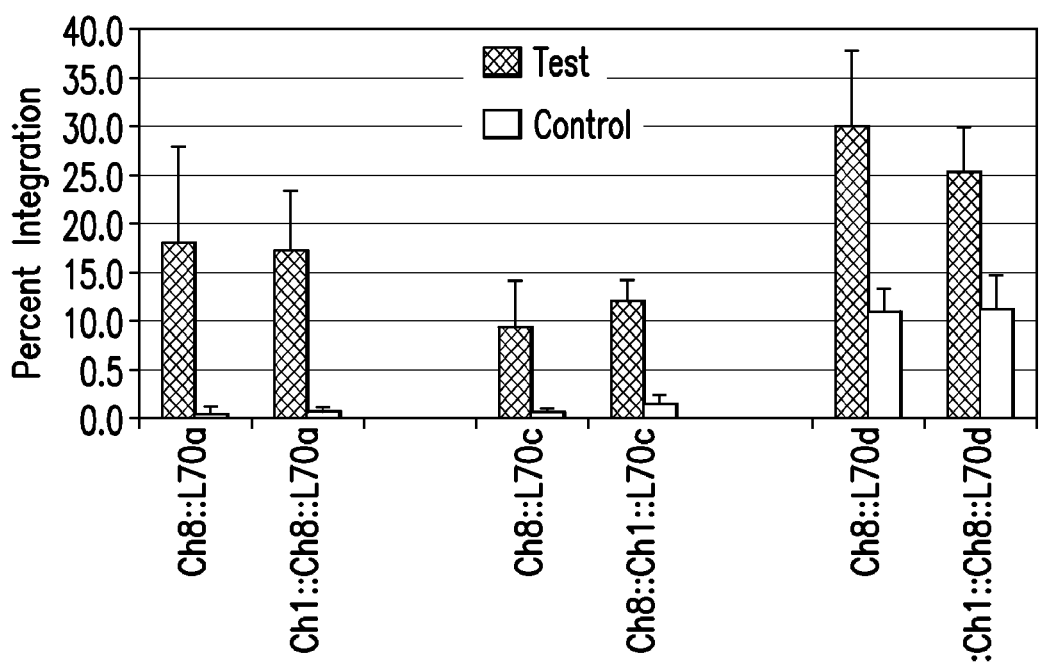

These results show that targeted integration rate at corn chromosomal site L70c when the sgRNA construct contains the Ch8::Ch1 chimeric promoter was slightly, to significantly higher compared to targeted integration rate when the sgRNA construct contains the ch8 U6 promoter (FIGS. 16A and 16B). These results also show that the targeted integration rate at corn chromosomal site L70a when the sgRNA construct contains the Ch1::Ch8 chimeric promoter is about equivalent compared to targeted integration rate when the sgRNA construct contains the ch8 U6 promoter (FIGS. 16A and 16B). Finally, these results show that the targeted integration rate at corn chromosomal site L70d when the sgRNA construct contains the ch8:ch2:ch1:ch8 chimeric promoter was lower compared to the targeted integration rate when the sgRNA construct contains the ch8 U6 promoter (FIGS. 16A and 16B). In conclusion, at least two of the three chimeric promoters were as good as, or better than, the best non-chimeric promoter in corn. These will have utility in multiplex targeting experiments, where the diversity of expression elements is indispensable.

Example 15

Targeted mutation in Tomato Invertase Inhibitor

The CRISPR/Cas9 system was used to knock out the apoplastic invertase inhibitor gene of tomato (INVINH1) by introducing targeted frameshift point mutations following imperfect repair of the targeted double-strand breaks by NHEJ. In an earlier study, knock-down of this gene by RNAi showed elevated fruit sugar content and increased seed weight (Jin et al. *Plant Cell* 21:2072-2089, 2009). Reducing or eliminating the invertase inhibitor activity by either targeted mutagenesis or RNA interference is useful to improve yield and/or quality traits in other crop species too (Braun et al. *J Exp Bot* 65: 1713-1735, 2014).

For these experiments tomato protoplasts were transfected with an expression construct containing a cassette encoding the SpCas9 with one NLS at the C-terminus (SEQ ID NO:28), and one expression construct encoding an sgRNA cassette where expression was driven by one of 4 separate tomato U6 promoters: promoter 1 encoded by SEQ ID NO:146 (which is a fragment of SEQ ID NO:10), promoter 2 encoded by SEQ ID NO:147 (which is a fragment of SEQ ID NO:11), promoter 3 encoded by SEQ ID NO:148 (which is a fragment of SEQ ID NO:9), or promoter 4 encoded by SEQ ID NO:149. The sgRNA were targeted to an invertase inhibitor site (site 1) without a SmlI site or to a site (labeled site 2) in the invertase inhibitor gene with a SmlI restriction endonuclease site. The site 2 sgRNA is encoded by SEQ ID NO:150. The CRISPR/Cas9 cleavage site within target site 2 contains a SmlI restriction endonuclease site. Upon CRISPR/Cas9 induced double-strand break at target site 2, the NHEJ repair will result in indels at this site, thus effectively removing the SmlI restriction endonuclease site. This mutation of the SmlI site was leveraged during the screening for targeted events by amplifying a 380 bp amplicon (SEQ ID NO:159) and subjecting the PCR amplicon to digestion with SmlI. If the SmlI site was not mutated, then the amplicon would be digested into two fragments of 181 bp and 199 bp. If the SmlI site was mutated, then the PCR amplicon would not be digested. This PCR scheme is illustrated in FIG. 17A.

Tomato protoplasts were transfected with the CRISPR/Cas9 system targeting the tomato invertase inhibitor and harvested 48 hours later and genomic DNA extracted. Negative control for the CRISPR/Cas9 system was omission of the expression construct encoding the Cas9 endonuclease. A negative control for the target site was use of a sgRNA to target site 1, and it is not expected that the SmlI site will be mutated with this sgRNA. PCR amplification was done with primers SEQ ID NO:157 and SEQ ID NO:158 and the resulting PCR amplicons were either undigested or digested with SmlI. The reactions were run on agarose gels and the results are shown in FIG. 17B. The negative controls of sgRNA to target site 1 and the omission of Cas9 endonuclease resulted only in PCR amplicons with the SmlI site intact. When the sgRNA was for target site 2, the SmlI site was mutated when the sgRNA cassette contained tomato U6 promoter 1, or tomato U6 promoter 2, or tomato U6 promoter 3, as evidenced by the full-length PCR amplicons (see FIG. 17B, arrows showing amplicons without a SmlI site). The sgRNA construct targeting site 2 and with U6 promoter 4 apparently did not show targeting.

To confirm that the PCR amplicons without a SmlI site were indeed due to CRISPR/Cas9 induced NHEJ mutation, these apparent mutated amplicons were gel-purified and pooled, and then they were sequenced. The multiple sequence alignment in FIG. 17C shows that these PCR amplicons without a SmlI site were from the target site 2 of the tomato invertase inhibitor and contained indels, consistent with CRISPR/Cas9 induced mutation. Specifically, in the multiple sequence alignment, SEQ ID NO:151 represents a region of the PCR amplicon (SEQ ID NO:159) without a mutation. SEQ ID NOs:152 and 153 illustrate indels where there was a 1 bp insertion at the cleavage site. SEQ ID NO:154 illustrates an indel with a 3 bp deletion at the cleavage site. SEQ ID NO:155 illustrates an indel with a 4 bp deletion at the cleavage site. SEQ ID NO:156 illustrates an indel with a 6 bp deletion at the cleavage site. In conclusion, these results indicate that the CRISPR/Cas9 system using tomato U6 promoter 1 (SEQ ID NO:146), or tomato U6 promoter 2 (SEQ ID NO:147), or tomato U6 promoter 3 (SEQ ID NO:148) to drive sgRNA induces mutation at the tomato invertase inhibitor gene target site 2.

Example 16

Promoters to Drive sgRNA Expression

To identify and select additional promoters which would be useful to drive expression of sgRNAs from expression cassettes introduced into dicots and monocots, RNA polymerase II (Pol II) and RNA polymerase III (Pol III) promoters (SEQ ID NOs:160-201 and SEQ ID NOs:247-283) were identified by comparing the sequence encoding U6, U3, U5, U2 and 7SL small nuclear RNA (snRNA) against soy and corn genomes using BLAST (see Table 10). From regions of this bioinformatic alignment, 200 or more nucleotides immediately upstream of the 5' end of the coding region of the respective snRNA was used for testing as putative promoters for driving expression of sgRNA from expression cassettes introduced into plant cells.

TABLE 10

SEQ ID NO of putative promoter sequence upstream of the snRNA genes and the source (tomato or soy or corn).

| Promoter SEQ ID NO: | snRNA | Promoter Source | Promoter + GUS + Terminator SEQ ID NO | Terminator |
|---|---|---|---|---|
| 148 | Promoter 3 | tomato | 202 | poly(T)7 |
| 160 | SoyU6a | soy | 203 | poly(T)7 |
| 161 | SoyU6c | soy | 204 | poly(T)7 |
| 162 | SoyU6d | soy | 205 | poly(T)7 |
| 163 | SoyU6e | soy | 206 | poly(T)7 |
| 164 | SoyU6f | soy | 207 | poly(T)7 |
| 165 | SoyU6g | soy | 208 | poly(T)7 |
| 166 | SoyU6i | soy | 209 | poly(T)7 |
| 167 | U3a | soy | 210 | poly(T)7 |
| 168 | U3b | soy | 211 | poly(T)7 |
| 169 | U3c | soy | 212 | poly(T)7 |
| 170 | U3d | soy | 213 | poly(T)7 |
| 171 | U3e | soy | 214 | poly(T)7 |
| 172 | 7SL_CR13 | soy | 215 | poly(T)7 |
| 173 | 7SL_CR14 | soy | 216 | poly(T)7 |
| 174 | 7SL_CR10 | soy | 217 | poly(T)7 |
| 175 | 7SLCR01 | corn | 218 | poly(T)7 |
| 176 | 7SLCR07 | corn | 219 | poly(T)7 |
| 177 | 7SLCR09 | corn | 220 | poly(T)7 |
| 178 | U3CR02 | corn | 221 | poly(T)7 |
| 179 | U3CR10 | corn | 222 | poly(T)7 |
| 180 | U3CR08 | corn | 223 | poly(T)7 |
| 181 | U3CR08b | corn | 224 | poly(T)7 |
| 182 | U3CR05 | corn | 225 | poly(T)7 |
| 183 | U2snRNA_P | corn | 226 | SEQ ID NO 237 |
| 184 | U2snRNA_I | corn | 227 | SEQ ID NO 237 |
| 185 | U2snRNA_B | corn | 228 | SEQ ID NO 237 |
| 186 | U2snRNA_G | corn | 229 | SEQ ID NO 237 |
| 187 | U2snRNA_A | corn | 230 | SEQ ID NO 237 |
| 188 | U5snRNA_A | corn | 231 | SEQ ID NO 237 |
| 189 | U5snRNA_C | corn | 232 | SEQ ID NO 237 |
| 190 | U5snRNA_D | corn | 233 | SEQ ID NO 237 |
| 191 | U5snRNA_E | corn | 234 | SEQ ID NO 237 |
| 192 | U2snRNA_C | corn | — | — |
| 193 | U2snRNA_D | corn | — | — |
| 194 | U2snRNA_E | corn | — | — |
| 195 | U2snRNA_F | corn | — | — |
| 196 | U2snRNA_H | corn | — | — |
| 197 | U2snRNA_K | corn | — | — |
| 198 | U2snRNA_L | corn | — | — |
| 199 | U2snRNA_M | corn | — | — |
| 200 | U6Chr08 | corn | 235 | poly(T)7 |
| 201 | U6Chr01 | corn | 236 | poly(T)7 |
| 247 | U2CR01a | Soy | — | — |
| 248 | U2CR01b | Soy | — | — |
| 249 | U2CR02 | Soy | — | — |
| 250 | U2CR03 | Soy | — | — |
| 251 | U2CR04 | Soy | — | — |
| 252 | U2CR05a | Soy | — | — |
| 253 | U2CR05b | Soy | — | — |
| 254 | U2CR06a | Soy | — | — |
| 255 | U2CR06b | Soy | — | — |
| 256 | U2CR06v | Soy | — | — |
| 257 | U2CR07 | Soy | — | — |
| 258 | U2CR08a | Soy | — | — |
| 259 | U2CR08b | Soy | — | — |
| 260 | U2CR08c | Soy | — | — |
| 261 | U2CR10a | Soy | — | — |
| 262 | U2CR10b | Soy | — | — |
| 263 | U2CR10c | Soy | — | — |
| 264 | U2CR13 | Soy | — | — |
| 265 | U2CR14 | Soy | — | — |
| 266 | U2CR15 | Soy | — | — |
| 267 | U2CR17a | Soy | — | — |
| 268 | U2CR17b | Soy | — | — |
| 269 | U2CR17c | Soy | — | — |
| 270 | U2CR17d | Soy | — | — |
| 271 | U2CR17e | Soy | — | — |
| 272 | U2CR17f | Soy | — | — |
| 273 | U2CR19a | Soy | — | — |
| 274 | U2CR19b | Soy | — | — |
| 275 | U2CR20 | Soy | — | — |
| 276 | U5CR07 | Soy | — | — |
| 277 | U5CR10 | Soy | — | — |
| 278 | U5CR10 | Soy | — | — |
| 279 | U5CR15 | Soy | — | — |
| 280 | U5CR19 | Soy | — | — |
| 281 | U5CR20a | Soy | — | — |
| 282 | U5CR20b | Soy | — | — |
| 283 | SoyU6b | Soy | — | — |

Example 17

Normalized RNA Transcript Level Assay

To assess the efficacy of the promoters listed in Table 10 to drive expression of sgRNAs, a series of constructs were generated which contained a cassette encoding one of the putative promoters (SEQ ID NO:154, and SEQ ID NOs: 160-201) operably linked to a 221 bp fragment of a beta-glucuronidase (GUS) open reading frame and either a poly (T)7 terminator for Pol III promoters (7SL, U6, and U3) or the sequence 5'-ACAATTCAAAACAAGTTTTAT-3' (SEQ ID NO:237) for the pol II U2 and U5 promoters (Table 10). The recombinant constructs (0.5 pmol) containing the promoter-GUS fragment fusions were transfected into soy cotyledon protoplasts (SEQ ID NO:202-217 or corn leaf protoplasts (SEQ ID NO: 218-236) along with 300 ng of a plasmid serving as a transformation control encoding Renilla Luciferase (RLUC) expressed using the CaMV promoter. The transfected protoplasts were harvested 18 hours after transfection and the RNA levels were measured via TaqMan assays using a probe and primers complementary to the GUS fragment. Internal controls used to normalized the TaqMan assay included (1) an 18S primer pair/probe set to control for RNA concentration and (2) RLUC luminescence as a transformation control.

Figure 18A:
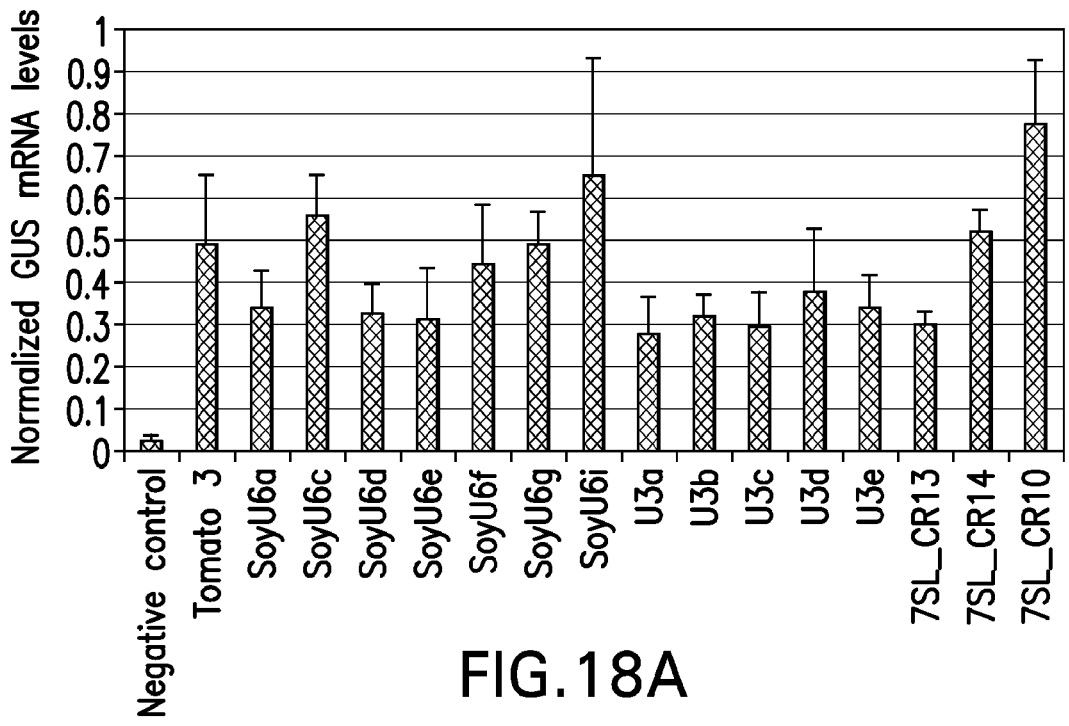
FIG. 18. 18A. Graphical representation of data showing normalized GUS mRNA levels from soybean cotyledon protoplast assays with recombinant expression constructs with U6, U3, and 7SL promoters. 18B. Graphical representation of data showing normalized GUS mRNA levels from corn leaf protoplast assays with recombinant expression constructs with U6, U3, 7SL, U2, or U5 promoters.
Figure 18B:
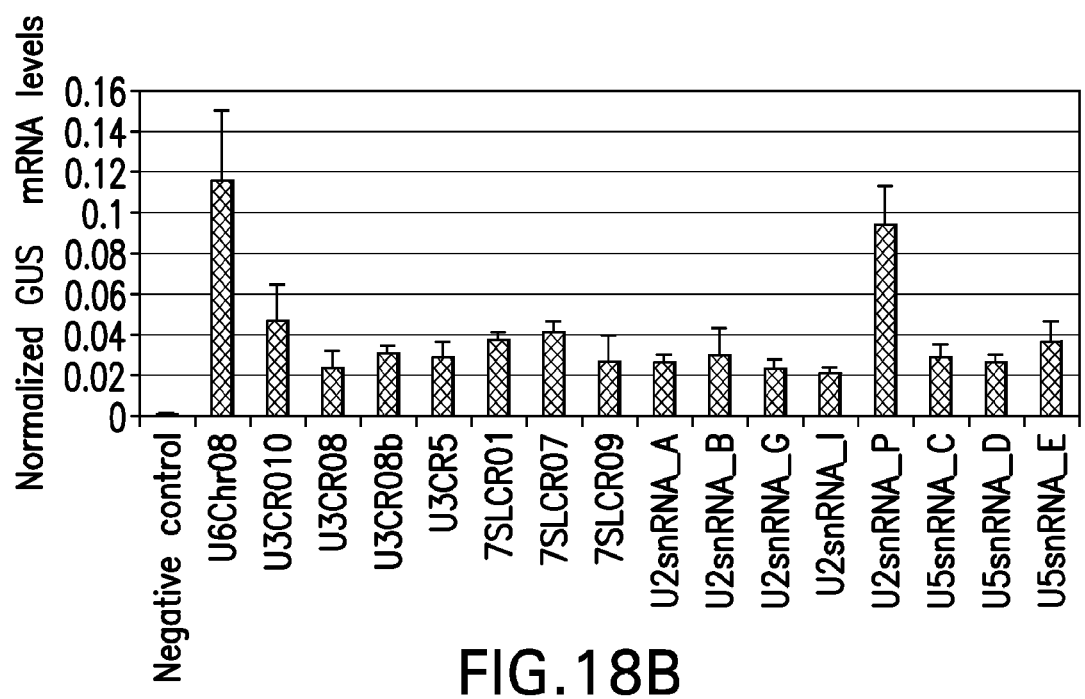

In soy cotyledon protoplasts, all promoters tested resulted in significantly higher normalized levels of GUS mRNA than the control (no GUS construct) (One-way ANOVA student t-test p value<0.05) (FIG. 18A). The lowest level of normalized GUS mRNA was with construct (SEQ ID NO:210) containing the U3a promoter (SEQ ID NO:167). The highest level of normalized GUS mRNA was with construct (SEQ ID NO:210) containing the 7SL_CR10 promoter (SEQ ID NO:174). The level of normalized GUS mRNA with all promoters tested with this assay ranged from 11-31 times higher expression levels that the no DNA negative control. No one class of promoters (U6, U3, or 7SL) performed better than the other, although the U3 promoters were generally in the lower range of expression observed in the experiment. U3 promoters have been successfully used by Liang et al. (*J. Genetics and Genomics* 41:63-68, 2014) to drive sgRNAs in corn. Thus, although these data indicate that the U3 promoters may be lower than U6 or 7SL, they are still viable candidates to drive sgRNA expression in soy. These data suggest that any of the U6, U3, or 7SL promoters identified here would be good candidates for making recombinant expression constructs to drive expression of sgRNA in plant cells. In corn leaf protoplast, all promoters tested resulted in significantly higher normalized levels of GUS mRNA compared to the control (One-way ANOVA student t-test p value<0.05) with values ranging from 26 fold to 141 fold higher expression than the negative control (FIG. 18B). The U6Chr08 promoter construct (SEQ ID NO:235) resulted in the highest normalized levels of GUS mRNA expression, and U2snRNA_I promoter construct (SEQ ID NO:227) resulted in the lowest, with approximately a 5.5-fold difference in normalized levels of GUS mRNA expression between them. The U2snRNA_P promoter construct (SEQ ID NO:226) also stood out as having high normalized levels of GUS mRNA expression. All the remaining promoters were within the same relative range having less than 2 fold difference between them (FIG. 18B). These data suggest that any of the U6, U3, 7S1, U2, or U5, promoters identified here would be good candidates for making recombinant expression constructs to drive expression of sgRNA in plant cells.

Example 18

GUS Expression Assay for sgRNA Expression

To determine how the difference in sgRNA expression levels impact Cas9 activity, an assay was used that relied on activating transcription from a minimal promoter upstream of the GUS open reading frame in a reporter construct transfected into corn leaf protoplasts. For this assay, a Cas9 nuclease from *S. thermophilus* was mutated at amino acid positions D9A and H599A of the native protein sequence, effectively creating a Cas9 without endonuclease cleavage activity (also referred to as a 'dead Cas9'). Additionally, this dead Cas9 was modified to encode one NLS domain (SEQ ID NO:120) at amino acid positions 2-11 of SEQ ID NO:239 and an activation domain from a TALE protein from amino acid positions 1135-1471 of SEQ ID NO:239. The polynucleotide sequence of the dead Cas9, represented by SEQ ID NO:238, included an intron at positions 507-695. A reporter construct was constructed where the uidA (GUS) reporter gene was driven by a minimal CaMV promoter with three adjacent sgRNA binding sites (SEQ ID NO:240) at nucleotide positions 80-98, 117-135, and 154-172 of the sequence SEQ ID NO:246. Also constructed were a set of sgRNA (based on the sgRNA of Cong et al. 2013 Science 339:819) expression constructs that consisted of the one of the promoters from each class of snRNA genes, namely U6, 7SL, U2, U5, and U3 (Table 11) and which would target the dead Cas9-TALE-AD to one or more of the sgRNA binding sites of the GUS reporter construct. The U6 and 7SL promoters normally initiate transcription on a G, and the U2, U5 and U3 promoters normally initiate transcription on an A. To ensure proper transcription initiation of the sgRNA, for constructs with either a U6 or 7SL promoter, a G was inserted between the promoter and spacer sequence. For constructs with a U2, U5 or U3 promoter, an A was inserted between the promoter and spacer sequence. When the dead Cas9-TALE-AD and sgRNA complex binds the GUS reporter construct, the TALE activation domain functions as a transcription factor activating the minimal CaMV promoter resulting in higher expression of the GUS transcript, and ultimately higher levels of GUS protein expression.

TABLE 11

SEQ ID NO corresponding to sgRNA expression constructs.

| Promoter + sgRNA SEQ ID NO: | Promoter | Promoter SEQ ID NO: |
| --- | --- | --- |
| 241 | U6Chr08 | 200 |
| 242 | 7SLCR07 | 176 |
| 243 | U2snRNA_I | 184 |
| 244 | U5snRNA_E | 191 |
| 245 | U3CR08b | 181 |

Figure 19:
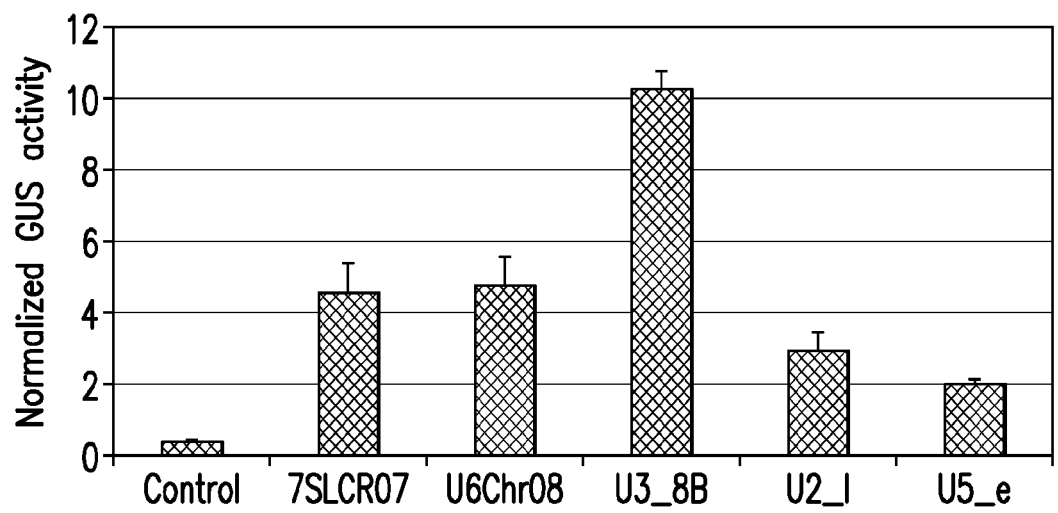
FIG. 19. Graphical representation of data from normalized GUS expression levels from corn leaf protoplast assays with, a recombinant expression constructs encoding 1) a GUS expression construct 2) a dead Cas9-TALE-AD expression construct, and 3) recombinant sgRNA expression constructs with 7SL, U6, U3, U2, or U5 promoters.

For the assay, corn leaf protoplasts were transfected with 0.8 pmol of dead Cas9-TALE-AD expression cassette, 0.5 pmol of the GUS expression cassette, 1.6 pmol of one of the sgRNA expression cassettes, 650 ng of Luciferase expression cassette, and 300 ng of Renilla Luciferase (RLUC) expression cassette. The transfected protoplasts were harvested 18 hours later and GUS activity was measured using the 4-methylumbelliferyl-beta-D-glucuronide (MUG, Sigma, St. Louis, Mo.) fluorimetric assay, and luciferase and RLUC activity was measured and used as control to normalize relative to transfection controls. The activity of GUS is a readout of the how often the dead Cas9-TALE-AD binds to the reporter plasmid. Each class of snRNA promoter driving sgRNA gave higher normalized GUS activity compared to the control (FIG. 19). The U3CR08b (U3_8B in FIG. 19) promoter resulted in the highest normalized GUS activity of about 10× over control. The two promoters 7SLCR07 and U6Chr08 both gave about the same normalized GUS activity of about 4× over control. The two promoters U2snRNA_I (Us_I in FIG. 19) and U5snRNA_E (U5_e in FIG. 19) were each at or slightly above 2× over control for normalized GUS activity. These results indicate that the 7SL, U6, U3, U2, and U5 snRNA promoters may be good to excellent candidates for use in sgRNA expression constructs for CRISPR/Cas9 system useful in genome modification.

The differences in normalized GUS expression observed using the dead Cas9-TALE-AD assay do not minor the normalized GUS mRNA levels shown in the corn leaf protoplast assay detailed in Example 17.

What is claimed is:

1. A recombinant DNA construct comprising a U6 snRNA promoter fragment, wherein said U6 snRNA promoter fragment is operably linked to:
   (i) a sequence encoding a single-guide RNA (sgRNA); or
   (ii) a sequence specifying a non-coding RNA;
   and wherein the sequence of said U6 snRNA promoter fragment consists of a sequence selected from the group consisting of SEQ ID NO:7 and SEQ ID NO:8, wherein the U6 snRNA promoter fragment and the sgRNA or the non-coding RNA come from different sources.

2. The recombinant DNA construct of claim 1, wherein the sequence of said U6 snRNA promoter fragment consists of the sequence of SEQ ID NO:7.

3. The recombinant DNA construct of claim 1, further comprising a transcription termination sequence.

4. The recombinant DNA construct of claim 1, further comprising a sequence encoding a promoter operably linked to a sequence encoding a clustered, regularly interspaced, short palindromic repeats (CRISPR)-associated Cas endonuclease gene product.

5. The recombinant DNA construct of claim 4, wherein the Cas endonuclease gene product is further operably linked to a nuclear localization sequence (NLS).

6. The recombinant DNA construct of claim 4, wherein the sequence encoding said Cas endonuclease is SEQ ID NO:27, SEQ ID NO:68, SEQ ID NO:97, SEQ ID NO:119, or SEQ ID NO:136.

7. The recombinant DNA construct of claim 1, wherein the non- coding RNA is a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), or a naturally occurring antisense siRNA (nat-siRNA).

8. A cell comprising the recombinant DNA construct of claim 1.

9. The cell of claim 8, wherein the cell is a plant cell.

10. A method of introducing a double-strand break in the genome of a cell, comprising introducing in said cell:
   a) at least one recombinant DNA construct of claim 1; and
   b) a second recombinant DNA construct comprising a sequence encoding a promoter operably linked to a sequence encoding a clustered, regularly interspaced, short palindromic repeats (CRISPR)-associated Cas endonuclease gene product operably linked to a nuclear localization sequence (NLS).

11. The method of claim 10, wherein the U6 snRNA promoter fragment consists essentially of the sequence of SEQ ID NO:7.

12. The method of claim 10, wherein the sequence encoding said Cas endonuclease is SEQ ID NO:27, SEQ ID NO:68, SEQ ID NO:97, SEQ ID NO:119, or SEQ ID NO:136.

13. A method of introducing a double-strand break in the genome of a cell, comprising introducing to said cell at least one recombinant DNA construct of claim 4.

14. The method of claim 13, wherein the U6 snRNA promoter fragment consists of the sequence of SEQ ID NO:7.

15. The method of claim 13, wherein the sequence encoding the Cas endonuclease is SEQ ID NO:27, SEQ ID NO:68, SEQ ID NO:97, SEQ ID NO:119, or SEQ ID NO:136.

16. A method of genome modification comprising:
   a) introducing a double-strand break in the genome of a plant cell by the method according to claim 10; and
   b) introducing into said plant cell a recombinant blunt-end double-strand DNA fragment,
wherein said recombinant blunt-end double-strand DNA fragment is incorporated into said double strand break by endogenous DNA repair.

17. A method of genome modification comprising:
   a) introducing a double-strand break in the genome of a plant cell by the method according to claim 13; and
   b) introducing into said plant cell a recombinant blunt-end double-strand DNA fragment,
wherein said recombinant blunt-end double-strand DNA fragment is incorporated into said double strand break by endogenous DNA repair.

* * * * *